United States Patent
Huigens, III et al.

(10) Patent No.: US 11,242,331 B2
(45) Date of Patent: Feb. 8, 2022

(54) ANALOGS OF YOHIMBINE AND USES THEREOF

(71) Applicant: University of Florida Research Foundation, Incorporated, Gainesville, FL (US)

(72) Inventors: Robert William Huigens, III, Williston, FL (US); Nicholas G. Paciaroni, Gainesville, FL (US); Hendrik Luesch, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/097,167

(22) PCT Filed: Apr. 28, 2017

(86) PCT No.: PCT/US2017/030171
§ 371 (c)(1),
(2) Date: Oct. 26, 2018

(87) PCT Pub. No.: WO2017/190038
PCT Pub. Date: Nov. 2, 2017

(65) Prior Publication Data
US 2019/0256490 A1    Aug. 22, 2019

Related U.S. Application Data

(60) Provisional application No. 62/427,772, filed on Nov. 29, 2016, provisional application No. 62/329,518, filed on Apr. 29, 2016.

(51) Int. Cl.
*C07D 401/04* (2006.01)
*A61P 35/00* (2006.01)
(Continued)

(52) U.S. Cl.
CPC ........ *C07D 401/04* (2013.01); *A61K 31/4745* (2013.01); *A61P 29/00* (2018.01);
(Continued)

(58) Field of Classification Search
CPC .. C07D 401/04; C07D 403/04; C07D 401/14; C07D 487/04
See application file for complete search history.

(56) References Cited

U.S. PATENT DOCUMENTS 3,219,661 A * 11/1965 Shavel, Jr. ............ C07D 471/20
546/18
3,576,004 A    4/1971 Albright et al.

FOREIGN PATENT DOCUMENTS

EP    0200436 A2    4/1986

OTHER PUBLICATIONS

Sheludko. Plant Cell Reports, 1999, 18, 911-18 (Year: 1999).*
(Continued)

*Primary Examiner* — Noble E Jarrell
(74) *Attorney, Agent, or Firm* — Wolf, Greenfield & Sacks, P.C.

(57) ABSTRACT

The present disclosure provides compounds of Formulae (I-A), (II'), (III-A), (IV'), and (V-A), wherein the compounds are derived from or based on yohimbine. The provided compounds may be useful in treating or preventing a disease (e.g., proliferative disease, cancers, inflammatory diseases, autoimmune diseases, and infectious diseases) in a subject in need thereof. The present disclosure provides methods of preparing compounds of Formulae (I-A), (II'), (III-A), (IV'), and (V-A). Also provided are pharmaceutical compositions, kits, methods, and uses that include or involve a compound described herein.

Formulae (I-A), (II'), (III-A), (IV') and (V-A)

(I-A)

(II')

(III-A)

(Continued)

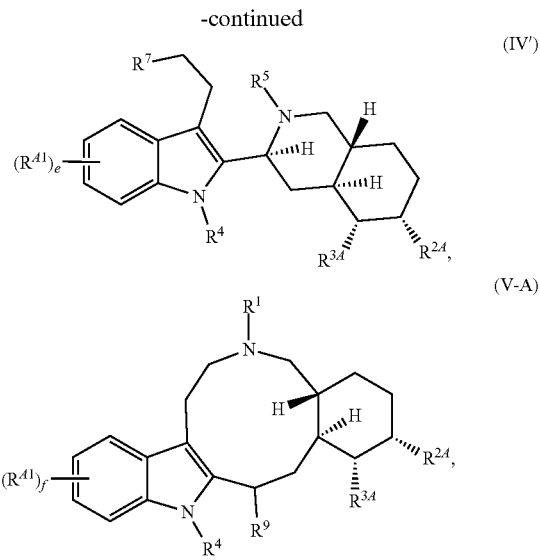

30 Claims, 32 Drawing Sheets

(51) Int. Cl.
| | |
|---|---|
| *C07D 401/14* | (2006.01) |
| *C07D 487/04* | (2006.01) |
| *A61K 31/4745* | (2006.01) |
| *A61P 29/00* | (2006.01) |
| *C07D 405/14* | (2006.01) |
| *C07D 409/14* | (2006.01) |
| *C07D 471/14* | (2006.01) |
| *C07D 498/16* | (2006.01) |
| *C07D 471/16* | (2006.01) |

(52) U.S. Cl.
CPC .............. *A61P 35/00* (2018.01); *C07D 401/14* (2013.01); *C07D 405/14* (2013.01); *C07D 409/14* (2013.01); *C07D 471/14* (2013.01); *C07D 471/16* (2013.01); *C07D 487/04* (2013.01); *C07D 498/16* (2013.01)

(56) References Cited

OTHER PUBLICATIONS

Paciaroni. Chemistry—A European Journal, 2017, 23, 4327-35 (Year: 2017).*
Greene. Protective Groups in Organic Synthesis, Third Edition, 1999, pp. 494-503 (Year: 1999).*
Huang. Journal of Nutritional Biochemistry, 2015, 26, 1401-1413 (Year: 2015).*
Takayama. Heterocycles, 1992, 33(1), 121-125 (Year: 1992).*
Olagnier. PLos Pathogens,.2011, 7(9), 1-14) (Year: 2011).*
Bhandari. Infectious Diseases and Therapy, 2014, 3, 159-174 (Year: 2014).*
International Search Report and Written Opinion, dated Sep. 7, 2017, in connection with International Application No. PCT/US2017/030171.
International Preliminary Report on Patentability, dated Nov. 8, 2018, in connection with International Application No. PCT/US2017/030171.
Albright et al., Alkaloid Studies, V. Reaction of Tertiary Amines with Cyanogen Bromide under Solvolytic Conditions. Journal of the American Chemical Society. 1969;91:4317-8.
Bhat et al., A structure-function relationship among reserpine and yohimbine analogues in their ability to increase expression of mdr1 and P-glycoprotein in a human colon carcinoma cell line. Mol Pharmacol. Oct. 1995;48(4):682-9.
Huigens et al., A ring-distortion strategy to construct stereochemically complex and structurally diverse compounds from natural products. Nat Chem. Mar. 2013;5(3):195-202. DOI: 10.1038/nchem.1549.
Kaushik et al., Biomedical importance of indoles. Molecules. Jun. 6, 2013;18(6):6620-62. DOI: 10.3390/molecules18066620.
O'Connor et al., Chemistry and biology of monoterpene indole alkaloid biosynthesis. Nat Prod Rep. Aug. 2006;23(4):532-47. DOI: 10.1039/B512615K.
Somei et al., 1-Hydroxyyohimbine and Its Derivatives: New Potent α2-Blockers for the Treatment of Erectile Dysfunction. Heterocycles. 2006;69(1):259-269. DOI: 10.3987/COM-06-S(O)26.
Somei et al., Synthesis of 1-Hydroxyyohimbine and Its Novel Skeletal Rearrangement Reaction into Oxindole Derivatives. Heterocycles. 2001;55(7):1237-1240. DOI: 10.3987/COM-01-9226.
Stahl et al., A Reinvestigation of the Oxidative Rearrangement of Yohimbane-Type Alkaloids. Part B. Formation of Oxindol (= 1,3-Dihydro-2H-indol-2-one) Derivatives. Helvetica Chimica Acta. 1996;79(5):1361-1378. DOI: 10.1002/hlca.19960790510.
Yang et al., Biosynthetically inspired divergent approach to monoterpene indole alkaloids: total synthesis of mersicarpine, leuconodines B and D, leuconoxine, melodinine E, leuconolam, and rhazinilam. Org Lett. Dec. 5, 2014;16(23):6216-9. DOI: 10.1021/ol503150c.
Zinnes et al., Yohimbane Derivatives. III. The Oxidative Rearrangement of Indole Alkaloids to Their Spirooxindole Analogs. Journal of Organic Chemistry. 1966;31:1765-1771.
Extended European Search Report dated Sep. 23, 2019, in connection with Application No. 17790565.0.

* cited by examiner

HIF-Dependent Anticancer Activity & Nitric Oxide Inhibition

Y7g

Nrf2-ARE Inhibition

Y6q

Y3e

Y1f

Nrf2-ARE Activation

Y5b

Y6u

ANALOGS OF YOHIMBINE AND USES THEREOF

RELATED APPLICATIONS

This application is a national stage filing under 35 U.S.C. § 371 of international application number PCT/US2017/030171, filed Apr. 28, 2017, and claims priority under 35 U.S.C. § 119(e) to U.S. Provisional Applications, U.S. Ser. No. 62/329,518, filed Apr. 29, 2016, and U.S. Ser. No. 62/427,772, filed Nov. 29, 2016, each of which is incorporated herein by reference.

BACKGROUND OF THE INVENTION

Indole-containing compounds span an array of chemical space from complex natural products to very simple compounds (FIG. 5, indoles 1-9). Interestingly, simple and complex indole-containing compounds demonstrate diverse biological activities due to the numerous biological targets that bind various indoles, making the indole nucleus a privileged scaffold that occupies an interesting and biologically relevant chemical space. Yohimbine is a complex indole alkaloid isolated from the bark of Pausinystalia trees and the Rauwolfia root that acts as an $\alpha_2$-adrenergic receptor antagonist. (Friesen, K.; Palatnick, W.; Tenebein, M. J. Emerg. Med. 1993, 11, 287-288). The alkaloid yohimbine is highly abundant and sold over-the-counter for its fat-burning, stimulatory, and aphrodisiac properties. Yohimbine has a highly complex ring system fused to an indole nucleus. This provides an opportunity to develop an innovative ring distortion strategy involving the basic reactivity of the indole heterocycle to rapidly generate complex and diverse small molecules for biological screening in diverse disease areas (e.g., cancer, inflammation, drug-resistant bacteria). New compounds based on or derived from yohimbine may be useful as potential antibacterial, anticancer, or antimalarial agents. These compounds may also be useful in other therapeutic areas. The disclosed synthetic strategy is useful for rapidly creating and screening structurally diverse small molecules for various biological activities and uses, including as treatment for proliferative disease (e.g., cancers, inflammatory diseases, autoimmune diseases), and infectious disease (e.g., bacterial infection (e.g., infections involving drug-resistant bacteria)).

SUMMARY OF THE INVENTION

Described herein are compounds of Formulae (I-A), (II'), (III-A), (IV'), and (V-A). The compounds of Formulae (I-A), (II'), (III-A), (IV'), (V-A) are derived from or based on yohimbine. The compounds described herein may be useful in treating and/or preventing a disease or condition, e.g., in treating and/or preventing a proliferative disease (e.g., cancers, inflammatory diseases, autoimmune diseases), or infectious disease, in a subject in need thereof. Also provided are methods of preparing compounds of Formulas (I-A), (II'), (III-A), (IV'), and (V-A), and salts, solvates, hydrates, polymorphs, co-crystals, tautomers, stereoisomers, isotopically labeled derivatives, and prodrugs thereof, or mixtures thereof. Also provided are pharmaceutical compositions and kits including a compound described herein.

In one aspect, the present disclosure provides compounds of Formula (I-A):

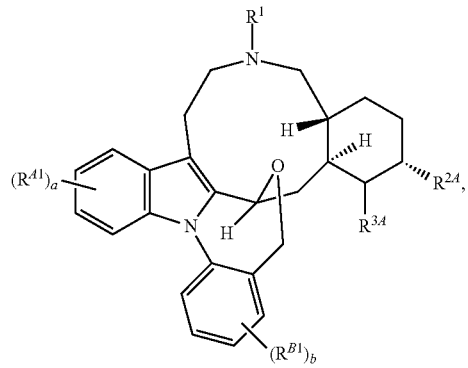

and pharmaceutically acceptable salts, solvates, hydrates, polymorphs, co-crystals, tautomers, stereoisomers, isotopically labeled derivatives, and prodrugs thereof, wherein a, b, $R^1$, $R^{A1}$, $R^{2A}$, $R^{3A}$, and $R^{B1}$ are as defined herein.

In one aspect, the present invention provides compounds of Formula (I):

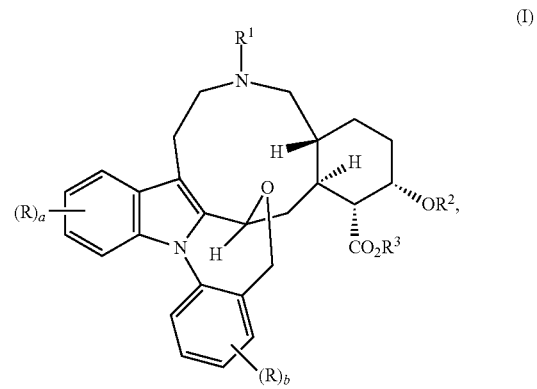

and pharmaceutically acceptable salts, solvates, hydrates, polymorphs, co-crystals, tautomers, stereoisomers, isotopically labeled derivatives, and prodrugs thereof, wherein a, b, R, $R^1$, $R^2$, and $R^3$ are as defined herein.

Exemplary compounds of Formulae (I-A) and (I) include, but are not limited to:

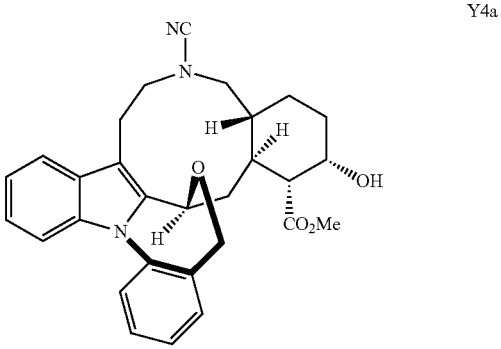

-continued

Y4b
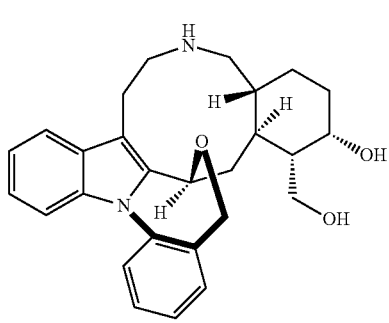

Y5a
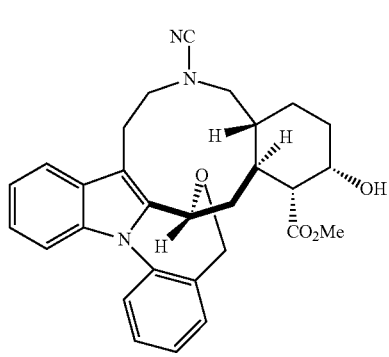

Y5b
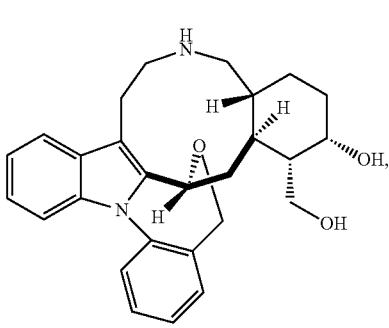

and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II'):

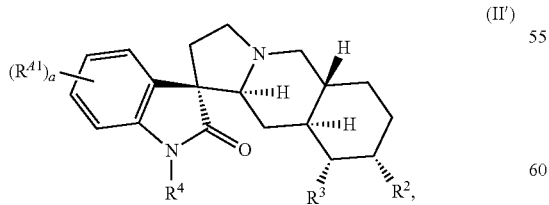
(II')

and pharmaceutically acceptable salts, solvates, hydrates, polymorphs, co-crystals, tautomers, stereoisomers, isotopically labeled derivatives, and prodrugs thereof, wherein a, $R^{2A}$, $R^{3A}$, $R^4$, and $R^{A1}$ are as defined herein.

In another aspect, the present disclosure provides compounds of Formula (II):

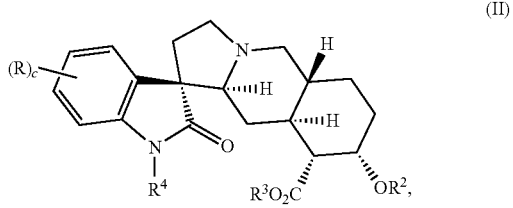
(II)

and pharmaceutically acceptable salts, solvates, hydrates, polymorphs, co-crystals, tautomers, stereoisomers, isotopically labeled derivatives, and prodrugs thereof, wherein c, R, $R^2$, $R^3$, and $R^4$ are as defined herein.

Exemplary compounds of Formulae (II') and (II) include, but are not limited to:

Y3a
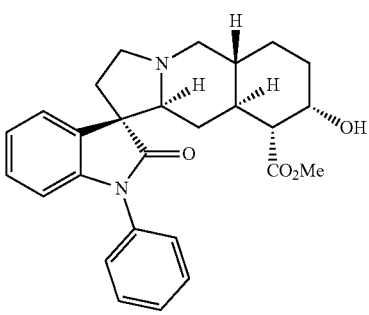

Y3b
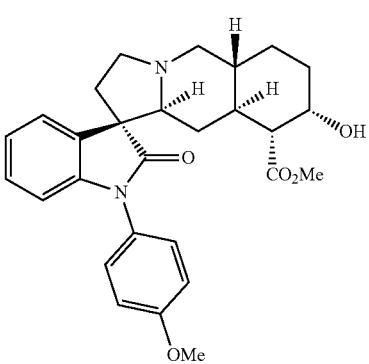

Y3c
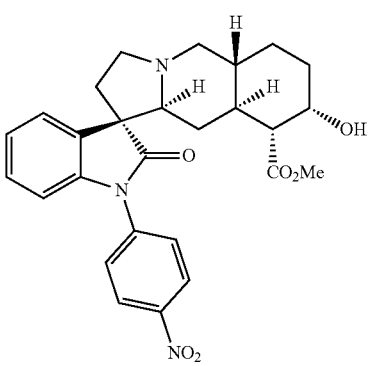

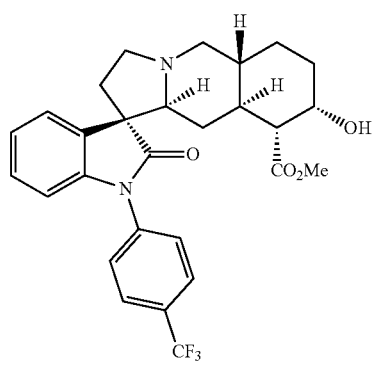
Y3d
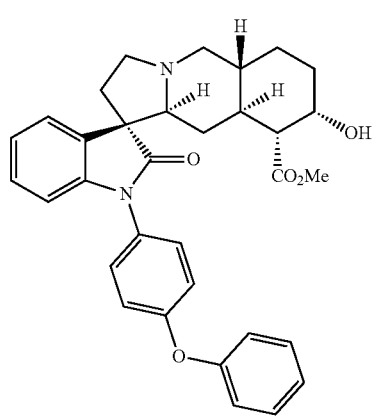
Y3e
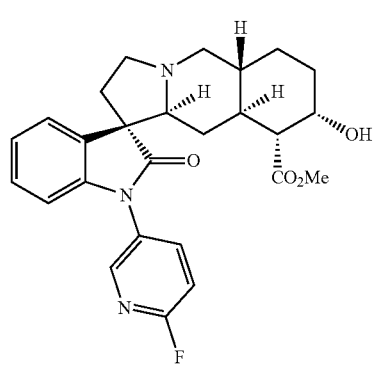
Y3f
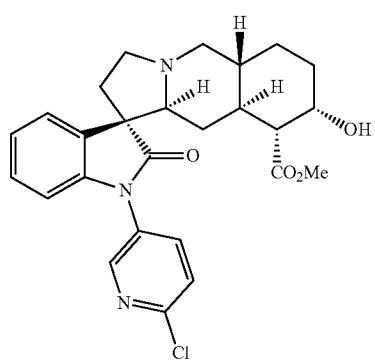
Y3g
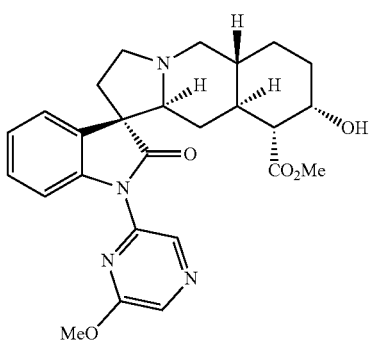
Y3h
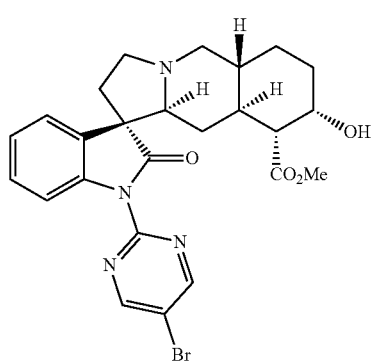
Y3i
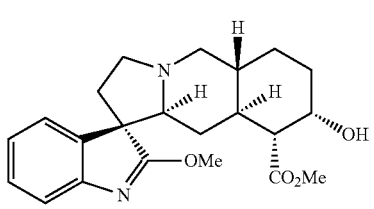
Y7a
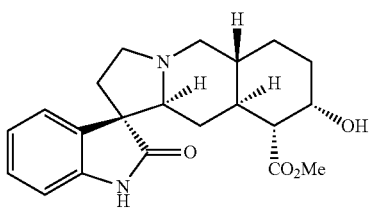
Y7b
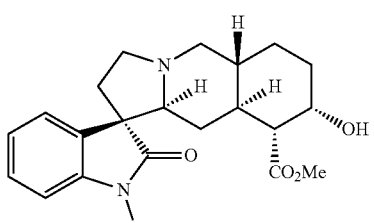
Y7c
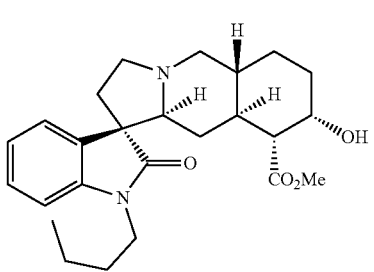
Y7d Y7e
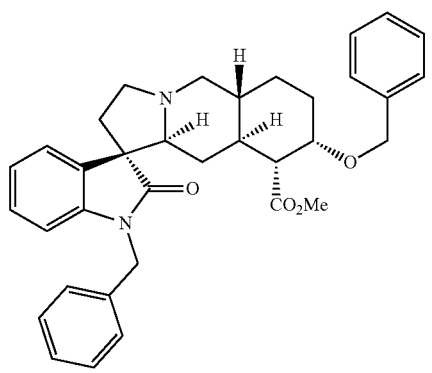
Y7f
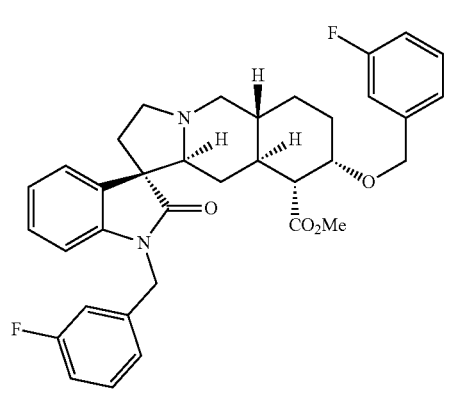
Y7g
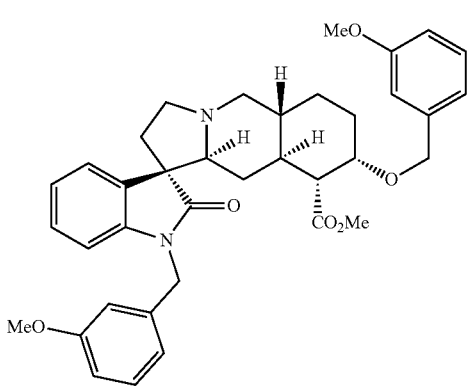
Y7h
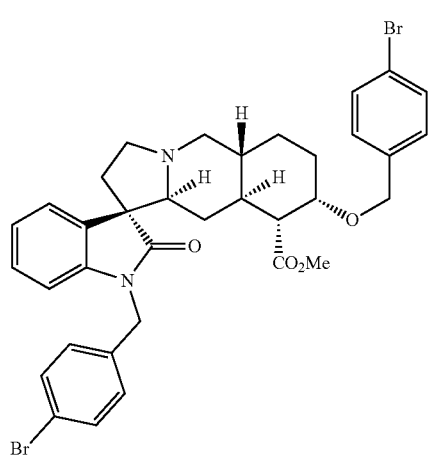
Y7i
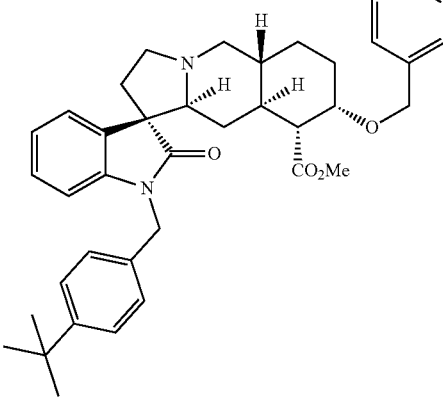
Y7j
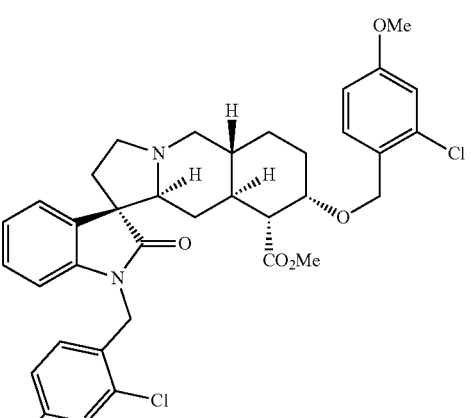
Y7k
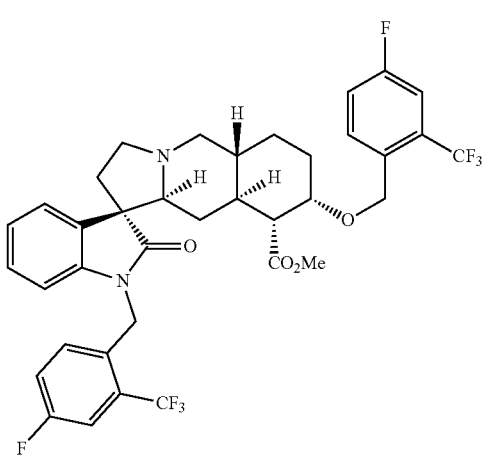

-continued

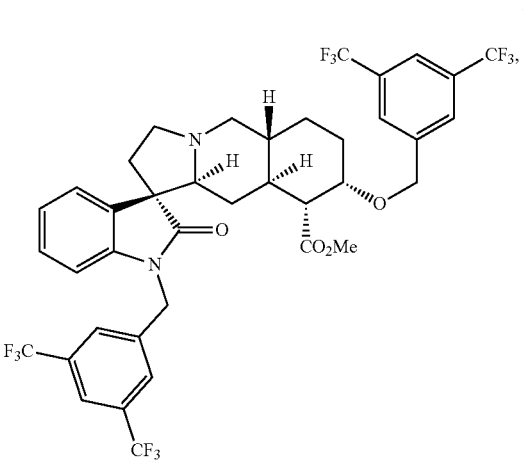
Y7l and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (III-A):

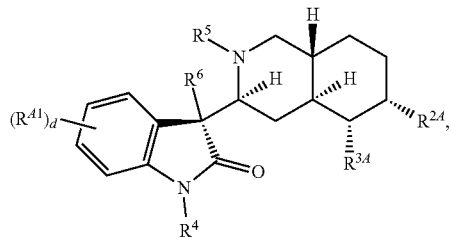
(III-A)

and pharmaceutically acceptable salts, solvates, hydrates, polymorphs, co-crystals, tautomers, stereoisomers, isotopically labeled derivatives, and prodrugs thereof, wherein d, $R^{2A}$, $R^{3A}$, $R^4$, $R^5$, $R^6$, and RAI are as defined herein.

In another aspect, the present disclosure provides compounds of Formula (III):

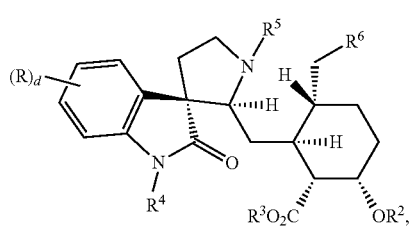
(III)

and pharmaceutically acceptable salts, solvates, hydrates, polymorphs, co-crystals, tautomers, stereoisomers, isotopically labeled derivatives, and prodrugs thereof, wherein d, $R^2$, $R^3$, $R^4$, $R^5$, $R^5$, and R are as defined herein.

Exemplary compounds of Formulae (III-A) and (III) include, but are not limited to:

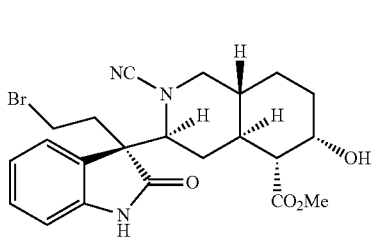
Y2a

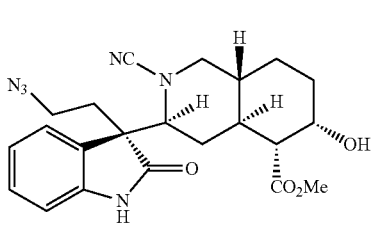
Y2b

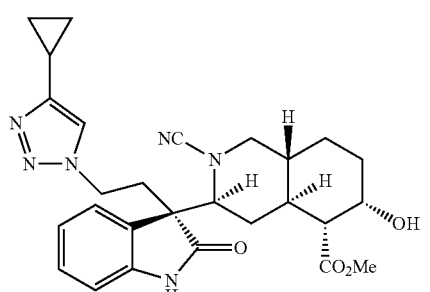
Y2c

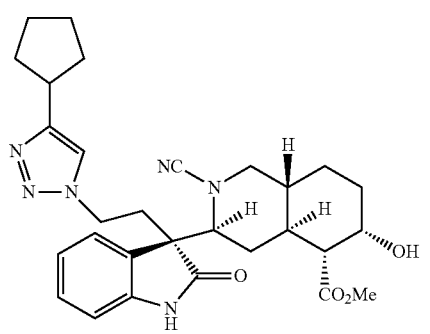
Y2d

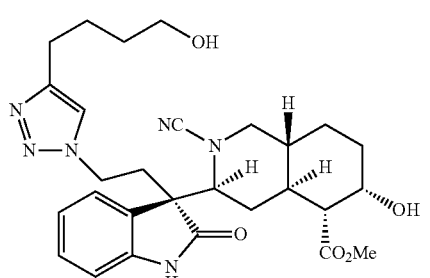
Y2e

Y2f
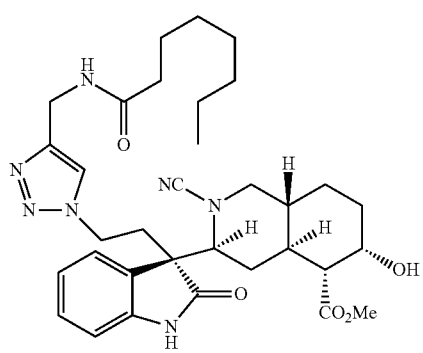
Y2g
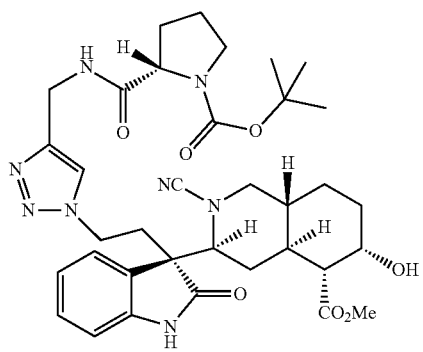
Y2h
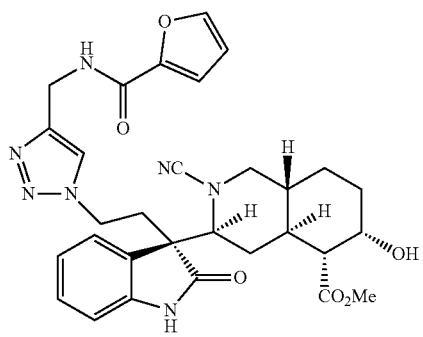
Y2i
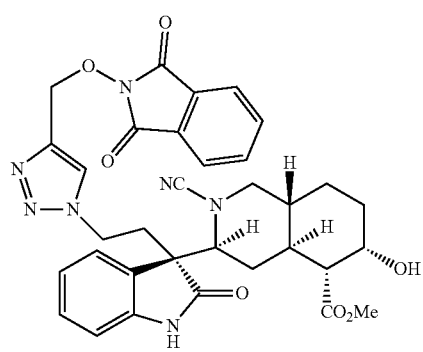
Y2j
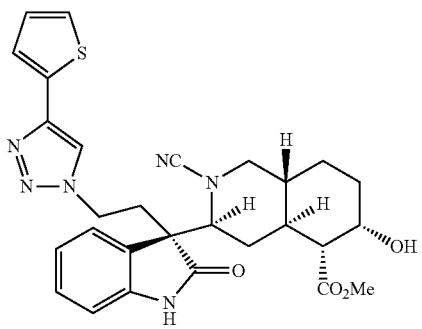
Y2k
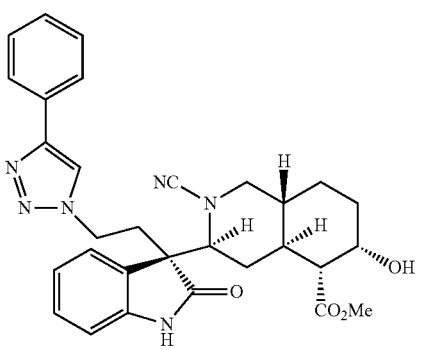
Y2l
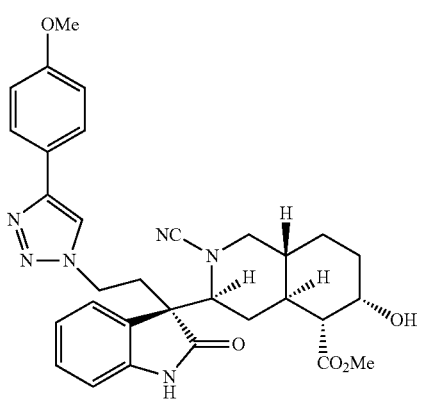
Y2m
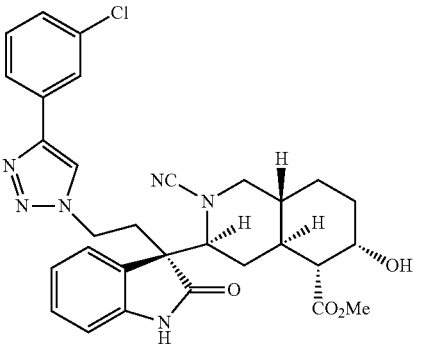

-continued

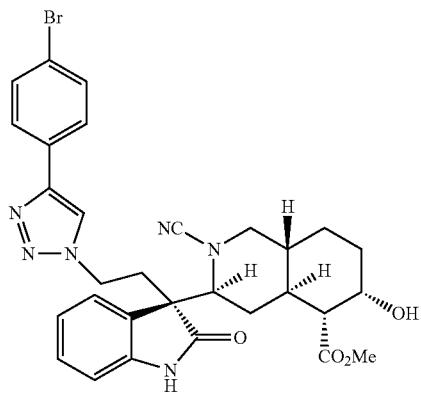

Y2n

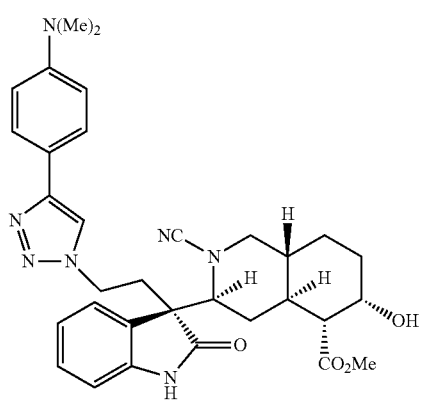

Y2o

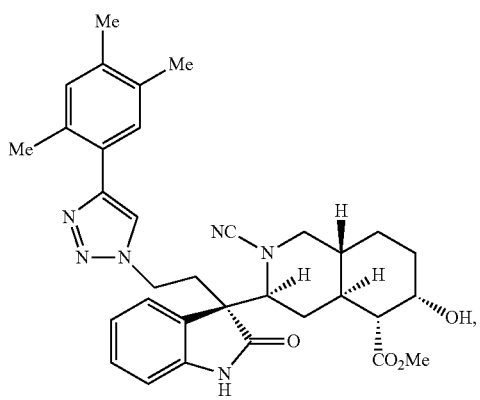

Y2p and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (IV'):

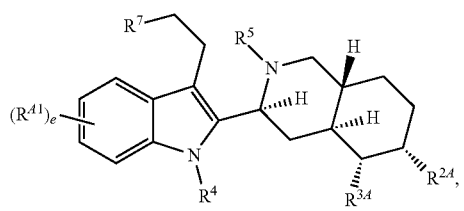

(IV')

and pharmaceutically acceptable salts, solvates, hydrates, polymorphs, co-crystals, tautomers, stereoisomers, isotopically labeled derivatives, and prodrugs thereof, wherein e, $R^{2A}$, $R^{3A}$, $R^4$, $R^5$, $R^7$, and $R^{A1}$ are as defined herein.

In another aspect, the present disclosure provides compounds of Formula (IV):

(IV)

and pharmaceutically acceptable salts, solvates, hydrates, polymorphs, co-crystals, tautomers, stereoisomers, isotopically labeled derivatives, and prodrugs thereof, wherein e, $R^2$, $R^3$, $R^4$, $R^7$, $R^8$, and R are as defined herein.

Exemplary compounds of Formulae (IV') and (IV) include, but are not limited to:

Y1a

Y1b

Y1c

-continued

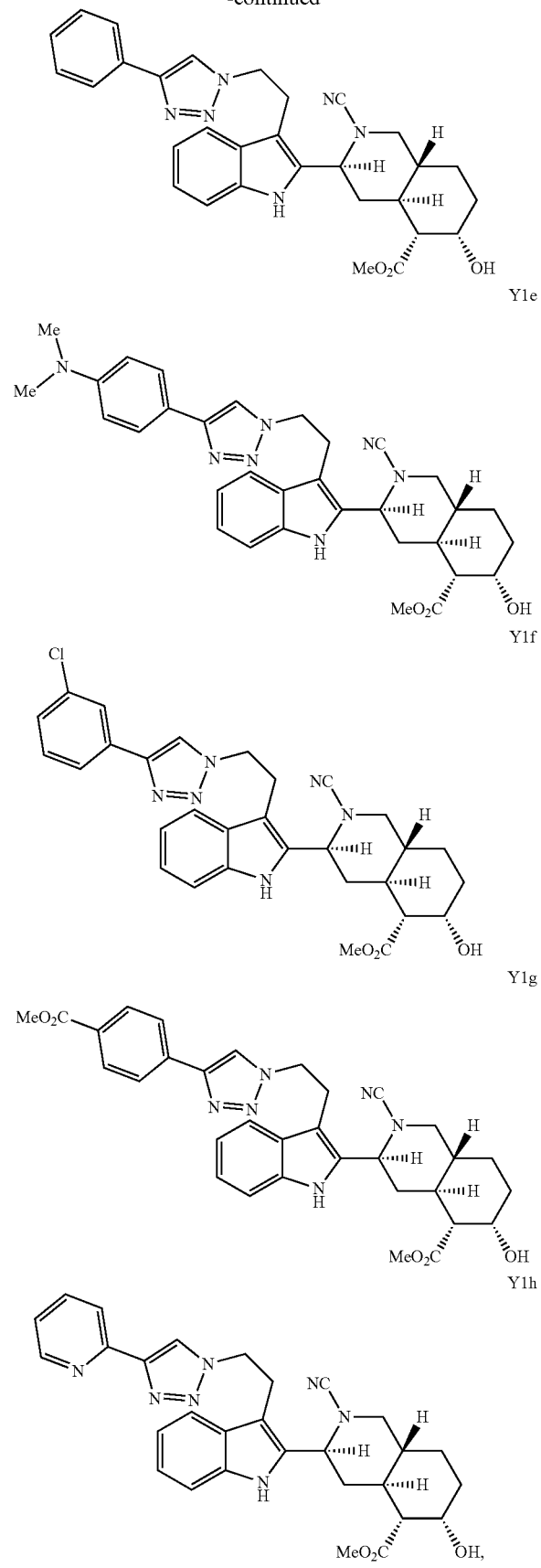

Y1e

Y1f

Y1g

Y1h and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (V-A):

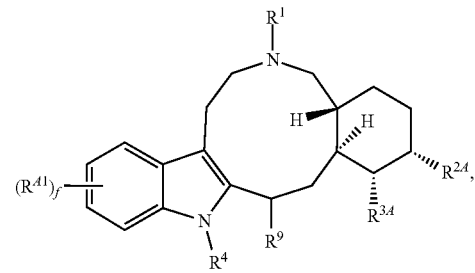

(V-A)

and pharmaceutically acceptable salts, solvates, hydrates, polymorphs, co-crystals, tautomers, stereoisomers, isotopically labeled derivatives, and prodrugs thereof, wherein f, $R^1$, $R^{2A}$, $R^{3A}$, $R^4$, $R^9$, and $R^{A1}$, are as defined herein.

In another aspect, the present disclosure provides compounds of Formula (V):

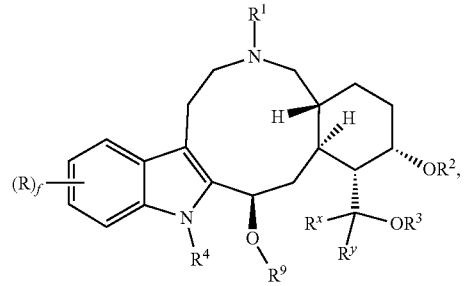

(V)

and pharmaceutically acceptable salts, solvates, hydrates, polymorphs, co-crystals, tautomers, stereoisomers, isotopically labeled derivatives, and prodrugs thereof, wherein f, $R^1$, $R^2$, $R^3$, $R^4$, $R^9$, R, $R^x$, and $R^y$ are as defined herein.

Exemplary compounds of Formulae (V-A) and (V) include, but are not limited to:

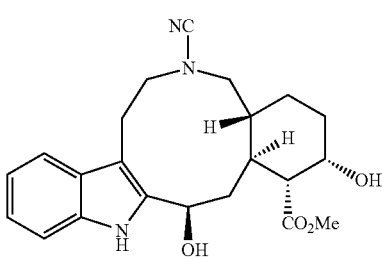

Y6a

Y6b
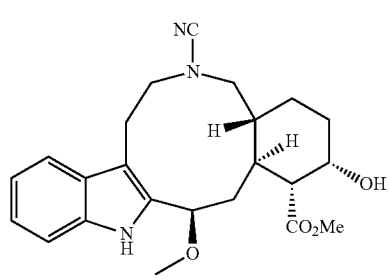
Y6c
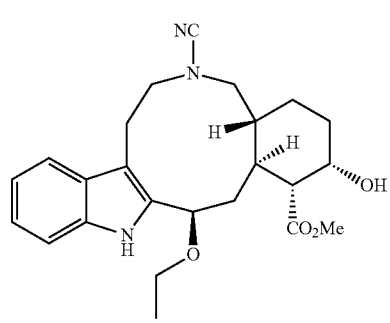
Y6d
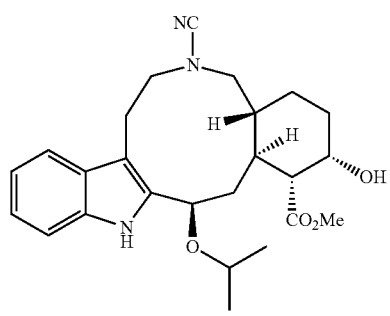
Y6e
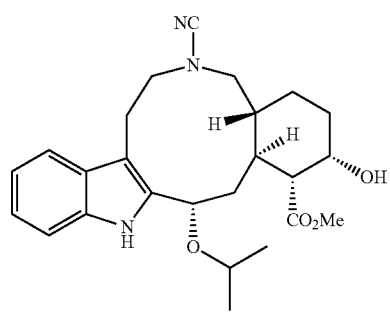
Y6f
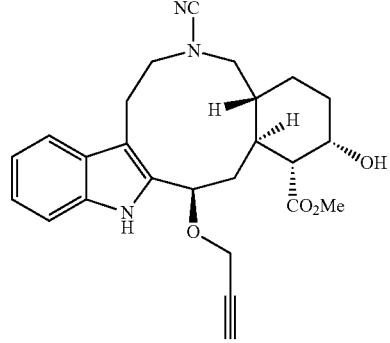
Y6g
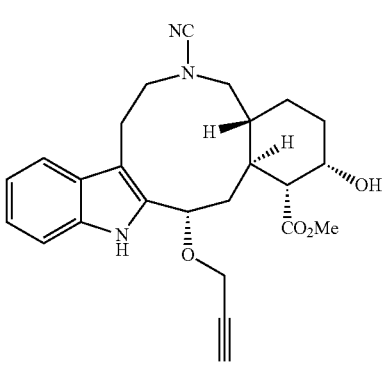
Y6h
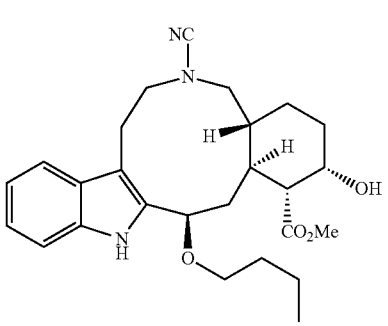
Y6i
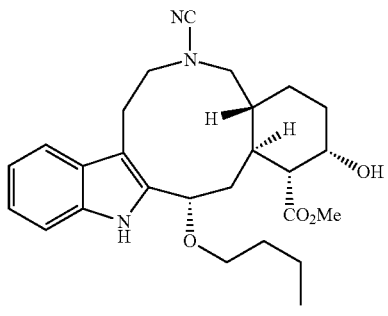
Y6j
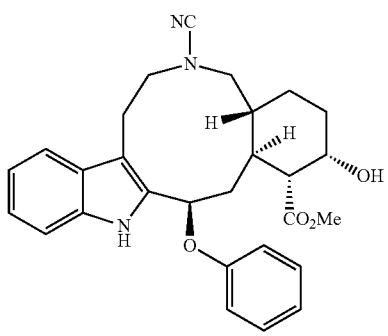
Y6k
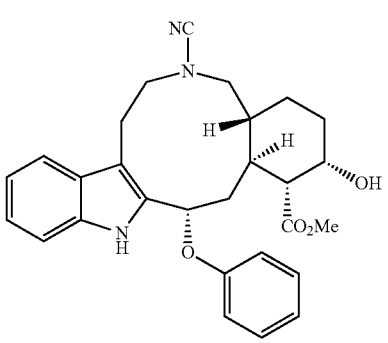

Y6l
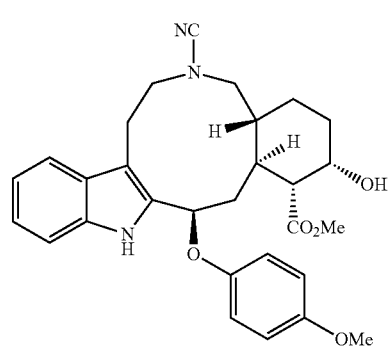
Y6m
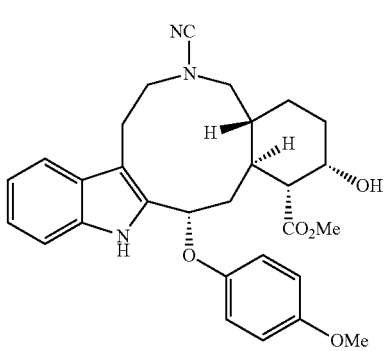
Y6n
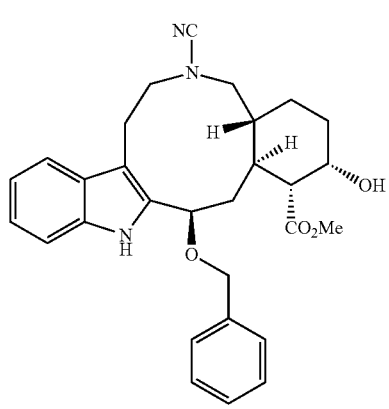
Y6o
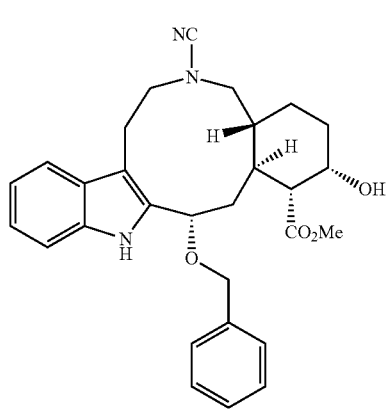
Y6p
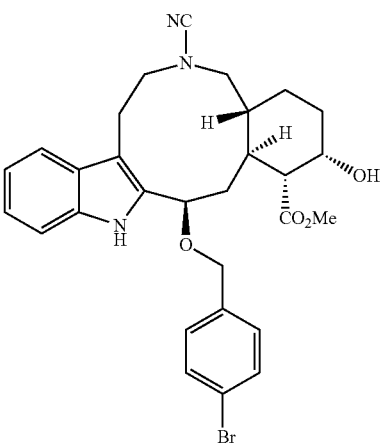
Y6q
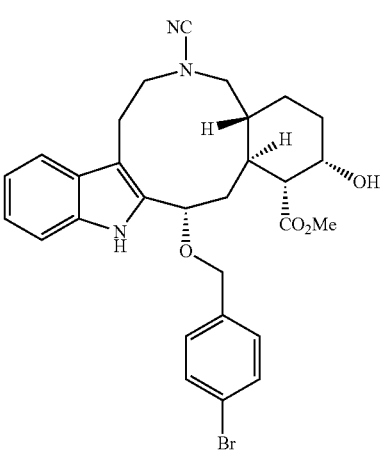
Y6r
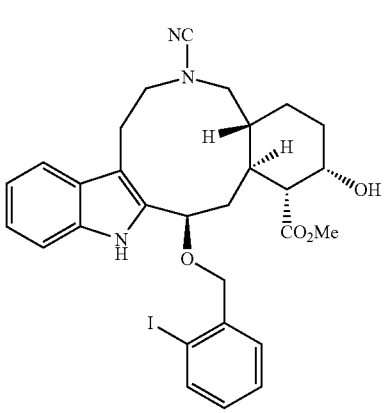

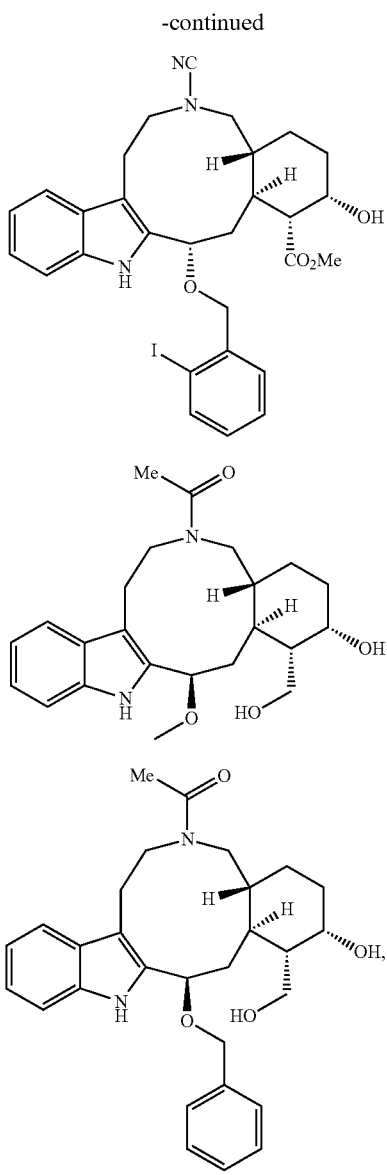

and pharmaceutically acceptable salts, solvates, hydrates, polymorphs, co-crystals, tautomers, stereoisomers, isotopically labeled derivatives, and prodrugs thereof.

In another aspect, the invention provides the synthesis of compounds of Formulae (I-A), (II'), (III-A), (IV'), and (V-A), and salts, solvates, hydrates, polymorphs, co-crystals, tautomers, stereoisomers, isotopically labeled derivatives, and prodrugs thereof. FIGS. 1-4 depict exemplary syntheses of compounds of the present invention, i.e., compounds of Formulae (I-A), (II'), (III-A), (IV'), and (V-A), and salts, solvates, hydrates, polymorphs, co-crystals, tautomers, stereoisomers, isotopically labeled derivatives, and prodrugs thereof, and mixtures thereof. And, in yet another aspect, the present invention provides synthetic intermediates useful in preparing the compounds described herein and useful in the synthetic methods described herein.

In another aspect, described herein are pharmaceutical compositions including a compound described herein, and optionally a pharmaceutically acceptable excipient. In certain embodiments, a pharmaceutical composition described herein includes an effective amount (e.g., therapeutically effective amount or prophylactically effective amount) of a compound described herein. The compounds may be useful in treating and/or preventing inflammatory diseases, treating and/or preventing proliferative diseases (e.g., cancer), treating and/or preventing autoimmune diseases, treating and/or preventing infections in a subject in need thereof (e.g., bacterial infections), or treating and/or preventing infectious diseases (e.g., malaria) in a subject in need thereof.

In certain embodiments, the disease being treated and/or prevented is an inflammatory disease. In certain embodiments, the disease being treated and/or prevented is an autoimmune disease. In certain embodiments, the disease being treated and/or prevented is a proliferative disease. In certain embodiments, the disease is a proliferative disease (e.g., cancer or inflammatory disease). In certain embodiments, the disease is cancer. In certain embodiments, the disease being treated and/or prevented is an infectious disease. In certain embodiments, the disease being treated and/or prevented is a plasmodial infection. In certain embodiments, the disease being treated and/or prevented is malaria.

In certain embodiments, the subject being administered a compound or pharmaceutical composition described herein is a human. In certain embodiments, the subject being administered a compound or pharmaceutical composition described herein is a non-human animal.

In still another aspect, described herein are kits including a container with a compound or pharmaceutical composition described herein. A kit described herein may include a single dose or multiple doses of the compound or pharmaceutical composition. The described kits may be useful in treating a disease (e.g., proliferative disease or infectious disease) in a subject in need thereof, and/or in preventing a disease (e.g., proliferative disease or infectious disease) in a subject in need thereof. In certain embodiments, a kit described herein further includes instructions for using the kit.

Another aspect of the present disclosure relates to methods of treating and/or preventing a disease in a subject in need thereof. The methods of the present disclosure include administering to the subject an effective amount of a compound or pharmaceutical composition described herein. In certain embodiments, the effective amount is a therapeutically effective amount. In certain embodiments, the effective amount is a prophylactically effective amount.

In yet another aspect, the present disclosure provides compounds and pharmaceutical compositions described herein for use in a method of the disclosure (e.g., a method of treating and/or preventing a disease (e.g., a proliferative or infectious disease)). In yet another aspect, the present disclosure provides compounds and pharmaceutical compositions described herein for use in treating and/or preventing a proliferative disease. In another aspect, the present disclosure provides compounds and pharmaceutical compositions described herein for use in treating and/or preventing an infectious disease.

The present application refers to various issued patents, published patent applications, journal articles, and other publications, all of which are incorporated herein by reference. The details of one or more embodiments of the invention are set forth herein. Other features, objects, and advantages of the invention will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_5$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 8 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-4}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-4}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-44}$ cycloalkyl. In certain embodiments, the cycloalkyl group is a substituted C$_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, substituted or unsubstituted. Substituted or unsubstituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R, —P(=O)(R$^{aa}$)$_2$, —P(=O)(OR$^{cc}$)$_2$, —OP(=O)(R$^{aa}$)$_2$, —OP(=O)(OR$^{aa}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{aa}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{aa}$)$_4$, —OP(OR$^{aa}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_6$i$_4$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ee}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$_{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ff}$, —C(=NR$^{ff}$)N(R$^{ff}$)$_2$, —OC(=NR$^{ff}$)N(R$^{f}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ff}$)$_2$, —P(=O)(R$^{ee}$)$_2$, —OP(=O)(R$^{ff}$)$_2$, —OP(=O)(OR$^{ff}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ff}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^L$- groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —SO$_2$R$^{aa}$, —SO$_2$OR$^{aa}$, —SO$_2$R$^{aa}$, —S(=O)R$^{aa}$, or —OS(=O)R$^{aa}$.

As used herein, the term "halo" or "halogen" refers to fluorine (fluoro, —F), chlorine (chloro, —Cl), bromine (bromo, —Br), or iodine (iodo, —I).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ haloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, n-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N $(R^{bb})_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3{}^+$X$^-$, —P(OR$^{cc}$)$_2$, —P(OR$^{cc}$)$_3{}^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —Raa, —N(Rbb)2, —C(=O)SRaa, —C(=O)Raa, —CO2Raa, —C(=O)N(Rbb)2, —C(=NRbb)Raa, —C(=NRbb)ORaa, —C(=NRbb)N(Rbb)2, —S(=O)Raa, —SO2Raa, —Si(Raa)3, —P(Rcc)2, —P(Rcc)3+X—, —P(ORcc)2, —P(ORcc)3+X—, —P(=O)(Raa)2, —P(=O)(ORcc)2, and —P(=O)(N(Rbb)2)2, wherein Raa, Rbb, and Rcc are as defined herein; wherein X— is a counterion. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), Crohn's disease, rheumatoid arthritis, psoriatic arthritis, ulcerative colitis, gouty arthritis, degenerative arthritis, tendonitis, bursitis, psoriasis, cystic fibrosis, arthrosteitis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

An "infection" or "infectious disease" refers to an infection with a microorganism, such as a protozoa, fungus, bacteria or virus. In certain embodiments, the infection is an infection with a protozoan parasite, i.e., a protozoan infection. In certain embodiments, the infection is an infection with a plasmodium protozoan parasite, e.g., a plasmodial infection. In certain embodiments, the infectious disease is malaria. Various infections include, but are not limited to, skin infections, GI infections, urinary tract infections, genito-urinary infections, sepsis, blood infections, and systemic infections. A "plasmodium" refers to a protozoan parasite of host organisms, such as mammals.

BRIEF DESCRIPTION OF THE DRAWINGS

FIG. 1 also shows an exemplary method of preparing a compound of Formula (V-A) and synthetic intermediate (V-B).

FIG. 2 also shows an exemplary method of preparing a compound of Formula (II') and synthetic intermediates (II-A), from yohimbine (compound 1).

FIG. 6 shows an exemplary ring distortion strategy based on two structural features connected through the tryptoline 9 substructure of yohimbine 1, where the ring distortion strategy involves: 1) the centrally positioned basic nitrogen with three C—N bonds indicated by dashed arrows drawn through the C—N bonds B, C and D, useful for diverse ring cleavage reactions to afford compounds 10-12; and 2) oxidative rearrangement of the 2,3-disubstituted indole nucleus to give ring-rearranged product Y7b (via bond A). As shown by dashed arrows in FIG. 6, C—N ring cleavage reactions of C—N bonds B, C, and D are used to afford compounds 10-12.

In FIG. 7, ring cleavage step G from yohimbine 1 yields Y1 derivatives (compounds of Formula (IV')) in 3 steps. In FIG. 7, step H via ring rearrangement and ring cleavage from yohimbine 1 yields Y2 derivatives (compounds of Formula (III-A)) in 6 steps. In FIG. 7, step J via ring rearrangement from yohimbine 1 yields Y3 or Y7 derivatives (compounds of Formula (II')) in 4 steps. In FIG. 7, step L via ring cleavage and ring fusion from yohimbine 1 yields Y4 derivatives (compounds of Formula (I-A)) in 2-3 steps. In FIG. 7, step M via ring cleavage and ring fusion from yohimbine 1 yields Y5 derivatives (compounds of Formula (I-A)) in 2-3 steps. In FIG. 7, step P indicates diastereomeric ring fusions. In FIG. 7, step N via ring cleavage from yohimbine 1 yields Y6 derivatives (compounds of Formula (V-A)) in 2-3 steps.

DETAILED DESCRIPTION OF CERTAIN EMBODIMENTS OF THE INVENTION

Figure 1:
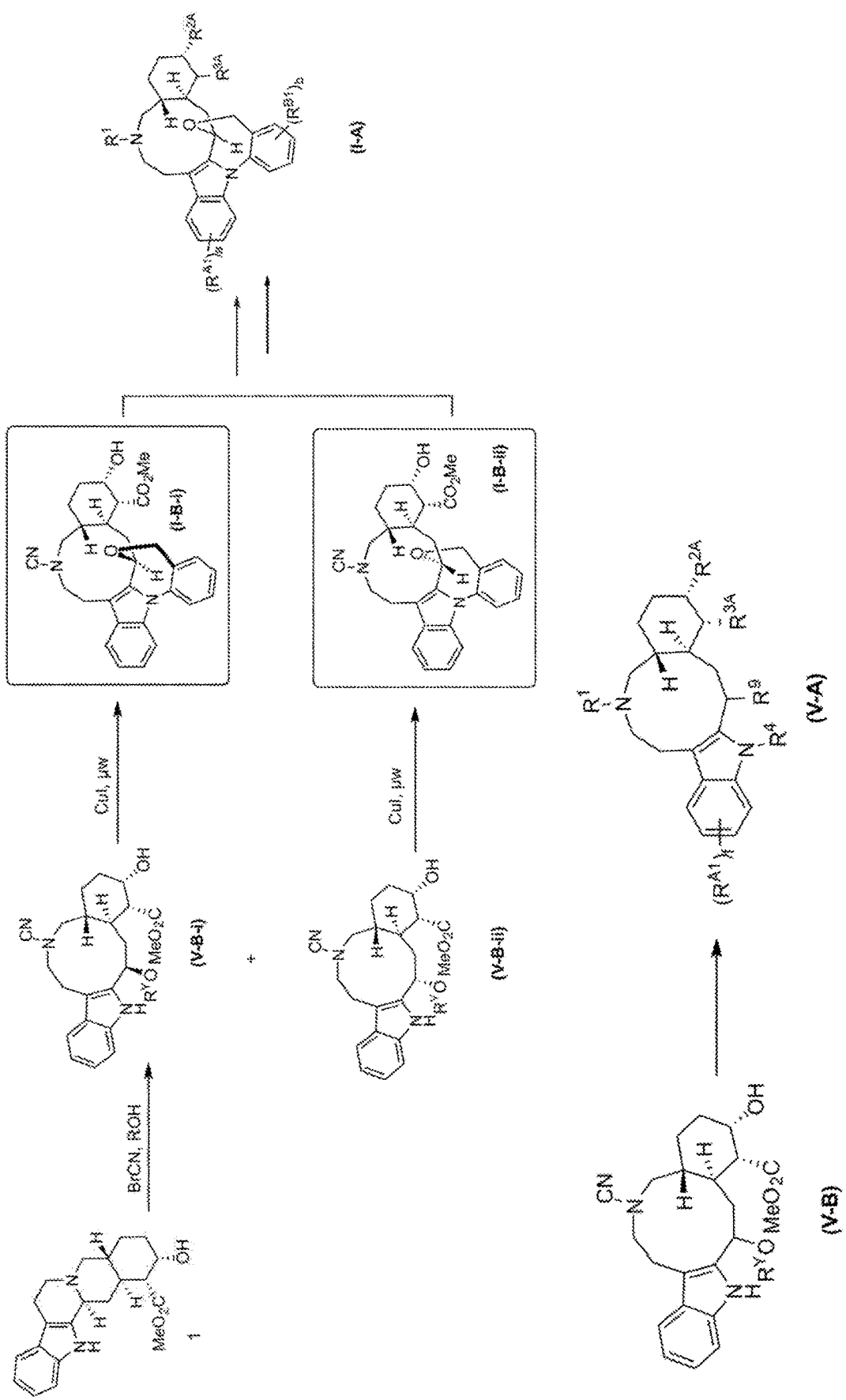
FIG. 1 shows an exemplary method of preparing a compound of Formula (I-A) and synthetic intermediates (I-B-i), (I-B-ii), (V-B), (V-B-i), and (V-B-ii), from yohimbine (compound 1).

Described herein are compounds of Formulae (I-A), (II'), (III-A), (IV'), (V-A), and pharmaceutically acceptable salts, solvates, hydrates, polymorphs, co-crystals, tautomers, stereoisomers, isotopically labeled derivatives, and prodrugs thereof. The compounds of Formulae (I-A), (II'), (III-A), (IV'), (V-A) are derived from or based on yohimbine. Certain compounds described herein may be useful in treating and/or preventing a disease (e.g., proliferative disease or infectious disease) in a subject in need thereof. The present invention also provides methods of preparing compounds of Formulae (I-A), (II'), (III-A), (IV'), and (V-A), and salts, solvates, hydrates, polymorphs, co-crystals, tautomers, stereoisomers, isotopically labeled derivatives, and prodrugs thereof, or mixtures thereof. Also provided are pharmaceutical compositions and kits including a compound described herein.

Compounds

Compounds of Formula (I-A) and Formula (I)

In one aspect, the present disclosure provides compounds of Formula (I-A):

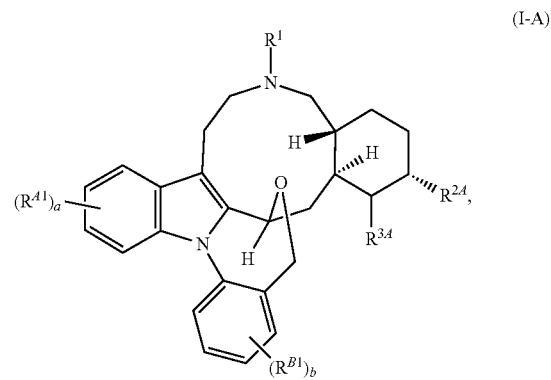

and pharmaceutically acceptable salts, solvates, hydrates, polymorphs, co-crystals, tautomers, stereoisomers, isotopically labeled derivatives, and prodrugs thereof, wherein:

$R^1$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$;

$R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^1$, —N(R$^b$)$_2$, or —SR$^a$; and each instance of $R^{A1}$ is independently hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of $R^{BI}$ is independently hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^1$, —N(R$^b$)$_2$, or —SR$^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl;

a is 0, 1, 2, 3, or 4; and b is 0, 1, 2, 3, or 4.

In one aspect, the present disclosure provides compounds of Formula (I):

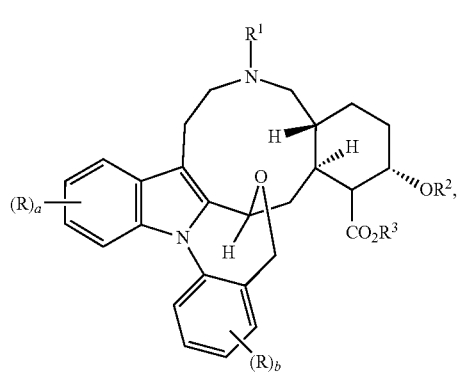

(I)

and pharmaceutically acceptable salts, solvates, hydrates, polymorphs, co-crystals, tautomers, stereoisomers, isotopically labeled derivatives, and prodrugs thereof, wherein:

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or —CN;

$R^2$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^3$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of R is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

a is 1, 2, 3, or 4; and b is 1, 2, 3, or 4.

Formula (I-A), (I), (V-A), (V) include substituent $R^1$. In certain embodiments, $R^1$ is hydrogen. In certain embodiments, $R^1$ is substituted or unsubstituted acyl. In certain embodiments, $R^1$ is —C(=O)(substituted or unsubstituted alkyl) (e.g., —C(=O)(substituted or unsubstituted $C_{1-6}$ alkyl)). In certain embodiments, $R^1$ is —C(=O)Me. In certain embodiments, $R^1$ is substituted or unsubstituted alkyl (e.g., substituted or unsubstituted $C_{1-6}$ alkyl). In certain embodiments, $R^1$ is substituted or unsubstituted methyl. In certain embodiments, $R^1$ is substituted or unsubstituted ethyl. In certain embodiments, $R^1$ is substituted or unsubstituted propyl. In certain embodiments, $R^1$ is substituted or unsubstituted alkenyl (e.g., substituted or unsubstituted $C_{2-6}$ alkenyl). In certain embodiments, $R^1$ is substituted or unsubstituted alkynyl (e.g., substituted or unsubstituted $C_{2-6}$ alkynyl). In certain embodiments, $R^1$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^1$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is substituted or unsubstituted aryl (e.g., substituted or unsubstituted, 6- to 10-membered aryl). In certain embodiments, $R^1$ is substituted benzyl. In certain embodiments, $R^1$ is unsubstituted benzyl. In certain embodiments, $R^1$ is substituted phenyl. In certain embodiments, $R^1$ is unsubstituted phenyl. In certain embodiments, $R^1$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^1$ is —CN.

Formula (I-A) includes substituent $R^{2A}$. Substituent $R^{2A}$ is described in the Detailed Description for Formula (II') below.

Formula (I), (II), (III), (IV), and (V) include substituent $R^2$. In certain embodiments, $R^2$ is hydrogen. In certain embodiments, $R^2$ is substituted or unsubstituted acyl. In certain embodiments, $R^2$ is —C(=O)(substituted or unsubstituted alkyl) (e.g., —C(=O)(substituted or unsubstituted $C_{1-6}$ alkyl)). In certain embodiments, $R^2$ is substituted or unsubstituted alkyl (e.g., substituted or unsubstituted $C_{1-6}$ alkyl). In certain embodiments, $R^2$ is substituted or unsubstituted methyl. In certain embodiments, $R^2$ is substituted or unsubstituted ethyl. In certain embodiments, $R^2$ is substituted or unsubstituted propyl. In certain embodiments, $R^2$ is substituted or unsubstituted alkenyl (e.g., substituted or unsubstituted $C_{2-6}$ alkenyl). In certain embodiments, $R^2$ is substituted or unsubstituted alkynyl (e.g., substituted or unsubstituted $C_{2-6}$ alkynyl). In certain embodiments, $R^2$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^2$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^2$ is substituted or unsubstituted aryl (e.g., substituted or unsubstituted, 6- to 10-membered aryl). In certain embodiments, $R^2$ is substituted benzyl. In certain embodiments, $R^2$ is unsubstituted benzyl. In certain embodiments, $R^2$ is substituted phenyl. In certain embodiments, $R^2$ is unsubstituted phenyl. In certain embodiments, $R^2$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^2$ is an oxygen protecting group (e.g., t-butyloxycarbonyl (BOC or Boc), methoxylmethyl (MOM) or methylthiomethyl (MTM)).

Formula (I-A) includes substituent $R^{3A}$. In certain embodiments, $R^{3A}$ is hydrogen. In certain embodiments, $R^{3A}$ is substituted or unsubstituted acyl. In certain embodiments, $R^{3A}$ is —C(=O)(substituted or unsubstituted alkyl) (e.g., —C(=O)(substituted or unsubstituted $C_{1-6}$ alkyl)). In certain embodiments, $R^{3A}$ is of formula

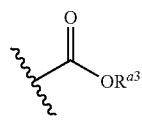

or —C(=O)NR$^{a4}$, wherein R$^{a3}$ is hydrogen or substituted or unsubstituted $C_{1-6}$ alkyl; and R$^{a4}$ is hydrogen, substituted or unsubstituted $C_{1-6}$ alkyl, or nitrogen protecting group. In certain embodiments, R$^{a3}$ is hydrogen. In certain embodiments, R$^{a3}$ is substituted or unsubstituted $C_{1-6}$ alkyl (e.g., substituted or unsubstituted methyl, substituted or unsubstituted ethyl, or substituted or unsubstituted propyl). In certain embodiments, R$^{a4}$ is hydrogen. In certain embodiments, R$^{a4}$ is substituted or unsubstituted $C_{1-6}$ alkyl (e.g., substituted or unsubstituted methyl, substituted or unsubstituted ethyl, or substituted or unsubstituted propyl). In certain embodiments, R$^{a4}$ is nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^{3A}$ is of formula

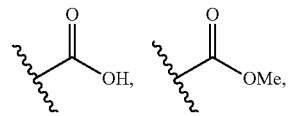

or —C(=O)NMe. In certain embodiments, $R^{3A}$ is —C(=O)Me. In certain embodiments, $R^{3A}$ is substituted or unsubstituted alkyl (e.g., substituted or unsubstituted $C_{1-6}$ alkyl). In certain embodiments, $R^{3A}$ is substituted or unsubstituted methyl. In certain embodiments, $R^{3A}$ is substituted methyl. In certain embodiments, $R^{3A}$ is —CF$_3$. In certain embodiments, $R^{3A}$ is unsubstituted methyl. In certain embodiments, $R^{3A}$ is of formula

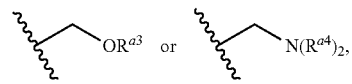

wherein R$^{a3}$ is hydrogen or substituted or unsubstituted $C_{1-6}$ alkyl; and R$^{a4}$ is hydrogen, substituted or unsubstituted $C_{1-6}$ alkyl, or nitrogen protecting group. In certain embodiments, $R^{3A}$ is of formula

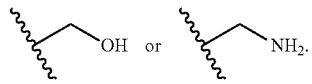

In certain embodiments, $R^{3A}$ is substituted or unsubstituted ethyl. In certain embodiments, $R^{3A}$ is substituted ethyl. In certain embodiments, $R^{3A}$ is unsubstituted ethyl. In certain embodiments, $R^{3A}$ is substituted or unsubstituted propyl. In certain embodiments, $R^{3A}$ is substituted or unsubstituted alkenyl (e.g., substituted or unsubstituted $C_{2-6}$ alkenyl). In certain embodiments, $R^{3A}$ is substituted or unsubstituted alkynyl (e.g., substituted or unsubstituted $C_{2-6}$ alkynyl). In certain embodiments, $R^{3A}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{3A}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{3A}$ is

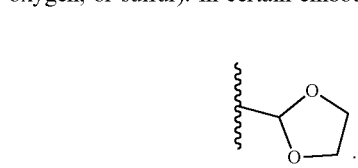

In certain embodiments, $R^{3A}$ is substituted or unsubstituted aryl (e.g., substituted or unsubstituted, 6- to 10-membered aryl). In certain embodiments, $R^{3A}$ is substituted benzyl. In certain embodiments, $R^{3A}$ is unsubstituted benzyl. In certain embodiments, $R^{3A}$ is substituted phenyl. In certain embodiments, $R^{3A}$ is unsubstituted phenyl. In certain embodiments, $R^{3A}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or
substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{3A}$ is —$OR^a$, wherein $R^a$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group (e.g., —OH or —OMe). In certain embodiments, $R^{3A}$ is —$O(R^a)$, and $R^a$ is hydrogen or substituted or unsubstituted $C_{1-6}$ alkyl. In certain embodiments, $R^{3A}$ is —OMe. In certain embodiments, $R^{3A}$ is —OEt. In certain embodiments, $R^{3A}$ is —O(Pr). In certain embodiments, $R^{3A}$ is —O(iPr). In certain embodiments, $R^{3A}$ is —$N(R^b)_2$ (e.g., —$NH_2$ or —$NMe_2$). In certain embodiments, $R^{3A}$ is —$SR^a$ (e.g., —SMe). In certain embodiments, $R^{3A}$ is an oxygen protecting group (e.g., t-butyloxycarbonyl (BOC or Boc), methoxylmethyl (MOM) or methylthiomethyl (MTM)).

Formula (I), (II), (III), (IV), and (V) include substituent $R^3$. In certain embodiments, $R^3$ is hydrogen. In certain embodiments, $R^3$ is substituted or unsubstituted acyl. In certain embodiments, $R^3$ is —C(=O)(substituted or unsubstituted alkyl) (e.g., —C(=O)(substituted or unsubstituted $C_{1-6}$ alkyl)). In certain embodiments, $R^3$ is substituted or unsubstituted alkyl (e.g., substituted or unsubstituted $C_{1-6}$ alkyl). In certain embodiments, $R^3$ is substituted or unsubstituted methyl. In certain embodiments, $R^3$ is substituted or unsubstituted ethyl. In certain embodiments, $R^3$ is substituted or unsubstituted propyl. In certain embodiments, $R^3$ is substituted or unsubstituted alkenyl (e.g., substituted or unsubstituted $C_{2-6}$ alkenyl). In certain embodiments, $R^3$ is substituted or unsubstituted alkynyl (e.g., substituted or unsubstituted $C_{2-6}$ alkynyl). In certain embodiments, $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is substituted or unsubstituted aryl (e.g., substituted or unsubstituted, 6- to 10-membered aryl). In certain embodiments, $R^3$ is substituted benzyl. In certain embodiments, $R^3$ is unsubstituted benzyl. In certain embodiments, $R^3$ is substituted phenyl. In certain embodiments, $R^3$ is unsubstituted phenyl. In certain embodiments, $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^3$ is an oxygen protecting group (e.g., t-butyloxycarbonyl (BOC or Boc), methoxylmethyl (MOM) or methylthiomethyl (MTM)).

Formula (I-A) includes substituent $R^4$. Substituent $R^4$ is described in the Detailed Description for Formula (II') below.

Formula (I-A) includes one or more instances of substituent $R^{41}$. In certain embodiments, a is 1. In certain embodiments, a is 2. In certain embodiments, a is 3. In certain embodiments, a is 4. In certain embodiments, b is 1. In certain embodiments, b is 2. In certain embodiments, b is 3. In certain embodiments, b is 4. In certain embodiments, at least one instance of $R^{41}$ is hydrogen. In certain embodiments, at least one instance of $R^{41}$ is substituted or unsubstituted acyl. In certain embodiments, at least one instance of $R^{41}$ is —C(=O)(substituted or unsubstituted alkyl) (e.g., —C(=O)(substituted or unsubstituted $C_{1-6}$ alkyl)). In certain embodiments, at least one instance of $R^{41}$ is —C(=O)Me. In certain embodiments, at least one instance of $R^{41}$ is substituted or unsubstituted alkyl (e.g., substituted or unsubstituted $C_{1-6}$ alkyl). In certain embodiments, at least one instance of $R^{41}$ is substituted or unsubstituted methyl. In certain embodiments, at least one instance of $R^{41}$ is substituted or unsubstituted ethyl. In certain embodiments, at least one instance of $R^{41}$ is substituted or unsubstituted propyl. In certain embodiments, at least one instance of $R^{41}$ is substituted or unsubstituted alkenyl (e.g., substituted or unsubstituted $C_{2-6}$ alkenyl). In certain embodiments, at least one instance of $R^{41}$ is substituted or unsubstituted alkynyl (e.g., substituted or unsubstituted $C_{2-6}$ alkynyl). In certain embodiments, at least one instance of $R^{41}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{41}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{41}$ is substituted or unsubstituted aryl (e.g., substituted or unsubstituted, 6- to 10-membered aryl). In certain embodiments, at least one instance of $R^{41}$ is substituted benzyl. In certain embodiments, at least one instance of $R^{41}$ is unsubstituted benzyl. In certain embodiments, at least one instance of $R^{41}$ is substituted phenyl. In certain embodiments, at least one instance of $R^{41}$ is unsubstituted phenyl. In certain embodiments, at least one instance of $R^{41}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{41}$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, at least one instance of $R^{41}$ is —CN. In certain embodiments, at least one instance of $R^{41}$ is —SCN. In certain embodiments, at least one instance of $R^{41}$ is —$NO_2$. In certain embodiments, at least one instance of $R^{41}$ is —$N_3$. In certain embodiments, at least one instance of $R^{41}$ is —$OR^a$ (e.g., —OH, —O(substituted or unsubstituted $C_{1-6}$ alkyl) (e.g., —OMe, —$OCF_3$, —OEt, —OPr, or —OBu). In certain embodiments, at least one instance of $R^{A1}$ is —N($R^b$)$_2$ (e.g., —NMe$_2$). In certain embodiments, at least one instance of $R^{A1}$ is —S$R^a$ (e.g., —SH, —S(substituted or unsubstituted C$_{1-6}$ alkyl) (e.g., —SMe, —SEt, —SPr, or —SBu).

Substituent $R^{A1}$ includes one or more instances of $R^a$. Substituent $R^{B1}$ includes one or more instances of $R^a$. In certain embodiments, at least one instance of $R^a$ is hydrogen. In certain embodiments, at least one instance of $R^a$ is substituted or unsubstituted acyl. In certain embodiments, at least one instance of $R^a$ is —C(=O)(substituted or unsubstituted alkyl) (e.g., —C(=O)(substituted or unsubstituted C$_{1-6}$ alkyl)). In certain embodiments, at least one instance of $R^a$ is —C(=O)Me. In certain embodiments, at least one instance of $R^a$ is substituted or unsubstituted alkyl (e.g., substituted or unsubstituted C$_{1-6}$ alkyl). In certain embodiments, at least one instance of $R^a$ is substituted or unsubstituted methyl. In certain embodiments, at least one instance of $R^a$ is substituted or unsubstituted ethyl. In certain embodiments, at least one instance of $R^a$ is substituted or unsubstituted propyl. In certain embodiments, at least one instance of $R^a$ is substituted or unsubstituted alkenyl (e.g., substituted or unsubstituted C$_{2-6}$ alkenyl). In certain embodiments, at least one instance of $R^a$ is substituted or unsubstituted alkynyl (e.g., substituted or unsubstituted C$_{2-6}$ alkynyl). In certain embodiments, at least one instance of $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted benzyl. In certain embodiments, at least one instance of $R^a$ is unsubstituted benzyl. In certain embodiments, at least one instance of $R^a$ is substituted phenyl. In certain embodiments, at least one instance of $R^a$ is unsubstituted phenyl. In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^a$ is an oxygen protecting group (e.g., t-butyloxycarbonyl (BOC or Boc), methoxylmethyl (MOM) or methylthiomethyl (MTM)) when attached to an oxygen atom. In certain embodiments, at least one instance of $R^a$ is an sulfur protecting group.

Substituent RAI includes one or more instances of $R^b$. Substituent $R^{BI}$ includes one or more instances of $R^b$. In certain embodiments, at least one instance of $R^b$ is hydrogen. In certain embodiments, at least one instance of $R^b$ is substituted or unsubstituted acyl. In certain embodiments, at least one instance of $R^b$ is —C(=O)(substituted or unsubstituted alkyl) (e.g., —C(=O)(substituted or unsubstituted C$_{1-6}$ alkyl)). In certain embodiments, at least one instance of $R^b$ is —C(=O)Me. In certain embodiments, at least one instance of $R^b$ is substituted or unsubstituted alkyl (e.g., substituted or unsubstituted C$_{1-6}$ alkyl). In certain embodiments, at least one instance of $R^b$ is substituted or unsubstituted methyl. In certain embodiments, at least one instance of $R^b$ is substituted or unsubstituted ethyl. In certain embodiments, at least one instance of $R^b$ is substituted or unsubstituted propyl. In certain embodiments, at least one instance of $R^b$ is substituted or unsubstituted alkenyl (e.g., substituted or unsubstituted C$_{2-6}$ alkenyl). In certain embodiments, at least one instance of $R^b$ is substituted or unsubstituted alkynyl (e.g., substituted or unsubstituted C$_{2-6}$ alkynyl). In certain embodiments, at least one instance of $R^b$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^b$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^b$ is substituted or unsubstituted aryl (e.g., substituted or unsubstituted, 6- to 10-membered aryl). In certain embodiments, at least one instance of $R^b$ is substituted benzyl. In certain embodiments, at least one instance of $R^b$ is unsubstituted benzyl. In certain embodiments, at least one instance of $R^b$ is substituted phenyl. In certain embodiments, at least one instance of $R^b$ is unsubstituted phenyl. In certain embodiments, at least one instance of $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^b$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two $R^b$ are joined together with the intervening atoms to form substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, two $R^b$ are joined together with the intervening atoms to form substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formulae (I), (II), (III), (IV), and (V) include one or more instances of substituent R. In certain embodiments, at least one instance of R is hydrogen. In certain embodiments, at least one instance of R is substituted or unsubstituted acyl. In certain embodiments, at least one instance of R is —C(=O)(substituted or unsubstituted alkyl) (e.g., —C(=O)(substituted or unsubstituted C$_{1-6}$ alkyl)). In certain embodiments, at least one instance of R is —C(=O)Me. In certain embodiments, at least one instance of R is substituted or unsubstituted alkyl (e.g., substituted or unsubstituted C$_{1-6}$ alkyl). In certain embodiments, at least one instance of R is substituted or unsubstituted methyl. In certain embodiments, at least one instance of R is substituted or unsubstituted ethyl. In certain embodiments, at least one instance of R is substituted or unsubstituted propyl. In certain embodiments, at least one instance of R is substituted or unsubstituted alkenyl (e.g., substituted or unsubstituted $C_{2-6}$ alkenyl). In certain embodiments, at least one instance of R is substituted or unsubstituted alkynyl (e.g., substituted or unsubstituted $C_{2-6}$ alkynyl). In certain embodiments, at least one instance of R is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of R is substituted or unsubstituted aryl (e.g., substituted or unsubstituted, 6- to 10-membered aryl). In certain embodiments, at least one instance of $R^A$ $R^1$ is substituted benzyl. In certain embodiments, at least one instance of R is unsubstituted benzyl. In certain embodiments, at least one instance of R is substituted phenyl. In certain embodiments, at least one instance of R is unsubstituted phenyl. In certain embodiments, at least one instance of R is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of R is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, at least one instance of R is —CN. In certain embodiments, at least one instance of R is —SCN. In certain embodiments, at least one instance of R is —NO$_2$. In certain embodiments, at least one instance of R is —N$_3$. In certain embodiments, at least one instance of R is —OR$^a$ (e.g., —OH, —O(substituted or unsubstituted $C_{1-6}$ alkyl) (e.g., —OMe, —OCF$_3$, —OEt, —OPr, or —OBu). In certain embodiments, at least one instance of R is —N(R$^b$)$_2$ (e.g., —NMe$_2$). In certain embodiments, at least one instance of R is —SR$^a$ (e.g., —SH, —S(substituted or unsubstituted $C_{1-6}$ alkyl) (e.g., —SMe, —SEt, —SPr, or —SBu).

In certain embodiments, the compound of Formula (I-A) is of the formula:

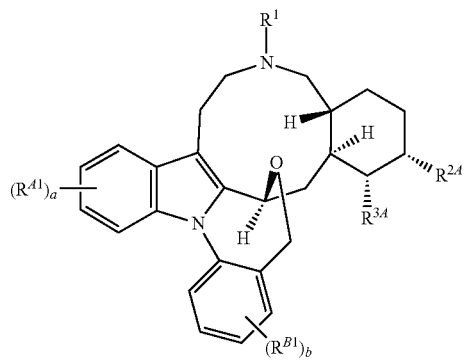

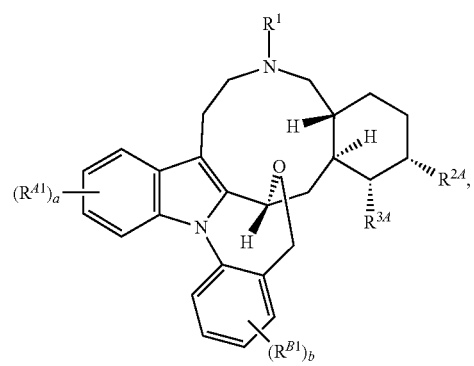

or a pharmaceutically acceptable salt, solvate, hydrate, polymorph, co-crystal, tautomer, stereoisomer, isotopically labeled derivative, or prodrug thereof.

In certain embodiments, the compound of Formula (I-A) is of the formula:

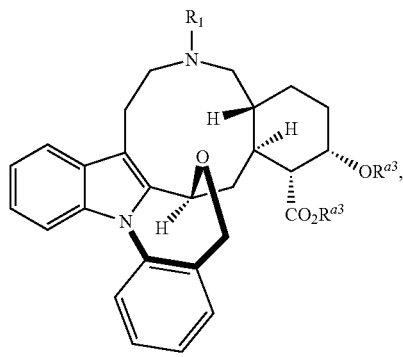

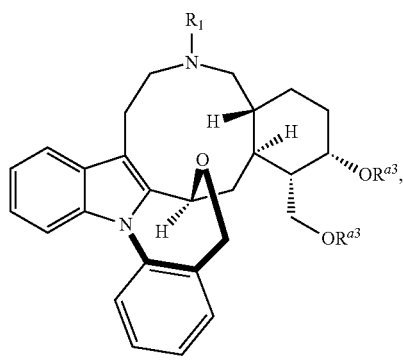

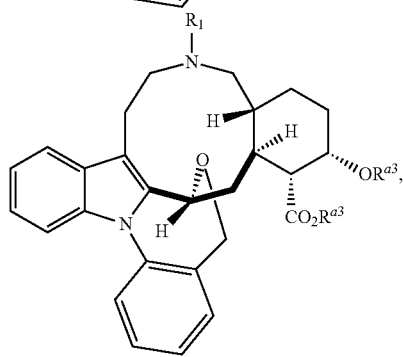

-continued

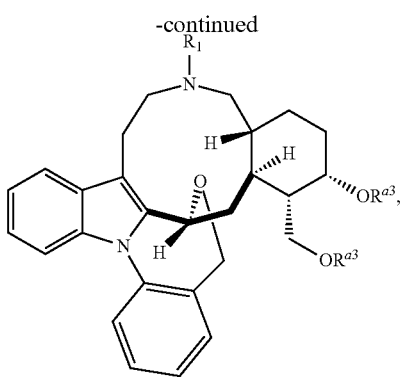

or a pharmaceutically acceptable salt, solvate, hydrate, polymorph, co-crystal, tautomer, stereoisomer, isotopically labeled derivative, or prodrug thereof.

In certain embodiments, the compound of Formula (I-A) is of the formula

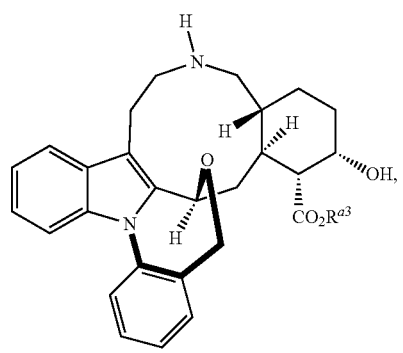

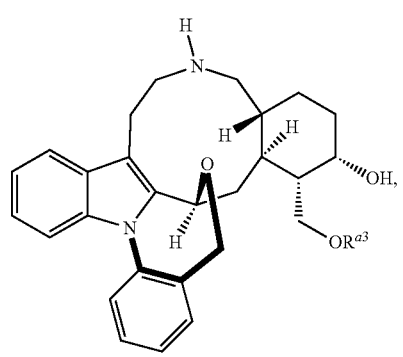

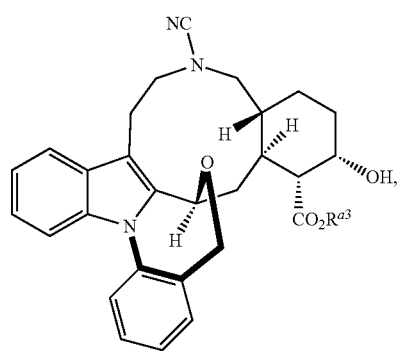

-continued

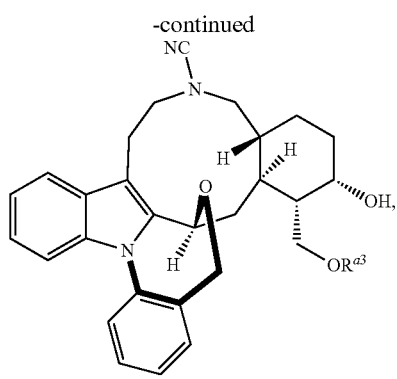

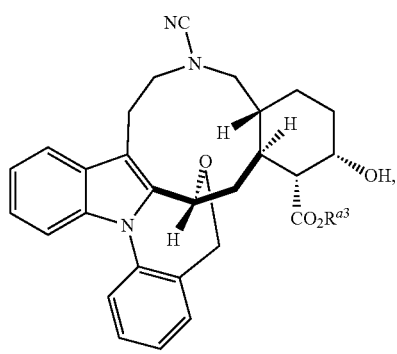

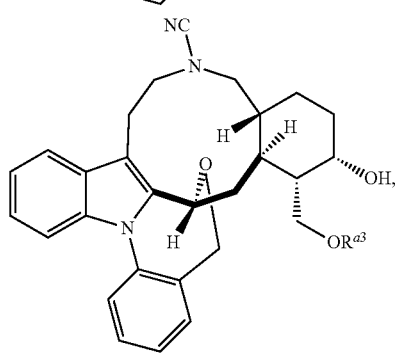

or a pharmaceutically acceptable salt, solvate, hydrate, polymorph, co-crystal, tautomer, stereoisomer, isotopically labeled derivative, or prodrug thereof.

In certain embodiments, exemplary compounds of Formulae (I-A) and (I) include, but are not limited to:

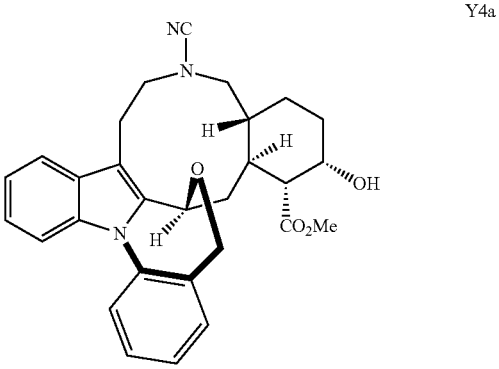

Y4a

-continued

Y4b
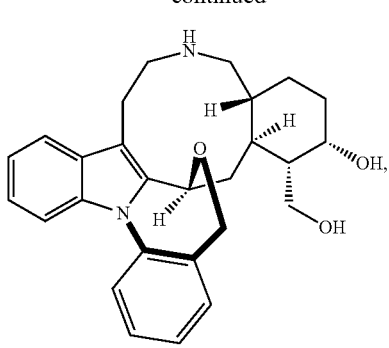

Y5a
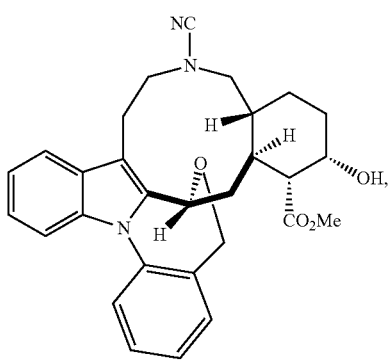

Y5b
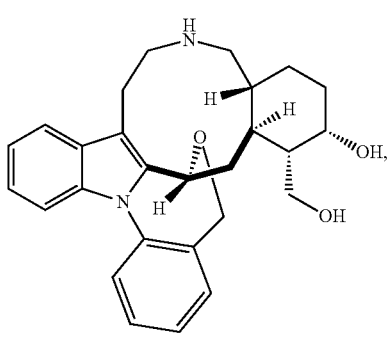

or a pharmaceutically acceptable salt, solvate, hydrate, polymorph, co-crystal, tautomer, stereoisomer, isotopically labeled derivative, or prodrug thereof.

Compounds of Formula (II') and Formula (II)

In one aspect, the present disclosure provides compounds of Formula (II'):

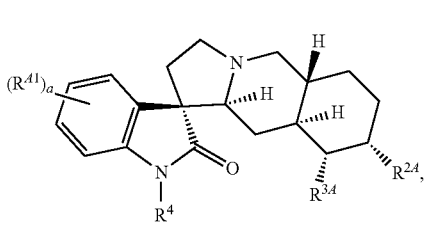

(II')

and pharmaceutically acceptable salts, solvates, hydrates, polymorphs, co-crystals, tautomers, stereoisomers, isotopically labeled derivatives, and prodrugs thereof, wherein:

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^b)_2$, or $-SR^a$;

$R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^b)_2$, or $-SR^a$;

$R^4$ is hydrogen, $-CN$, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

each instance of $R^{A1}$ is independently hydrogen, halogen, $-CN$, $-SCN$, $-NO_2$, $-N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, $-OR^a$, $-N(R^b)_2$, or $-SR^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl; and c is 0, 1, 2, 3, or 4.

In one aspect, the present disclosure provides compounds of Formula (II):

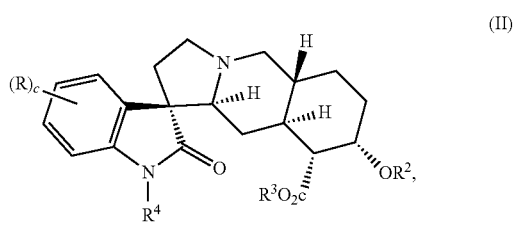

(II)

and pharmaceutically acceptable salts, solvates, hydrates, polymorphs, co-crystals, tautomers, stereoisomers, isotopically labeled derivatives, and prodrugs thereof, wherein:

$R^2$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^3$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^4$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl; and c is 1, 2, 3, or 4.

Formula (II') includes substituent $R^{2A}$. In certain embodiments, $R^{2A}$ is hydrogen. In certain embodiments, $R^{2A}$ is substituted or unsubstituted acyl. In certain embodiments, $R^{2A}$ is —C(=O)(substituted or unsubstituted alkyl) (e.g., —C(=O)(substituted or unsubstituted C$_{1-6}$ alkyl)). In certain embodiments, R$^2$ is substituted or unsubstituted alkyl (e.g., substituted or unsubstituted C$_{1-6}$ alkyl). In certain embodiments, $R^{2A}$ is substituted or unsubstituted methyl. In certain embodiments, $R^{2A}$ is substituted or unsubstituted ethyl. In certain embodiments, $R^{2A}$ is substituted or unsubstituted propyl. In certain embodiments, R$^2$ is substituted or unsubstituted alkenyl (e.g., substituted or unsubstituted C$_{2-6}$ alkenyl). In certain embodiments, $R^{2A}$ is substituted or unsubstituted alkynyl (e.g., substituted or unsubstituted C$_{2-6}$ alkynyl). In certain embodiments, $R^{2A}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{2A}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{2A}$ is substituted or unsubstituted aryl (e.g., substituted or unsubstituted, 6- to 10-membered aryl). In certain embodiments, $R^{2A}$ is substituted benzyl. In certain embodiments, $R^{2A}$ is unsubstituted benzyl. In certain embodiments, $R^{2A}$ is substituted phenyl. In certain embodiments, $R^{2A}$ is unsubstituted phenyl. In certain embodiments, $R^{2A}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{2A}$ is an oxygen protecting group (e.g., t-butyloxycarbonyl (BOC or Boc), methoxylmethyl (MOM) or methylthiomethyl (MTM)). In certain embodiments, $R^{2A}$ is —OR$^a$, —N(R$^b$)$_2$, or —SR$^a$. In certain embodiments, $R^{2A}$ is —OR$^a$, wherein R$^a$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group (e.g., —OH or —OMe). In certain embodiments, $R^{2A}$ is —O(R$^a$), and R$^a$ is hydrogen or substituted or unsubstituted C$_{1-6}$ alkyl. In certain embodiments, R$^2$ is —OMe. In certain embodiments, $R^{2A}$ is —OEt. In certain embodiments, $R^{2A}$ is —O(Pr). In certain embodiments, $R^{2A}$ is —O(iPr). In certain embodiments, $R^{2A}$ is of the formula: —O(CH$_2$)$_z$R$^{6b}$, wherein: R$^{6b}$ is substituted or unsubstituted C$_{1-6}$ alkyl, substituted or unsubstituted heterocyclyl, substituted or unsubstituted aryl, or substituted or unsubstituted heteroaryl; and z is 0, 1, 2, 3, or 4. In certain embodiments, z is 0. In certain embodiments, z is 1. In certain embodiments, z is 2. In certain embodiments, z is 3. In certain embodiments, z is 4. In certain embodiments, R$^{6b}$ is substituted or unsubstituted C$_{1-6}$ alkyl (e.g., substituted or unsubstituted methyl, ethyl, or propyl). In certain embodiments, R$^{6b}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{6b}$ is substituted or unsubstituted aryl (e.g., substituted or unsubstituted, 6- to 10-membered aryl). In certain embodiments, R$^{6b}$ is substituted benzyl. In certain embodiments, $R^{2A}$ is of the formula:

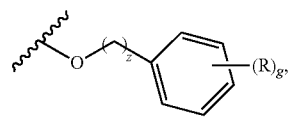

wherein: R is H, halogen, substituted or unsubstituted C$_{1-6}$ alkyl, or —OR$^a$; R$^a$ is substituted or unsubstituted C$_{1-6}$ alkyl; z is 0 or 1; and g is 1, 2, 3, 4, or 5. In certain embodiments, R$^{6b}$ is unsubstituted benzyl. In certain embodiments, R$^{6b}$ is substituted phenyl. In certain embodiments, R$^{6b}$ is unsubstituted phenyl. In certain embodiments, z is 0. In certain embodiments, z is 1. In certain embodiments, g is 1. In certain embodiments, g is 2. In certain embodiments, g is 3. In certain embodiments, g is 4. In certain embodiments, g is 5. In certain embodiments, at least one instance of R is H. In certain embodiments, at least one instance of R is halogen (e.g., F, Cl, Br, or I). In certain embodiments, at least one instance of R is F. In certain embodiments, at least one instance of R is Cl. In certain embodiments, at least one instance of R is Br. In certain embodiments, at least one instance of R is I. In certain embodiments, at least one instance of R is substituted or unsubstituted C$_{1-6}$ alkyl (e.g., substituted or unsubstituted methyl, ethyl, or propyl). In certain embodiments, at least one instance of R is —CF$_3$. In certain embodiments, at least one instance of R is —OR$^a$, and R$^a$ is substituted or unsubstituted C$_{1-6}$ alkyl. In certain embodiments, at least one instance of R is —OMe. In certain embodiments, R is —OEt. In certain embodiments, R$^{2A}$ is of the formula:

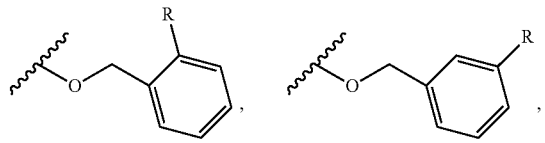

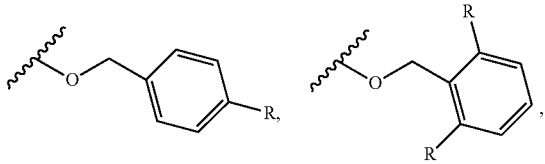

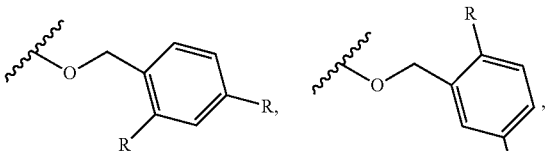

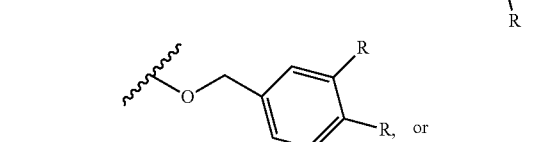

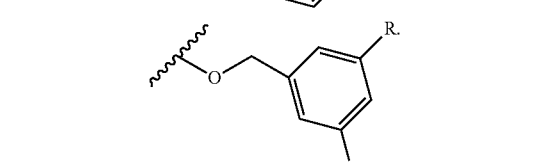

In certain embodiments, R$^{2A}$ is of the formula:

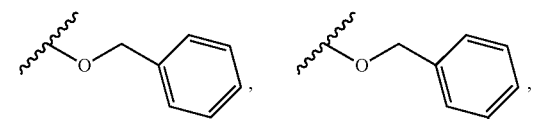

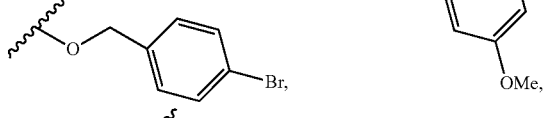

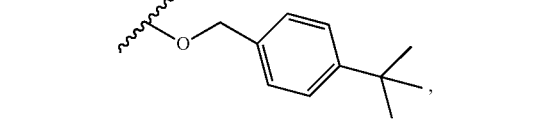

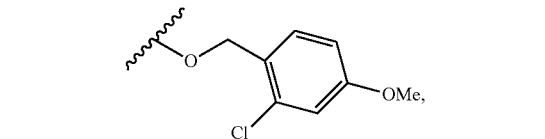

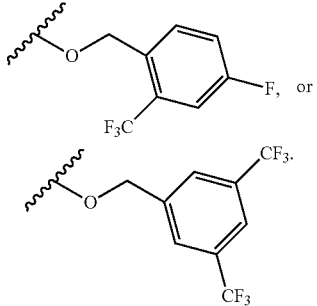

In certain embodiments, R$^{2A}$ is of the formula:

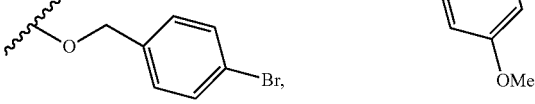

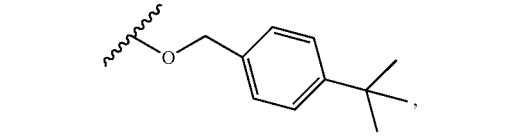

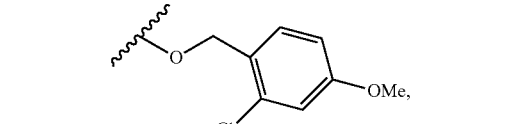

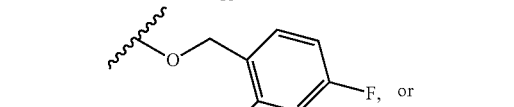

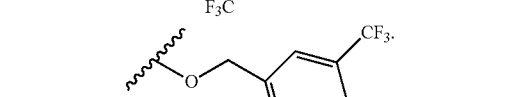

In certain embodiments, R$^{6b}$ is substituted or unsubstituted heteroaryl e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, R$^{2A}$ is —N(R$^b$)$_2$ (e.g., —NH$_2$ or —NMe$_2$). In certain embodiments, R$^{2A}$ is —SR$^a$ (e.g., —SMe).

Formula (II') includes substituents R$^{3A}$ and R$^A$. Substituents R$^{3A}$ and R$^{A1}$ are described in the Detailed Description for Formula (I-A) above. Formula (II') includes one or more instances of substituent $R^{A1}$. In certain embodiments, c is 1. In certain embodiments, c is 2. In certain embodiments, c is 3. In certain embodiments, c is 4.

Formula (II') includes substituent $R^4$. In certain embodiments, $R^4$ is hydrogen. In certain embodiments, $R^4$ is substituted or unsubstituted acyl. In certain embodiments, $R^4$ is —C(═O)(substituted or unsubstituted alkyl) (e.g., —C(═O)(substituted or unsubstituted $C_{1-6}$ alkyl)). In certain embodiments, $R^4$ is —C(═O)Me. In certain embodiments, $R^4$ is substituted or unsubstituted alkyl (e.g., substituted or unsubstituted $C_{1-6}$ alkyl). In certain embodiments, $R^4$ is substituted or unsubstituted methyl. In certain embodiments, $R^4$ is unsubstituted methyl. In certain embodiments, $R^4$ is substituted or unsubstituted ethyl. In certain embodiments, $R^4$ is substituted ethyl. In certain embodiments, $R^4$ is unsubstituted ethyl. In certain embodiments, $R^4$ is substituted or unsubstituted propyl. In certain embodiments, $R^4$ is of the formula:

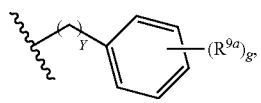

wherein: $R^9$ is H, halogen, substituted or unsubstituted $C_{1-6}$ alkyl, —$OR^a$, or —$NO_2$; $R^a$ is substituted or unsubstituted $C_{1-6}$ alkyl or substituted or unsubstituted aryl; Y is 0 or 1; d is 1, 2, 3, or 4; and g is 1, 2, 3, 4, or 5. In certain embodiments, Y is 0. In certain embodiments, Y is 1. In certain embodiments, g is 1. In certain embodiments, g is 2. In certain embodiments, g is 3. In certain embodiments, g is 4. In certain embodiments, g is 5. In certain embodiments, at least one instance of $R^{9a}$ is H. In certain embodiments, at least one instance of $R^{9a}$ is halogen (e.g., F, Cl, Br, or I). In certain embodiments, at least one instance of $R^{9a}$ is F. In certain embodiments, at least one instance of $R^{9a}$ is Cl. In certain embodiments, at least one instance $R^{9a}$ R is Br. In certain embodiments, at least one instance of $R^{9a}$ is I. In certain embodiments, at least one instance of $R^{9a}$ is substituted or unsubstituted $C_{1-6}$ alkyl (e.g., substituted or unsubstituted methyl, ethyl, or propyl). In certain embodiments, at least one instance of $R^{9a}$ is —$CF_3$. In certain embodiments, at least one instance of $R^{9a}$ R is —$OR^a$, and $R^a$ is substituted or unsubstituted $C_{1-6}$ alkyl or substituted or unsubstituted aryl. In certain embodiments, at least one instance of $R^{9a}$ is —OMe. In certain embodiments, $R^{9a}$ is —OEt. In certain embodiments, at least one instance of $R^{9a}$ is —OPh. In certain embodiments, at least one instance of $R^{9a}$ is —$NO_2$. In certain embodiments, $R^4$ is —CN. In certain embodiments, $R^4$ is of the formula:

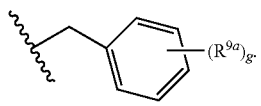

In certain embodiments, $R^4$ is of the formula:

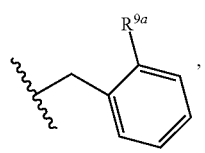 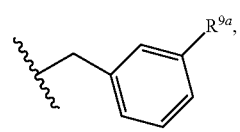

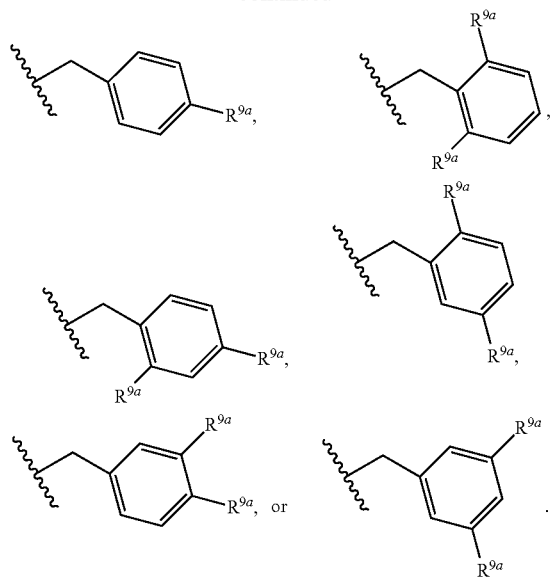

In certain embodiments $R^4$ is of the formula:

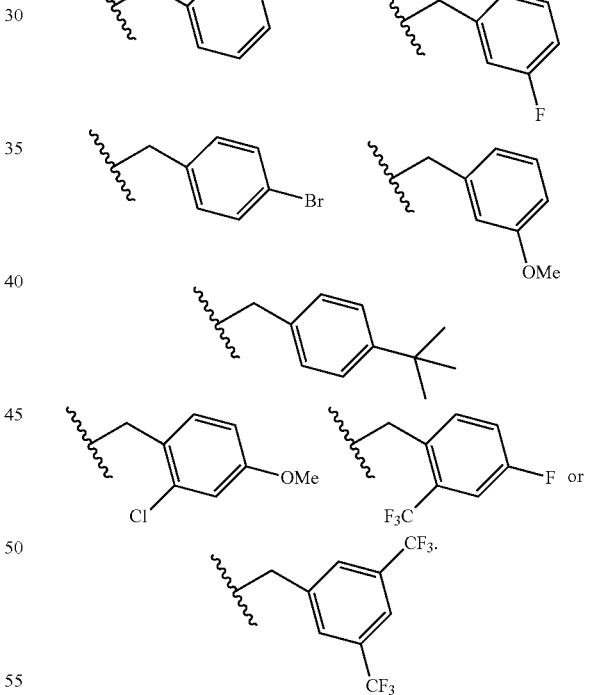

In certain embodiments, $R^4$ is of the formula:

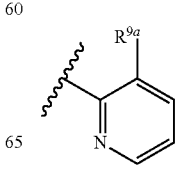 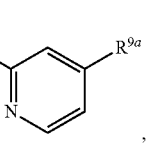 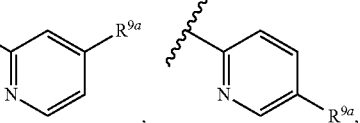

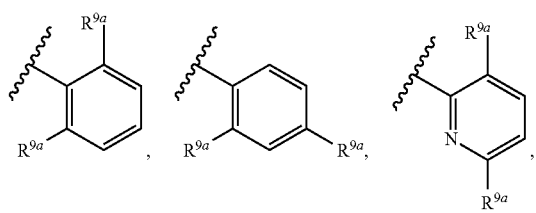

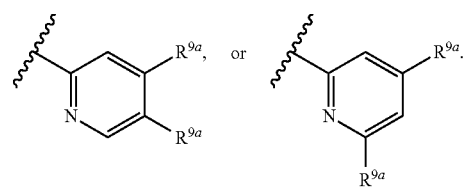

In certain embodiments, R⁴ is of the formula:

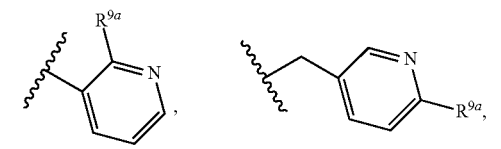

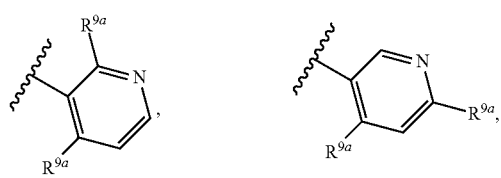

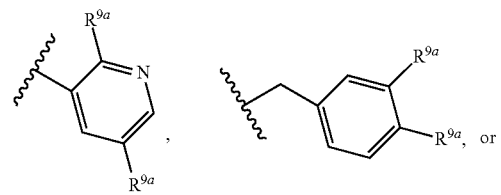

In certain embodiments, R⁴ is of the formula:

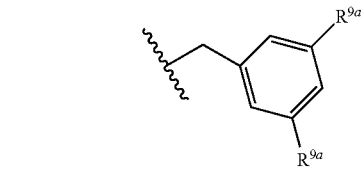

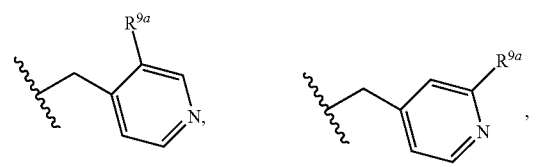

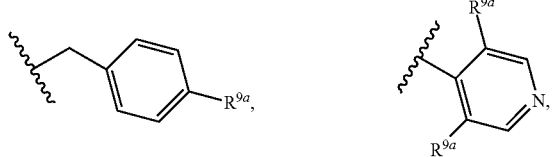

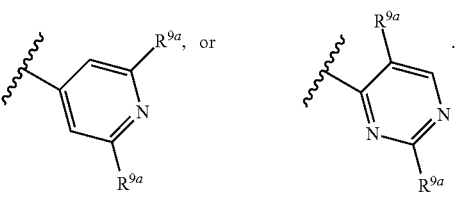

In certain embodiments, R⁴ is of the formula:

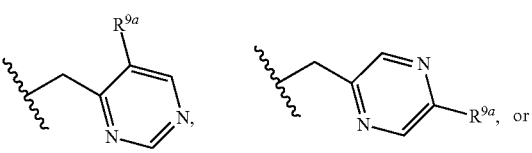

In certain embodiments, R⁴ is of the formula:

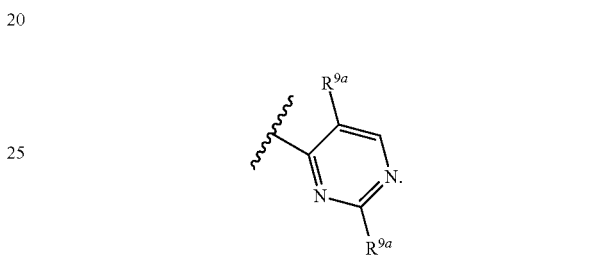

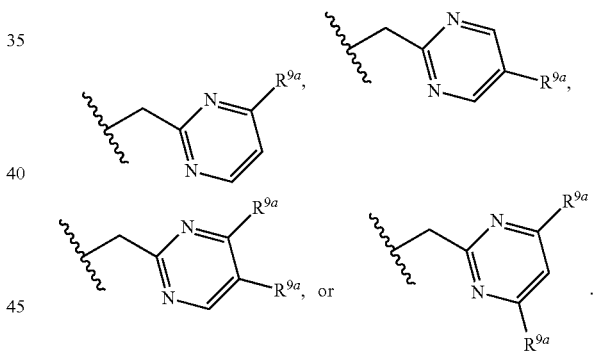

In certain embodiments, R⁴ is substituted or unsubstituted alkenyl (e.g., substituted or unsubstituted $C_{2-6}$ alkenyl). In certain embodiments, R⁴ is substituted or unsubstituted alkynyl (e.g., substituted or unsubstituted $C_{2-6}$ alkynyl). In certain embodiments, R⁴ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R⁴ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R⁴ is substituted or unsubstituted aryl (e.g., substituted or unsubstituted, 6- to 10-membered aryl). In certain embodiments, R⁴ is substituted benzyl. In certain embodiments, R⁴ is unsubstituted benzyl. In certain embodiments, R⁴ is substituted phenyl. In certain embodiments, R⁴ is of the formula:

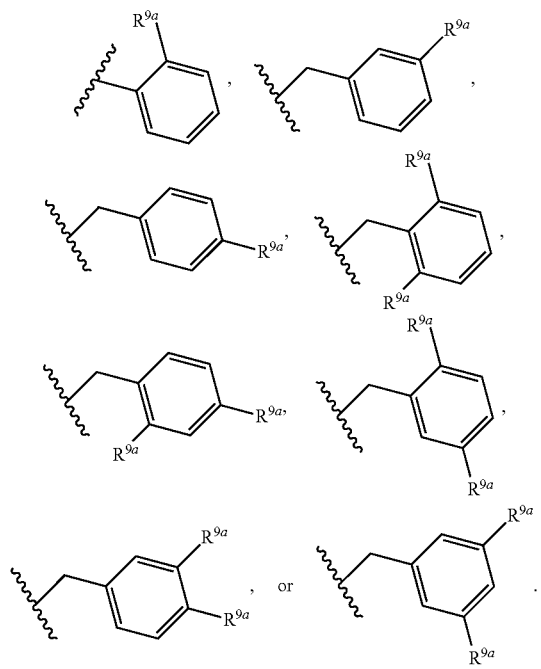

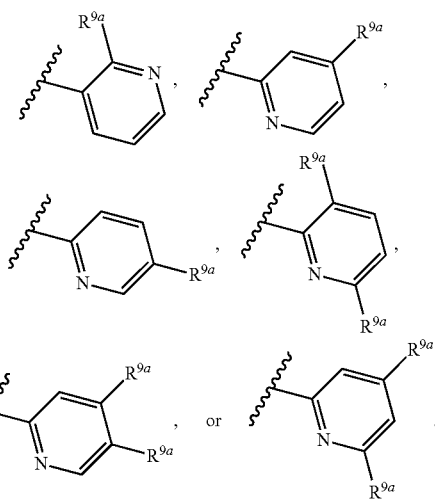

In certain embodiments, $R^4$ is of the formula:

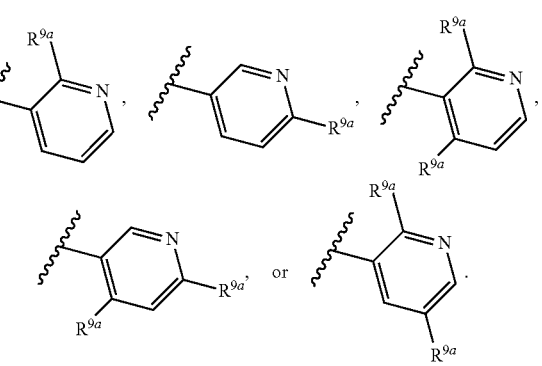

In certain embodiments, $R^4$ is unsubstituted phenyl. In certain embodiments, $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^4$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^4$ is substituted or unsubstituted pyridine. In certain embodiments, $R^4$ is substituted or unsubstituted pyrimidine. In certain embodiments, $R^4$ is substituted or unsubstituted pyrazine. In certain embodiments, $R^4$ is of the formula:

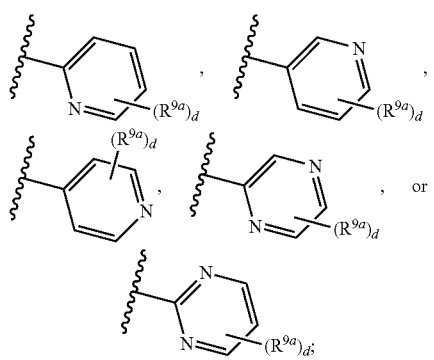

wherein: $R^{9a}$ is H, halogen, substituted or unsubstituted $C_{1-6}$ alkyl, $-OR^a$, or $-NO_2$; $R^a$ is substituted or unsubstituted $C_{1-6}$ alkyl or substituted or unsubstituted aryl; Y is 0 or 1; d is 1, 2, 3, or 4; and g is 1, 2, 3, 4, or 5. In certain embodiments, $R^4$ is of the formula:

In certain embodiments, $R^4$ is of the formula:

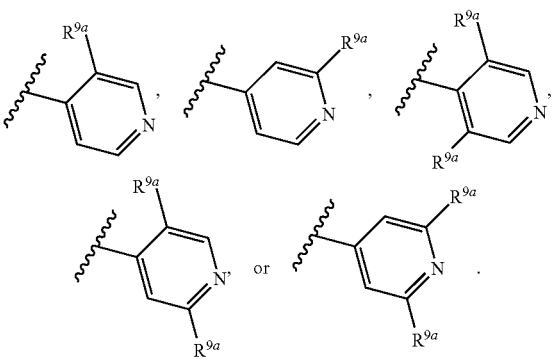

In certain embodiments, $R^4$ is of the formula:

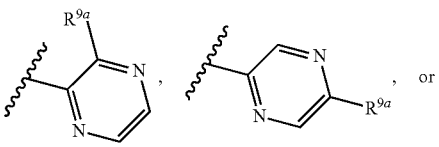

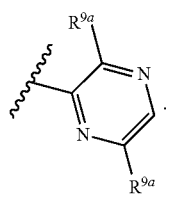

In certain embodiments, R⁴ is of the formula:

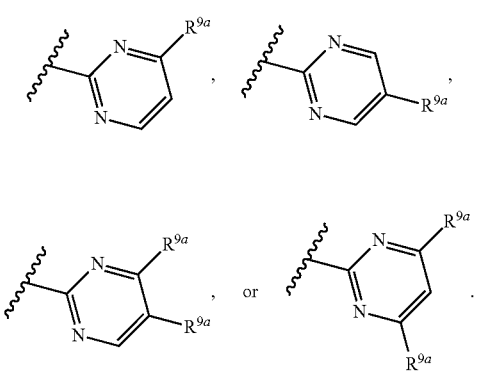

In certain embodiments, R⁴ is of the formula:

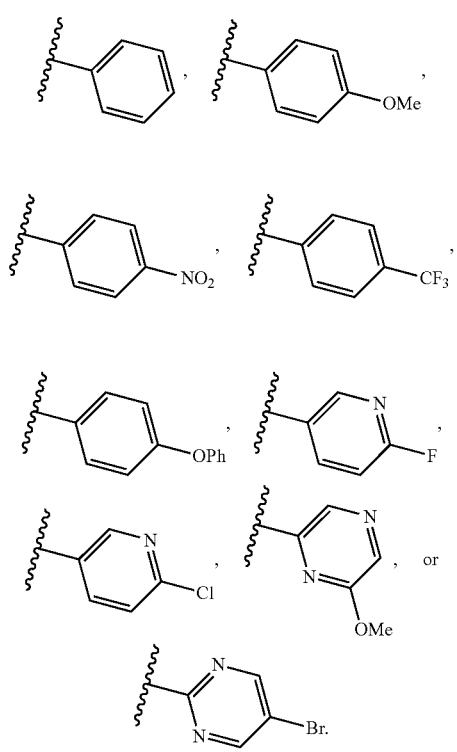

In certain embodiments, R⁴ is an oxygen protecting group (e.g., t-butyloxycarbonyl (BOC or Boc), methoxylmethyl (MOM) or methylthiomethyl (MTM)).

In certain embodiments, the compound of Formula (II') is of the formula:

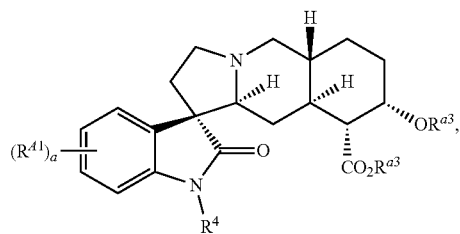

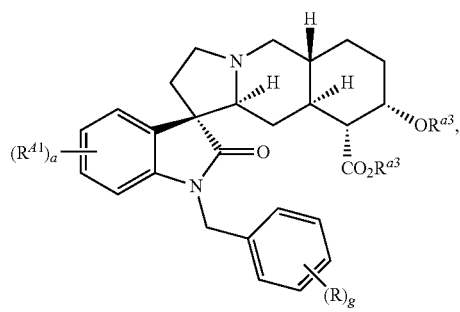

or a pharmaceutically acceptable salt, solvate, hydrate, polymorph, co-crystal, tautomer, stereoisomer, isotopically labeled derivative, or prodrug thereof.

In certain embodiments, the compound of Formula (II') is of the formula:

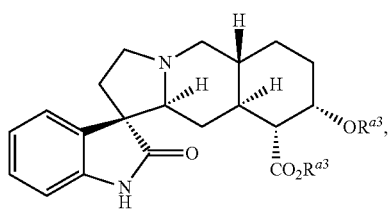

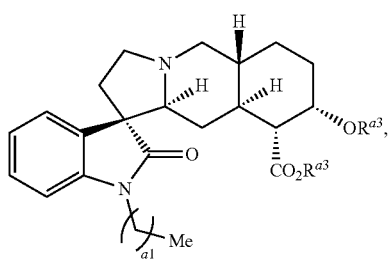

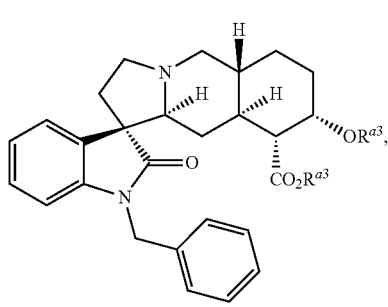

-continued

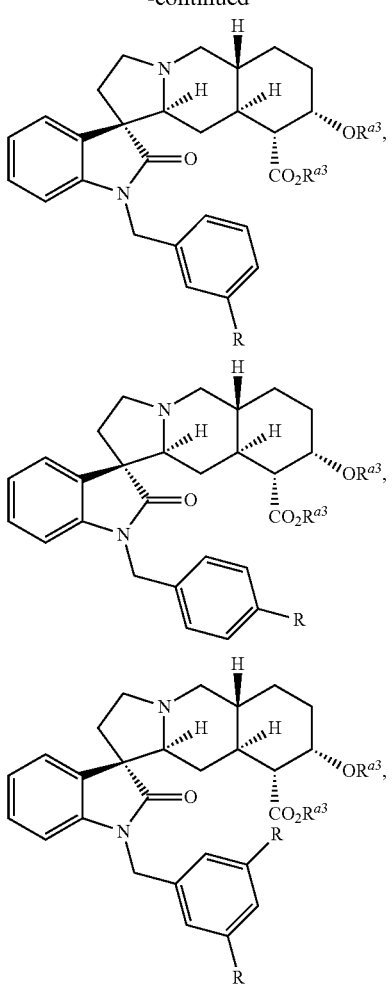

wherein a1 is 0, 1, 2, or 3; or a pharmaceutically acceptable salt, solvate, hydrate, polymorph, co-crystal, tautomer, stereoisomer, isotopically labeled derivative, or prodrug thereof.

In certain embodiments, the compound of Formula (II') is of the formula:

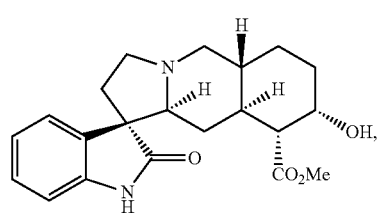

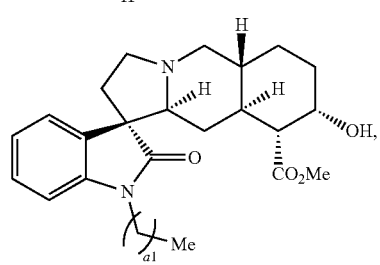

-continued

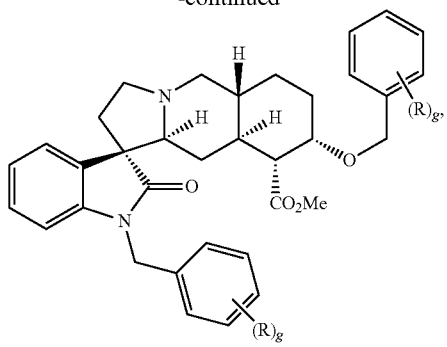

or a pharmaceutically acceptable salt, solvate, hydrate, polymorph, co-crystal, tautomer, stereoisomer, isotopically labeled derivative, or prodrug thereof.

In certain embodiments, the compound of Formula (II') is of the formula:

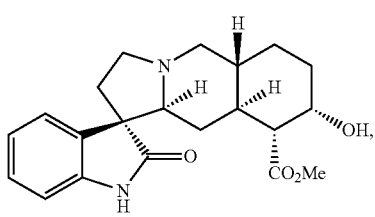

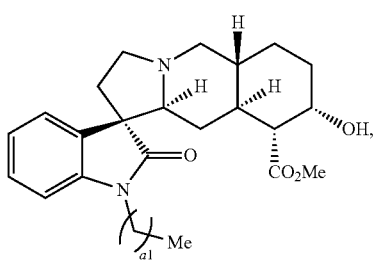

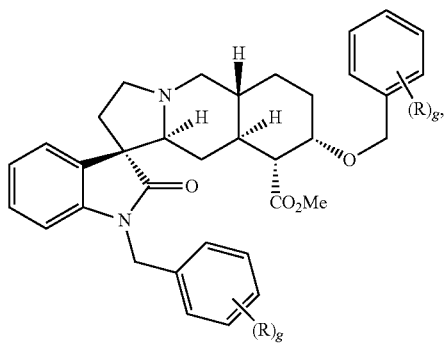

or a pharmaceutically acceptable salt, solvate, hydrate, polymorph, co-crystal, tautomer, stereoisomer, isotopically labeled derivative, or prodrug thereof.

In certain embodiments, exemplary compounds of Formulae (II') and (II) include, but are not limited to:

| | |
|---|---|
| Y3a 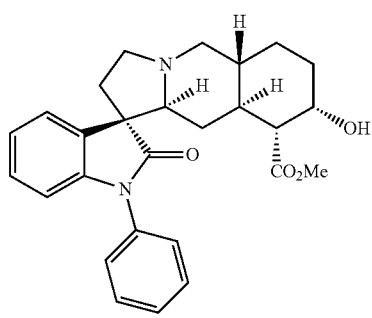 | Y3e 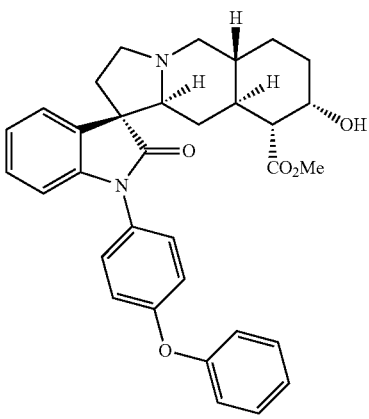 |
| Y3b 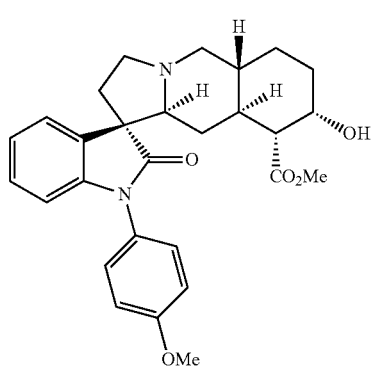 | Y3f 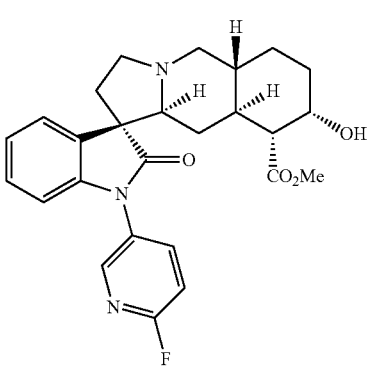 |
| Y3c 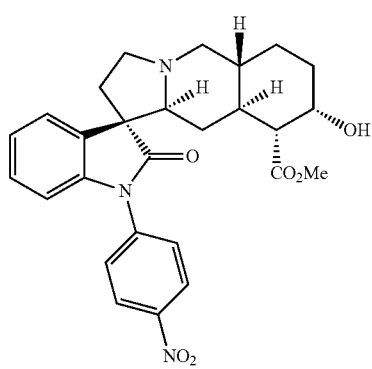 | Y3g 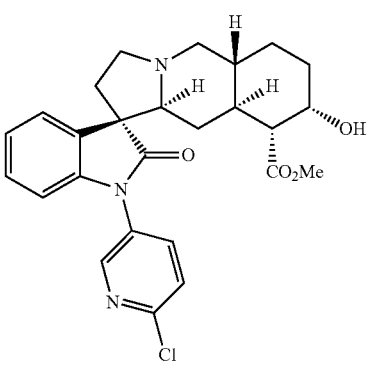 |
| Y3d 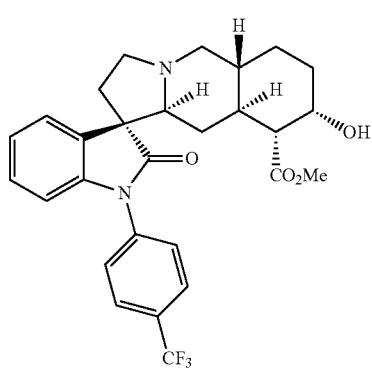 | Y3h 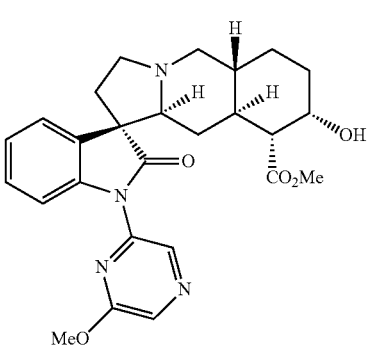 |

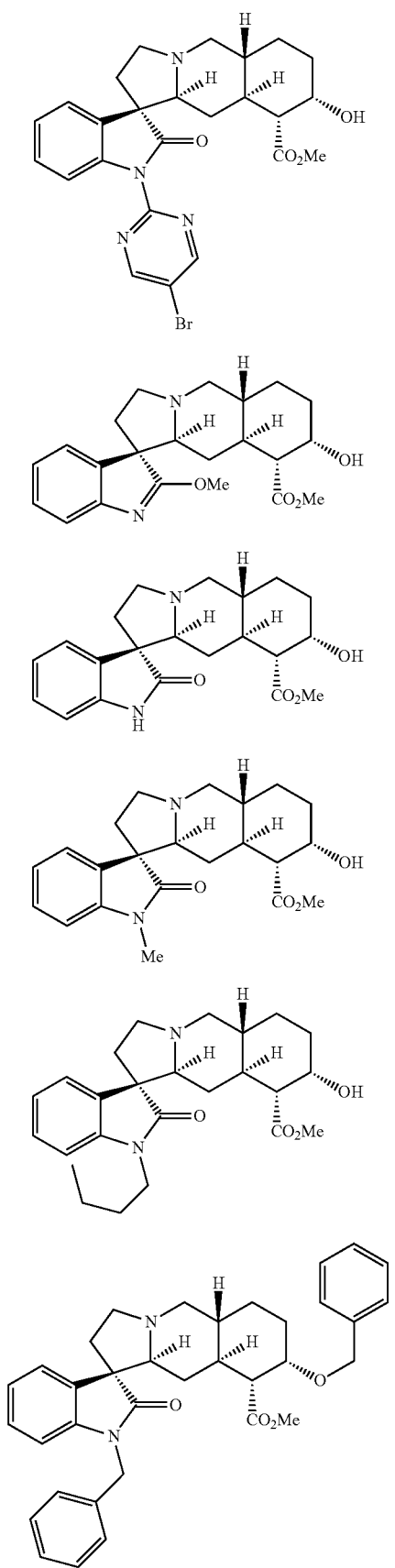
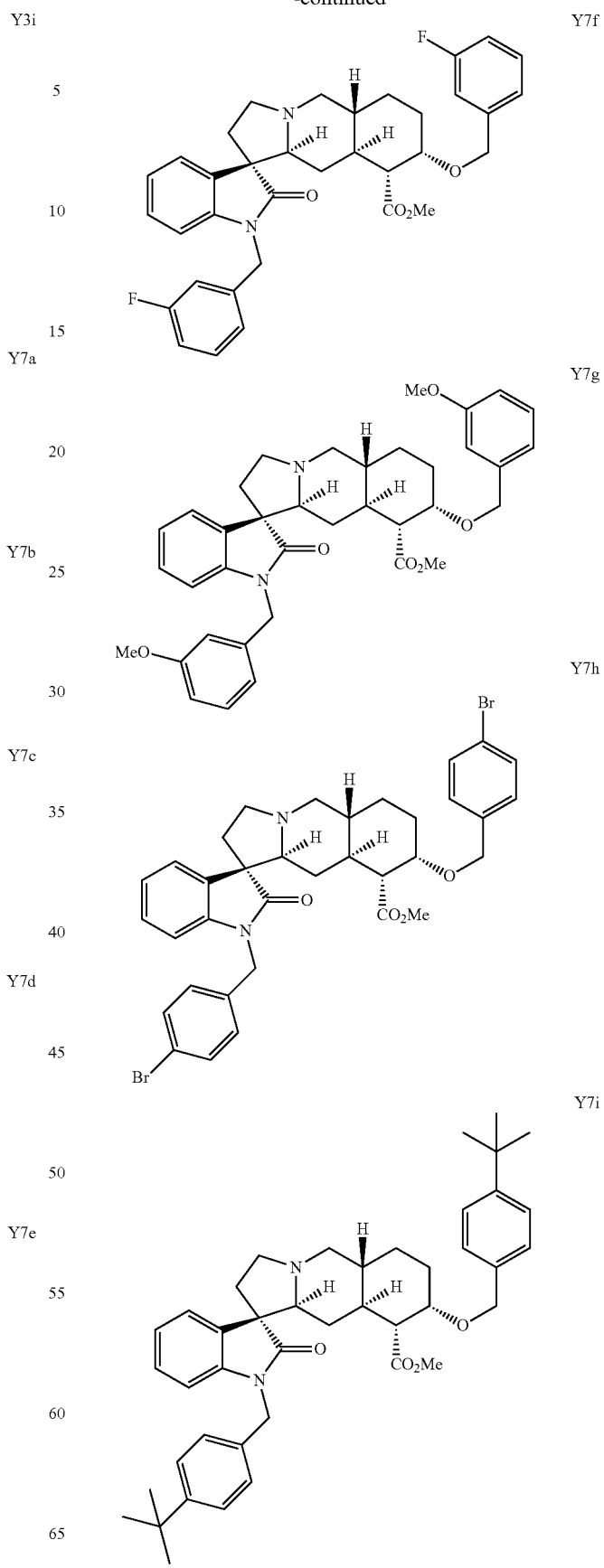

-continued

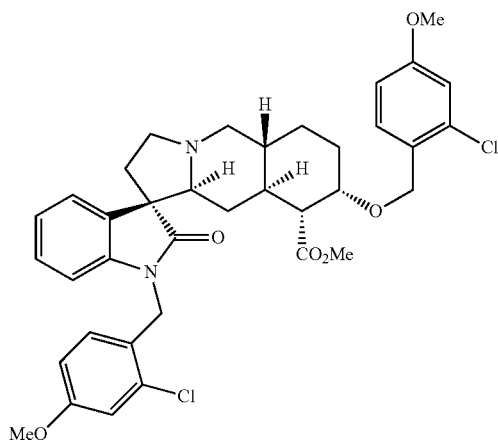

Y7j

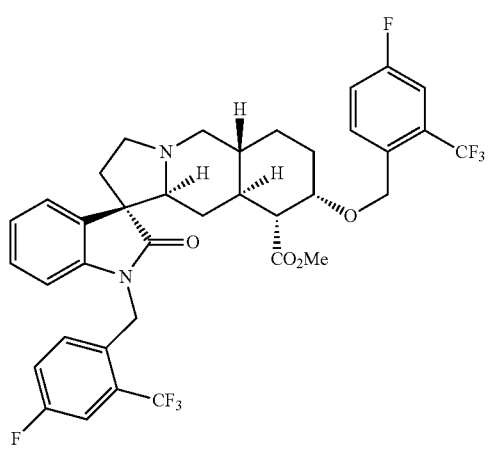

Y7k

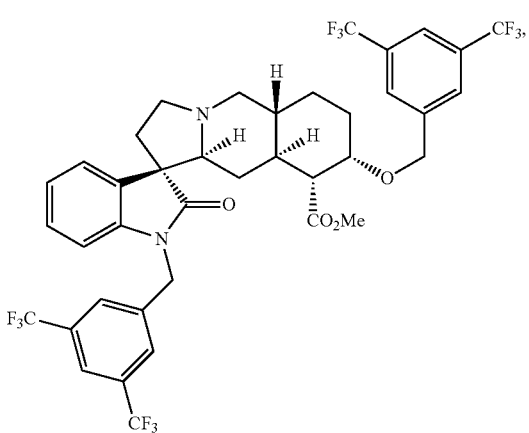

Y7l or a pharmaceutically acceptable salt, solvate, hydrate, polymorph, co-crystal, tautomer, stereoisomer, isotopically labeled derivative, or prodrug thereof. Compounds of Formula (III-A) and Formula (III)

In certain embodiments, the compound is of Formula (III-A):

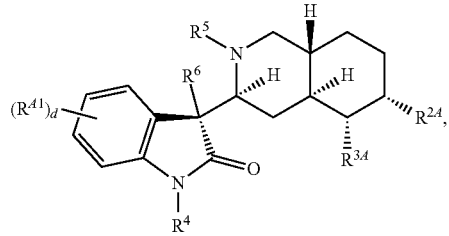

(III-A)

and pharmaceutically acceptable salts, solvates, hydrates, polymorphs, co-crystals, tautomers, stereoisomers, isotopically labeled derivatives, and prodrugs thereof, wherein:

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group; and $R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

$R^4$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^5$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^6$ is hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted acyl, substituted or unsubstituted sulfonyl, —OR$^a$, —N(R$^b$)$_2$, or —SR$^a$;

each instance of R is independently hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl; and d is 1, 2, 3, or 4.

In certain embodiments, the compound is of Formula (III):

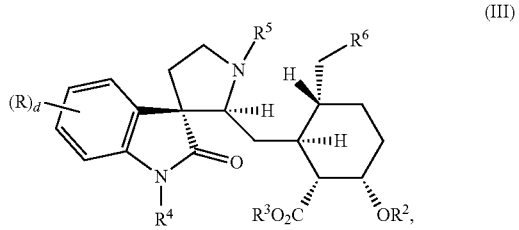

(III)

and pharmaceutically acceptable salts, solvates, hydrates, polymorphs, co-crystals, tautomers, stereoisomers, isotopically labeled derivatives, and prodrugs thereof, wherein:

$R^2$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^3$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^4$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^5$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^6$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl; and d is 1, 2, 3, or 4.

Formulae (III-A), (III), and (IV') include substituent $R^5$. In certain embodiments, $R^5$ is hydrogen. In certain embodiments, $R^5$ is substituted or unsubstituted acyl. In certain embodiments, $R^5$ is —C(=O)(substituted or unsubstituted alkyl) (e.g., —C(=O)(substituted or unsubstituted $C_{1-6}$ alkyl)). In certain embodiments, $R^5$ is —C(=O)Me. In certain embodiments, $R^5$ is substituted or unsubstituted alkyl (e.g., substituted or unsubstituted $C_{1-6}$ alkyl). In certain embodiments, $R^5$ is substituted or unsubstituted methyl. In certain embodiments, $R^5$ is substituted or unsubstituted ethyl. In certain embodiments, $R^5$ is substituted or unsubstituted propyl. In certain embodiments, $R^5$ is substituted or unsubstituted alkenyl (e.g., substituted or unsubstituted $C_{2-6}$ alkenyl). In certain embodiments, $R^5$ is substituted or unsubstituted alkynyl (e.g., substituted or unsubstituted $C_{2-6}$ alkynyl). In certain embodiments, $R^5$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^5$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^5$ is substituted or unsubstituted aryl (e.g., substituted or unsubstituted, 6- to 10-membered aryl). In certain embodiments, $R^5$ is substituted benzyl. In certain embodiments, $R^5$ is unsubstituted benzyl. In certain embodiments, $R^5$ is substituted phenyl. In certain embodiments, $R^5$ is unsubstituted phenyl. In certain embodiments, $R^5$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^5$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^5$ is —CN.

Formula (III-A) includes substituent $R^6$. In certain embodiments, $R^6$ is hydrogen. In certain embodiments, $R^6$ is substituted or unsubstituted acyl. In certain embodiments, $R^6$ is —C(=O)(substituted or unsubstituted alkyl) (e.g., —C(=O)(substituted or unsubstituted $C_{1-6}$ alkyl)). In certain embodiments, $R^6$ is —C(=O)Me. In certain embodiments, $R^6$ is substituted or unsubstituted alkyl (e.g., substituted or unsubstituted $C_{1-6}$ alkyl). In certain embodiments, $R^6$ is of formula $—(CH_2)_n R^{6A}$, wherein: $R^{6A}$ is halogen, —CN, —SCN, —NO₂, —N₃, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)₂, or —SR$^a$; each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of R$^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two R$^b$ are joined together with the intervening atoms to form substituted or unsubstituted heterocyclyl or substituted or unsubstituted heteroaryl; and n is 1, 2, 3, or 4. In certain embodiments, n is 1. In certain embodiments, n is 2. In certain embodiments, n is 3. In certain embodiments, n is 4.

In certain embodiments, $R^6$ is of formula:

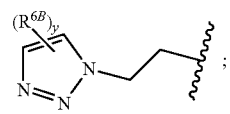

wherein $R^{6B}$ is halogen, substituted or unsubstituted $C_{1-6}$ alkyl, substituted or unsubstituted carbocyclyl, substituted or unsubstituted phenyl, substituted or unsubstituted $C_{3-6}$ heteroaryl; and y is 0, 1, or 2. In certain embodiments, $R^{6B}$ is halogen (e.g., F, Cl, Br, or I). In certain embodiments, $R^{6B}$ is substituted or unsubstituted $C_{1-6}$ alkyl (e.g., substituted or unsubstituted $C_{1-6}$ alkyl). In certain embodiments, $R^{6B}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{6B}$ is substituted or unsubstituted phenyl. In certain embodiments, $R^{6B}$ is substituted or unsubstituted $C_{3-6}$ heteroaryl. In certain embodiments, y is 0. In certain embodiments, y is 1. In certain embodiments, y is 2.

In certain embodiments, $R^6$ is of formula:

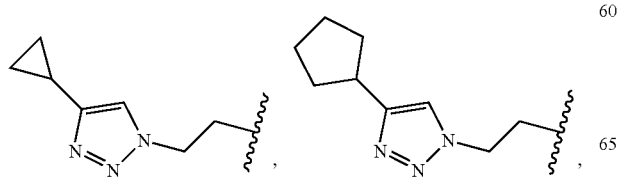

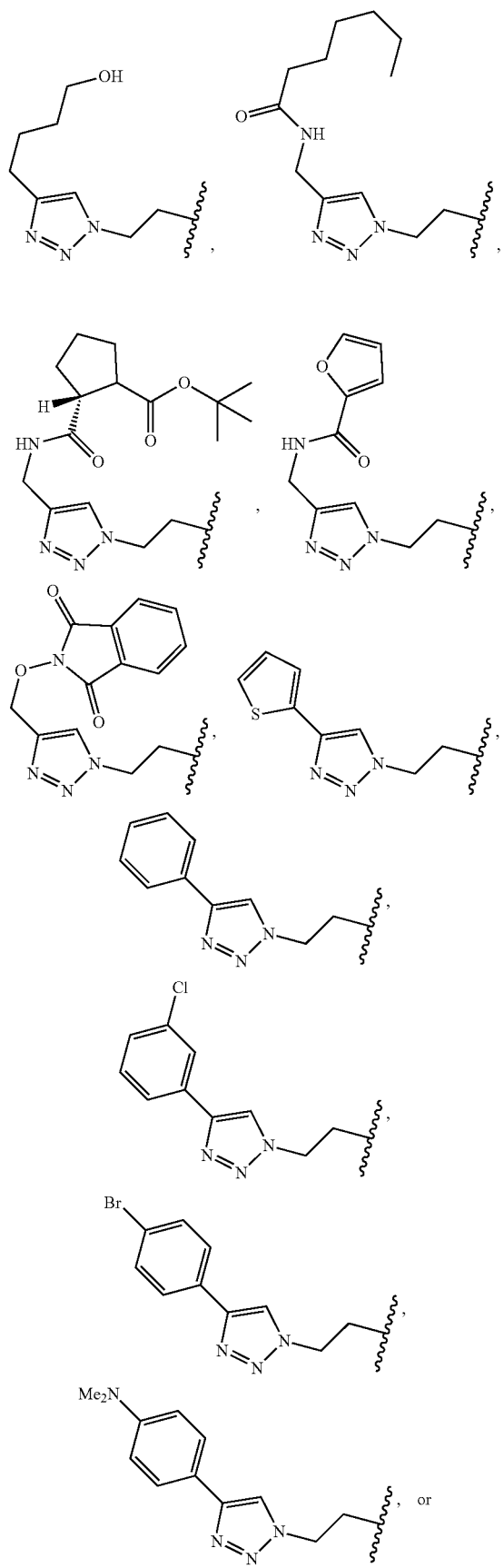

-continued

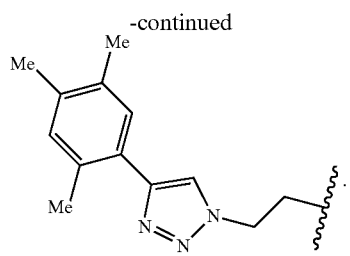

In certain embodiments, $R^6$ is of formula —$(CH_2)_zOR^{6b}$ or —$(CH_2)_zNHC(=O)R^{6c}$, wherein: $R^{6b}$ is H, substituted or unsubstituted $C_{1-6}$ alkyl, substituted or unsubstituted heterocyclyl, or substituted or unsubstituted heteroaryl; $R^{6c}$ is substituted or unsubstituted $C_{1-6}$ alkyl; substituted or unsubstituted heterocyclyl, or substituted or unsubstituted heteroaryl;

and z is 0, 1, 2, 3, or 4. In certain embodiments, z is 0. In certain embodiments, z is 1. In certain embodiments, z is 2. In certain embodiments, z is 3. In certain embodiments, z is 4. In certain embodiments, $R^{6b}$ is H. In certain embodiments, $R^{6b}$ is substituted or unsubstituted $C_{1-6}$ alkyl (e.g., Me, Et, or Pr). In certain embodiments, $R^{6b}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{6b}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{6c}$ is substituted or unsubstituted $C_{1-6}$ alkyl (e.g., Me, Et, or Pr). In certain embodiments, $R^{6c}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{6c}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^6$ is of formula

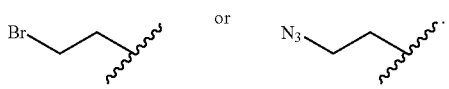

In certain embodiments, $R^6$ is substituted or unsubstituted methyl. In certain embodiments, $R^6$ is substituted or unsubstituted ethyl. In certain embodiments, $R^6$ is substituted or unsubstituted propyl. In certain embodiments, $R^6$ is substituted or unsubstituted alkenyl (e.g., substituted or unsubstituted $C_{2-6}$ alkenyl). In certain embodiments, $R^6$ is substituted or unsubstituted alkynyl (e.g., substituted or unsubstituted $C_{2-6}$ alkynyl). In certain embodiments, $R^6$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^6$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^6$ is substituted or unsubstituted aryl (e.g., substituted or unsubstituted, 6- to 10-membered aryl). In certain embodiments, $R^6$ is substituted benzyl. In certain embodiments, $R^6$ is unsubstituted benzyl. In certain embodiments, $R^6$ is substituted phenyl. In certain embodiments, $R^6$ is unsubstituted phenyl. In certain embodiments, $R^6$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^6$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, the compound of Formula (III-A) is of the formula:

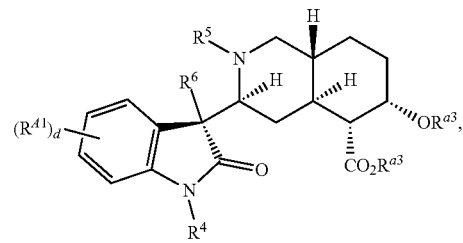

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

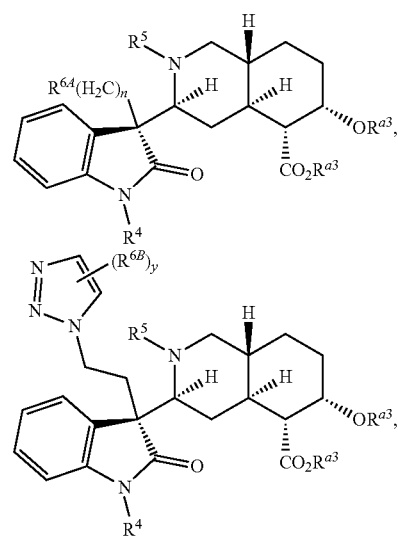

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

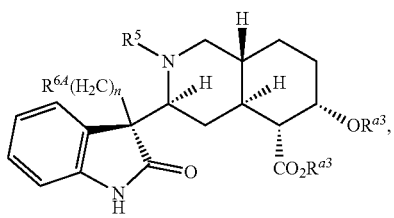

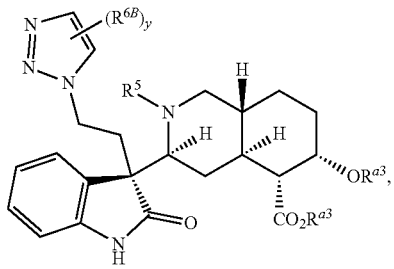

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

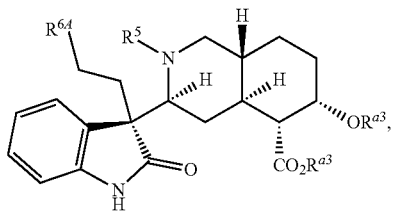

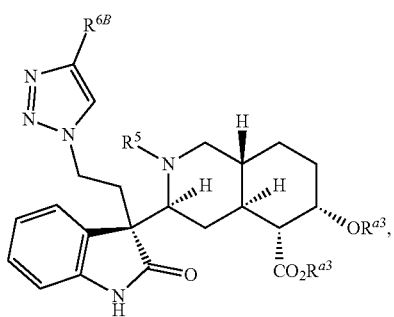

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

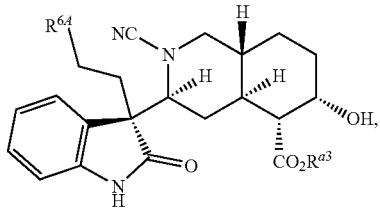

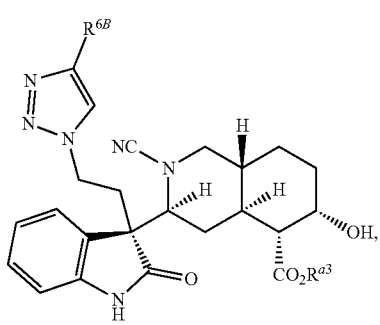

or a pharmaceutically acceptable salt, solvate, hydrate, polymorph, co-crystal, tautomer, stereoisomer, isotopically labeled derivative, or prodrug thereof.

In certain embodiments, exemplary compounds of Formulae (III-A) and (III) include, but are not limited to:

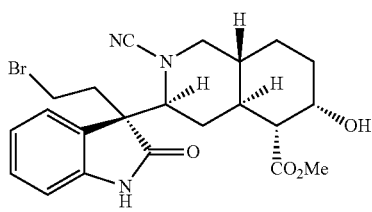

Y2a

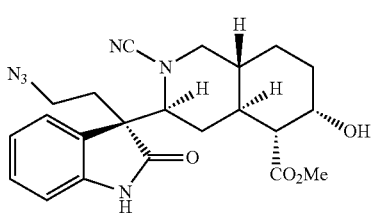

Y2b

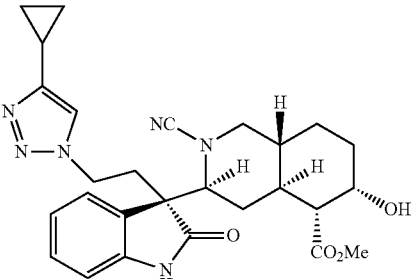

Y2c

91
-continued
Y2d
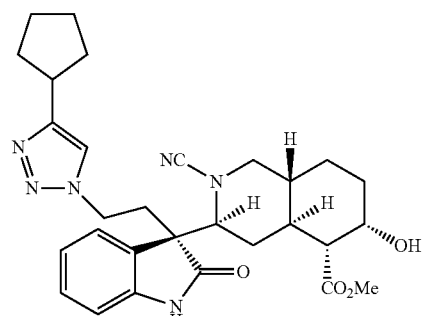
Y2e
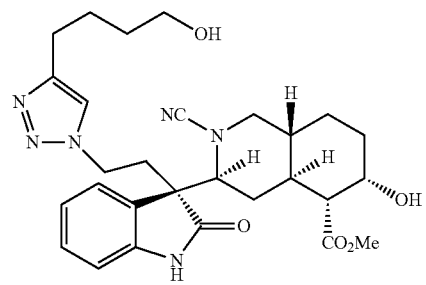
Y2f
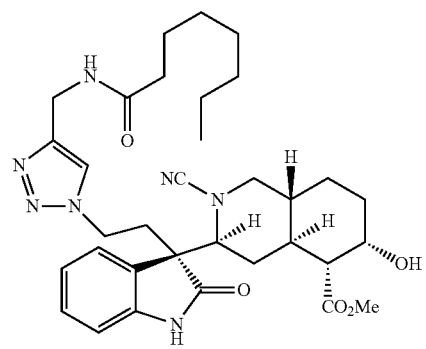
Y2g
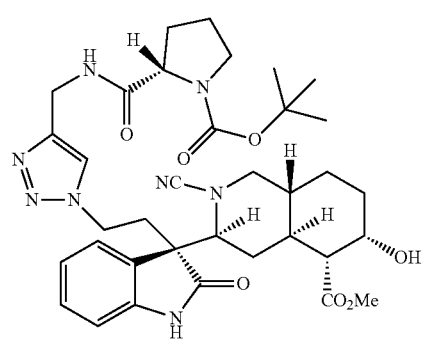
Y2h
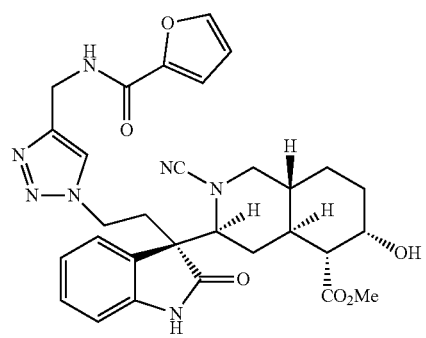
92
-continued
Y2i
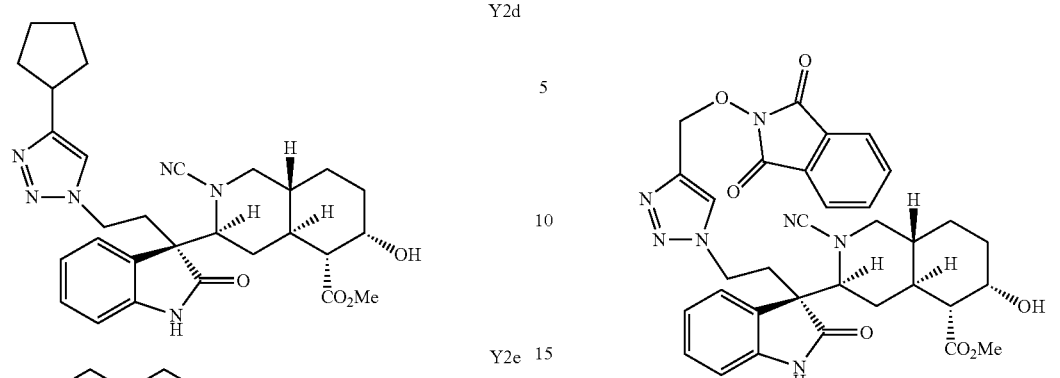
Y2j
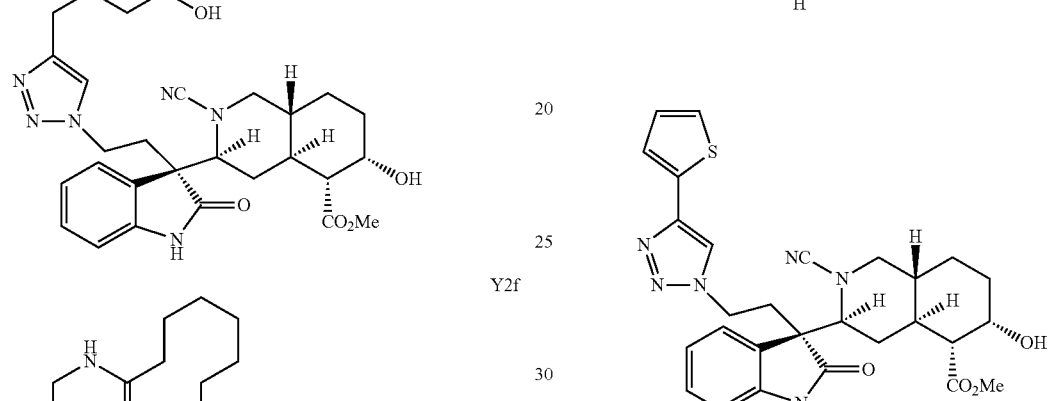
Y2k
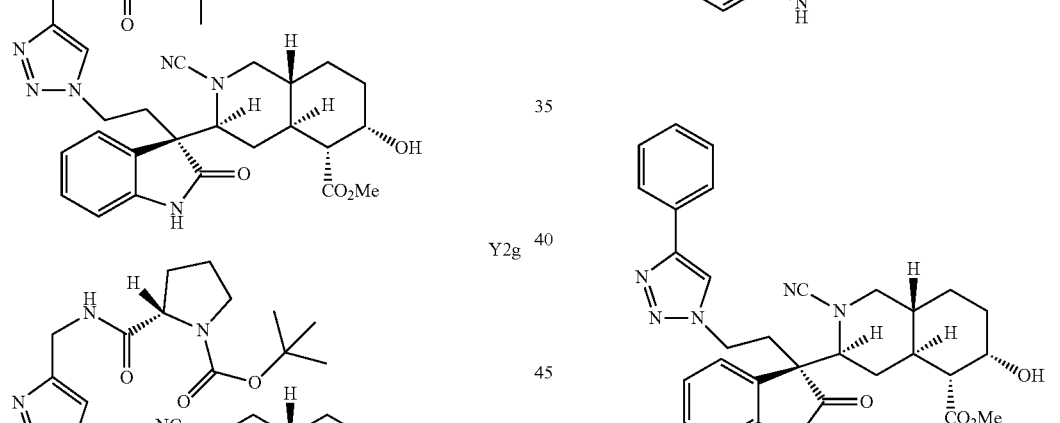
Y2l
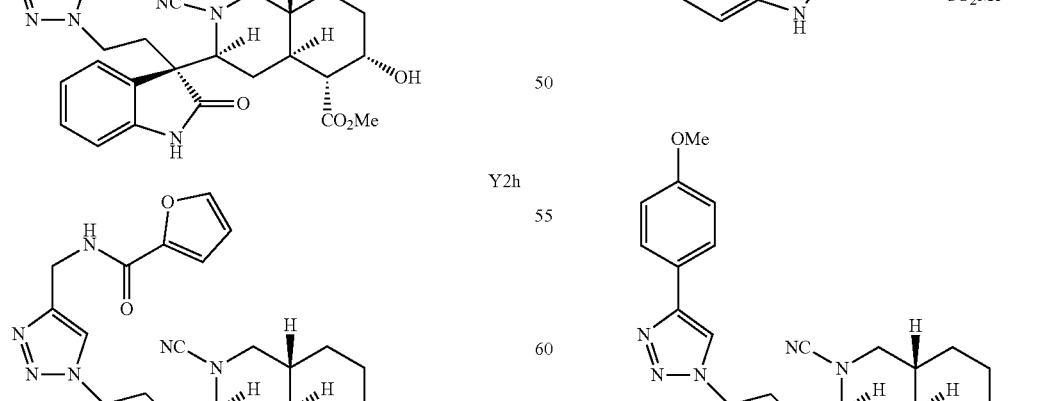

-continued

Y2m 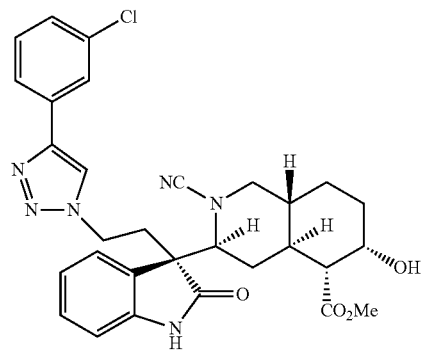

Y2n 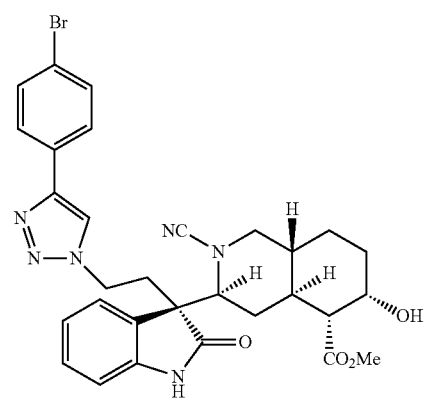

Y2o 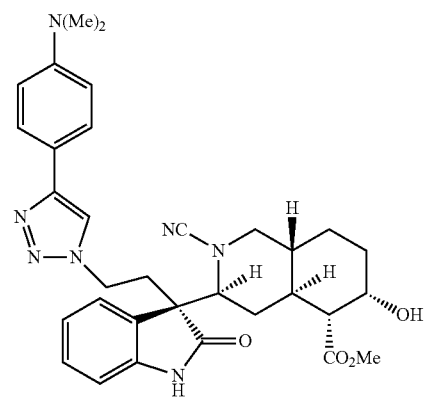

Y2p 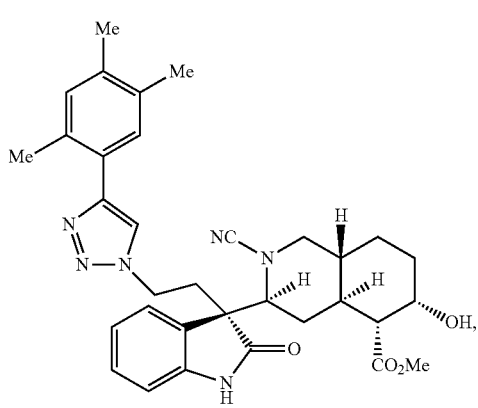

or a pharmaceutically acceptable salt, solvate, hydrate, polymorph, co-crystal, tautomer, stereoisomer, isotopically labeled derivative, or prodrug thereof.

Compounds of Formula (IV') and Formula (IV)

In one aspect, the present disclosure provides compounds of Formula (IV'):

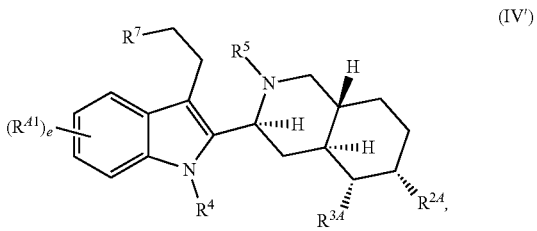

(IV')

and pharmaceutically acceptable salts, solvates, hydrates, polymorphs, co-crystals, tautomers, stereoisomers, isotopically labeled derivatives, and prodrugs thereof, wherein:

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$; and $R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

$R^4$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^7$ is hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted acyl, substituted or unsubstituted sulfonyl, —$OR^a$, —$N(R^b)_2$, or —$SR^a$ $R^5$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

each instance of $R^{41}$ is independently hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —$OR^a$, —$N(R^b)_2$, or —$SR^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl; and e is 0, 1, 2, 3, or 4.

In one aspect, the present disclosure provides compounds of Formula (IV):

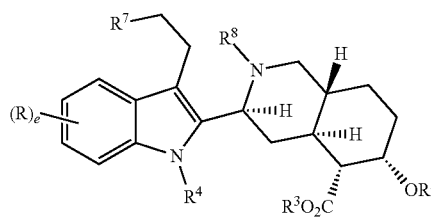

(IV)

and pharmaceutically acceptable salts, solvates, hydrates, polymorphs, co-crystals, tautomers, stereoisomers, isotopically labeled derivatives, and prodrugs thereof, wherein:

$R^2$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and $R^3$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^4$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^7$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^8$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl; and d is 1, 2, 3, or 4.

Formula (IV') includes substituents $R^{2A}$, $R^{3A}$, $R^4$, $R^5$, $R^7$, $R^9$, and $R^{A1}$. Substituents $R^{2A}$, $R^{3A}$, and $R^{A1}$ are described in the Detailed Description for Formula (I-A) above. Formula (IV') includes zero or more instances of substituent $R^{A1}$. In certain embodiments, e is 0. In certain embodiments, e is 1. In certain embodiments, e is 2. In certain embodiments, e is 3. In certain embodiments, e is 4. Substituent $R^4$ is described in the Detailed Description for Formula (II') above. Substituent $R^5$ is described in the Detailed Description for Formula (III-A) above.

Formula (IV') and (IV) include substituent $R^7$. In certain embodiments, $R^7$ is hydrogen. In certain embodiments, $R^7$ is halogen (e.g., F, Cl, Br, or I). In certain embodiments, $R^7$ is —Br. In certain embodiments, $R^7$ is substituted or unsubstituted acyl. In certain embodiments, $R^7$ is —C(=O)(substituted or unsubstituted alkyl) (e.g., —C(=O)(substituted or unsubstituted C$_{1-6}$ alkyl)). In certain embodiments, $R^7$ is —C(=O)Me. In certain embodiments, $R^7$ is substituted or unsubstituted alkyl (e.g., substituted or unsubstituted C$_{1-6}$ alkyl). In certain embodiments, $R^7$ is substituted or unsubstituted methyl. In certain embodiments, $R^7$ is substituted or unsubstituted ethyl. In certain embodiments, $R^7$ is substituted or unsubstituted propyl. In certain embodiments, $R^7$ is substituted or unsubstituted alkenyl (e.g., substituted or unsubstituted C$_{2-6}$ alkenyl). In certain embodiments, $R^7$ is substituted or unsubstituted alkynyl (e.g., substituted or unsubstituted C$_{2-6}$ alkynyl). In certain embodiments, $R^7$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^7$ is substituted or unsubstituted cyclopropyl. In certain embodiments, $R^7$ is substituted or unsubstituted cyclobutyl. In certain embodiments, $R^7$ is substituted or unsubstituted cyclopentyl. In certain embodiments, $R^7$ is substituted or unsubstituted cyclohexyl. In certain embodiments, $R^7$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^7$ is substituted or unsubstituted aryl (e.g., substituted or unsubstituted, 6- to 10-membered aryl). In certain embodiments, $R^7$ is substituted benzyl. In certain embodiments, $R^7$ is unsubstituted benzyl. In certain embodiments, $R^7$ is substituted phenyl. In certain embodiments, $R^7$ is unsubstituted phenyl. In certain embodiments, $R^7$ is of formula:

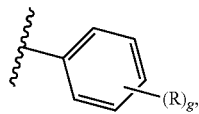

wherein R is H, halogen, substituted or unsubstituted alkyl, substituted or unsubstituted acyl, or —N($R^b$)$_2$; each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, or substituted or unsubstituted heterocyclyl; and g is 1, 2, 3, 4, or 5. In certain embodiments, g is 1. In certain embodiments, g is 2. In certain embodiments, g is 3. In certain embodiments, g is 4. In certain embodiments, g is 5.

In certain embodiments, $R^7$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^7$ is substituted or unsubstituted $C_{3-6}$ heteroaryl. In certain embodiments, $R^7$ is of formula

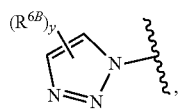

wherein: $R^{6B}$ is substituted or unsubstituted $C_{1-6}$ alkyl, substituted or unsubstituted $C_{3-6}$ carbocyclyl, substituted or unsubstituted phenyl, or substituted or unsubstituted $C_{3-7}$ heteroaryl; and y is 0, 1, or 2. In certain embodiments, $R^7$ includes zero or more instances of $R^{6B}$. In certain embodiments, y is 0. In certain embodiments, y is 1. In certain embodiments, y is 2. In certain embodiments, $R^{6B}$ is substituted or unsubstituted $C_{1-6}$ alkyl (e.g., substituted or unsubstituted $C_{1-6}$ alkyl). In certain embodiments, $R^{6B}$ is substituted or unsubstituted $C_{3-6}$ carbocyclyl. In certain embodiments, $R^{6B}$ is unsubstituted cyclopentyl. In certain embodiments, $R^{6B}$ is substituted or unsubstituted phenyl. In certain embodiments, $R^{6B}$ is unsubstituted phenyl. In certain embodiments, $R^{6B}$ is substituted phenyl. In certain embodiments, $R^{6B}$ is substituted or unsubstituted $C_{3-6}$ heteroaryl. In certain embodiments, $R^{6B}$ is substituted or unsubstituted pyridyl. In certain embodiments, $R^{6B}$ is unsubstituted pyridyl.

In certain embodiments, $R^7$ is of formula

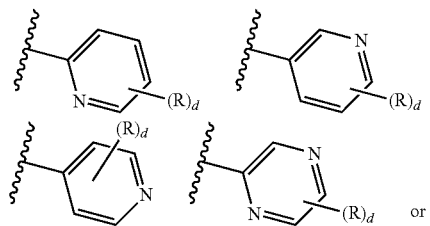

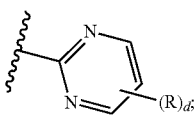

wherein R is H, halogen, substituted or unsubstituted alkyl, substituted or unsubstituted acyl, or —N($R^b$)$_2$; each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, or substituted or unsubstituted heterocyclyl; and d is 1, 2, 3, or 4. In certain embodiments, d is 1. In certain embodiments, d is 2. In certain embodiments, d is 3. In certain embodiments, d is 4. In certain embodiments, $R^7$ is of formula

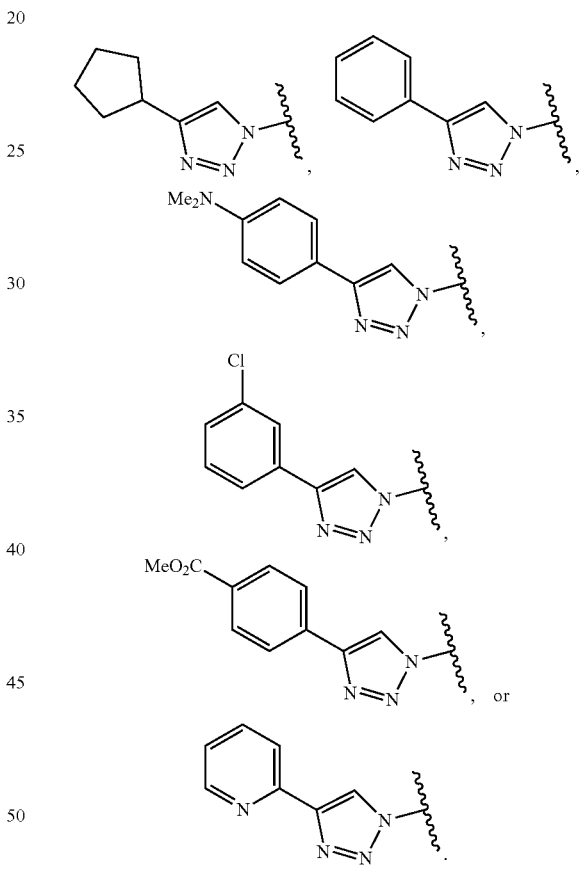

In certain embodiments, $R^7$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^7$ is —CN. In certain embodiments, $R^7$ is —SCN. In certain embodiments, $R^7$ is —NO$_2$. In certain embodiments, $R^7$ is —N$_3$. In certain embodiments, $R^7$ is —OR$^a$ (e.g., —OH, —O(substituted or unsubstituted $C_{1-6}$ alkyl) (e.g., —OMe, —OCF$_3$, —OEt, —OPr, or —OBu). In certain embodiments, $R^7$ is —N($R^b$)$_2$ (e.g., —NMe$_2$). In certain embodiments, $R^7$ is —SR$^a$ (e.g., —SH, —S(substituted or unsubstituted $C_{1-6}$ alkyl) (e.g., —SMe, —SEt, —SPr, or —SBu).

Formula (IV) includes substituent R⁸. In certain embodiments, R⁸ is hydrogen. In certain embodiments, R⁸ is substituted or unsubstituted acyl. In certain embodiments, R⁸ is —C(=O)(substituted or unsubstituted alkyl) (e.g., —C(=O)(substituted or unsubstituted $C_{1-6}$ alkyl)). In certain embodiments, R⁸ is substituted or unsubstituted alkyl (e.g., substituted or unsubstituted $C_{1-6}$ alkyl). In certain embodiments, R⁸ is substituted or unsubstituted methyl. In certain embodiments, R⁸ is substituted or unsubstituted ethyl. In certain embodiments, R⁸ is substituted or unsubstituted propyl. In certain embodiments, R⁸ is substituted or unsubstituted alkenyl (e.g., substituted or unsubstituted $C_{2-6}$ alkenyl). In certain embodiments, R⁸ is substituted or unsubstituted alkynyl (e.g., substituted or unsubstituted $C_{2-6}$ alkynyl). In certain embodiments, R⁸ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R⁸ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R⁸ is substituted or unsubstituted aryl (e.g., substituted or unsubstituted, 6- to 10-membered aryl). In certain embodiments, R⁸ is substituted benzyl. In certain embodiments, R⁸ is unsubstituted benzyl. In certain embodiments, R⁸ is substituted phenyl. In certain embodiments, R⁸ is unsubstituted phenyl. In certain embodiments, R⁸ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R⁸ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, the compound of Formula (IV') is of the formula:

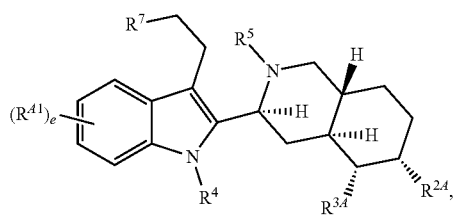

or a pharmaceutically acceptable salt, solvate, hydrate, polymorph, co-crystal, tautomer, stereoisomer, isotopically labeled derivative, or prodrug thereof.

In certain embodiments, the compound of Formula (IV') is of the formula:

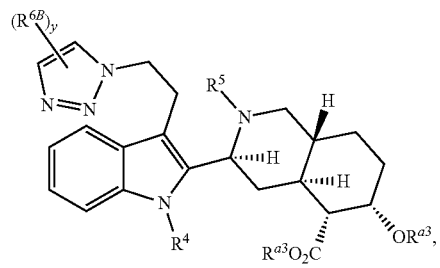

or a pharmaceutically acceptable salt, solvate, hydrate, polymorph, co-crystal, tautomer, stereoisomer, isotopically labeled derivative, or prodrug thereof.

In certain embodiments, the compound of Formula (IV') is of the formula:

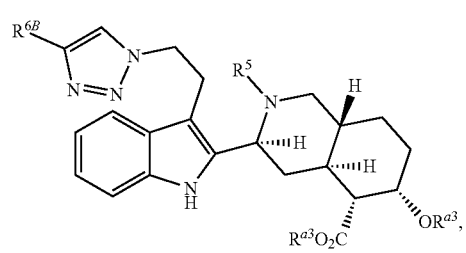

or a pharmaceutically acceptable salt, solvate, hydrate, polymorph, co-crystal, tautomer, stereoisomer, isotopically labeled derivative, or prodrug thereof.

In certain embodiments, the compound of Formula (IV') is of the formula:

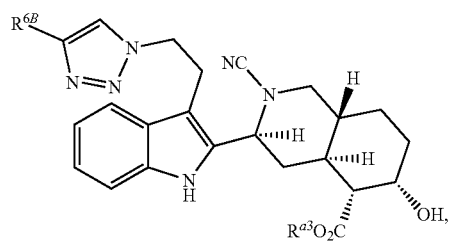

or a pharmaceutically acceptable salt, solvate, hydrate, polymorph, co-crystal, tautomer, stereoisomer, isotopically labeled derivative, or prodrug thereof.

In certain embodiments, exemplary compounds of Formulae (IV') and (IV) include, but are not limited to:

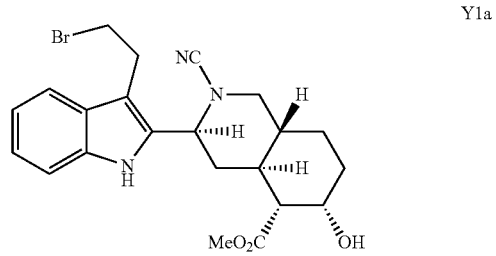

Y1a

-continued

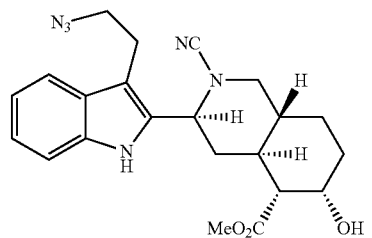
Y1b

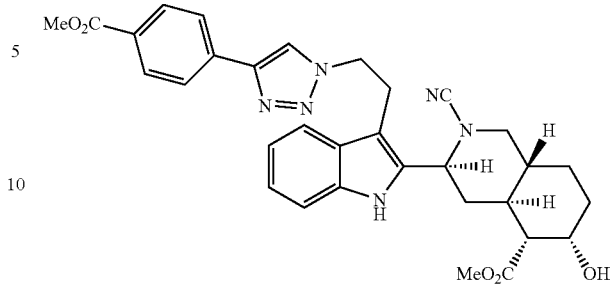
Y1g

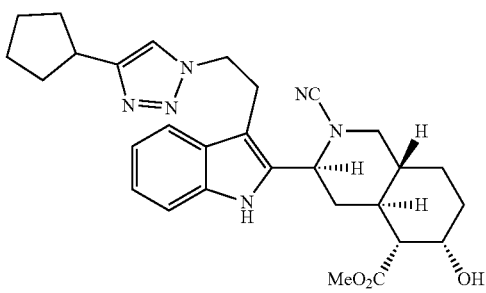
Y1c

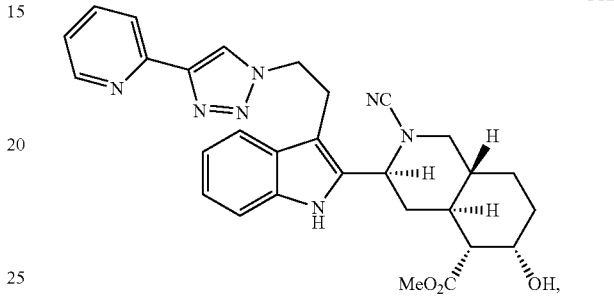
Y1h

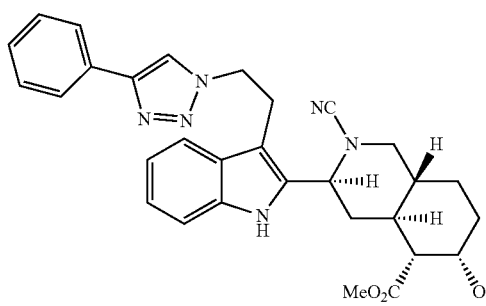
Y1d

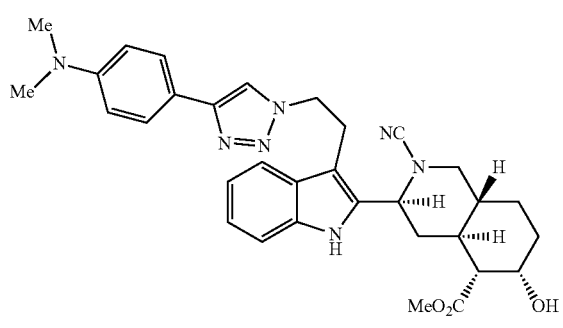
Y1e

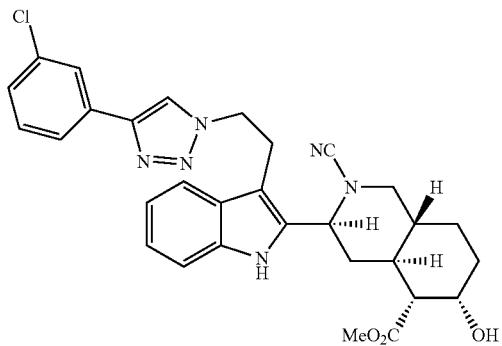
Y1f

Compounds of Formula (V-A) and Formula (V)

In one aspect, the present disclosure provides compounds of Formula (V-A):

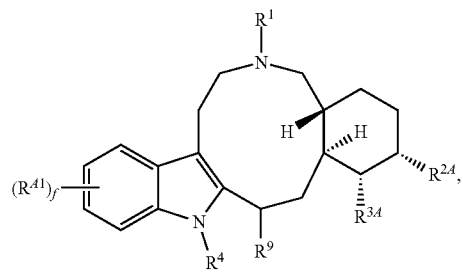

(V-A)

and pharmaceutically acceptable salts, solvates, hydrates, polymorphs, co-crystals, tautomers, stereoisomers, isotopically labeled derivatives, and prodrugs thereof, wherein:

$R^1$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$; and $R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

R⁴ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R⁹ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$;

each instance of R$^{A1}$ is independently hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of R$^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two R$^b$ are joined together with the intervening atoms to form substituted or unsubstituted heterocyclyl or substituted or unsubstituted heteroaryl; and f is 0, 1, 2, 3, or 4.

In one aspect, the present disclosure provides compounds of Formula (V):

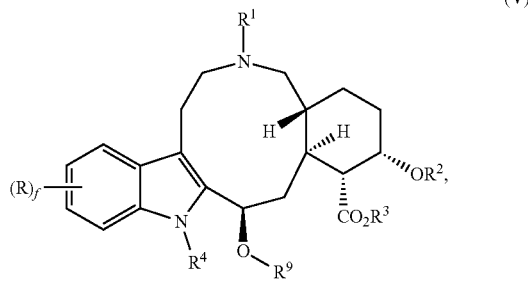

(V)

and pharmaceutically acceptable salts, solvates, hydrates, polymorphs, co-crystals, tautomers, stereoisomers, isotopically labeled derivatives, and prodrugs thereof, wherein:

R¹ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or —CN;

R² is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and R³ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R⁴ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R⁹ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of R is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl; and f is 1, 2, 3, or 4.

Formula (V-A) includes substituents R¹, R$^{2A}$, R$^{3A}$, R⁴, R⁹, and R$^{A1}$. Substituents R¹, R$^{2A}$, R$^{3A}$, and R$^{A1}$ are described in the Detailed Description for Formula (I-A) above. Substituent R⁴ is described in the Detailed Description for Formula (II′) above. Formula (V-A) includes zero or more instances of substituent R$^{A1}$. In certain embodiments, f is 0. In certain embodiments, f is 1. In certain embodiments, f is 2. In certain embodiments, f is 3. In certain embodiments, f is 4.

Formula (V-A) and Formula (V) include substituent R⁹. In certain embodiments, R⁹ is hydrogen. In certain embodiments, R⁹ is substituted or unsubstituted acyl. In certain embodiments, R⁹ is substituted or unsubstituted alkyl (e.g., substituted or unsubstituted C$_{1-6}$ alkyl). In certain embodiments, R⁹ is —OR$^a$, and R$^a$ is H, substituted or unsubstituted C$_{1-6}$ alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^9$ is —OH. In certain embodiments, $R^9$ is —OMe. In certain embodiments, $R^9$ is —OEt. In certain embodiments, $R^9$ is —O(iPr). In certain embodiments, $R^9$ is —O(Bu). In certain embodiments, $R^9$ is of formula

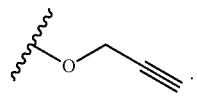 [SMILES: *OCC#C]

In certain embodiments, $R^9$ is of formula:

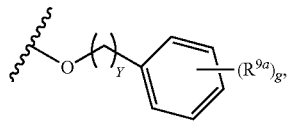

wherein: $R^{9a}$ is H, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^c$, —$N(R^d)_2$, or —$SR^c$; $R^c$ is H, substituted or unsubstituted $C_{1-6}$ alkyl, or an oxygen protecting group when attached to an oxygen atom, or a sulfur protecting group when attached to a sulfur atom; $R^d$ is H, substituted or unsubstituted $C_{1-6}$ alkyl, or a nitrogen protecting group; Y is 0, 1, 2, 3, 4, 5, or 6; and g is 0, 1, 2, 3, 4, or 5. In certain embodiments, Y is 0. In certain embodiments, Y is 1. In certain embodiments, Y is 2. In certain embodiments, Y is 3. In certain embodiments, Y is 4. In certain embodiments, Y is 5. In certain embodiments, Y is 6. In certain embodiments, $R^9$ includes zero or more instances of R. In certain embodiments, g is 0. In certain embodiments, g is 1. In certain embodiments, g is 2. In certain embodiments, g is 3. In certain embodiments, g is 4. In certain embodiments, g is 5. In certain embodiments, $R^{9a}$ is H. In certain embodiments, $R^{9a}$ is halogen (e.g., F, Cl, Br, or I). In certain embodiments, $R^{9a}$ is F. In certain embodiments, $R^{9a}$ is Cl. In certain embodiments, $R^{9a}$ is Br. In certain embodiments, $R^{9a}$ is I. In certain embodiments, $R^{9a}$ is substituted or unsubstituted acyl (e.g., —C(=O)Me). In certain embodiments, $R^{9a}$ is substituted or unsubstituted alkyl (e.g., substituted or unsubstituted $C_{1-6}$ alkyl). In certain embodiments, $R^{9a}$ is substituted or unsubstituted alkenyl (e.g., substituted or unsubstituted $C_{2-6}$ alkenyl). In certain embodiments, $R^{9a}$ is substituted or unsubstituted alkynyl (e.g., substituted or unsubstituted $C_{2-6}$ alkynyl). In certain embodiments, $R^{9a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{9a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{9a}$ is substituted or unsubstituted aryl (e.g., substituted or unsubstituted, 6- to 10-membered aryl). In certain embodiments, $R^{9a}$ is benzyl. In certain embodiments, $R^{9a}$ is substituted or unsubstituted phenyl. In certain embodiments, $R^{9a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{9a}$ is —ORC (e.g., —OMe). In certain embodiments, $R^{9a}$ is —OMe. In certain embodiments, $R^{9a}$ is —$N(R^d)_2$ (e.g., —$NMe_2$). In certain embodiments, $R^{9a}$ is —$SR^c$ (e.g., —SMe). In certain embodiments, $R^9$ is of formula:

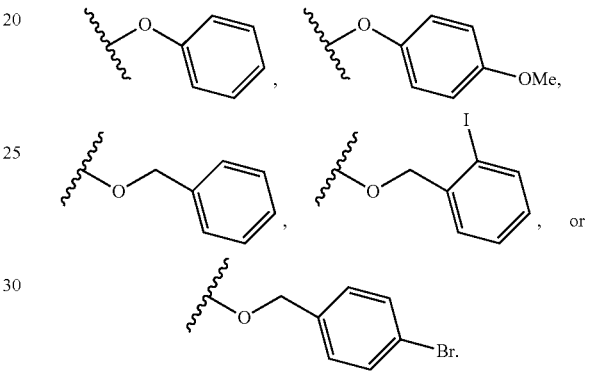

In certain embodiments, $R^9$ is substituted or unsubstituted alkenyl (e.g., substituted or unsubstituted $C_{2-6}$ alkenyl). In certain embodiments, $R^9$ is substituted or unsubstituted alkynyl (e.g., substituted or unsubstituted $C_{2-6}$ alkynyl). In certain embodiments, $R^9$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^9$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur).

In certain embodiments, $R^9$ is substituted or unsubstituted aryl (e.g., substituted or unsubstituted, 6- to 10-membered aryl). In certain embodiments, $R^9$ is benzyl. In certain embodiments, $R^9$ is substituted or unsubstituted phenyl. In certain embodiments, $R^9$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^9$ is —$OR^a$ (e.g., —OH or —OMe). In certain embodiments, $R^9$ is —$N(R^b)_2$ or —$SR^a$.

In certain embodiments, the compound of Formula (V-A) is of the formula:

107

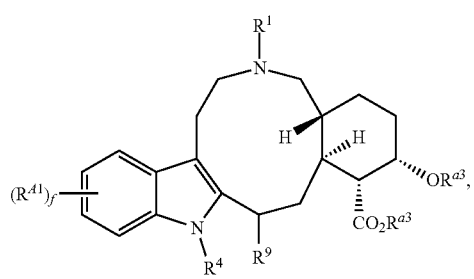

or a pharmaceutically acceptable salt, solvate, hydrate, polymorph, co-crystal, tautomer, stereoisomer, isotopically labeled derivative, or prodrug thereof.

In certain embodiments, the compound of Formula (V-A) is of the formula:

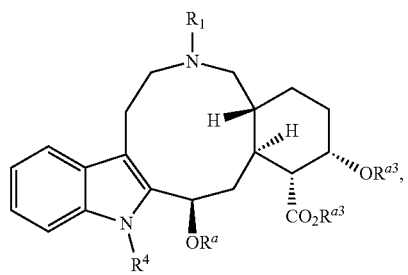

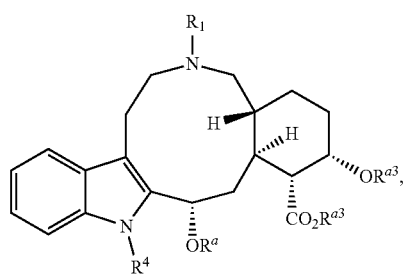

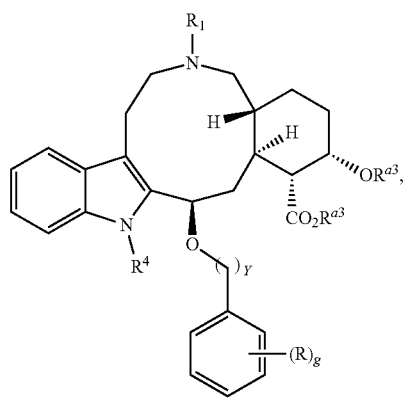

108

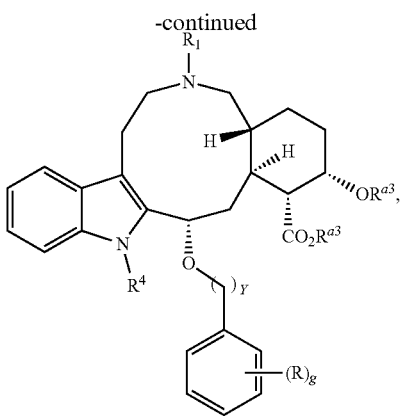

or a pharmaceutically acceptable salt, solvate, hydrate, polymorph, co-crystal, tautomer, stereoisomer, isotopically labeled derivative, or prodrug thereof.

In certain embodiments, the compound of Formula (V-A) is of the formula:

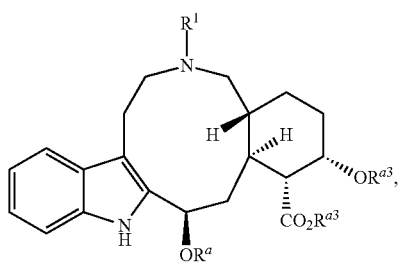

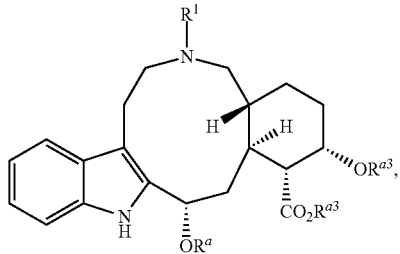

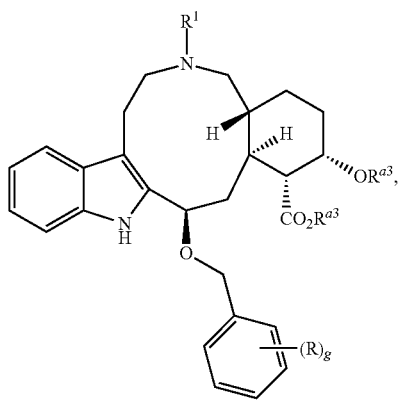

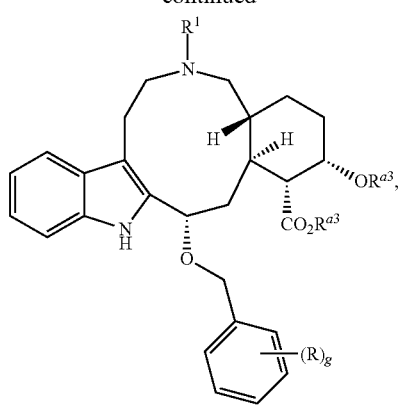
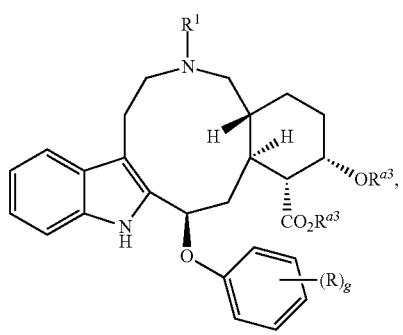
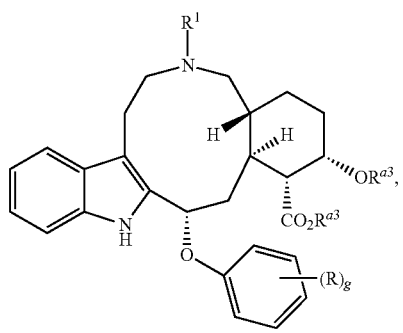
or a pharmaceutically acceptable salt, solvate, hydrate, polymorph, co-crystal, tautomer, stereoisomer, isotopically labeled derivative, or prodrug thereof.
In certain embodiments, the compound of Formula (V-A) is of the formula:
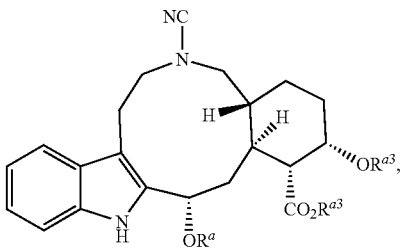
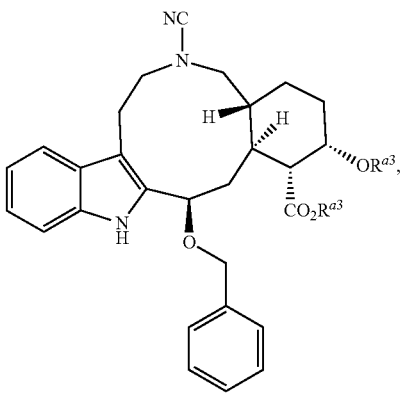
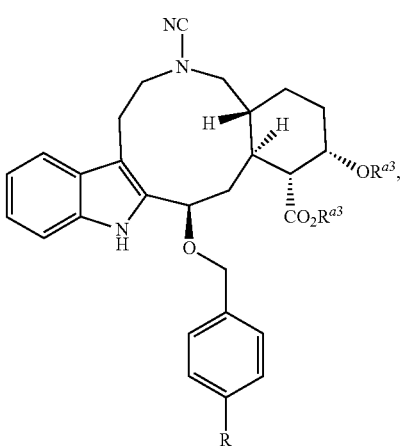
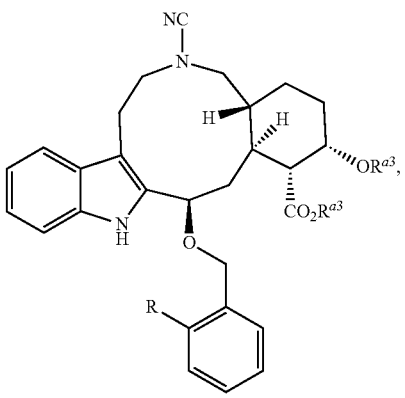

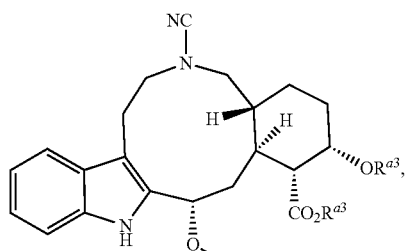
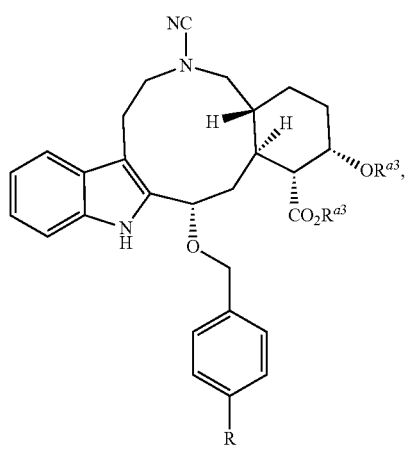
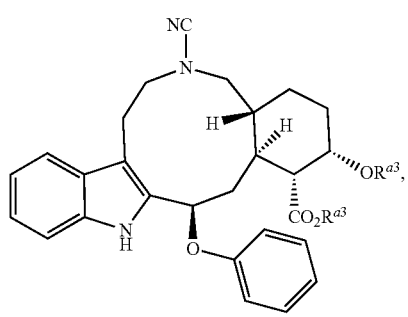
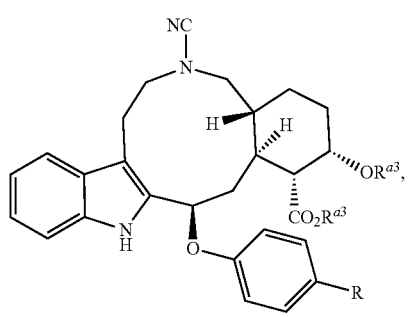
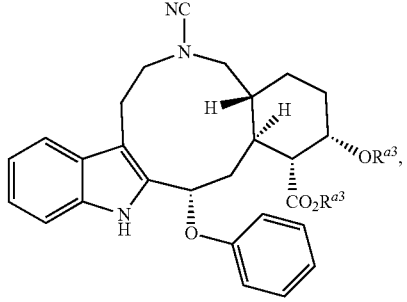
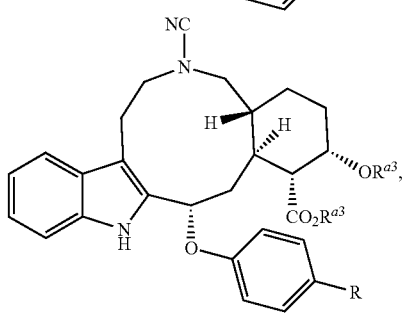
or a pharmaceutically acceptable salt, solvate, hydrate, polymorph, co-crystal, tautomer, stereoisomer, isotopically labeled derivative, or prodrug thereof.
In certain embodiments, the compound of Formula (V-A) is of the formula:
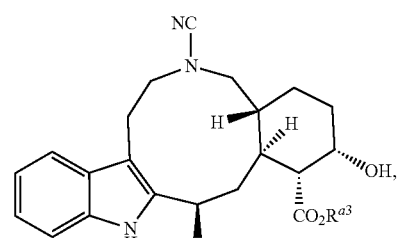
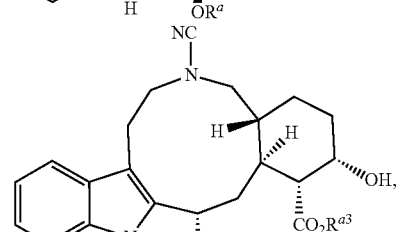
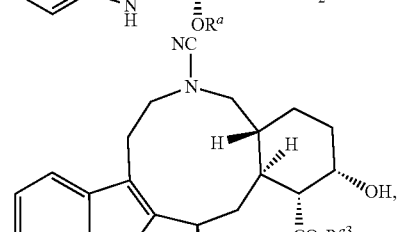
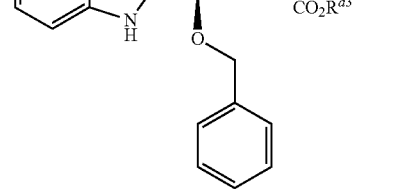

-continued
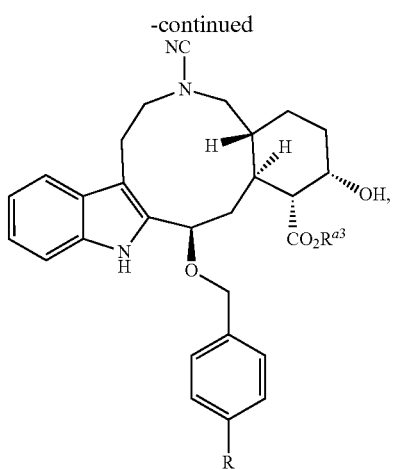
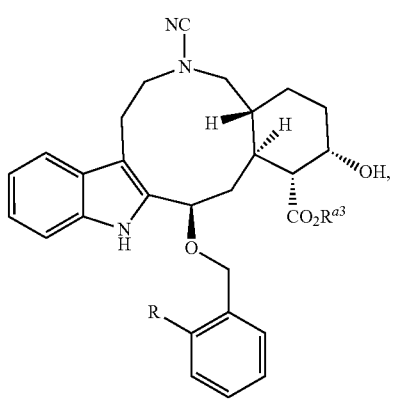
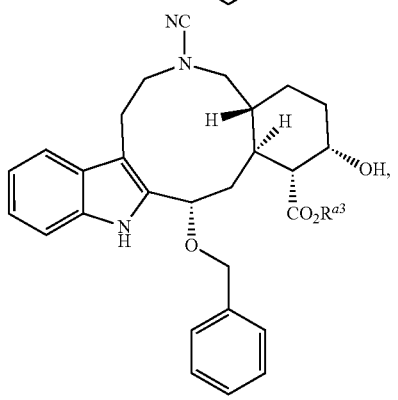
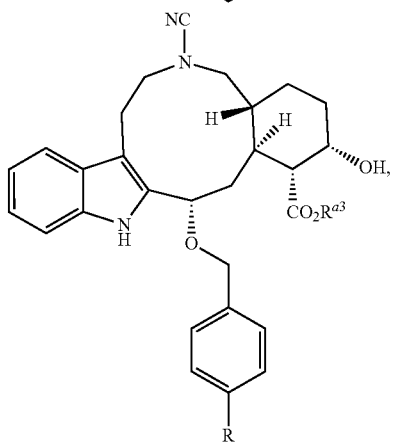
-continued
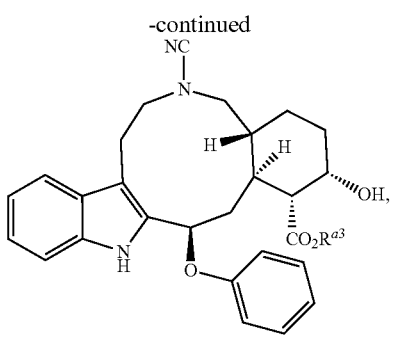
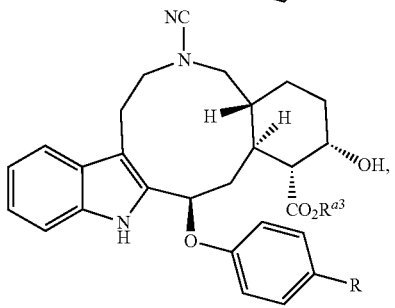
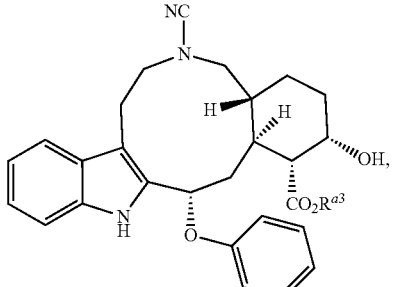
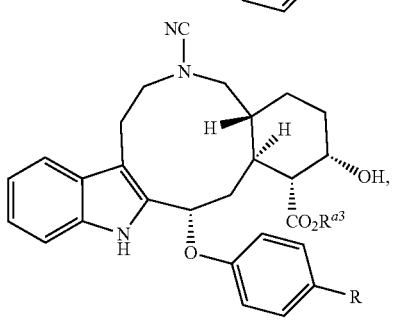
or a pharmaceutically acceptable salt, solvate, hydrate, polymorph, co-crystal, tautomer, stereoisomer, isotopically labeled derivative, or prodrug thereof.
In certain embodiments, exemplary compounds of Formulae (V-A) and (V) include, but are not limited to:
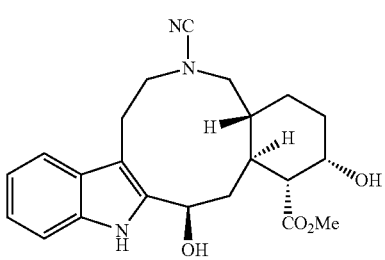
Y6a Y6b
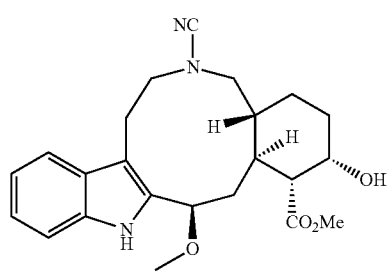
Y6c
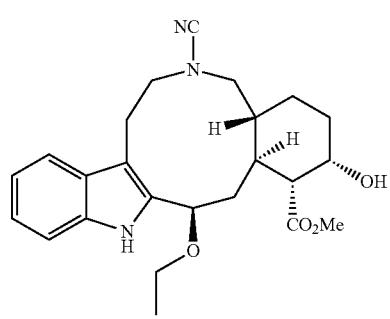
Y6d
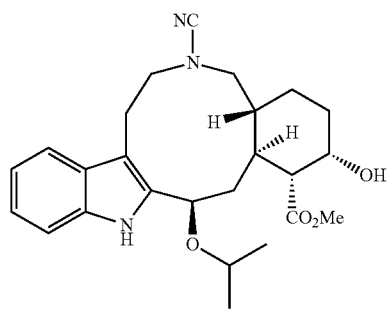
Y6e
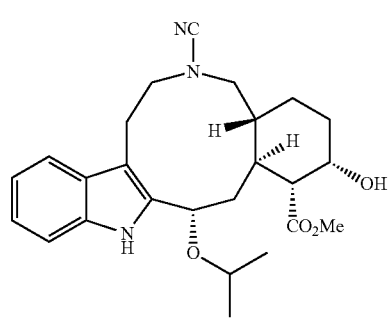
Y6f
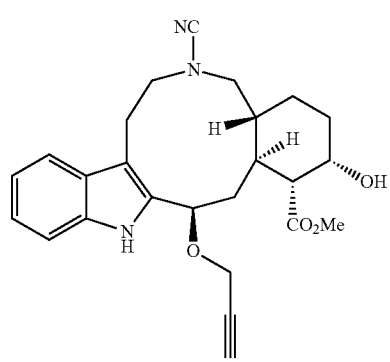
Y6g
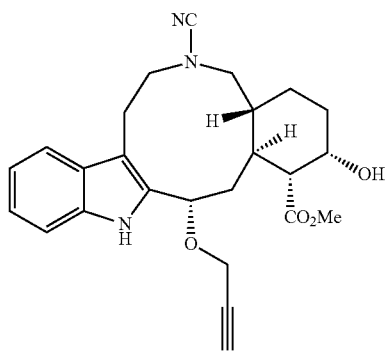
Y6h
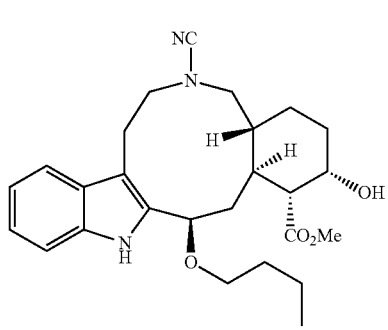
Y6i
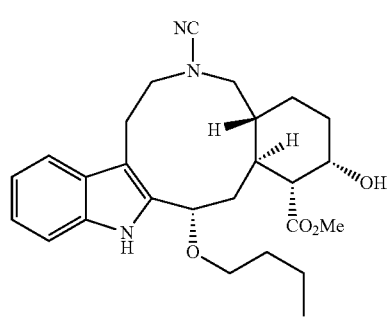
Y6j
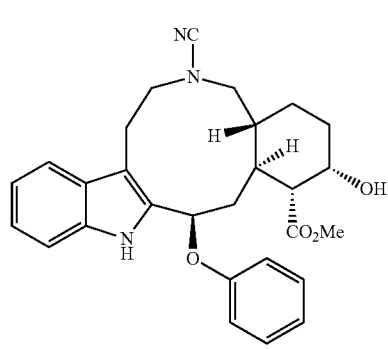
Y6k
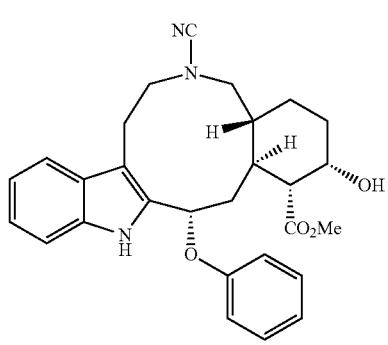

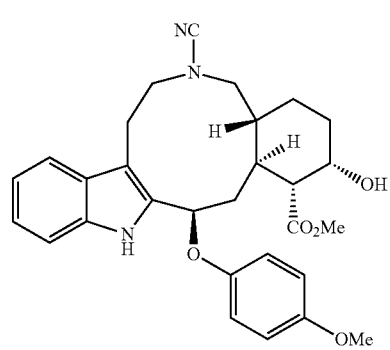
Y6l
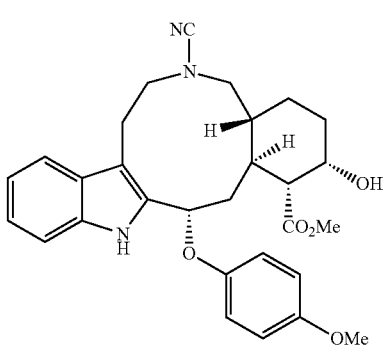
Y6m
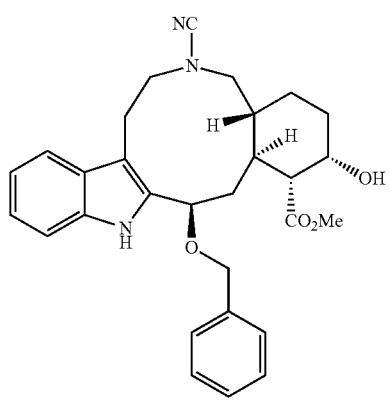
Y6n
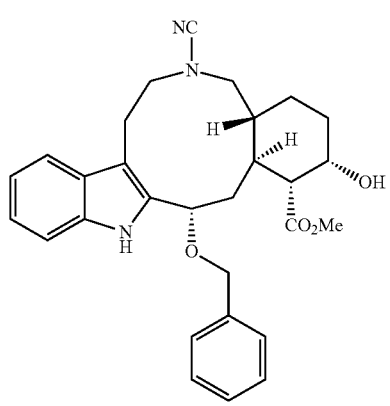
Y6o
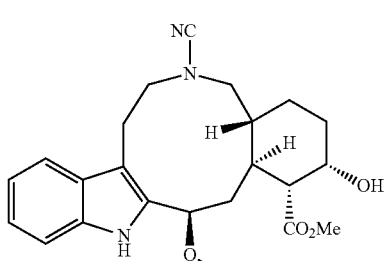
Y6p
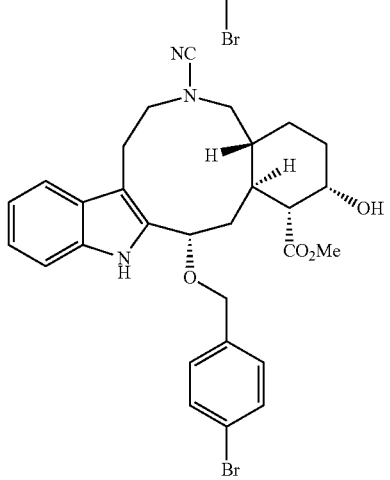
Y6q
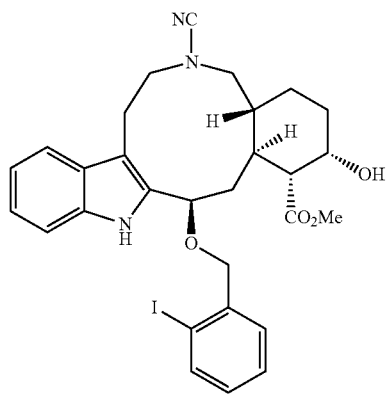
Y6r
Y6s -continued

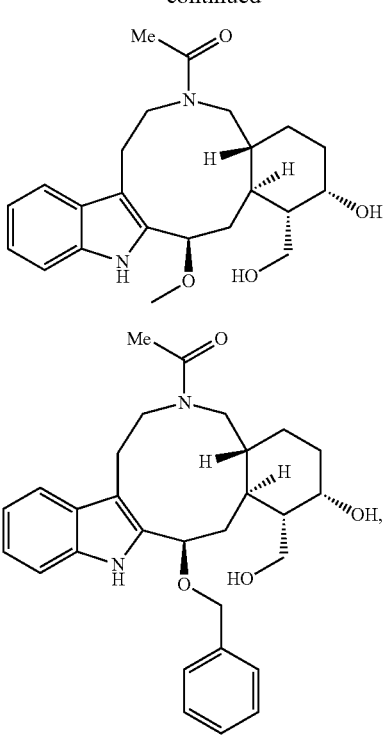

or a pharmaceutically acceptable salt, solvate, hydrate, polymorph, co-crystal, tautomer, stereoisomer, isotopically labeled derivative, or prodrug thereof.

Methods of Preparation

The present invention further provides methods of preparing compounds of the present invention, e.g., compounds of Formulae (I-A), (II'), (III-A), (IV'), and (V-A), and salts, solvates, hydrates, polymorphs, co-crystals, tautomers, stereoisomers, isotopically labeled derivatives, and prodrugs thereof, or mixtures thereof, as described herein. The compounds of Formulae (I-A), (II'), (III-A), (IV'), (V-A) are derived from or based on yohimbine. Exemplary methods of preparing the compounds are depicted in FIGS. 1-4 and 6-10.

For example, in one aspect, provided is a method of preparing a compound of Formula (I-A):

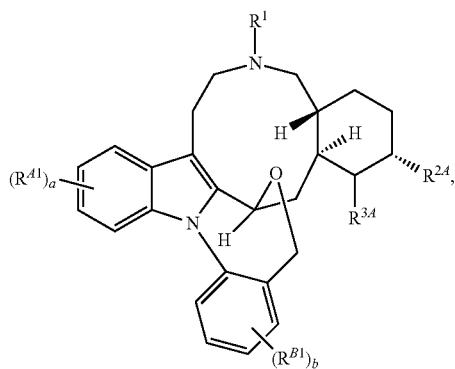

or a pharmaceutically acceptable salt thereof, wherein:

$R^1$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

$R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$; and each instance of $R^{A1}$ is independently hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —$OR^a$, —$N(R^b)_2$, or —$SR^a$;

each instance of $R^{B1}$ is independently hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —$OR^a$, —$N(R^b)_2$, or —$SR^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl;

a is 0, 1, 2, 3, or 4; and b is 0, 1, 2, 3, or 4;

the method comprising adding to yohimbine, cyanogen bromide and an alcohol of formula $R^Y$—OH, wherein $R^Y$ is hydrogen, substituted or unsubstituted alkyl, substituted or unsubstituted aryl, or substituted or unsubstituted heteroaryl; to provide a compound of Formula V-B),

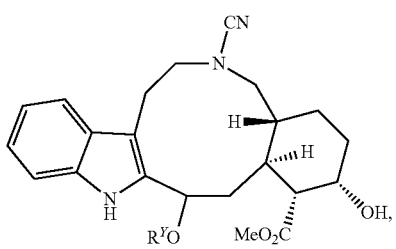

(V-B)

or a pharmaceutically acceptable salt thereof;
followed by modification of the compound of Formula (V-B) to provide a compound of formula (V-A):

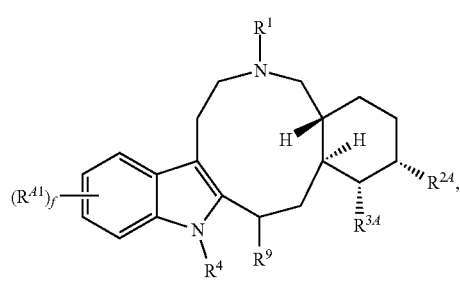

(V-A)

or a pharmaceutically acceptable salt thereof, wherein:
$R^1$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$; and $R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

$R^4$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^9$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

each instance of $R^{A1}$ is independently hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —$OR^a$, —$N(R^b)_2$, or —$SR^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl; R; and f is 0, 1, 2, 3, or 4;
followed by copper iodide-catalyzed intramolecular C—N coupling,
to provide a compound of Formula (I-B),

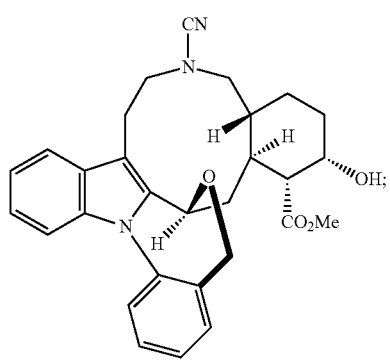

(I-B)

followed by subsequent modification to provide a compound of Formula (I-A), or a pharmaceutically acceptable salt thereof.

In certain embodiments, the modification of the compound of Formula (V-B) to provide a compound of Formula (V-A) comprises modification of the CN group in Formula (V-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group as the $R^1$ substituent in Formula (V-A). In certain embodiments, the modification of the compound of Formula (V-B) to provide a compound of Formula (V-A) comprises modification of the —OH group in Formula (V-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$ as the R$^{2A}$ substituent in Formula (V-A). In certain embodiments, the modification of the compound of Formula (V-B) to provide a compound of Formula (V-A) comprises reduction of the —CO$_2$Me ester group in Formula (V-B) to form

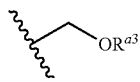

as the R$^{3A}$ substituent in Formula (V-A). In certain embodiments, the modification of the compound of Formula (V-B) to provide a compound of Formula (V-A) comprises conversion of the —CO$_2$Me ester group in Formula (V-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$ as the R$^{3A}$ substituent in Formula (V-A).

In certain embodiments, the modification of the compound of Formula (V-B) to provide a compound of Formula (V-A) comprises modification of the O(R$^Y$) group in Formula (V-B) into a hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$ as the R$^9$ substituent in Formula (V-A).

In certain embodiments, the copper iodide-catalyzed intramolecular C—N coupling to provide a compound of Formula (I-B) is catalyzed by copper (I) iodide.

In certain embodiments, a compound of Formula (V-B):

(V-B)

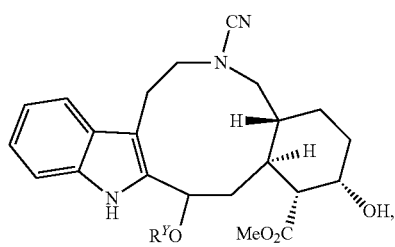

or a pharmaceutically acceptable salt thereof, is a compound of Formula (V-B-i):

(V-B-i)

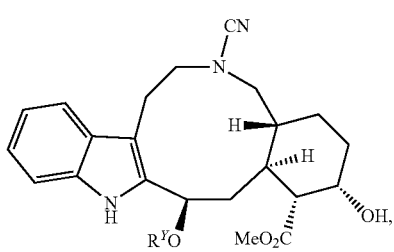

or a compound of Formula (V-B-ii):

(V-B-ii)

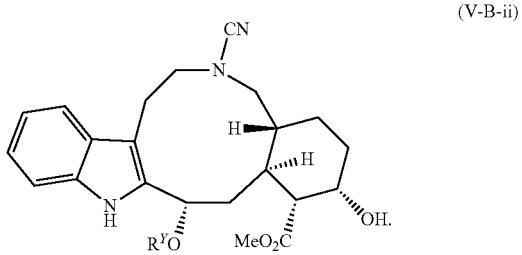

In certain embodiments, a compound of Formula (V-B) is modified to provide a compound of Formula (V-A):

(V-A)

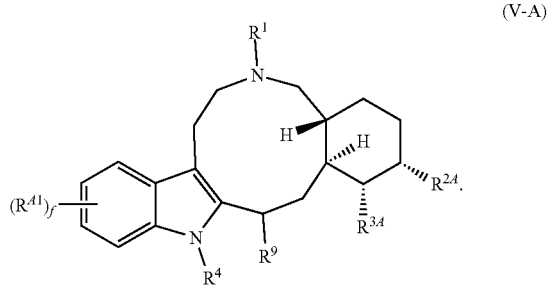

In certain embodiments, the methyl ester substituent on the cyclohexyl ring of a compound of Formula (V-B) is reduced to an alcohol substituent to provide a compound of Formula (V-A), wherein R$^{3A}$ is

and R$^{a3}$ is hydrogen or substituted or unsubstituted C$_{1-6}$ alkyl.

In certain embodiments, a compound of Formula (I-A):

(I-A)

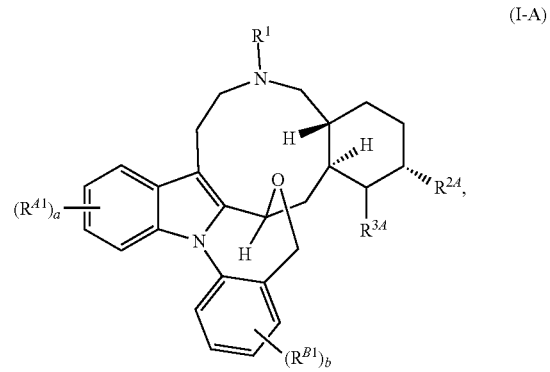

or a pharmaceutically acceptable salt thereof, is prepared by copper iodide-catalyzed intramolecular C—N coupling of a compound of Formula (V-A):

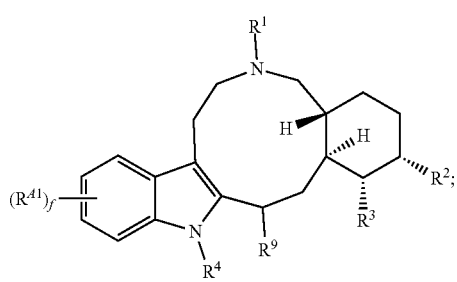
(V-A)

to provide a compound of Formula (I-B):

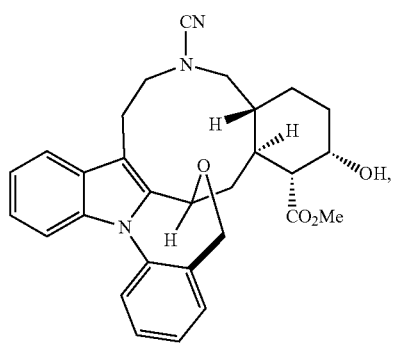
(I-B)

followed by subsequent modification to provide a compound of Formula (I-A), or a pharmaceutically acceptable salt thereof.

In certain embodiments, the copper iodide-catalyzed intramolecular C—N coupling of a compound of Formula (V-A) to provide a compound of Formula (I-B) is catalyzed by copper (I) iodide. In certain embodiments, copper iodide-catalyzed intramolecular C—N coupling of a compound of Formula (V-A) is performed using microwave irradiation. In certain embodiments, copper (I) iodide-catalyzed intramolecular C—N coupling of a compound of Formula (V-A) is performed using microwave irradiation.

In certain embodiments, the modification of the compound of Formula (I-B) to provide a compound of Formula (I-A) comprises modification of the CN group in Formula (I-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group as the $R^1$ substituent in Formula (I-A).

In certain embodiments, the modification of the compound of Formula (I-B) to provide a compound of Formula (I-A) comprises modification of the —OH group in Formula (I-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$ as the $R^{2A}$ substituent in Formula (I-A). In certain embodiments, the modification of the compound of Formula (I-B) to provide a compound of Formula (I-A) comprises reduction of the —$CO_2Me$ ester group in Formula (I-B) to form

as the $R^{3A}$ substituent in Formula (I-A). In certain embodiments, the modification of the compound of Formula (I-B) to provide a compound of Formula (I-A) comprises conversion of the —$CO_2Me$ ester group in Formula (I-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$ as the $R^{3A}$ substituent in Formula (I-A).

In certain embodiments, a compound of Formula (I-B) is a compound of Formula (I-B-i):

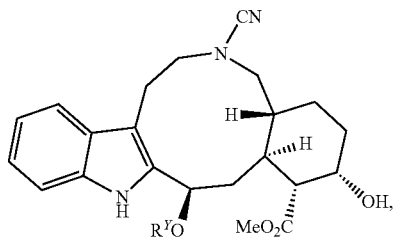

or a compound of Formula (I-B-i)

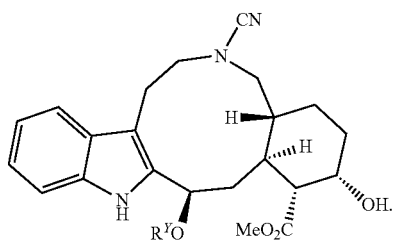

In another aspect, provided is a method of preparing a compound of Formula (II'):

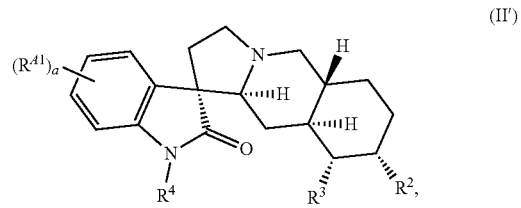
(II')

or a pharmaceutically acceptable salt thereof, wherein:

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

$R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$;

R$^4$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

each instance of R$^{41}$ is independently hydrogen, halogen, —CN, —SCN, —N$_{O2}$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of R$^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two R$^b$ are joined together with the intervening atoms to form substituted or unsubstituted heterocyclyl or substituted or unsubstituted heteroaryl; and c is 0, 1, 2, 3, or 4;

the method comprising adding to yohimbine, a chlorinating agent followed by treatment with a base and then an acid to provide a compound of Formula (II-A):

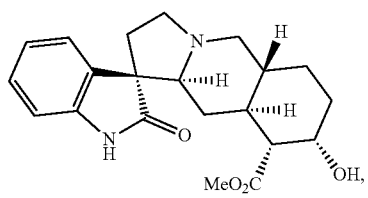
(II-A)

or a pharmaceutically acceptable salt thereof; and adding an alkyl halide to provide a compound of Formula (II'), or a pharmaceutically acceptable salt thereof.

In certain embodiments, the chlorinating agent is N-chlorosuccinimide (NCS). In certain embodiments, the base does not affect the —CO$_2$Me ester group or the c proton in Formula (II'). In certain embodiments, the base is sodium methoxide (NaOMe). In certain embodiments, the base is sodium hydride or sodium tert-butoxide. In certain embodiments, the acid is trifluoroacetic acid (TFA).

In another aspect, provided is a method of preparing a compound of Formula (III-B):

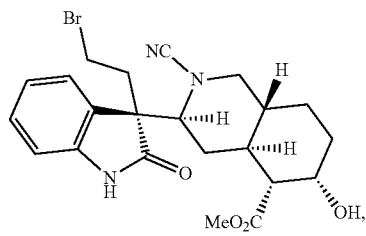
(III-B)

or a pharmaceutically acceptable salt thereof; the method comprising adding to a compound of Formula (II-A) cyanogen bromide and using microwave irradiation to provide a compound of Formula (III-B), or a pharmaceutically acceptable salt thereof.

In another aspect, provided is a method of preparing a compound of Formula (III-A):

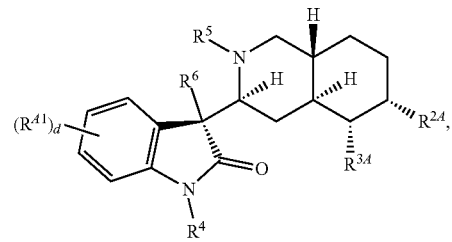
(III-A)

or a pharmaceutically acceptable salt thereof, wherein:

R$^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$; and R$^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$;

R$^4$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^5$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

R$^6$ is hydrogen, halogen, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted acyl, substituted or unsubstituted sulfonyl, —OR$^a$, —N(R$^b$)$_2$, or —SR$^a$;

each instance of $R^{A1}$ is independently hydrogen, halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two R$^b$ are joined together with the intervening atoms to form substituted or unsubstituted heterocyclyl or substituted or unsubstituted heteroaryl; and d is 0, 1, 2, 3, or 4;

the method comprising adding to a compound of Formula (II-A), cyanogen bromide and sodium azide to provide a compound of Formula (III-D),

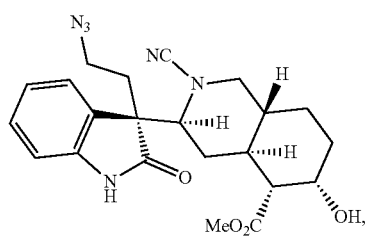

or a pharmaceutically acceptable salt thereof;

followed by a copper-catalyzed Click reaction with an alkyne of formula

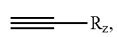

wherein

R$^z$ is substituted or unsubstituted alkyl, substituted or unsubstituted carbocyclyl, substituted or unsubstituted heterocyclyl, substituted or unsubstituted aryl, or substituted or unsubstituted heteroaryl; to provide a compound of Formula (III-C),

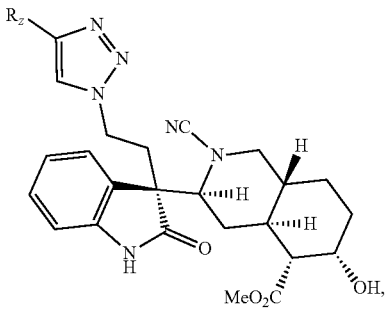

or a pharmaceutically acceptable salt thereof;

followed by modification of a compound of Formula (III-C) to provide a compound of Formula (III-A), or a pharmaceutically acceptable salt thereof.

In certain embodiments, the modification of the compound of Formula (III-C) to provide a compound of Formula (III-A) comprises modification of the CN group in Formula (III-C) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group as the R$^5$ substituent in Formula (III-A).

In certain embodiments, the modification of the compound of Formula (III-C) to provide a compound of Formula (III-A) comprises modification of the —OH group in Formula (III-C) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$ as the R$^{2A}$ substituent in Formula (III-A). In certain embodiments, the modification of the compound of Formula (I-B) to provide a compound of Formula (I-A) comprises reduction of the —CO$_2$Me ester group in Formula (III-C) to form

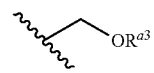

as the R$^{3A}$ substituent in Formula (I-A). In certain embodiments, the modification of the compound of Formula (I-B) to provide a compound of Formula (III-A) comprises conversion of the —CO$_2$Me ester group in Formula (I-B) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^b$)$_2$, or —SR$^a$ as the R$^{3A}$ substituent in Formula (III-A). In certain embodiments, the Click reaction is catalyzed by copper (I) iodide.

In another aspect, provided is a method of preparing a compound of Formula (IV-A):

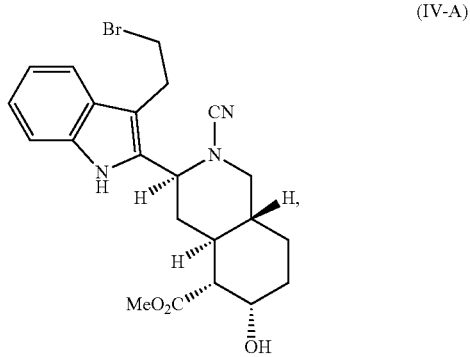

(IV-A)

or a pharmaceutically acceptable salt thereof, the method comprising adding to yohimbine, cyanogen bromide and using microwave irradiation to provide a compound of Formula (IV-A), or a pharmaceutically acceptable salt thereof.

In one aspect, provided is a method of preparing a compound of Formula (IV')

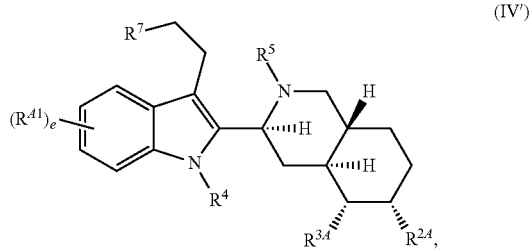

(IV')

or a pharmaceutically acceptable salt thereof, wherein:

$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$; and $R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

$R^4$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^7$ is hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted acyl, substituted or unsubstituted sulfonyl, —$OR^a$, —$N(R^b)_2$, or —$SR^a$;

$R^5$ is hydrogen, —CN, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

each instance of $R^{A1}$ is independently hydrogen, halogen, —CN, —SCN, —$NO_2$, —$N_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —$OR^a$, —$N(R^b)_2$, or —$SR^a$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom;

each instance of $R^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two $R^b$ are joined together with the intervening atoms to form substituted or unsubstituted heterocyclyl or substituted or unsubstituted heteroaryl; and e is 0, 1, 2, 3, or 4;

the method comprising adding to a compound of Formula (IV-A) sodium azide to provide a compound of Formula (IV-D),

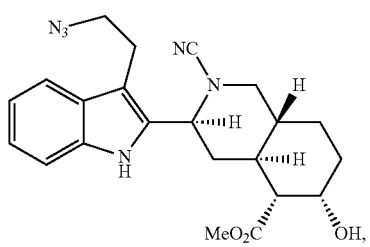

or a pharmaceutically acceptable salt thereof;

followed by a copper-catalyzed Click reaction with an alkyne of formula ≡—$R^z$, wherein $R^z$ is substituted or unsubstituted alkyl, substituted or unsubstituted carbocyclyl, substituted or unsubstituted heterocyclyl, substituted or unsubstituted aryl, or substituted or unsubstituted heteroaryl; to provide a compound of Formula (IV-C),

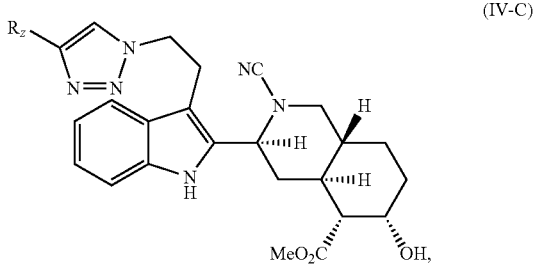
(IV-C)

or a pharmaceutically acceptable salt thereof;

followed by modification of a compound of Formula (IV-C) to provide a compound of Formula (IV'), or a pharmaceutically acceptable salt thereof.

In certain embodiments, the modification of the compound of Formula (IV-C) to provide a compound of Formula (IV') comprises modification of the CN group in Formula (III-C) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group as the $R^5$ substituent in Formula (IV').

In certain embodiments, the modification of the compound of Formula (IV-C) to provide a compound of Formula (IV') comprises modification of the —OH group in Formula (IV-C) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$ as the $R^{2A}$ substituent in Formula (IV'). In certain embodiments, the modification of the compound of Formula (IV-C) to provide a compound of Formula (IV') comprises reduction of the —$CO_2Me$ ester group in Formula (IV-C) to form

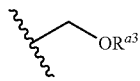

as the $R^{3A}$ substituent in Formula (IV'). In certain embodiments, the modification of the compound of Formula (IV-C) to provide a compound of Formula (IV') comprises conversion of the —$CO_2Me$ ester group in Formula (IV-C) into hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$ as the $R^{3A}$ substituent in Formula (IV'). In certain embodiments, the Click reaction is catalyzed by copper (I) iodide.

Pharmaceutical Compositions, Kits, and Administration

The present disclosure provides pharmaceutical compositions comprising a compound of Formulae (I-A), (II'), (III-A), (IV'), and (V-A), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical composition described herein comprises a compound of Formulae (I-A), (II'), (III-A), (IV'), and (V-A), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof.

In certain embodiments, the subject being administered a compound or composition described herein is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is present in vitro. In certain embodiments, the cell being contacted with a compound or composition described herein is present in vivo.

An effective amount of a compound described herein may vary from about 0.001 mg/kg to about 1000 mg/kg in one or more dose administrations for one or several days (depending on the mode of administration), wherein mg/kg is mg of compound to kg weight of the subject. In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste); gelatin; sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in inhibiting the activity of a protein kinase (e.g., SIK) in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which are different from the compound or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-musculoskeletal disease agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-musculoskeletal disease agent. In certain embodiments, the additional pharmaceutical agent is an anti-cancer agent. In certain embodiments, the additional pharmaceutical agent is an anti-viral agent. In certain embodiments, the additional pharmaceutical agent is an binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, cancers, inflammatory diseases, and infectious diseases) in a subject in need thereof. In certain embodiments, the kits are useful for preventing a disease (e.g., proliferative disease, cancers, inflammatory diseases, and infectious diseases) in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, cancers, inflammatory diseases, and infectious diseases) in a subject in need thereof. In certain embodiments, the kits and instructions provide for preventing a disease (e.g., proliferative disease, cancers, inflammatory diseases, and infectious diseases) in a subject in need thereof. A kit described herein may include one or more additional pharmaceutical agents described herein as a separate composition.

Methods of Treatment and Uses

The present disclosure provides methods for the treatment of a wide range of diseases, such as proliferative diseases, inflammatory diseases, autoimmune diseases, cancers, and infectious diseases in a subject in need thereof.

Another aspect of the present disclosure relates to methods of treating and/or preventing a disease in a subject in need thereof. In certain embodiments, the disease is a proliferative disease. In certain embodiments, the disease is cancer. In certain embodiments, the disease is a benign neoplasm. In certain embodiments, the disease is associated with pathological angiogenesis. In certain embodiments, the disease is an inflammatory disease. In certain embodiments, the disease is an autoimmune disease. In certain embodiments, the disease is an infectious disease. In certain embodiments, the disease is a bacterial infection. In certain embodiments, the disease is a plasmodial infection. In certain embodiments, the disease is malaria.

In certain embodiments, the methods of the disclosure include administering to a subject in need thereof an effective amount of a compound or pharmaceutical composition described herein. In certain embodiments, the subject being administered a compound or pharmaceutical composition described herein is a human. In certain embodiments, the subject being administered a compound or pharmaceutical composition described herein is a non-human animal.

In certain embodiments, the methods of the disclosure include administering to a subject in need thereof a therapeutically effective amount of a compound or pharmaceutical composition described herein. In certain embodiments, the methods of the disclosure include administering to a subject in need thereof a prophylactically effective amount of a compound or pharmaceutical composition described herein. In certain embodiments, the methods of the disclosure include contacting a cell with an effective amount of a compound or pharmaceutical composition described herein.

In another aspect, the present disclosure provides the compounds described herein for use in a method described herein, such as a method of treating a disease (e.g., proliferative disease, cancers, inflammatory diseases, and infectious diseases), or a method of preventing a disease (e.g., proliferative disease, cancers, inflammatory diseases, and infectious diseases).

In still another aspect, the present disclosure provides the pharmaceutical compositions described herein for use in a method described herein such as a method of treating a disease (e.g., proliferative disease, cancers, inflammatory diseases, autoimmune diseases, and infectious diseases), or a method of preventing a disease (e.g., proliferative disease, cancers, inflammatory diseases, autoimmune diseases, and infectious diseases). In another aspect, the present disclosure provides the pharmaceutical compositions described herein for use in treating a disease (e.g., proliferative disease, cancers, inflammatory diseases, autoimmune diseases, and infectious diseases). In another aspect, the present disclosure provides the pharmaceutical compositions described herein for use as a medicament in treating a disease. In certain embodiments, the disease is a proliferative disease, cancer, inflammatory disease, autoimmune disease, or an infectious disease.

In another aspect, the present disclosure provides the compounds described herein for use in a method described herein, such as a method of treating and/or preventing a disease (e.g., proliferative disease, cancers, inflammatory diseases, autoimmune diseases, and infectious diseases), the use comprising administering to the subject an effective amount of a compound of Formulae (I-A), (II'), (III-A), (IV'), and (V-A) described herein.

EXAMPLES

In order that the disclosure may be more fully understood, the following examples are set forth. The examples described in this application are offered to illustrate the compounds, pharmaceutical compositions, uses, and methods provided herein and are not to be construed in any way as limiting their scope.

All reactions were carried out under an atmosphere of argon unless otherwise specified. Reagents were purchased from commercial sources and used without further purification. Anhydrous solvents were transferred via syringe to flame-dried glassware, which was cooled under a stream of dry argon. All microwave reactions were carried out in sealed tubes in an Anton Paar Monowave 300 Microwave Synthesis Reactor. A constant power was applied to ensure reproducibility. Temperature control was automated via IR sensor and all indicated temperatures correspond to the maximal temperature reached during each experiment. Analytical thin layer chromatography (TLC) was performed using 250 μm Silica Gel 60 F254 pre-coated plates (EMD Chemicals Inc.). Flash column chromatography was performed using 230-400 Mesh 60A Silica Gel (Sorbent Technologies).

NMR experiments were recorded on Varian Unity spectrometer (400 MHz for $^1$H NMR; 100 MHz for $^{13}$C NMR). All spectra are presented using MestReNova 8.1 (Mnova) software and are displayed without the use of the signal suppression function. Spectra were obtained in the following solvents (reference peaks also included for $^1$H and $^{13}$C NMRs): CDCl$_3$ ($^1$H NMR: 7.26 ppm; $^{13}$C NMR: 77.23 ppm), d$_6$-DMSO ($^1$H NMR: 2.50 ppm; $^{13}$C NMR: 39.52 ppm). NMR samples where the respective solvent peaks were buried in the sample signals referenced TMS at 0.00 ppm for $^1$H NMR experiments. NMR experiments were performed at room temperature unless otherwise indicated. Chemical shift values (δ) are reported in parts per million (ppm) for all $^1$H NMR and $^{13}$C NMR spectra. $^1$H NMR multiplicities are reported as: s=singlet, d=doublet, t=triplet, q=quartet, p=pentet, m=multiplet, br=broad. Melting points were obtained on a Mel-Temp II capillary melting point apparatus and were uncorrected. High-resolution mass spectra were obtained from the Mass Spectrometry Facility in the Chemistry Department at the University of Florida.

Yohimbine and yohimbine-derived compounds were dissolved as 20 mM DMSO stock solutions in 96-well plates for primary biological screening. Each biological screen was performed in three independent experiments at concentrations of 1, 10, 100 or 200 μM. All hit compounds identified in primary screens were then evaluated in follow-up assays to validate/confirm the initial screening results.

Experimental Procedures

Example 1. Selected Compounds and Biological Activity

Selected compounds of Formulas (I-A), (II'), (III-A), (IV'), and (V-A) of the library of compounds derived from yohimbine were screened in several phenotypic and focused pathway-specific screens related to cancer and inflammation as well as pathogenic bacteria (FIG. 11). The screen aimed to identify selective antiproliferative agents that preferentially act on cancer cells with functional hypoxia-inducible factors (HIF) pathways. HIF transcription factor mediated signaling is known to be activated in cancer and linked to angiogenesis, cell growth, survival and metastasis. Isogenic HCT116 colorectal cancer cell lines were employed, including parental HCT116 and HCT116 double knockout cells lacking HIF-1α and HIF-2α,[36,37] and the library was screened for differential antiproliferative activity. Of the 70 compounds tested, Y7g stood out as the most selective antiproliferative agent upon dose-response analysis (FIG. 11B), suggesting that this compound could be a starting point for the development of selective and more potent HIF inhibitors. Chronic inflammation is a known factor in the etiology of colorectal cancer and, intriguingly, the same compound (Y7g) also showed the most selective anti-inflammatory activity in RAW264.7 macrophage cells based on the inhibition of nitric oxide (NO) production (FIG. 2C). Cell viability was almost unaffected in this cell type, further supporting the cancer cell selectivity of Y7g.

Figure 11A:
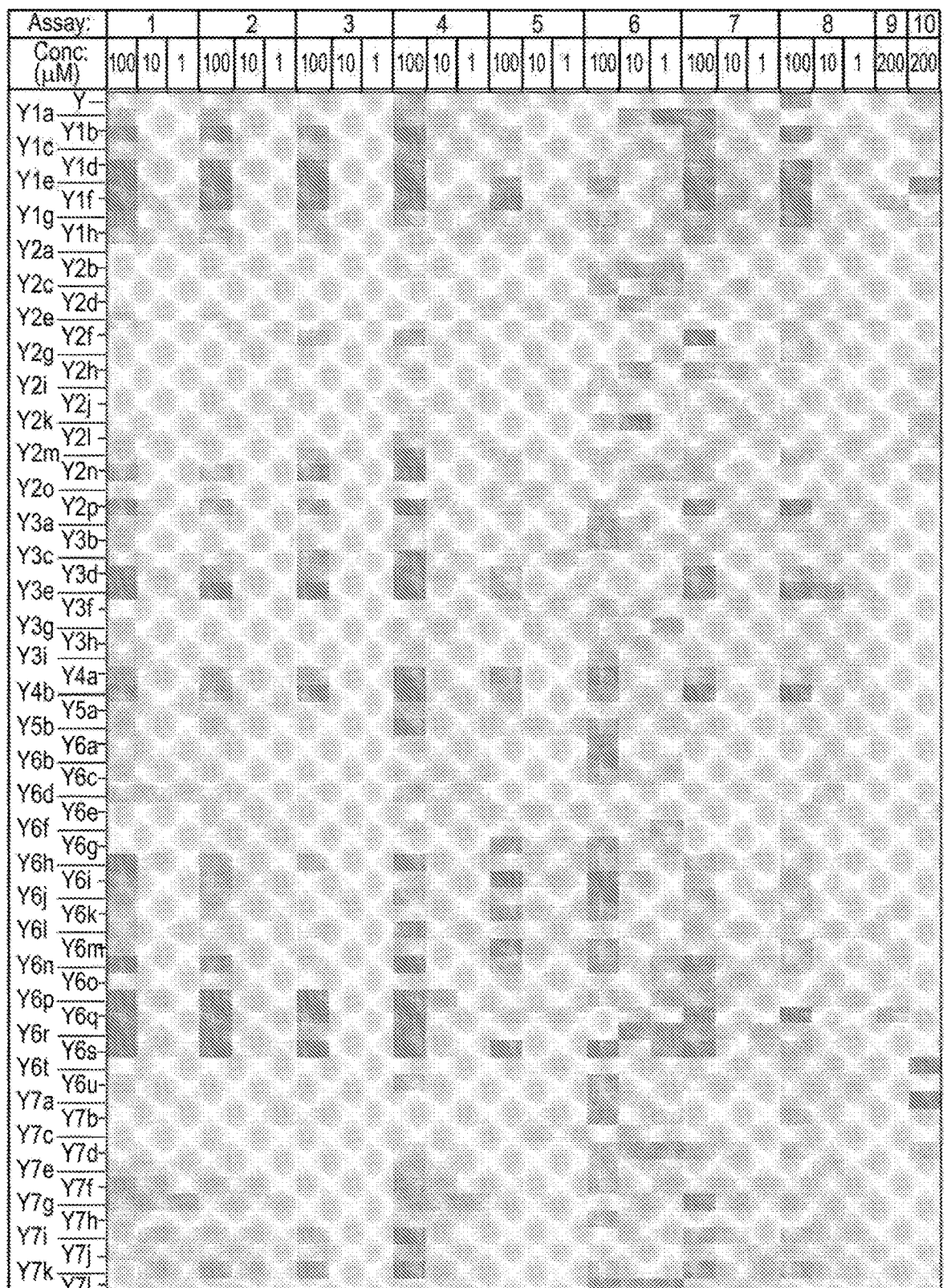
FIG. 11A. Heat map matrix summarizing primary biological screening results of the yohimbine ring distortion library (biological activity scale key: red=inhibition; yellow=no change; green=activation), including the structures of six validated hit compounds. Rows correspond to compounds tested. Columns correspond to primary biological activity screens (1-10) and concentrations tested (200, 100, 10 and 1 μM). 1) Parental HCT116 and 2) HCT116$^{HIF-1\alpha-/-HIF-2\alpha-/-}$ cell viability; 3) RAW264.7 cell viability; 4) RAW264.7 NO production; 5) LNCaP cell viability; 6) LNCaP cell ARE activity; 7) MDA-MB-231-ARE-luc cell viability; 8) MDA-MB-231-ARE-luc cell ARE activity; 9) *S. aureus* and 10) *A. baumannii* growth. B)-E) Validation experiments of hit compounds.
Figure 11B:
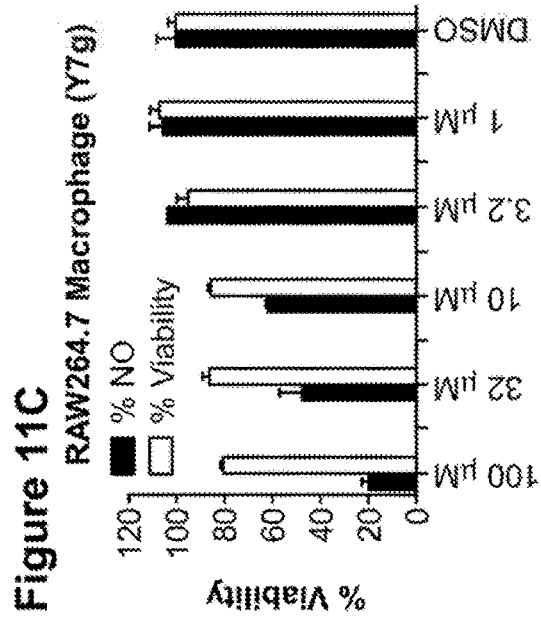
FIG. 11B. HIF-dependent anticancer activity. Cell viability of parental HCT16 and HCT116$^{HIF-1\alpha-/-HIF-2\alpha-/-}$ cells was determined after 48 h exposure using MTT assay (p-values: ≤0.01 **, ≤0.05 *; pairwise student t-test comparing cell viability between parental HCT116 and HCT116$^{HIF-1\alpha-/-HIF-2\alpha-/-}$ cells at a given concentration).
Figure 11C:
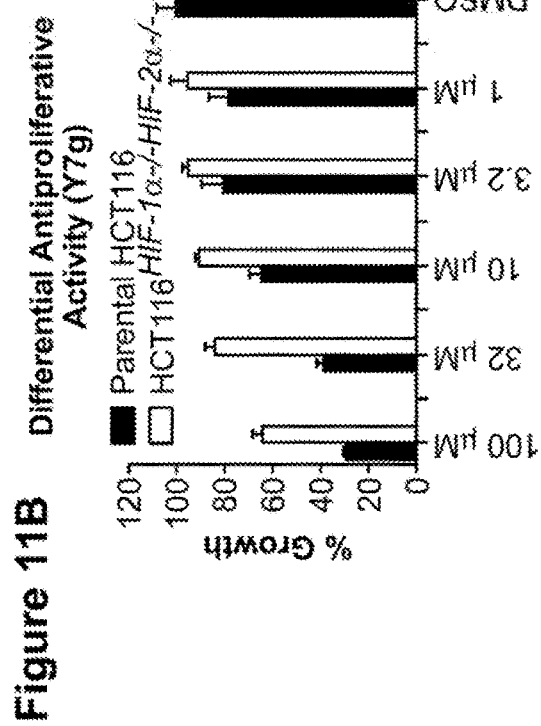
FIG. 11C. NO production and cell viability. Production of NO and cell viability of RAW264.7 cells were determined after 24 h exposure using Griess reagent and MTT assay, respectively (p-values: ≤0.01 **, ≤0.05 *; pairwise student t-test comparing relative NO production and viability of RAW264.7 cells at a given concentration).
Figure 11D:
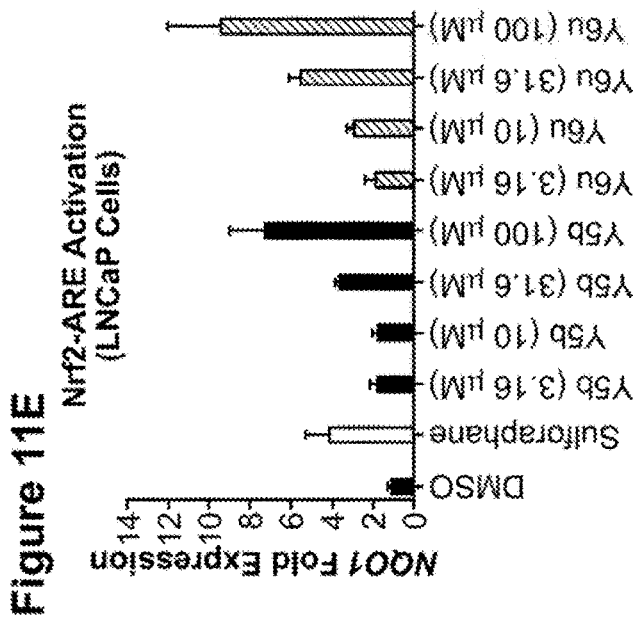
FIG. 11D. MDA-231-ARE-luc cell ARE activity and FIG. 11E. LNCaP cell ARE activity. ARE inhibition in MDA-MB-231-ARE-luc and ARE activation in LNCaP cells after 24 h exposure were validated by effects on endogenous NQO1 transcript levels measured by RT-qPCR. ACBT expression was used as an internal control for normalization. All validation data are presented relative to vehicle control (0.5% DMSO). Brusatol (125 nM) and sulforaphane (10 μM) served as positive controls for MDA-MB-231-ARE-luc ARE inhibition and LNCaP ARE activation assays, respectively.

The library compounds were then assessed for the potential to modulate the activity of another key transcription factor, NF-E2-related factor 2 (Nrf2), which acts on the antioxidant response element (ARE) in the promoter region upstream of antioxidant and phase II detoxification enzymes. Activators of the Nrf2-ARE pathway have potential as cancer preventive agents because of their ability to increase antioxidant status of the cell and protect from oxidative damage that could lead to cancer. Inhibitors in turn may increase the susceptibility of cancer cells to chemotherapeutic agents and overcome drug resistance since Nrf2 is commonly activated in cancer.[44] To screen for Nrf2 inhibitors, MDA-MB-231 breast cancer cells (a model for invasive, triple negative breast cancer) stably transfected with the ARE-luciferase reporter were used, where the promoter region is derived from the human NQO1 gene.[45] As a control, cell viability was monitored to ensure the identification of false positives in the reporter gene assay that are a result of concomitant reduced cell viability. Y3e, Y6q and Y1f were selected for validation by RT-qPCR, assessing the effects of the compounds on the transcription of the endogenous Nrf2 target gene, NQO1, in comparison with brusatol.[46] All three compounds downregulated NQO1 transcription (FIG. 11D).

Figure 11E:
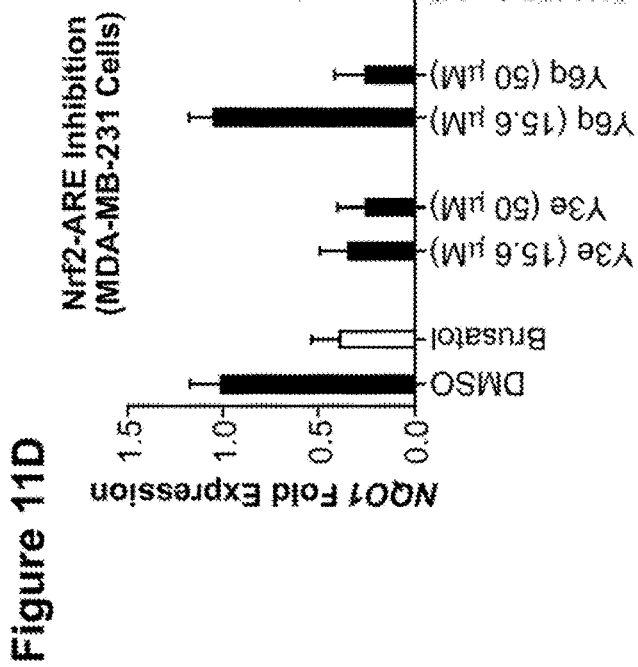
Figure 12A:
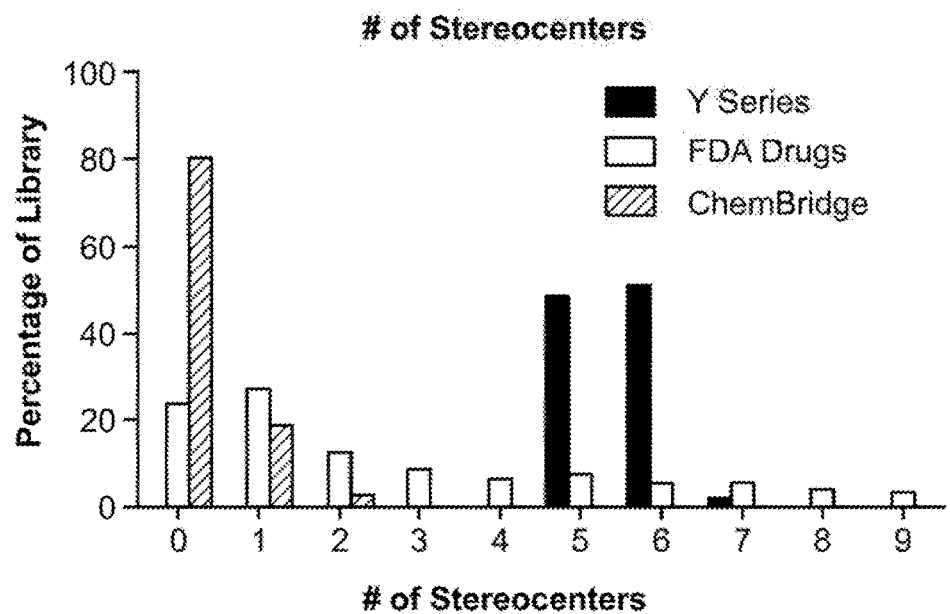
FIG. 12A. Analysis of the stereochemical complexity of the yohimbine ring distortion library (Y Series) compared to FDA Drugs and a ChemBridge library.
Figure 12B:
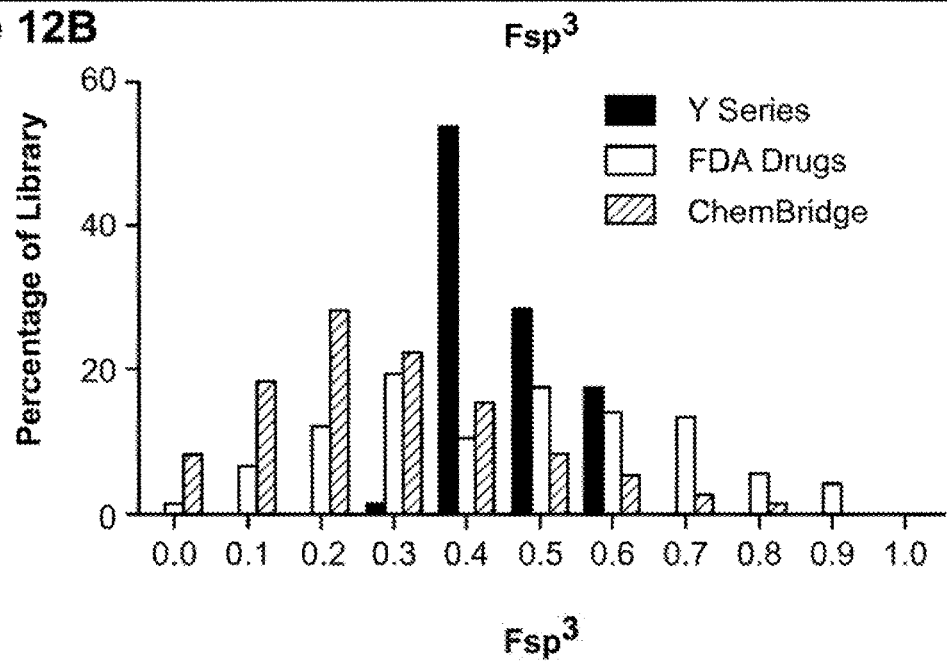
FIG. 12B. Comparison of the Fsp$^3$ character of the yohimbine library (Y Series), FDA Drugs and a ChemBridge library.
Figure 12C:
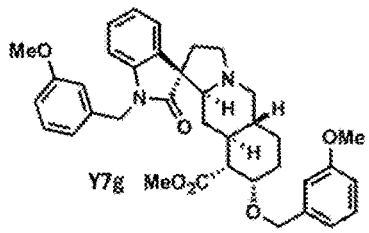
FIG. 12C. Structure of selected compounds used in biological screening for HIF-Dependent anticancer activity & nitric oxide inhibition; Nrf2-ARE inhibition; and Nrf2-ARE activation.
Figure 12C:
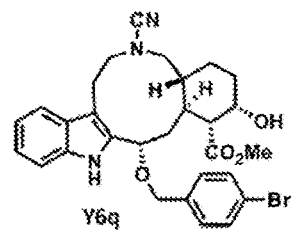
Figure 12C:
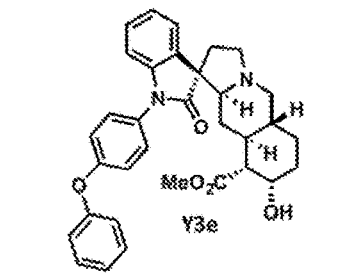
Figure 12C:
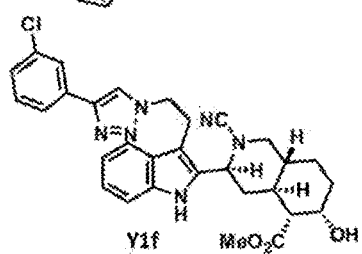
Figure 12C:
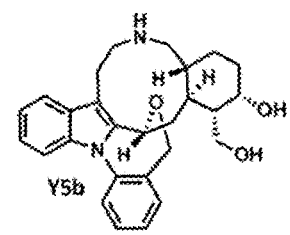
Figure 12C:
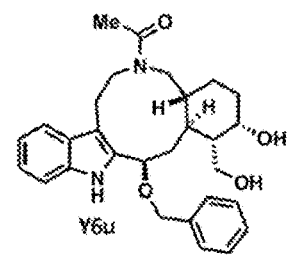
Figure 13:
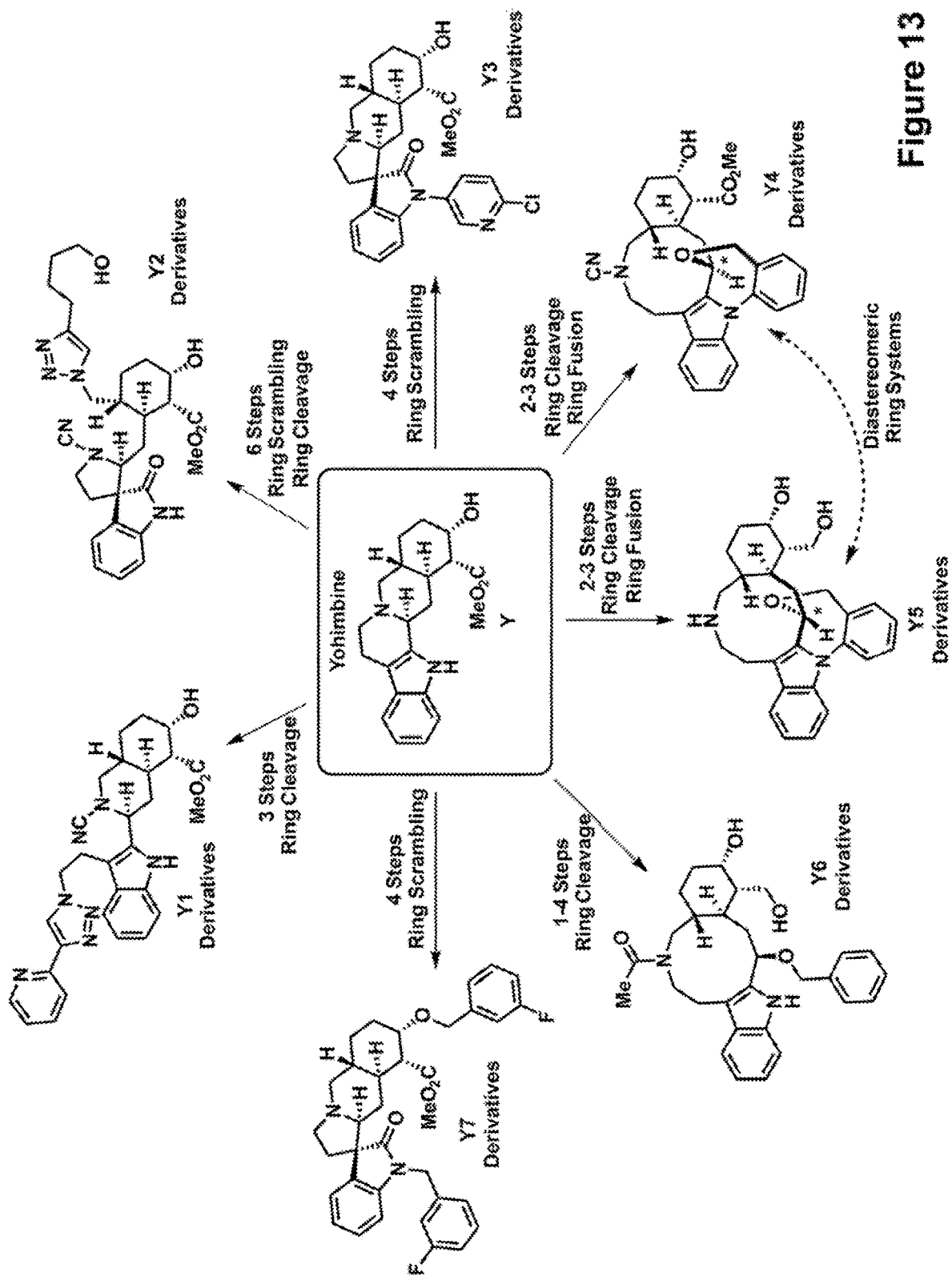
FIG. 13. Diverse and Complex Small Molecules Derived from Yohimbine
Figure 14:
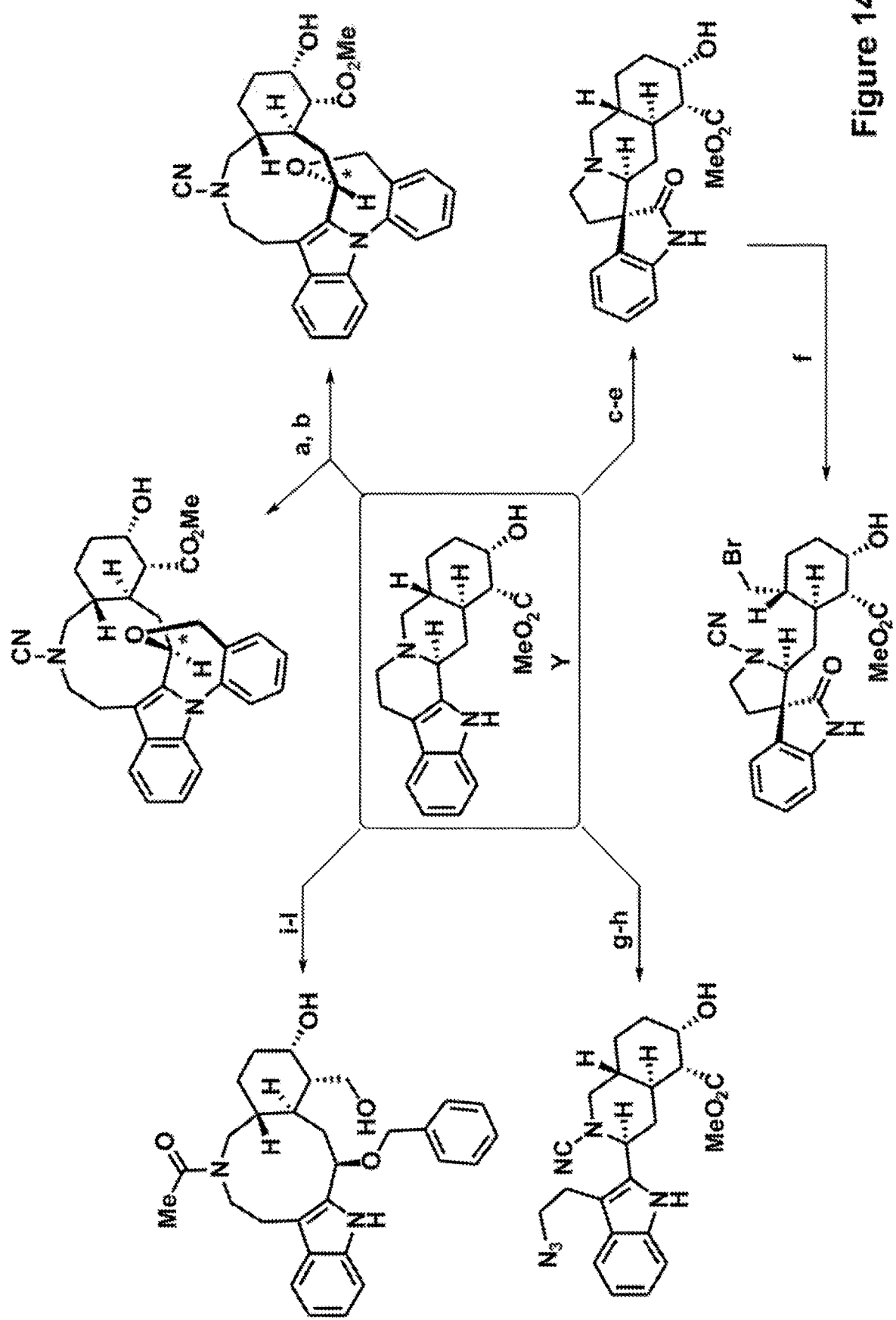
FIG. 14. Ring Distortion of Yohimbine. Step a) 3 M CNBr (3.0 eq), 2-iodo-benyl alcohol (3.0 eq), CHCl₃, rt, 3 h; b) CuI (0.35 eq), MeNH(CH₂)₂HNMe (0.7 eq), K₂CO₃ (1.5 eq), MeCN, μw, 160° C., 13 min; c) NCS, CH₂Cl₂, −40° C., 0.75 h, quant.; d) 0.5 N NaOMe/MeOH, room temperature, 2.25 h, 51%; e) 10% TFA, reflux, 1 h, 58%; f) 3M CNBr (3.0 eq), DMF, room temperature—60° C., 22 h, 54%; g) 3M CNBr, DMF, μw, 100° C., 2.75 min, 56%; h) NaN₃ (2.5 eq), DMF, room temperature—75° C., 24 h, 91%; i) 3M CNBr (3.0 eq), benzyl alcohol (3.0 eq), CHCl₃, room temperature—50° C., 4.5 h, 37%; j) LAH (6.0 eq), THF, 0° C. to room temperature, 1.5 h; k) Ac₂O (6.0 eq), cat. DMAP, pyridine (0.4 eq), DCM, room temperature, 30 min; l) K₂CO₃ (6.0 eq), MeOH, room temperature, 12 h.
Figures 15A, 15B:
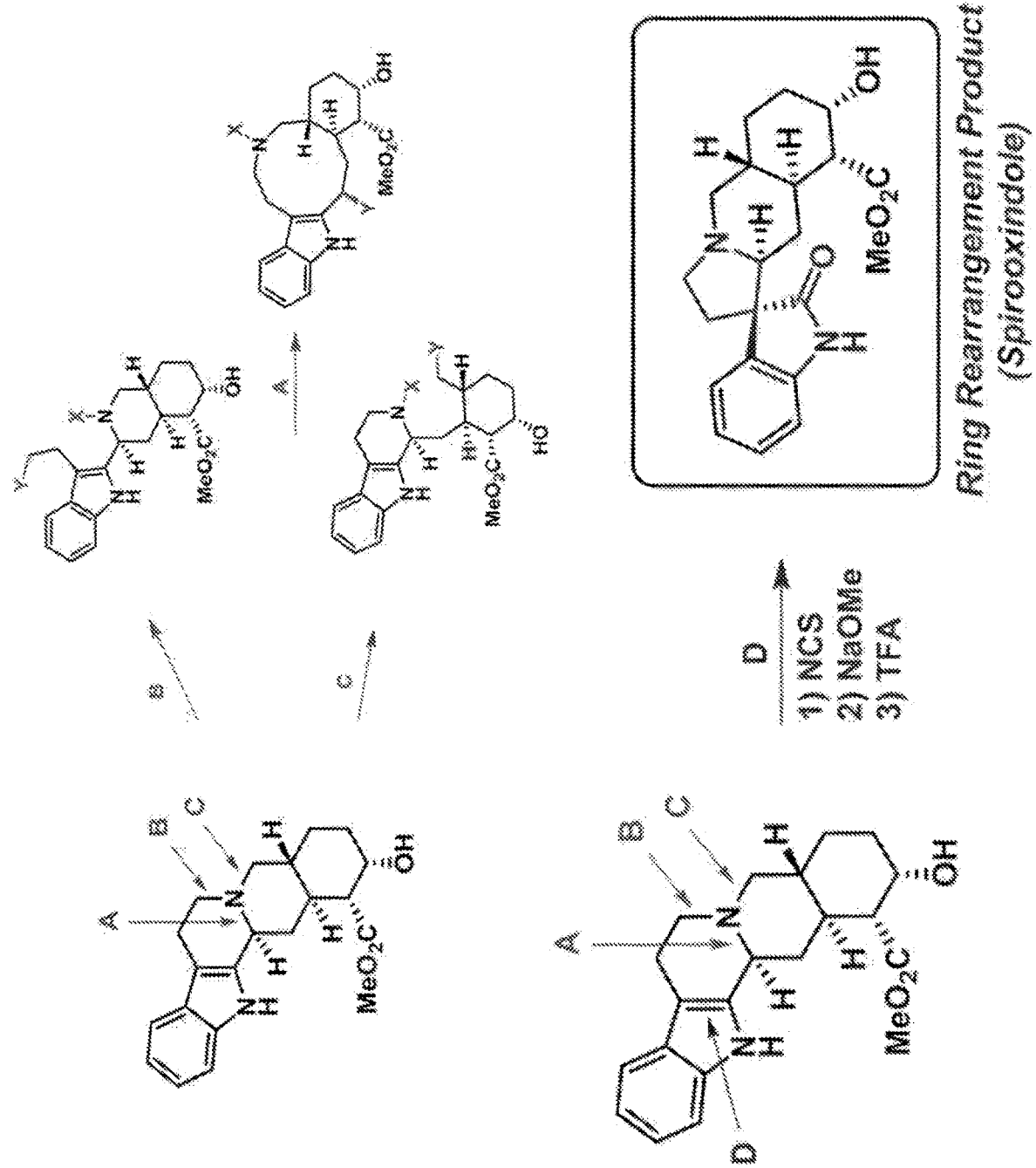
FIG. 15A. Ring Distortion Strategy for Yohimbine.
FIG. 15B. additional Ring Distortion Strategy for Yohimbine.
Figure 16:
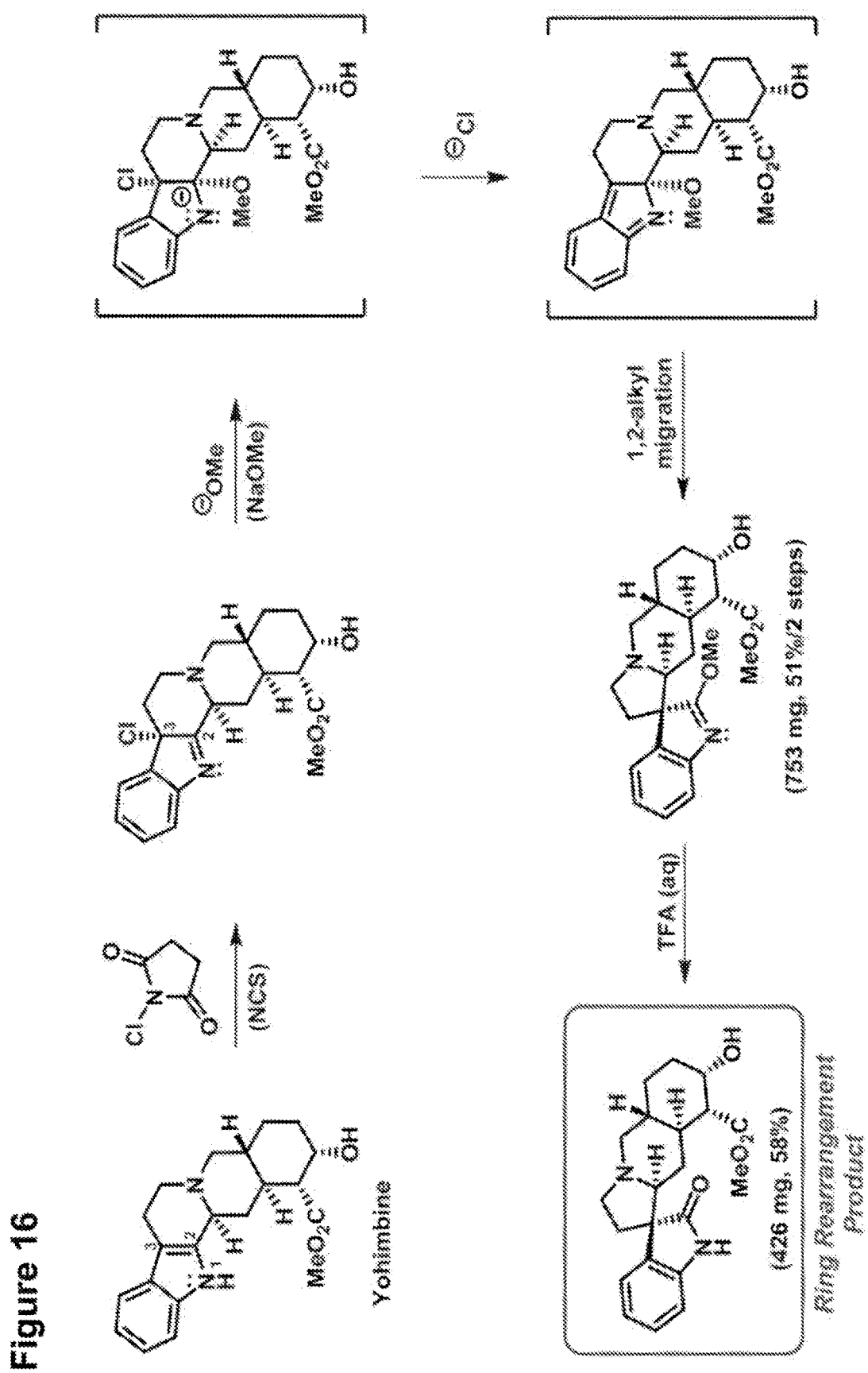
FIG. 16. Mechanism for Yohimbine Ring Rearrangement
Figure 17:
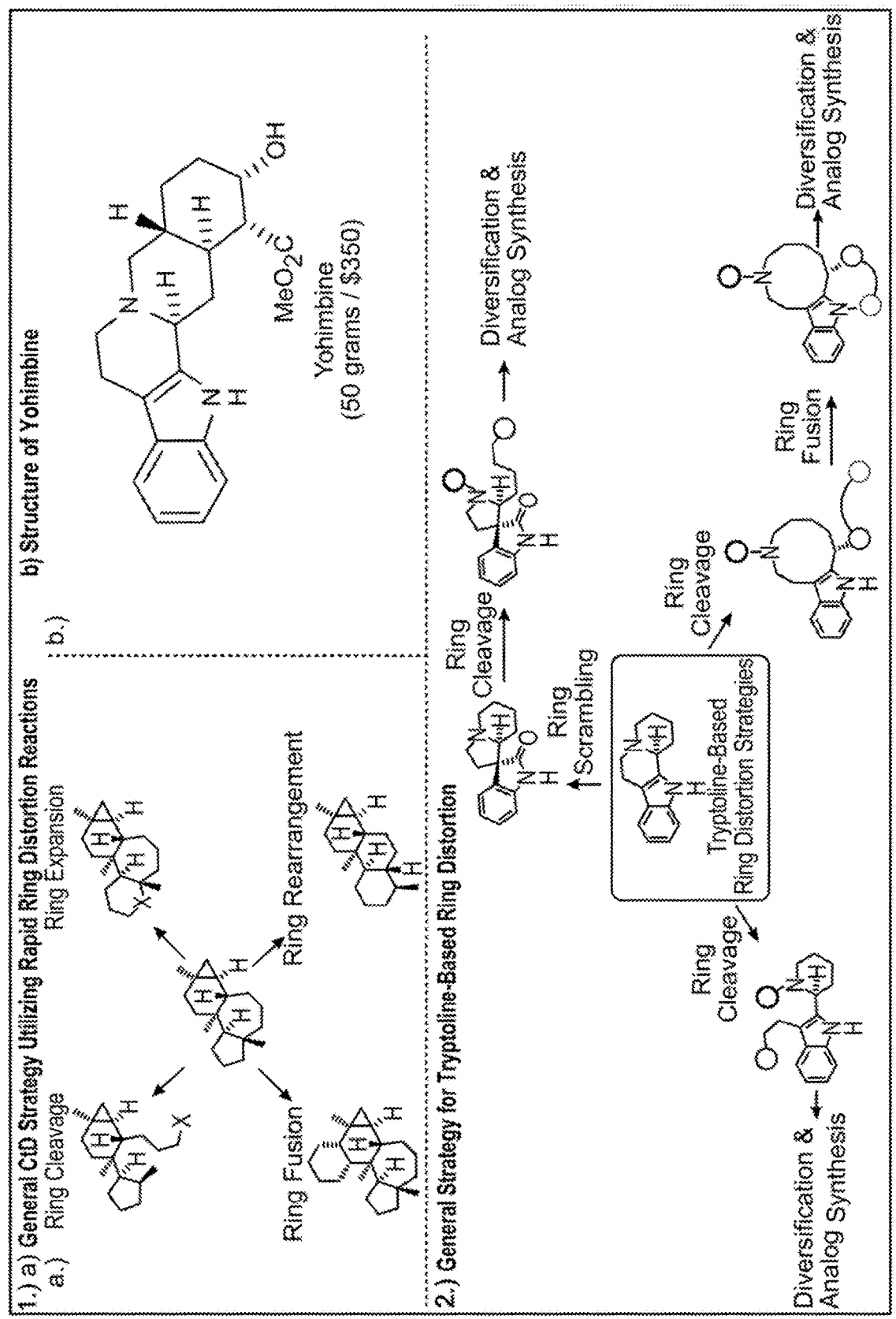
FIG. 17. Complex to Diversity (CtD) Strategy: Approach & Application
Figure 18A:
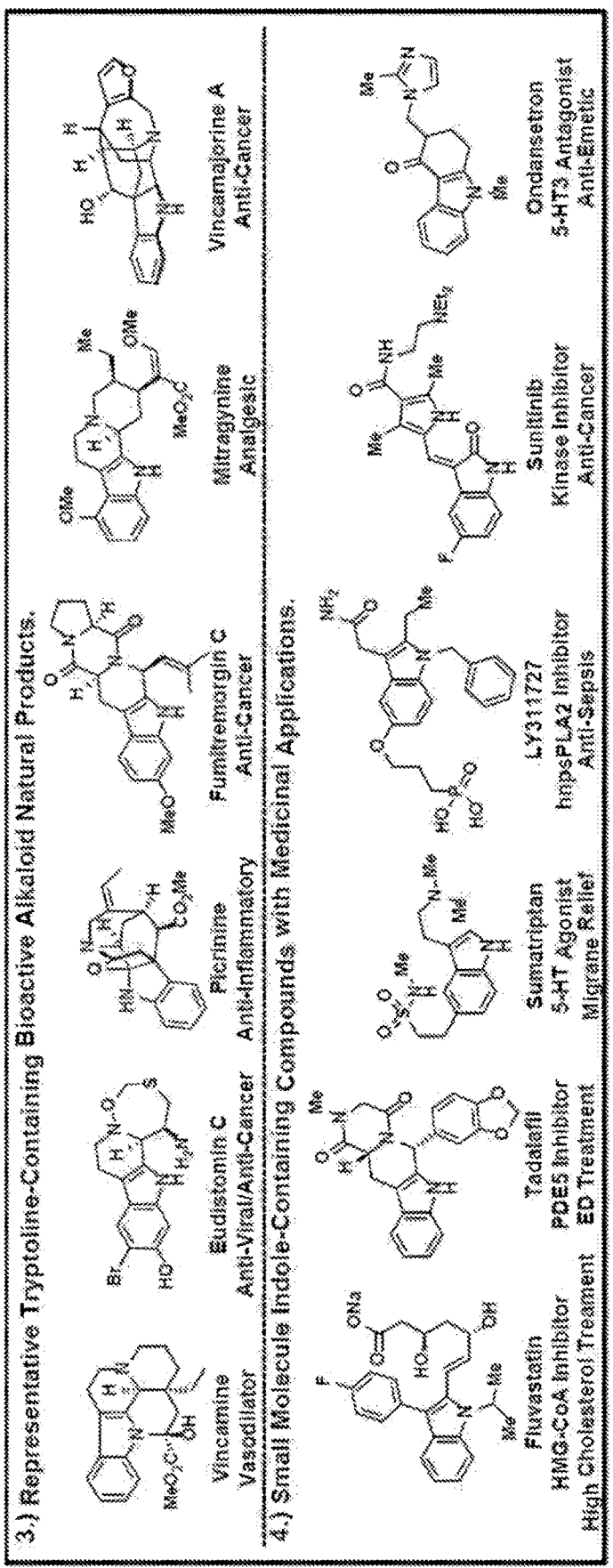
FIG. 18A. Indole Natural Products and Drug Molecules.
Figure 18B:
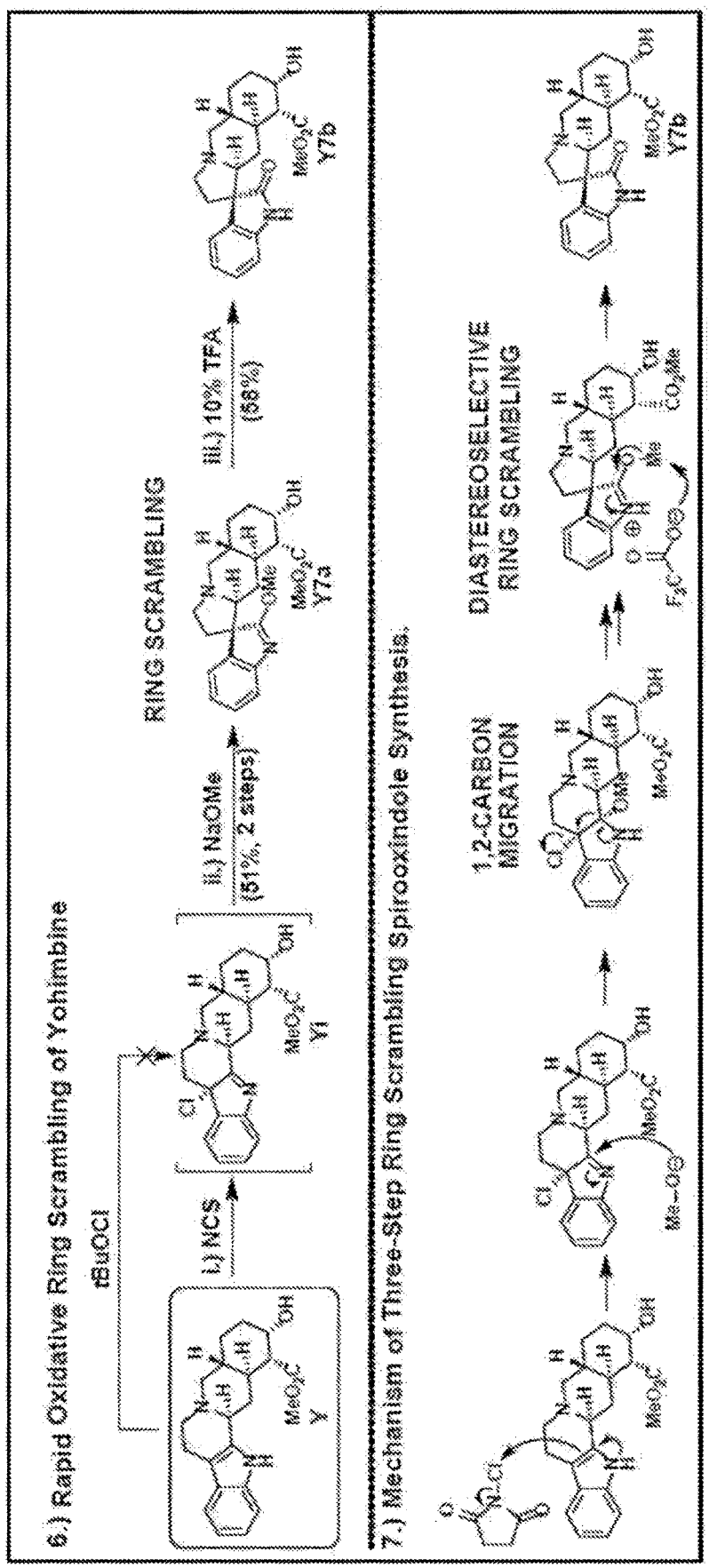
FIG. 18B. Spirooxindole Small Molecules from Yohimbine FIG. 19. Spirooxindole Small Molecules from Yohimbine FIG. 20A. Ring Cleavage and Diversification from Yohimbine.
Figure 19:
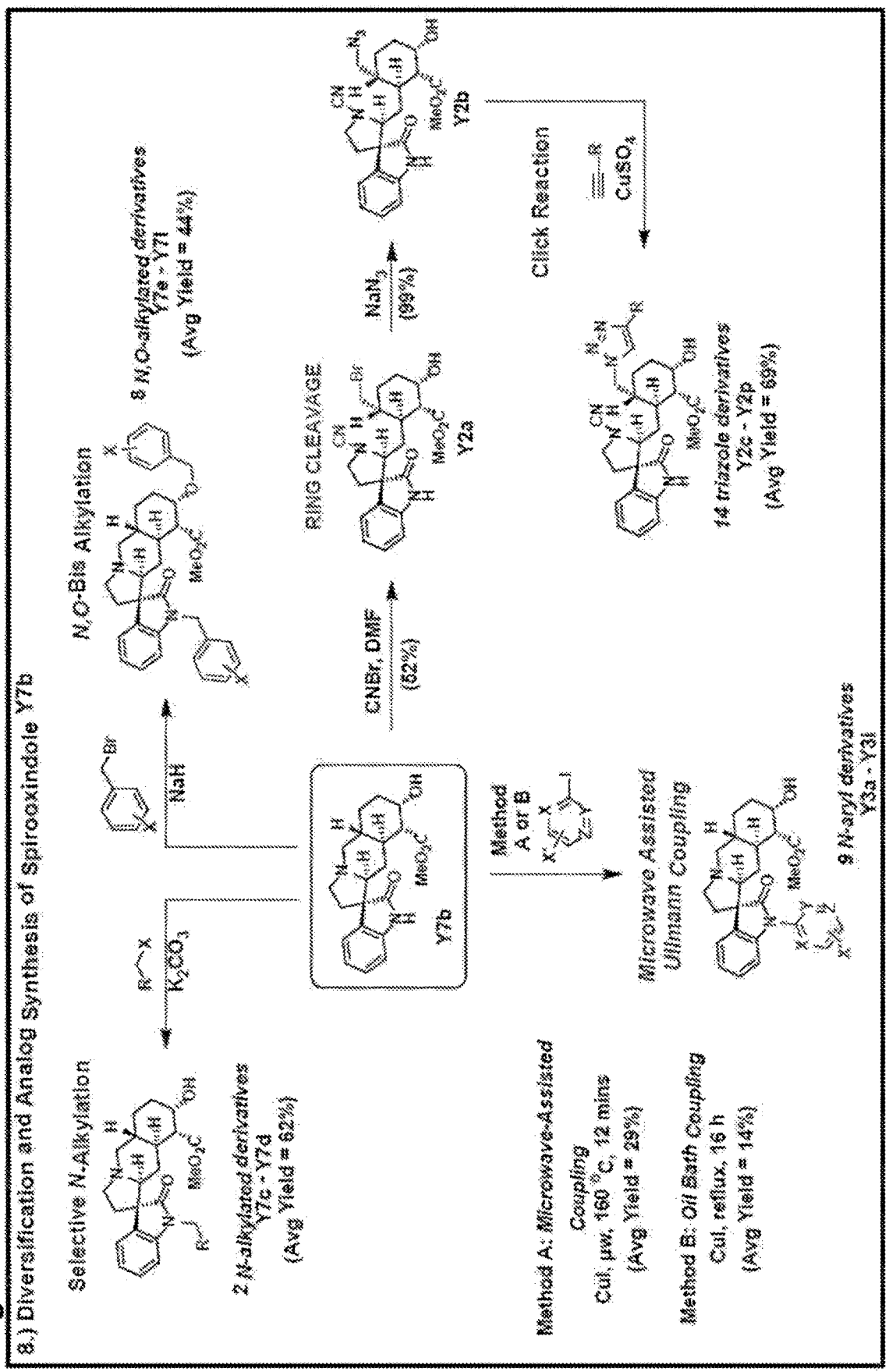
Figure 20A:
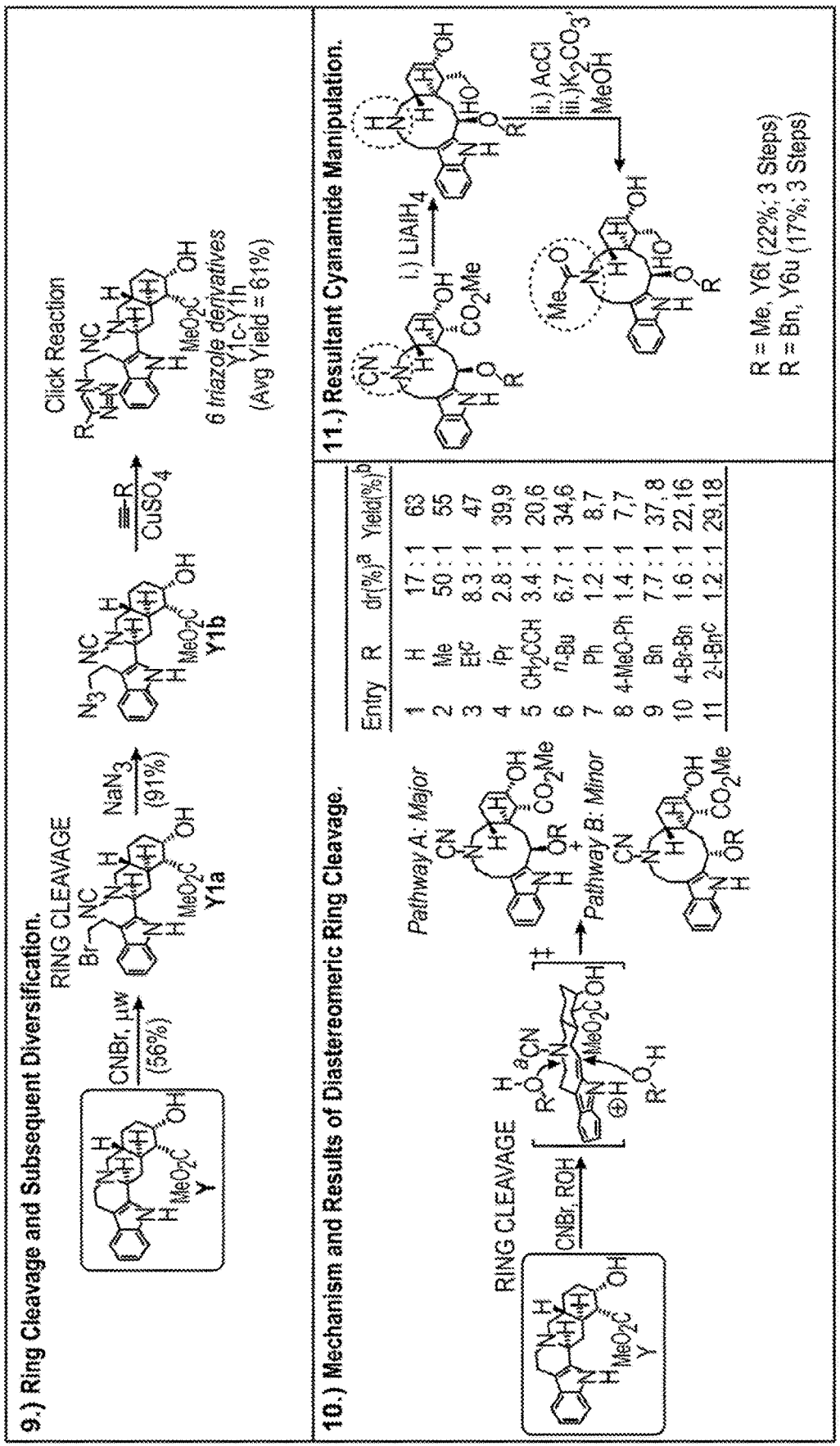
FIG. 20B. Stereochemistry of ether derivatives; ring fusion; and derivative synthesis.
Figure 20B:
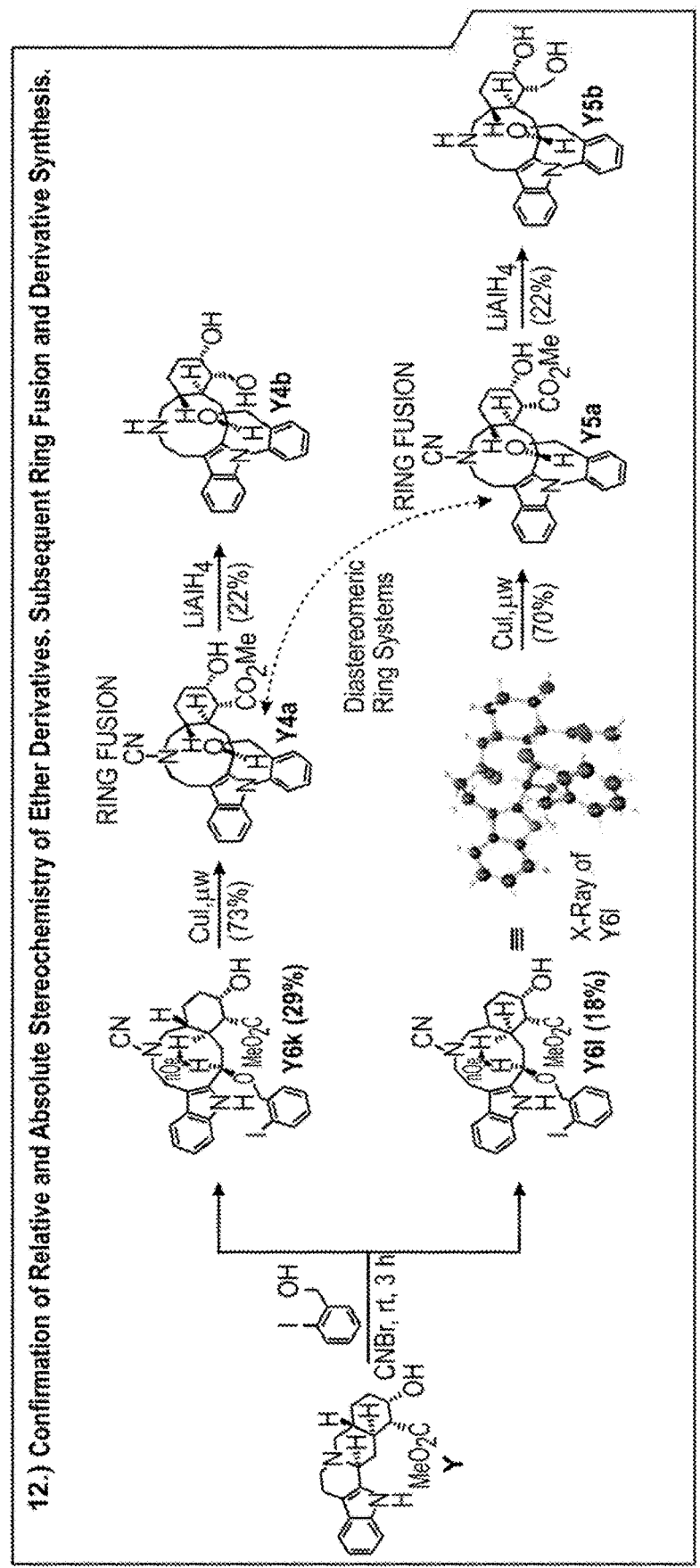
Figure 21:
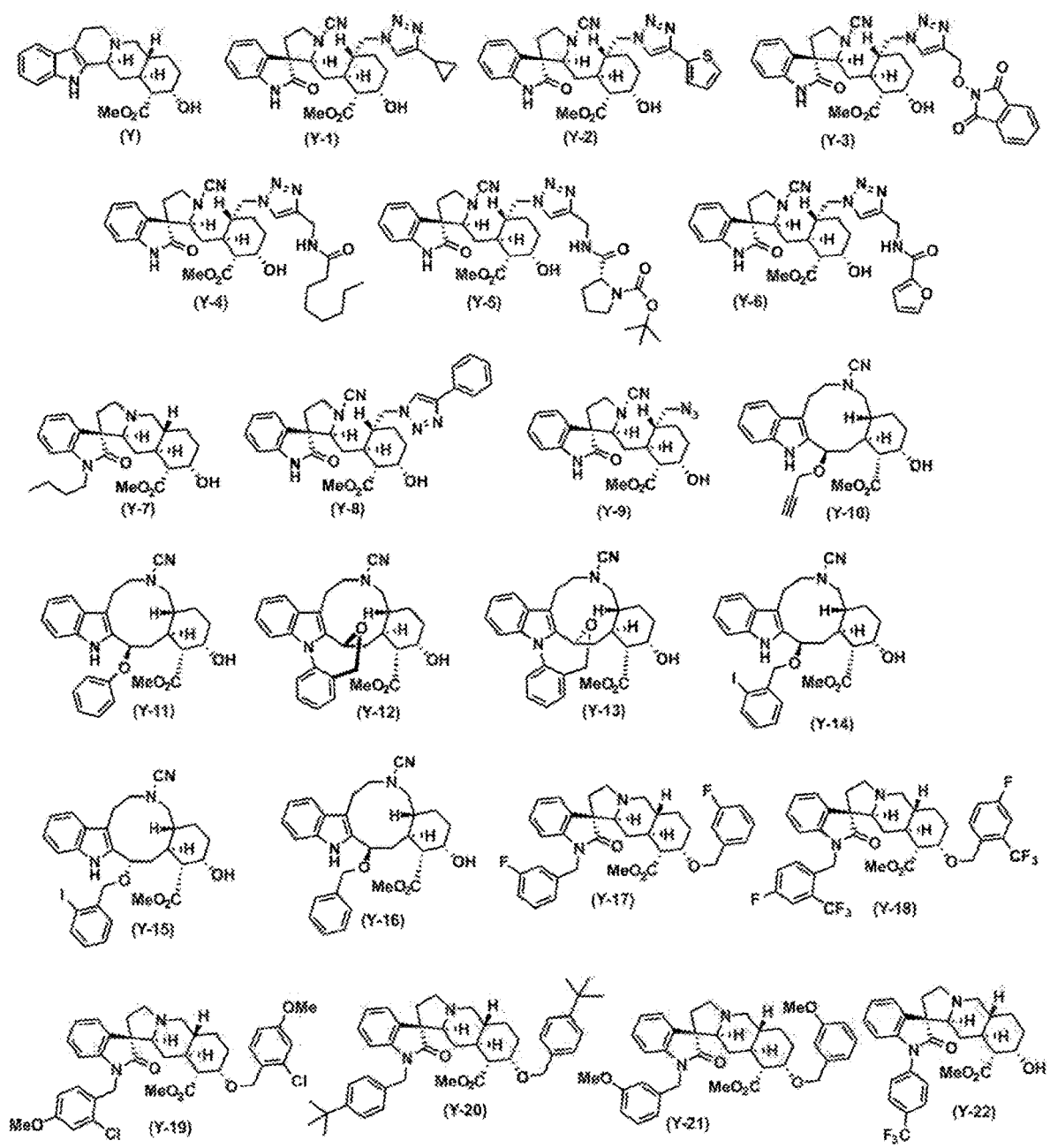
FIG. 21. Exemplary compounds of Formulae (I-A), (I), (II'), (II), (III-A), (III), (IV'), (IV), (V-A), or (V).
Figure 22:
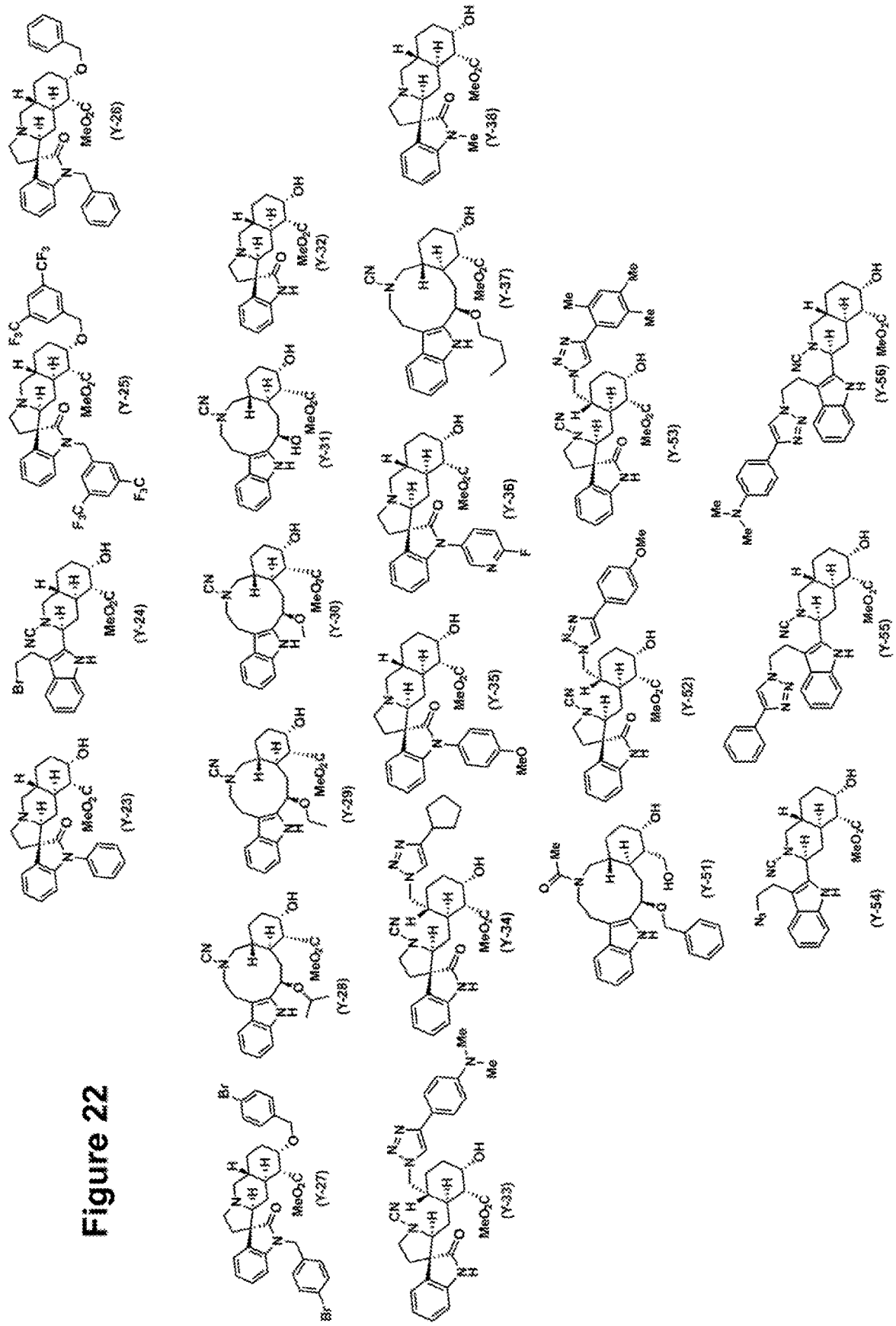
FIG. 22. Exemplary compounds of Formulae (I-A), (I), (II'), (II), (III-A), (III), (IV'), (IV), (V-A), or (V).
Figure 23:
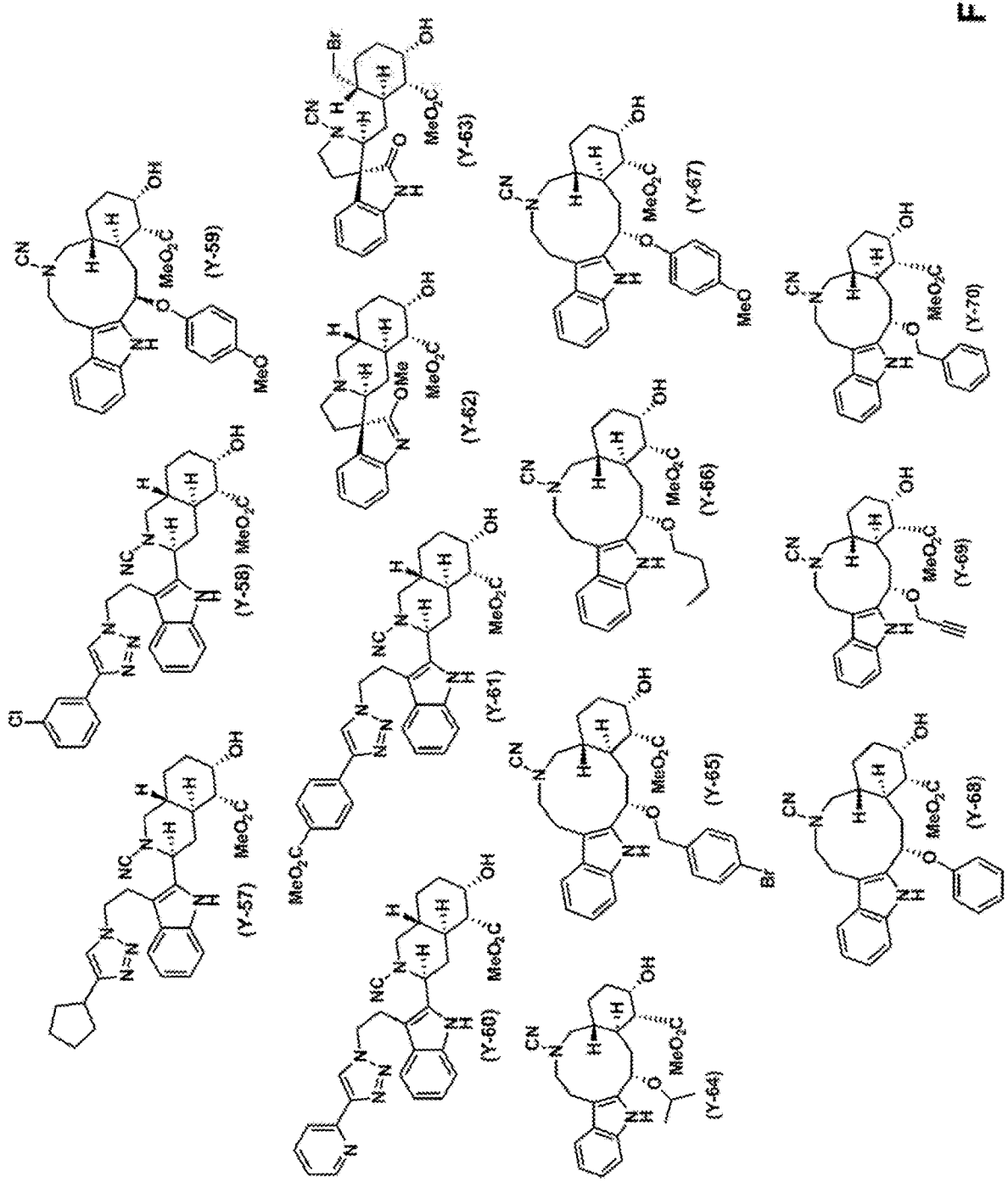
FIG. 23. Exemplary compounds Formulae (I-A), (I), (II'), (II), (III-A), (III), (IV'), (IV), (V-A), or (V).
Figure 24:
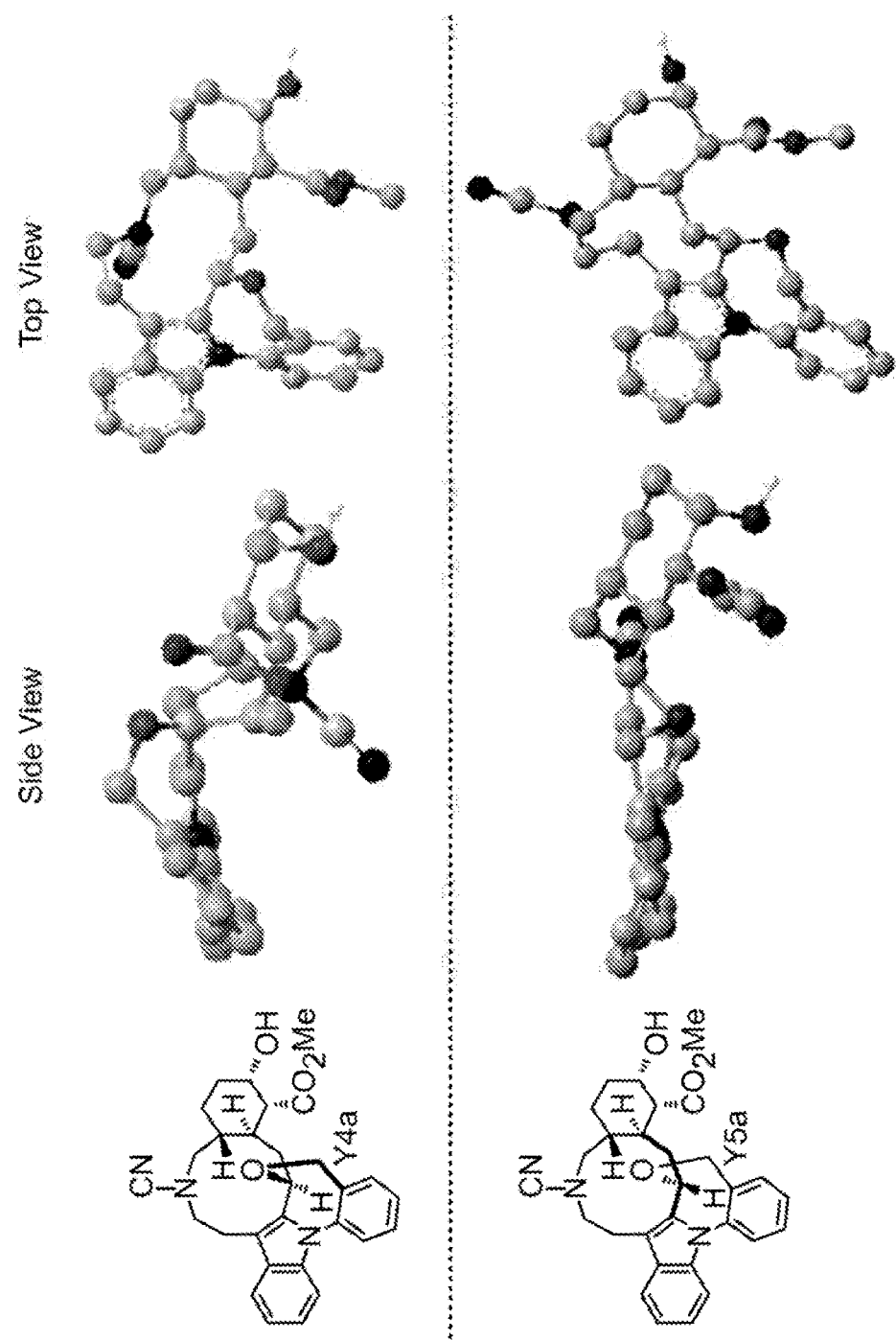
FIG. 24. Molecular models of compounds Y4a and Y5a highlighting diverse diastereomeric ring fused systems FIG. 25A. Compound Y6s crystallized from CDCl3 in an NMR tube after 12 hours at room temperature.
Figure 25A:
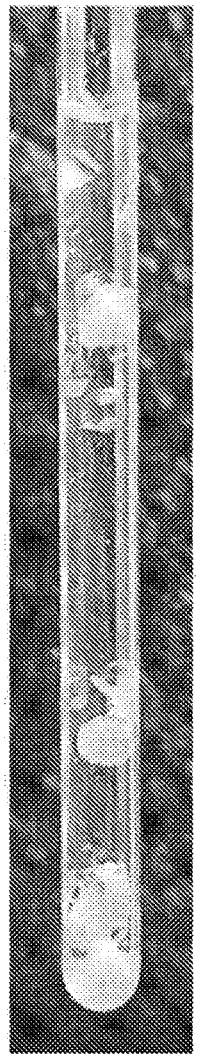
FIG. 25B. Raw crystal data and atomic numbering for compound Y6S.
FIG. 25C. Refined crystal image of Y6s. Refined images were generated from Ortep3 and POV-Ray v3.7 programs from the raw X-Ray CIF file. X-ray crystals were obtained by dissolving 518 mg of Y6s in 450 μL of deuterated chloroform. The solution was kept at room temperature in an NMR tube for 12 hours which precipitated colorless crystals of suitable quality for x-ray diffraction analysis.
Figure 25C:
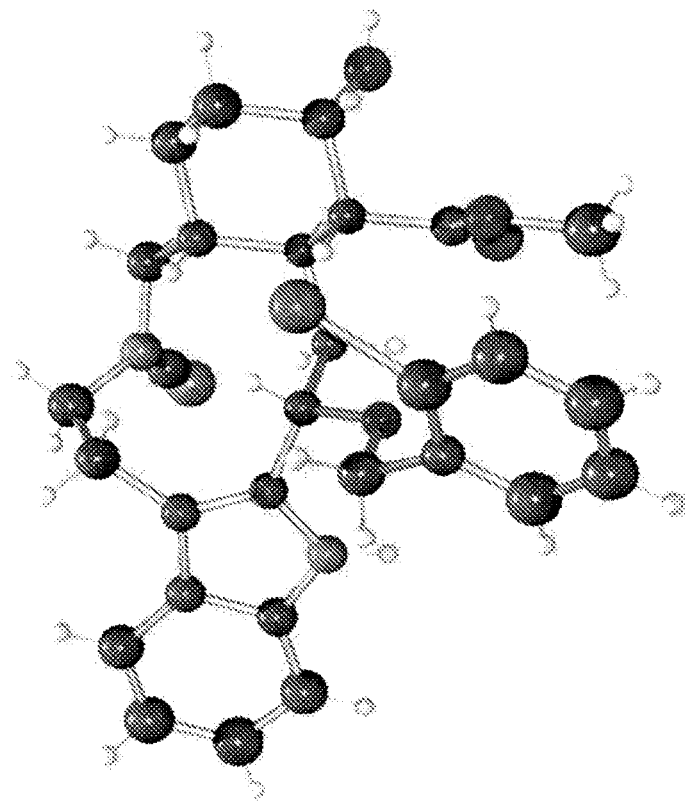
Figure 25B:
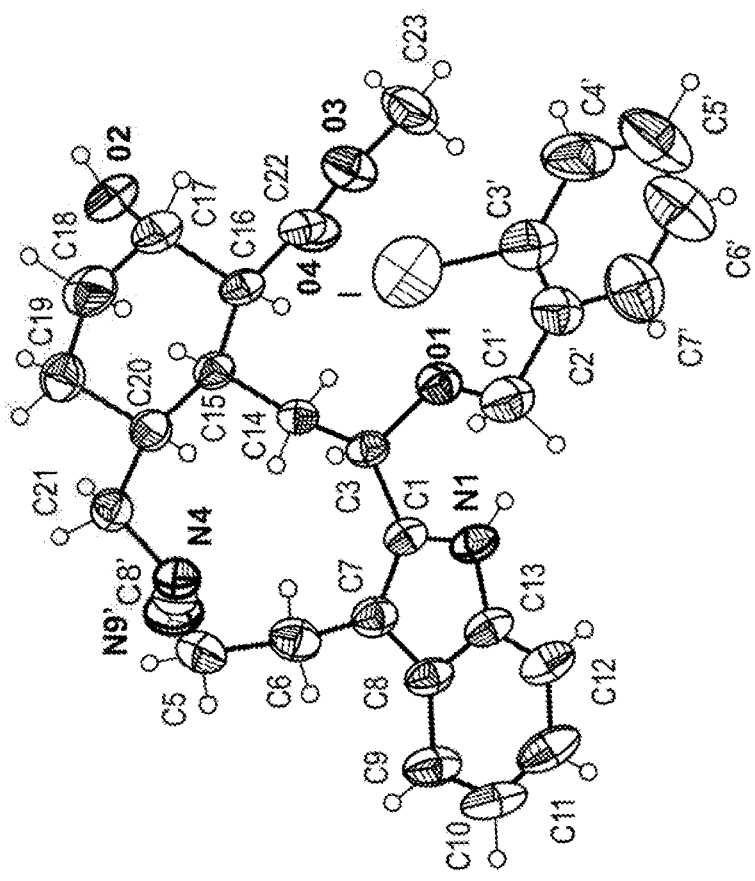
Figure 26:
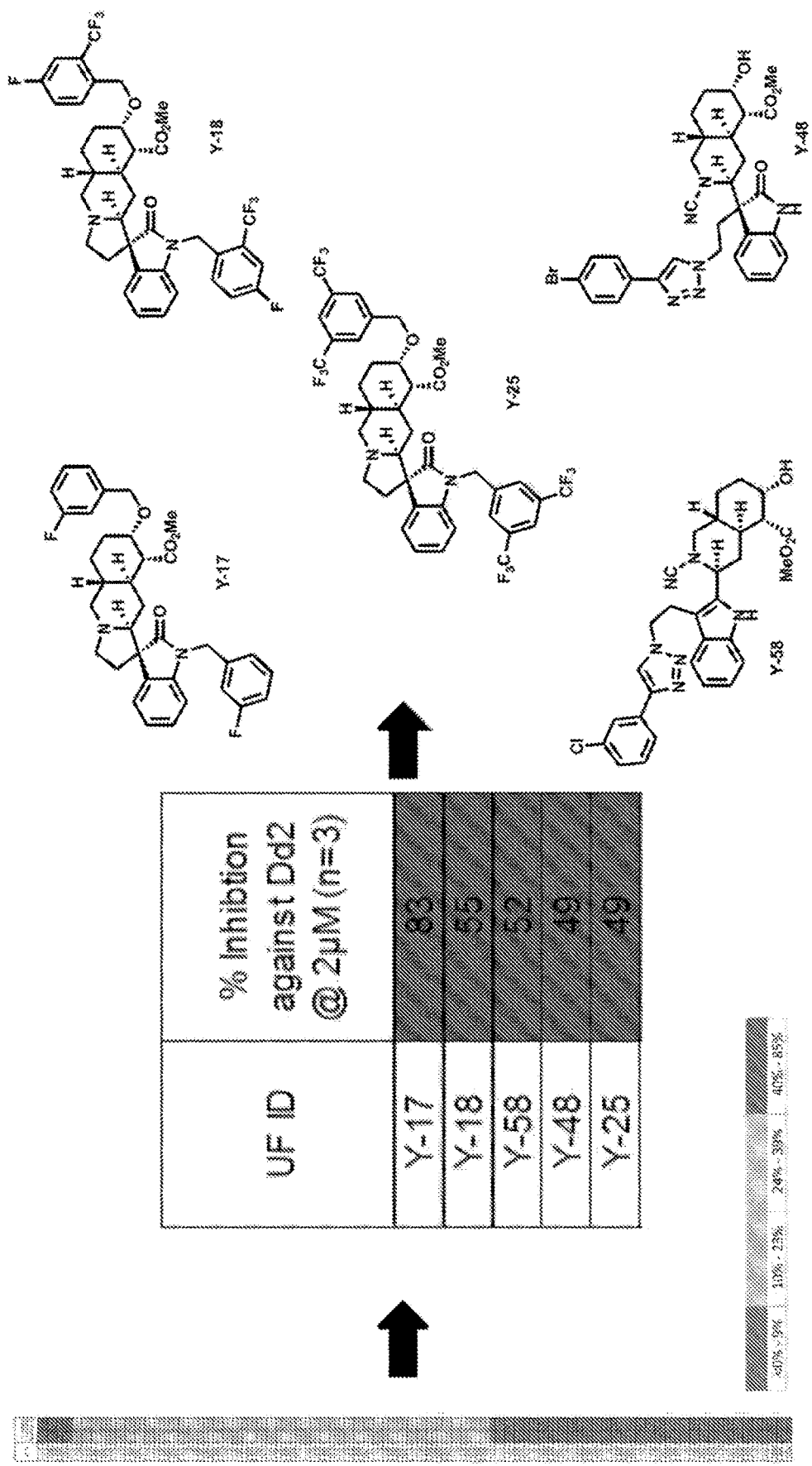
FIG. 26. Initial screening results of an assay for antimalarial (anti-plasmodial) activity for exemplary compounds. For FIGS. 26-28, the anti-plasmodial assay was conducted with the following standard assay conditions in a SYBR Green I-Based Fluorescence Assay to test for anti-plasmodial activity, and drug-resistant Dd2 *P. falciparum* strain (resistant against chloroquine, pyrimethamine, mefloquine) was used to obtain $EC_{50}$ values for the exemplary compounds. See Assessment and Continued Validation of the Malaria SYBR Green I-Based Fluorescence Assay for Use in Malaria Drug Screening, *Antimicrob. Agents Chemother.*, 2007 June; 51(6): 1926-1933, incorporated herein by reference.
Figure 27:
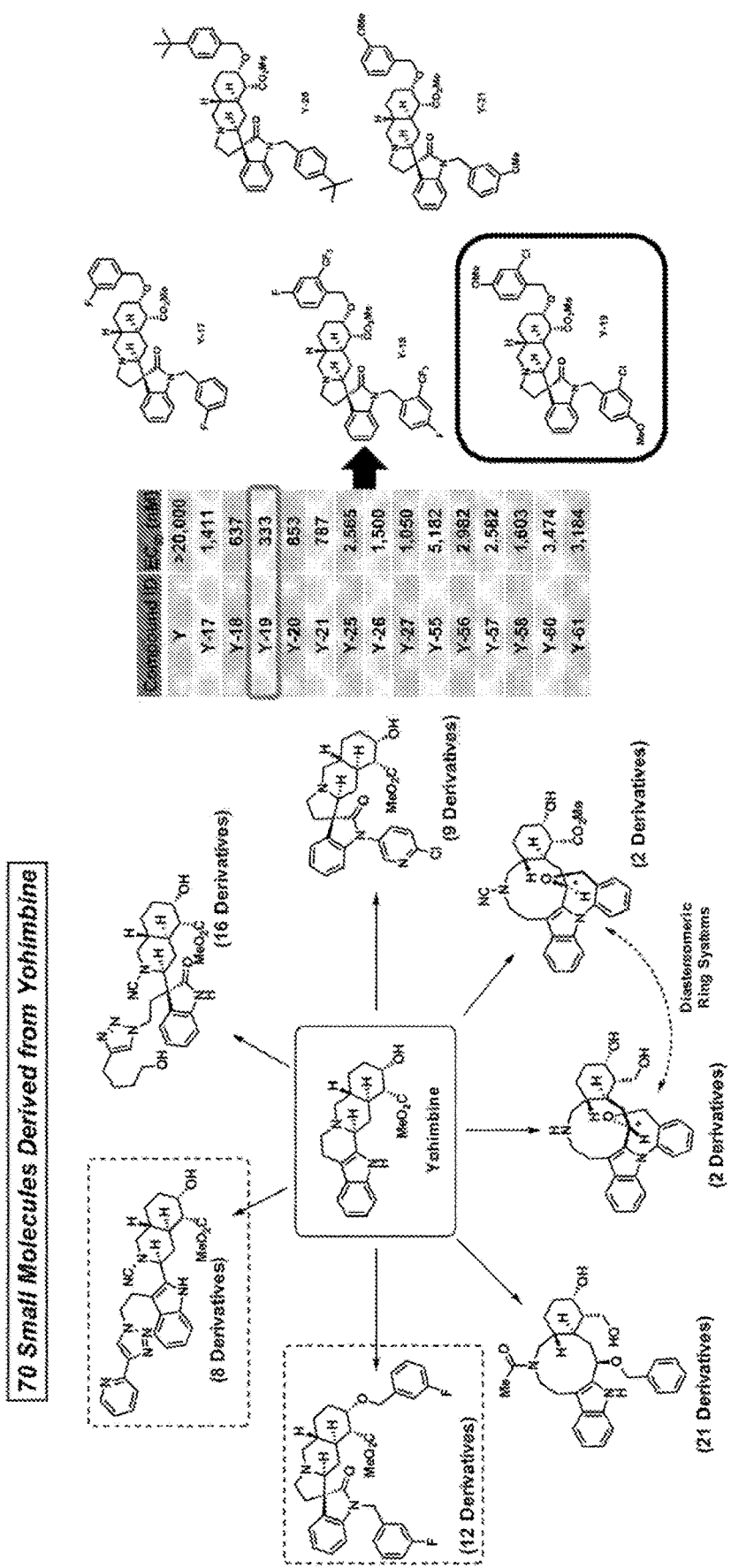
FIG. 27. Retest from dry stocks for $EC_{50}$ values and identification of two compound scaffolds with anti-plasmodial activity ($EC_{50}$ values), with top 5 hits from a single compound scaffold.
Figure 28:
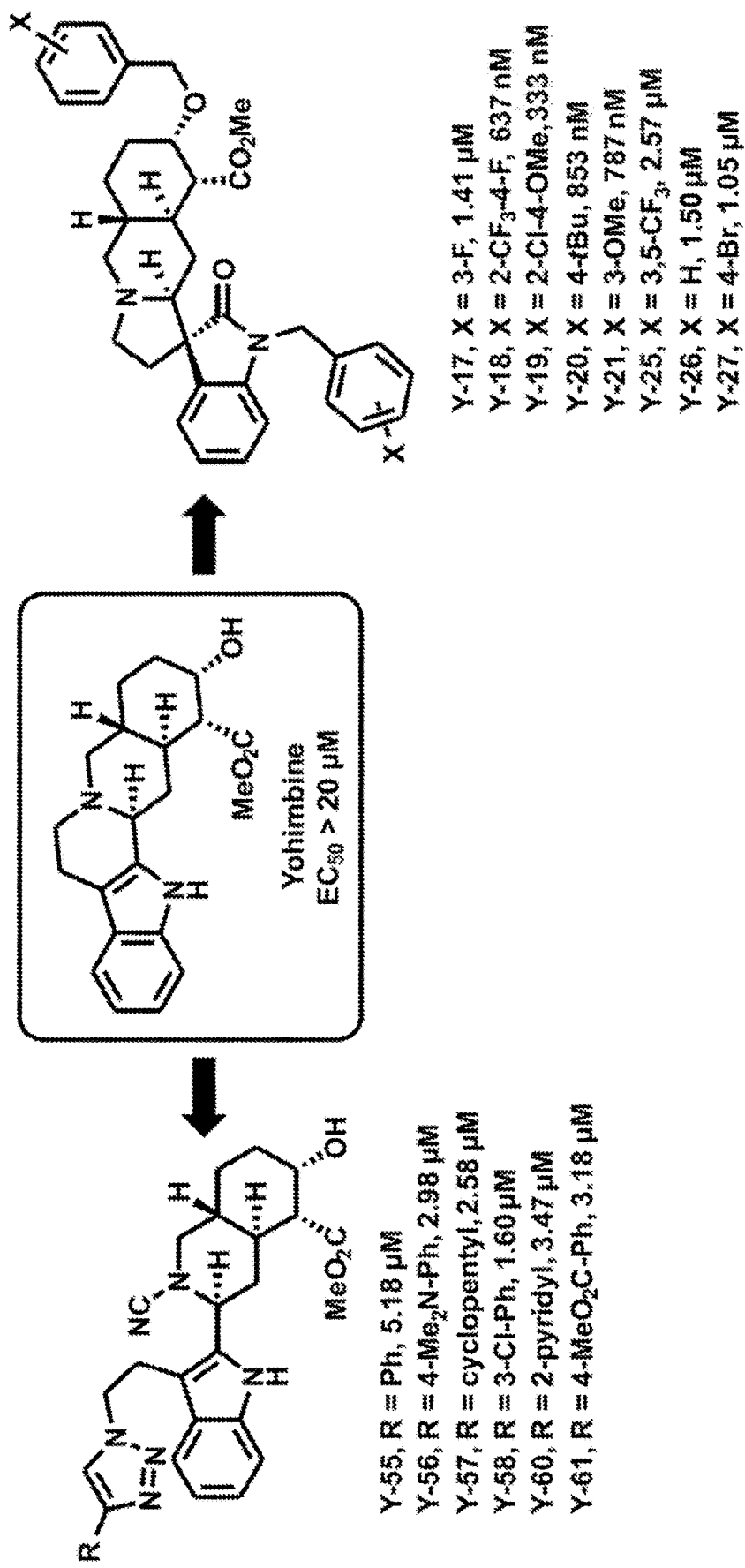
FIG. 28. $EC_{50}$ values for active exemplary compounds retested in $EC_{50}$ assays.

To identify activators of Nrf2, the transiently transfection of LNCaP androgen-sensitive prostate cancer cells with ARE-luciferase reporter based on the human NQO1 promoter4,4[1] was conducted and then challenged with the yohimbine derivative library. As a control, LNCaP viability was monitored in parallel (FIG. 11E). While many compounds activated the ARE at 100 μM potentially as a stress response, Y5b and Y6u were also active at lower concentrations when the hits were validated by RT-qPCR for levels of endogenous NQO1. These compounds were only slightly less potent than the positive control, sulforaphane.

Figure 2:
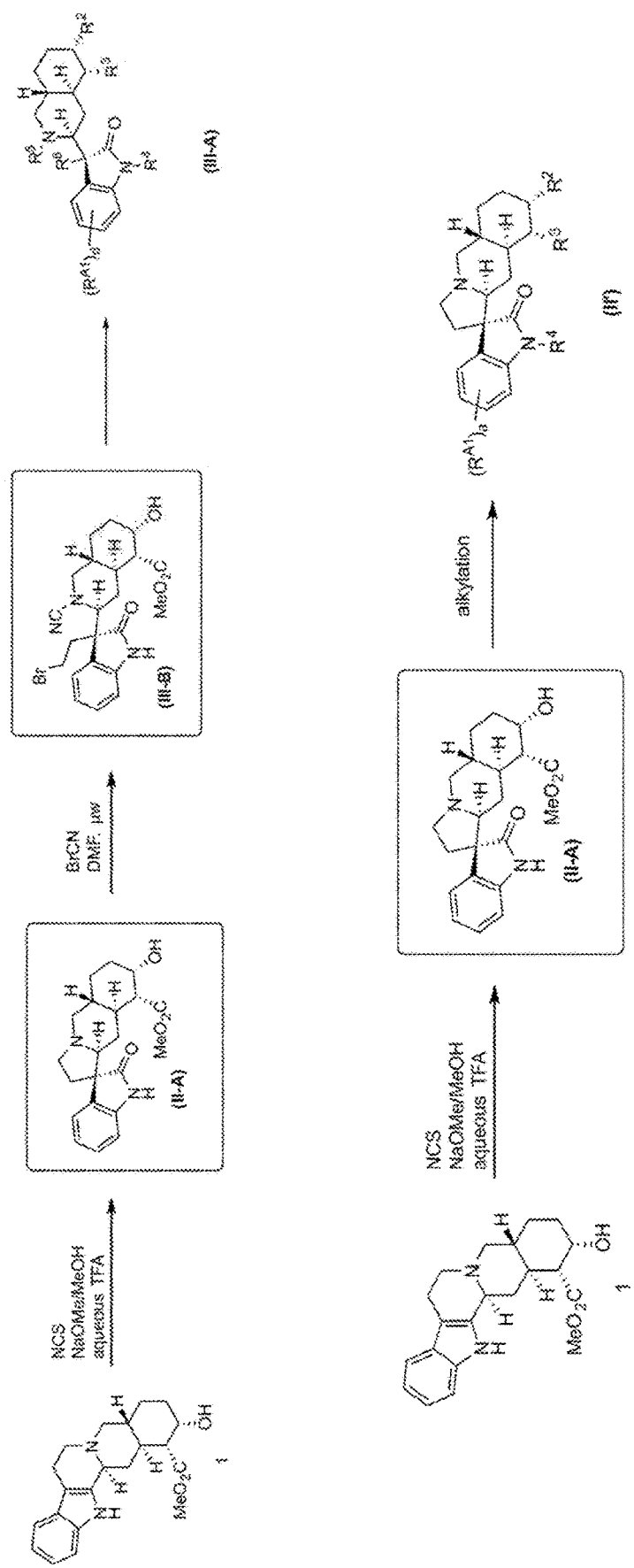
FIG. 2 shows an exemplary method of preparing a compound of Formula (III-A) and synthetic intermediates (II-A) and (III-B), from yohimbine (compound 1).
Figure 3:
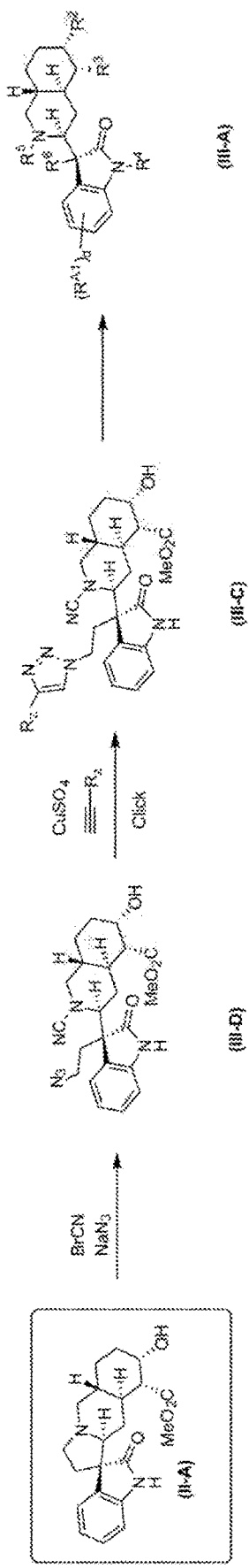
FIG. 3 shows an exemplary method of preparing a compound of Formula (III-A) and synthetic intermediates (III-C) and (III-D) from synthetic intermediate (II-A).
Figure 4:
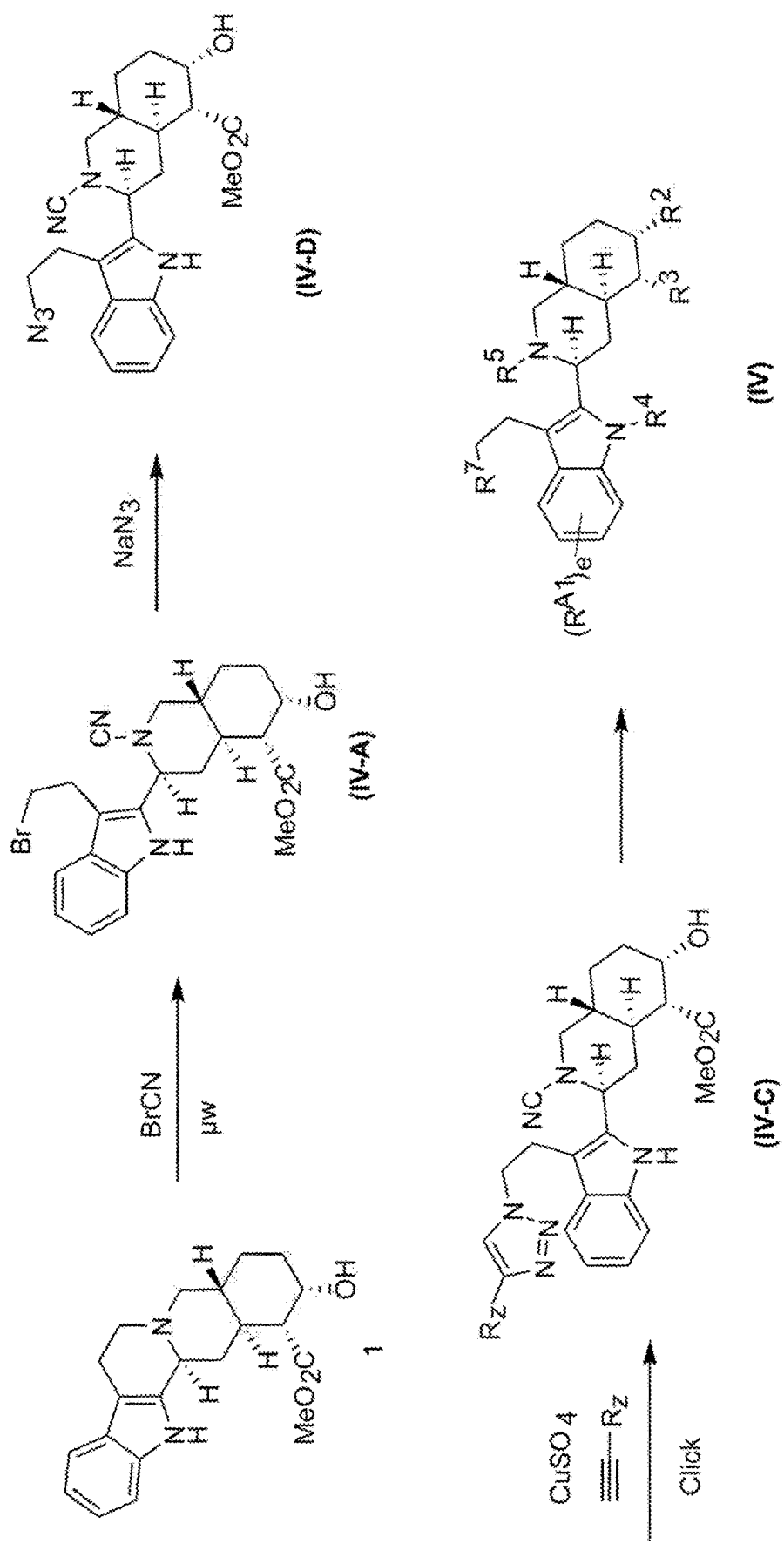
FIG. 4 shows an exemplary method of preparing a compound of Formula (IV') and synthetic intermediates (IV-A), (IV-C), and (IV-D), from yohimbine (compound 1).
Figure 5:
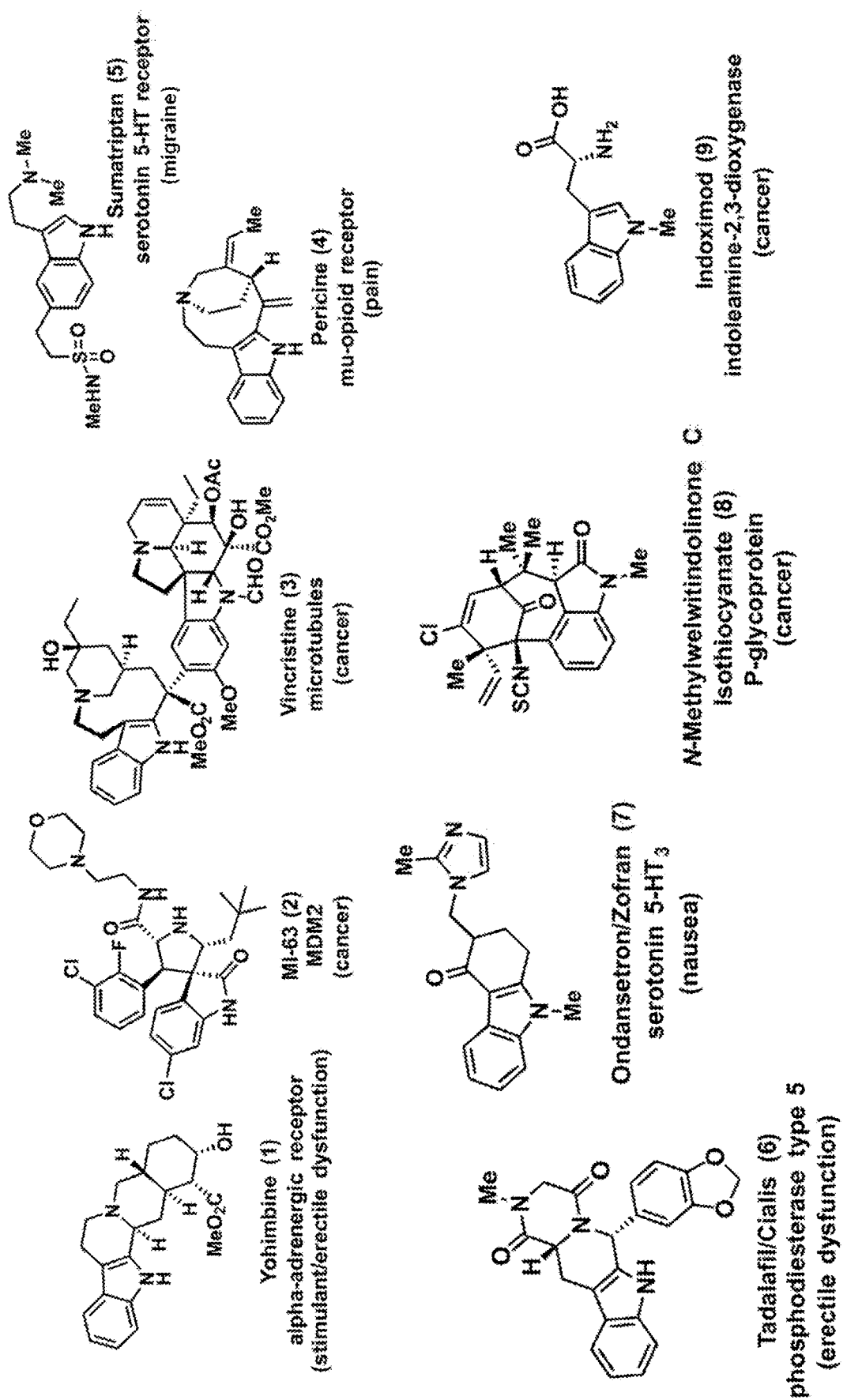
FIG. 5 shows biologically active and therapeutic indole-containing and indole-related molecules.
Figure 6:
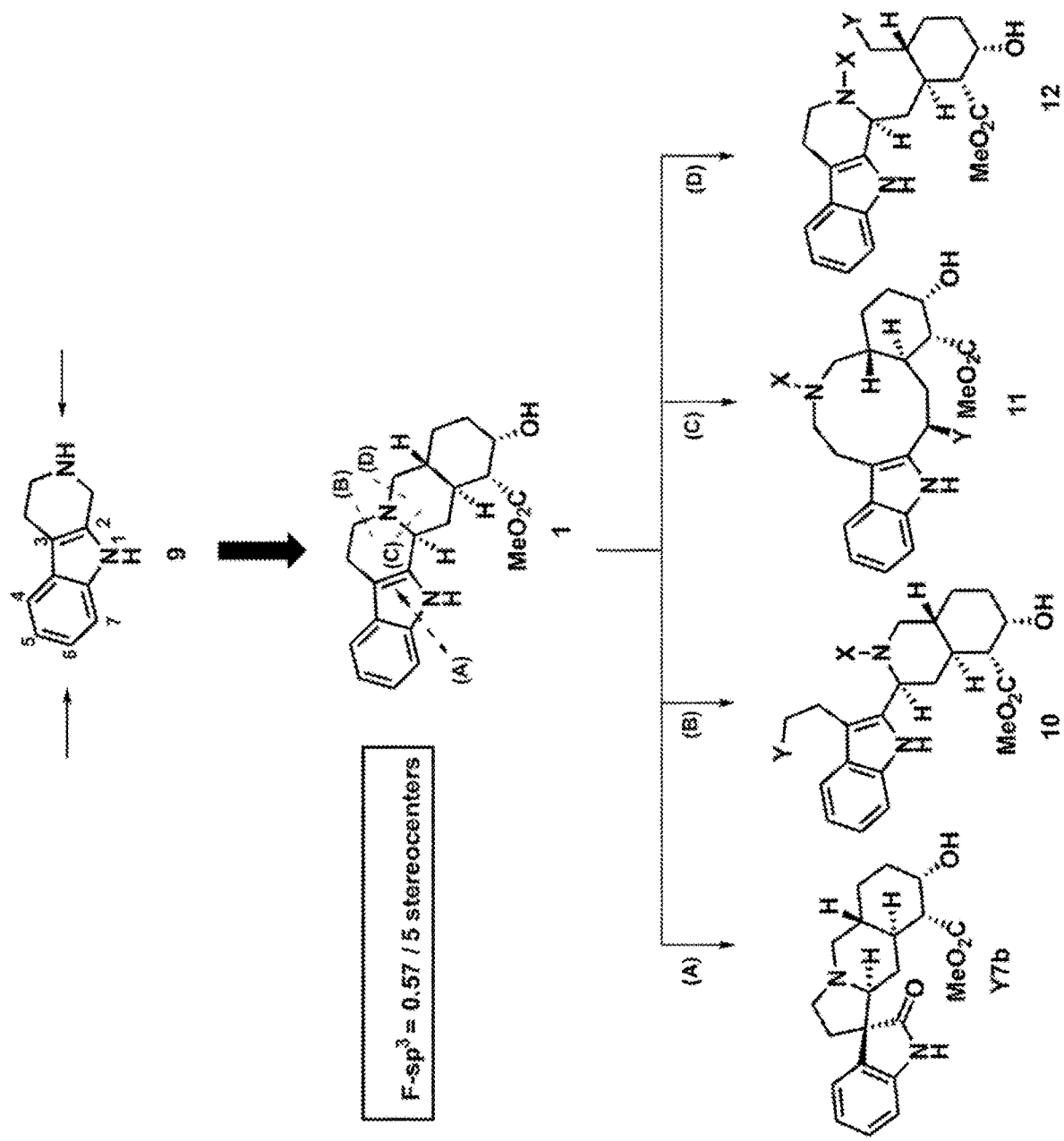
FIG. 6 shows an exemplary tryptoline ring distortion strategy applied to the indole alkaloid yohimbine.
Figure 7:
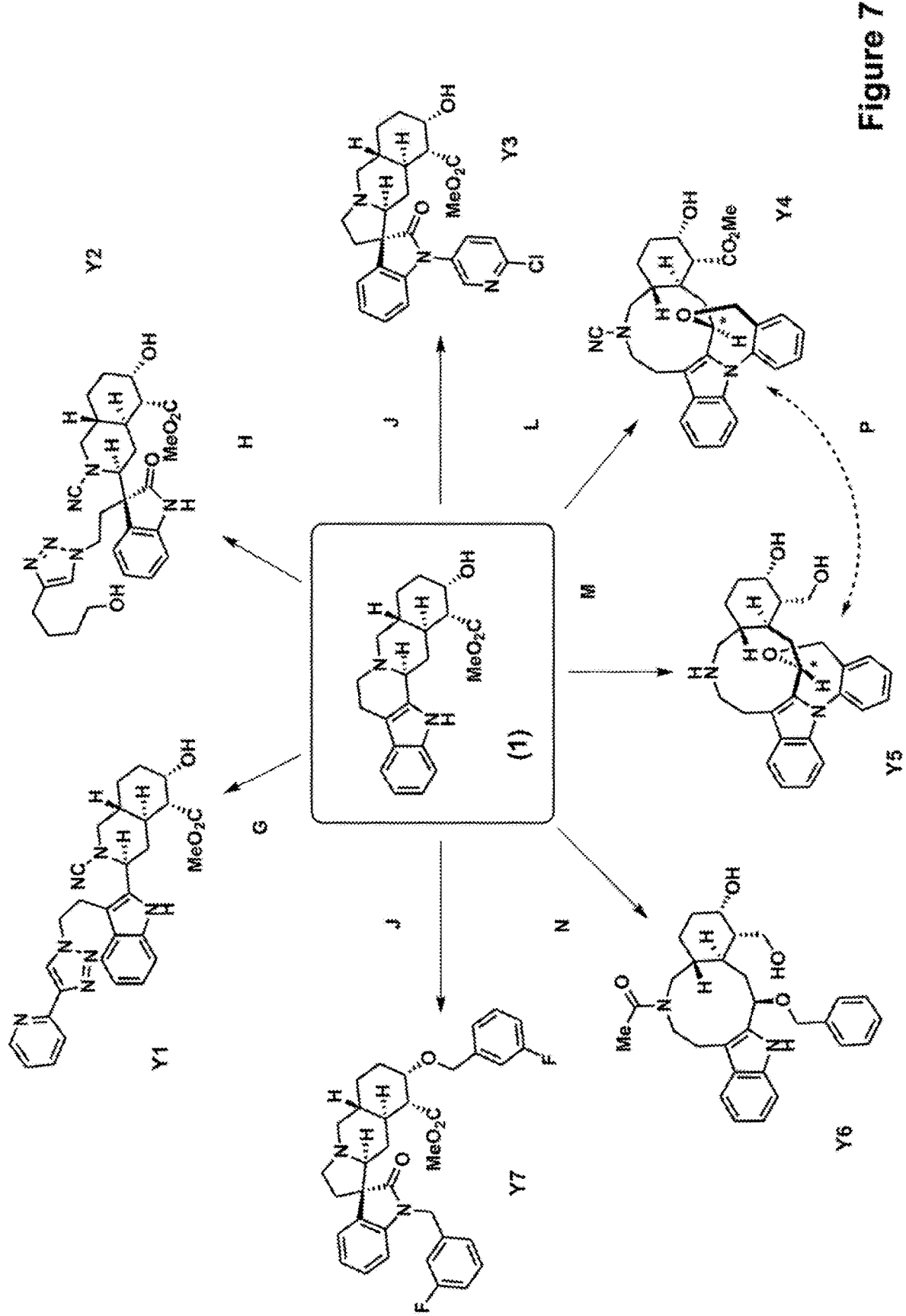
FIG. 7 shows an exemplary scheme for rapid synthesis of complex and diverse small molecules from yohimbine.

The yohimbine derivative library was also screened against *Staphylococcus aureus* (Gram-positive pathogen) and *Acinetobacter baumannii* (Gram-negative); however, only a few compounds demonstrated weak antibacterial activities (i.e., partial growth inhibition) against *A. baumannii* at 200 μM. The antibacterial screen was insightful to cross-reference activity profiles of validated hit compounds with selective antiproliferative, NO inhibition and Nrf2-ARE modulation. Of the six validated hit compounds identified during these biological investigations (Y7g, Y6q, Y3e, Y1f, Y5b, Y6u; FIG. 2), only Y1f and Y6q demonstrated slight (~20%) growth inhibition activities at 200 μM against *S. aureus*. Interestingly, yohimbine 1 does not possess any of these activities inherently, illustrating the potential for yohimbine, and other natural products, to reach beyond their own biological capabilities using this ring distortion approach. Overall, yohimbine ring-distorted small molecules cover a biologically relevant chemical space as evident by the diverse array of active compounds identified in a library of 70 compounds. ARE luciferase assay in LNCaP and MDA-MB-231-ARE-Luc cells The antioxidant response element (ARE) expression induction assay with LNCaP cells was performed as previously described.[6] The ARE expression inhibition assay was performed with MDA-MB-231-ARE-Luc cells that stably express the ARE reporter construct.7 MDA-MB-231-ARE-Luc cells were seeded in 96 well plates at $1.5 \times 10^4$ cells/well in DMEM medium (GIBCO) containing 10% FCS and 1% antibiotic-antimycotic (GIBCO), and allowed to attach overnight. Test compounds were screened in triplicate at three concentrations (100, 10 and 1 μM) and ARE expression was quantified on the EnVision plate reader (Perkin-Elmer) using the BriteLite plus luciferase reporter assay system (Perkin-Elmer) after 24 h exposure in a humidified incubator at 37° C. with 5% $CO_2$. In both cell line assays the luciferase expression for compound-treated wells was expressed relative the 0.5% DMSO carrier solvent control. A parallel viability assay was performed with the Cell Titer 96 Non-radioactive Cell Proliferation Assay (Promega) and the data expressed in the same manner as above. Compounds that inhibited ARE expression 20% more than viability, or induced ARE expression more than three-fold were re-tested in a seven-point, two-fold serial dilution dose-response assay (100-1.56 μM). Compounds that displayed activity comparable to the primary screen were assessed for their effect on the expression of Nqo1 by RT-qPCR.

RT-qPCR Validation

In order to validate the ARE modulatory effects of compounds from the primary screen, the expression of the target Nrf2 target gene, Ngo1, was quantified by RT-qPCR. LNCaP and MDA-MB-231-ARE-Luc cells were seeded in 6 well plates at $5 \times 10^5$ and $7 \times 10^5$ cells per well, in EMEM and DMEM media containing 10% FCS and 1% antibiotic-antimycotic (GIBCO) respectively. Cells were allowed to attach overnight before the addition of test compounds. After 24 h exposure in a humidified incubator at 37° C. with 5% $CO_2$, RNA was isolated using the RNeasy kit (Qiagen) and quantified using a NanoDrop spectrophotometer (Thermo Fisher Scientific). cDNA was synthesized from 2 μg of RNA using Oligo(dT)12-18 (Life Technologies) primer and SuperScript II (Thermo Fisher Scientific) on the Mastercycler Gradient PCR machine (Eppendorf) for 1 h at 42° C. following a 10 min denaturation at 65° C. Gene expression was quantified on the 7300 Real Time PCR machine (Applied Biosystems) using TaqMan Gene Expression Master Mix (Thermo Fisher Scientific) and probes for the target gene Nqo1 (Hs02512143_s1, Thermo Fisher Scientific) and reference gene ActB (Hs99999903_m1, Thermo Fisher Scientific). Real time PCR was performed with the following thermal cycle: 1. 50° C. for 2 min; 2. 95° C. for 10 min; 3. 40 cycles of 95° C. for 15 sec followed by 60° C. for 1 min.

Cell Viability Assay

Human colorectal cancer cell lines HCT116, HCT116$^{HIF-1\alpha-/-HIF-2\alpha-/-}$, and HCT 116$^{WT\ KRAS}$ were cultured in Dulbecco's Modified Eagle Medium (DMEM) supplemented with 10% fetal bovine serum and maintained in 5% $CO_2$ at 37° C. The cells were seeded in a 96-well plate (10,000 cells/well) and treated with different concentrations of test compounds or solvent control (0.5% DMSO) after 24 h. Cell viability was measured 48 h following treatment with MTT dye using the manufacturer's protocol (Promega).

Nitric Oxide Assay

Mouse macrophage, RAW264.7 cells were cultured in Dulbecco's Modified Eagle Medium (DMEM) supplemented with 10% fetal bovine serum and maintained in 5% $C_{O2}$ at 37° C. Cells were seeded in 96-well plates (20,000 cells/well) and after 24 h pretreated for 1 hour with different concentrations of test compounds in triplicate or solvent control (0.5% DMSO) before adding LPS (1 μg/mL in PBS). Nitric oxide (NO) production in culture supernatant was assessed after 24 h following treatment by measuring nitrite concentration, an oxidative product of NO. Nitrite production was measured by mixing 50 mL of culture supernatant with 50 mL of Griess reagent (Promega), absorbance measured at 540 nm and NO % calculated against a calibration curve generated for fresh sodium nitrite standard. Cells were used for measuring viability (24 h) as above.

Bacterial Growth Inhibition Assay

Bacterial growth inhibition was determined by screening all yohimbine-derived compounds at 200 µM in 96-well plates. Briefly, 2 µL of a 20 mM DMSO stock solution (test compound) was added to 98 µL of media (tryptic soy broth with 0.5% glucose for *S. aureus*; LB for *A. baumannii*) before each well was treated with an additional 100 µL of inoculated media (giving ~$10^5$ colony forming units per milliliter) prepared from a fresh log-phase culture ($OD_{600}$ of 0.8 to 1.0). The inoculated 96-well plates were then covered and placed in a humidifying chamber and allowed to incubate at 37° C. for 16-18 hours. Bacterial growth was then determined using a spectrophotometer plate reader ($OD_{600}$) to quantify turbidity (growth) in each treated and untreated well of the 96-well plates. Turbidity for treated wells were compared to a 1% v/v DMSO vehicle and recorded in the screening heat map. All compounds were tested in three independent experiments.

Example II. Preparation of Selected Compounds

Figure 8:
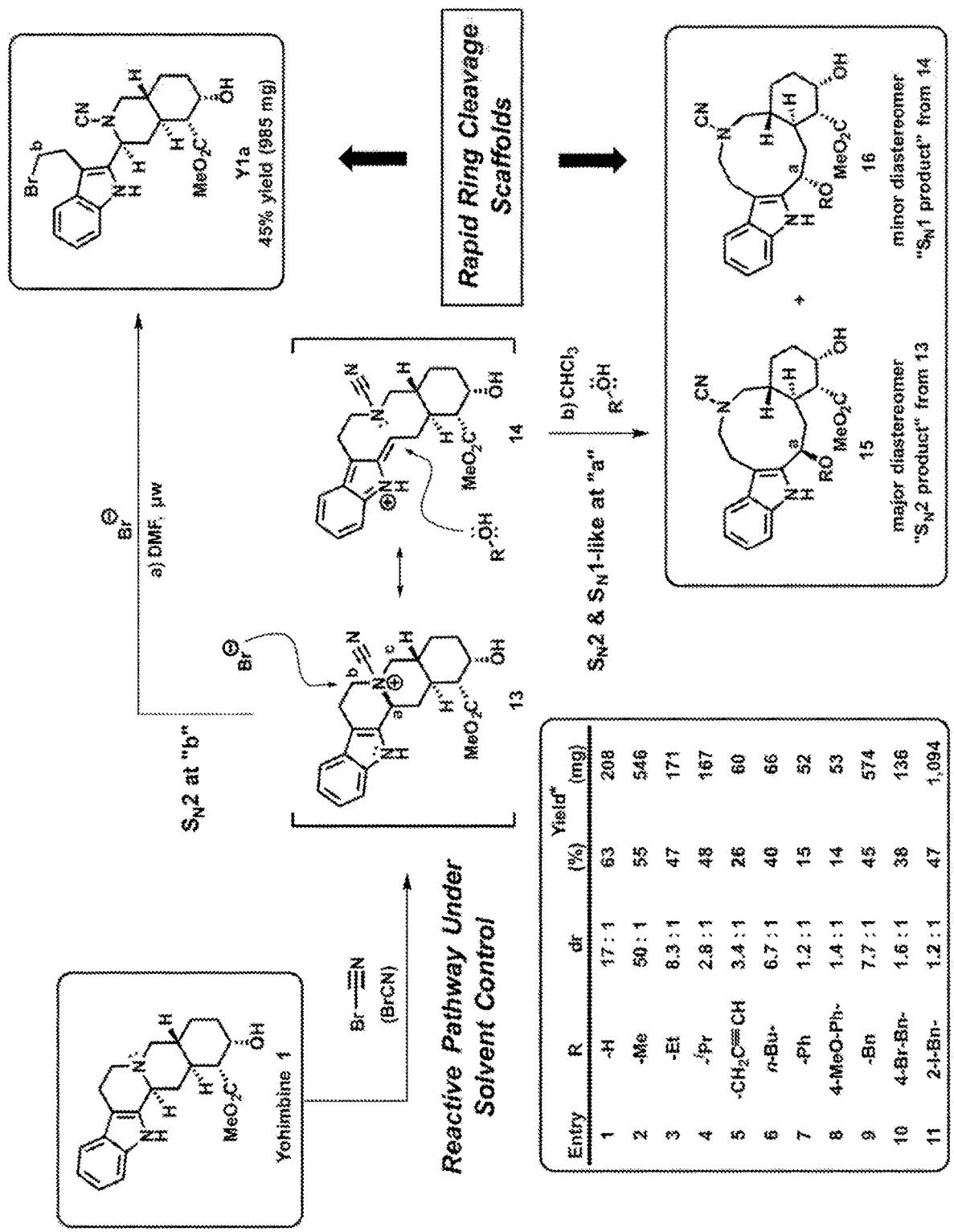
FIG. 8 shows exemplary selective C—N ring cleavage pathways under solvent control using cyanogen bromide.

FIG. 8 shows exemplary selective C—N Ring cleavage pathways under solvent control using cyanogen bromide. Using cyanogen bromide (BrCN), the basic nitrogen of yohimbine 1 was activated to give intermediate 13 (FIG. 8), from which numerous diverted ring-distorted compounds were generated. Two of the C—N bonds of 1 could be selectively cleaved with cyanogen bromide through careful selection of solvent. The table in FIG. 8 indicates the R group of the alcohol solvent used during cyanogen bromide cleavage, the diastereomeric ratio (dr), and percentage and amount yield of the product after treatment with a 3:1 chloroform:alcohol solvent mixture.

Cyanogen bromide C—N ring cleavage of yohimbine 1 proceeds through an $S_N2$ pathway in dimethylformamide (DMF; FIG. 8). The liberated bromide anion generated upon formation of intermediate 13 attacks the most accessible "b" carbon adjacent to the activated central nitrogen of intermediate 13 in only 3 minutes using microwave irradiation resulting in compound Y1a (a compound of Formula (IV')) as the only observed product. This reaction was carried out on a 985 milligram scale (45% yield), which was useful for subsequent analogue synthesis.

Contrasting to the $S_N^2$ pathway, as shown in FIG. 8, a 3:1 chloroform:alcohol solvent mixture results in an $S_N1$-like pathway in which the alcohol is a nucleophile and attacks the "a" carbon of intermediate 13. This reaction has been previously described;[34] however, this reaction was extended by utilizing diverse alcohol solvent/nucleophiles, which react with intermediate 13/14 (resonance structures) to yield diastereomeric mixtures of ethers 15 ("$S_N^2$ product"; inverted stereochemistry at "a") and 16 ("$S_N1$ product"; retention of stereochemistry at "a"). Diastereomers produced from this reaction can be readily separated via chromatography and tested in biological screens. Interestingly, less sterically encumbered alcohols (i.e., methanol) gave "$S_N^2$ products" (i.e., 15) as the major diastereomer (3.4:1 to 50:1 drs; FIG. 8), which can be rationalized by considering that 13 and 14 can permit less hindered nucleophiles to undergo "back-side attack" at carbon "a" of resonance structure 13. Alcohols with more steric bulk (i.e., 2-iodobenzyl alcohol) gave an approximately 1:1 mixtures of diastereomeric products, which can be explained by, but is not limited to, an $S_N1$-like mechanism involving nucleophilic attack of both faces on resonance-stabilized carbocation 14. This ring-cleavage reaction proceeded in 14-63% yield (11 examples yielded 19 ethers) and the major diastereomers were isolated on scales between 6.9 and 576 milligrams, which is useful for additional ring distortion reactions, analogue synthesis and biological screening.

Figures 9A, 9B:
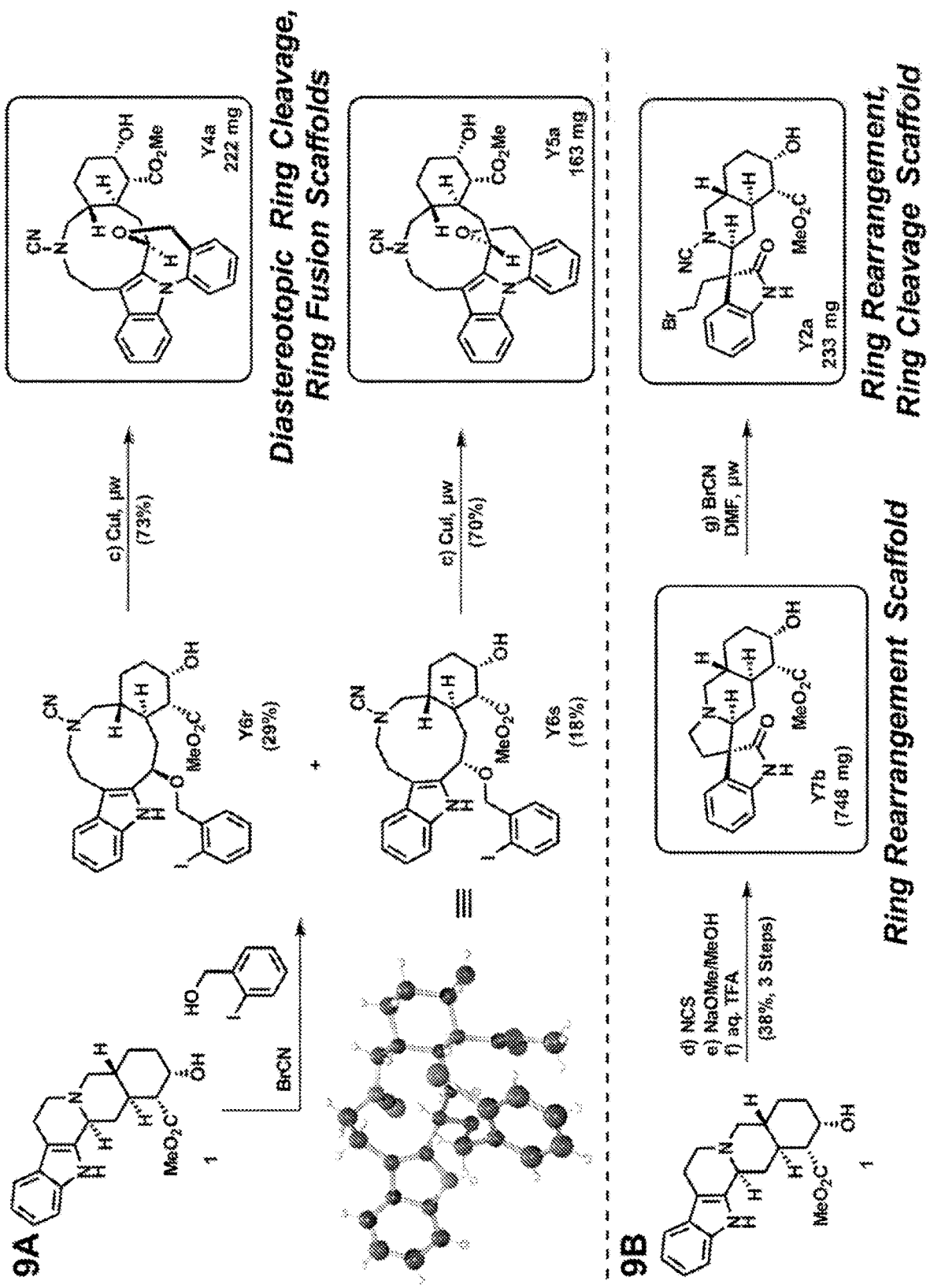
FIG. 9A shows the exemplary synthesis of topologically diverse compounds Y4a and Y5a (compounds of Formula (I-A)) from yohimbine through ring cleavage and ring fusion.
FIG. 9B shows an exemplary synthetic scheme to provide compounds Y2a, a compound of Formula (III-A), and compound Y7a, a compound of Formula (II'), in an exemplary synthetic pathway from yohimbine involving ring rearrangement and ring cleavage.

As shown in FIG. 9A, the lack of diastereocontol of cyanogen bromide/alcohol ring cleavage to generate diverted ring fusion products Y4a and Y5a (compounds of Formula (I-A)), which have unique complex molecular architectures. Yohimbine was initially subjected to cyanogen bromide ring cleavage in chloroform:2-iodobenzyl alcohol to give a 1.2:1 diastereomeric mixture of Y6r and Y6s (47% combined yield) (compounds of Formula (V-A)). The diastereomeric mixture was readily separated and each diastereomer was taken forward and subjected to copper(I) iodide-catalyzed intramolecular C—N coupling between the aryl iodide and indole nitrogen to give diverted ring fusion products Y4a (70%) and Y5a (73%) on a 163-222 milligram scale.

Indole heterocycles can undergo oxidation with subsequent alkyl migration, translating to a ring rearrangement of 1. An oxidative rearrangement such as this allows use of the intrinsic reactivity of the indole ring, which was a critical aspect of the tryptoline ring distortion strategy. A three-step, oxidative-rearrangement of yohimbine to afford ring-rearranged spirooxindole Y7b (FIG. 9B) was previously reported.[41] As shown in FIG. 9B, using N-chlorosuccinimide (NCS) afforded clean chlorination at the 3-position of the indole of yohimbine 1. This was followed by treatment with sodium methoxide (NaOMe) to induce stereospecific alkyl migration and expulsion of the 3-chloro group. Final treatment with trifluoroacetic acid (TFA) afforded ring-rearranged product Y7b (38%/3 steps). 748 milligrams of Y7b were generated in one run through this three step route.

Ring-rearrangement product Y7b was subjected to cyanogen bromide ring cleavage in DMF to afford Y2a as a single product in 52% yield (233 milligrams; FIG. 9B). The propensity of bromide to cleave attack the "b" carbon of Y7b can be rationalized by an $S_N^2$ attack, but is not limited by this theory, of the least sterically encumbered carbon atom of the respective cyanamide intermediate (not shown).

The rapid, tryptoline-based ring distortion pathways developed during these investigations were highly efficient in the generation of several new scaffolds in 1 to 4 steps from yohimbine 1. During these investigations, multiple C—N bonds to the central nitrogen atom of yohimbine 1 were selectively cleaved with cyanogen bromide, an oxidative rearrangement of the indole heterocycle of yohimbine 1 was utilized and C—N bond coupling reactions were used in ring fusion reactions to generate diverted complex scaffolds. Overall, this tryptoline ring-distortion platform enabled the rapid synthesis of novel complex and diverse chemotypes that are important to biological screening and drug discovery efforts.

Figure 10:
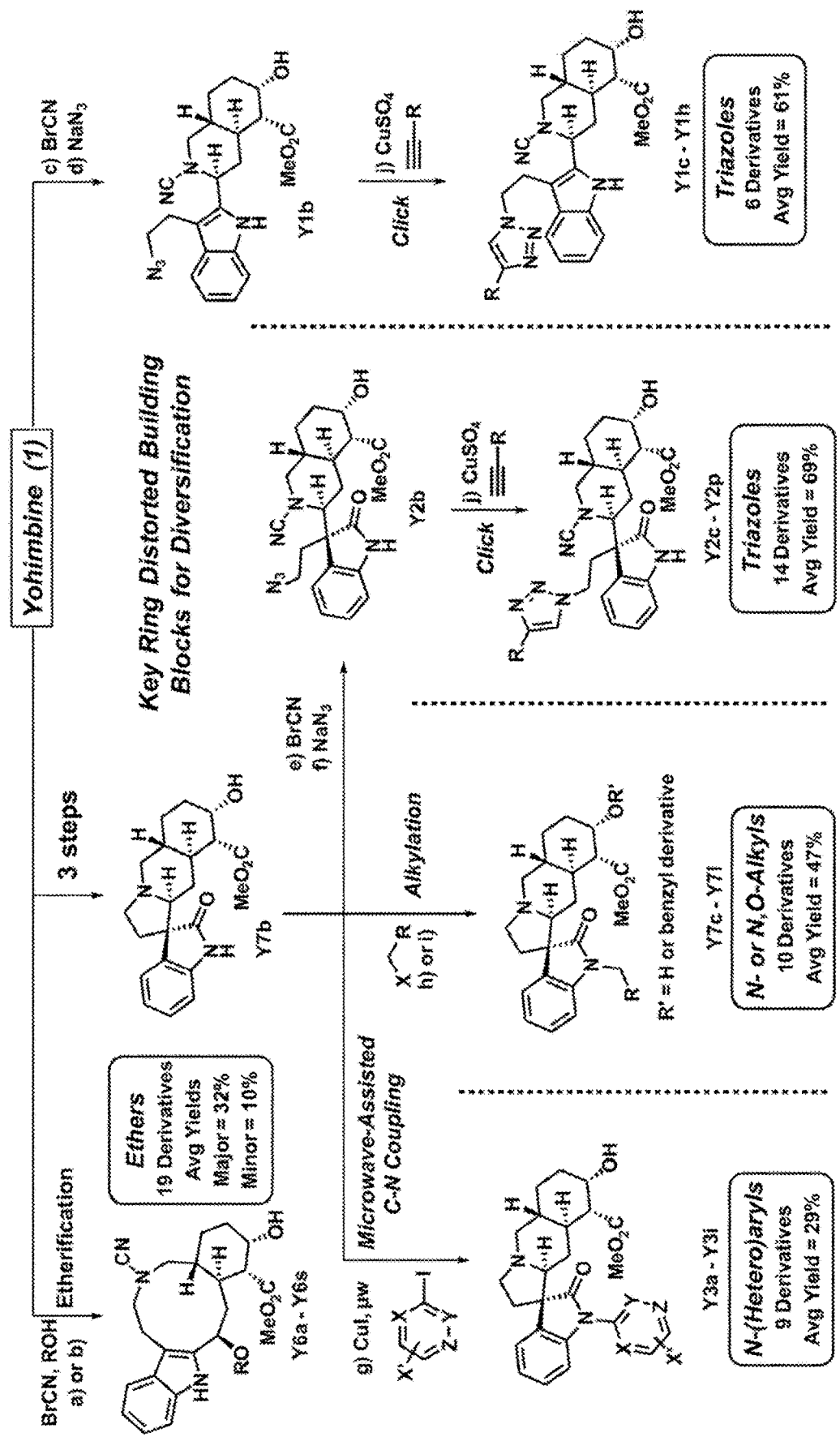
FIG. 10 shows the exemplary synthesis of yohimbine derivatives via ring distortion, C—N coupling, alkylation, or click reactions of intermediates derived from yohimbine.

As shown in FIG. 10, given the synthetic utility of cyanogen bromide in ring cleavage reactions, multiple ring-cleaved compounds contained primary bromides (Y1a and Y2a) which were subjected to sodium azide displacement ($S_N^2$) to yield azides Y1b and Y2b, respectively (FIG. 10). Each azide was then subjected to copper(I)-catalyzed click reactions with a diverse panel of available terminal alkynes to generate two diverse triazole sub-libraries (Y1c-Y1h, 6 examples, 61% average yield; Y2c-Y2p, 14 examples, 69% average yield).

Ring-rearranged compound Y7b was very useful in diverted library synthesis due to the amide and hydroxyl functional groups readily available as synthetic handles. Ten mono- or dialkylated products of Y7b were synthesized with available alkyl halides (Y7c-Y7l, 47% average yield;

Scheme 2). Y7b was also diversified using copper(I)-catalyzed C—N coupling between the amide nitrogen and nine diverse (hetero)aryl iodides (29% average yield).

Chemical Synthesis and Characterization

Scheme 1. Synthesis of Compounds Y3a-Y3i (Compounds of Formula (II'))

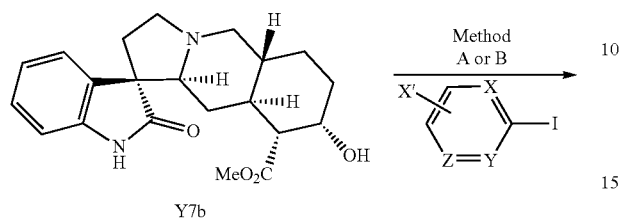

Y7b

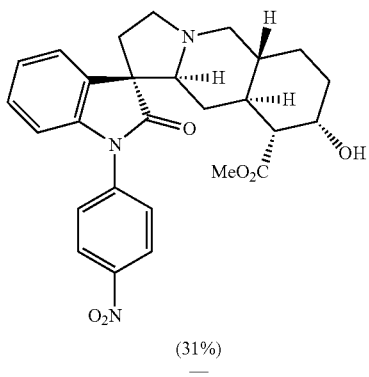

9 N-(hetero)aryl derivatives
Y3a - Y3i

Method A: Microwave-Assisted C—N Coupling CuI, μw, 160° C., 12 mins (Avg Yield = 29%)

Method B: Oil Bath C—N Coupling CuI, reflux, 16 h (Avg Yield = 14%)

Y3a (26%)
(40%)

Y3b

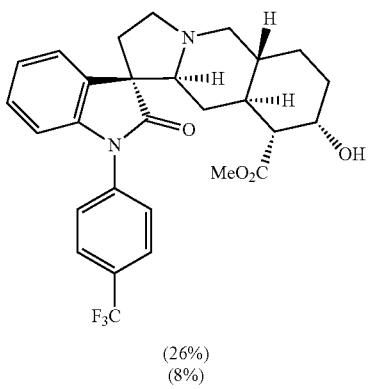

(24%)
(0%)

Y3c (31%)
—

Y3d

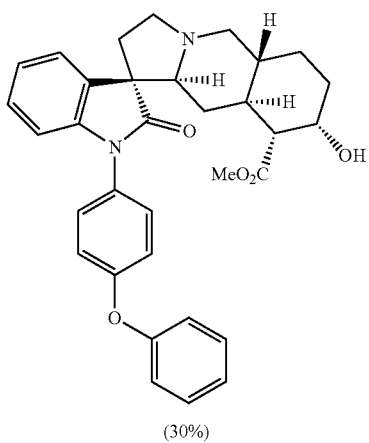

(26%)
(8%)

Y3e (30%)
—

Y3f

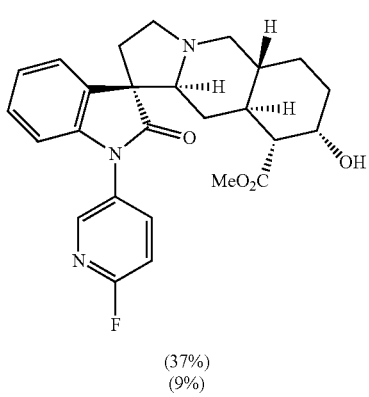

(37%)
(9%)

153
-continued
Y3g
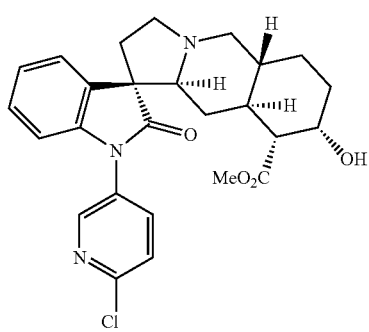
(25%)
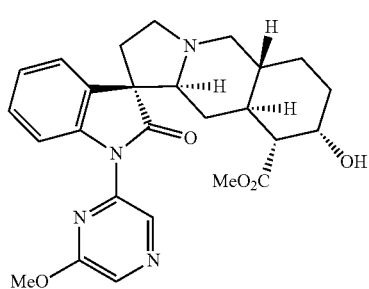
(27%)
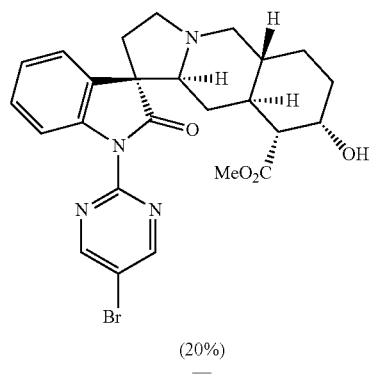
(20%)
Scheme 2. Synthesis of Compounds Y2c-Y2p (Compounds of Formula (III-A))
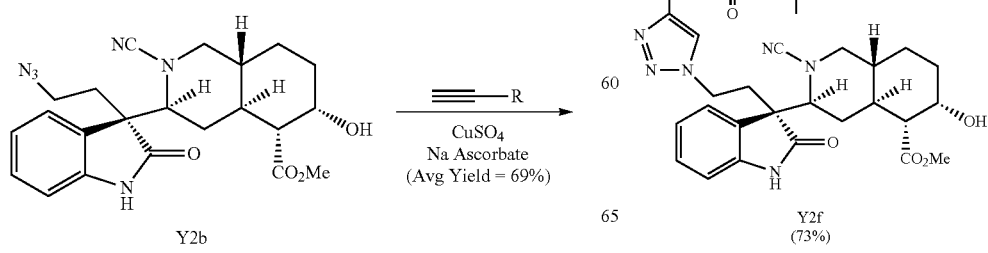
154
-continued
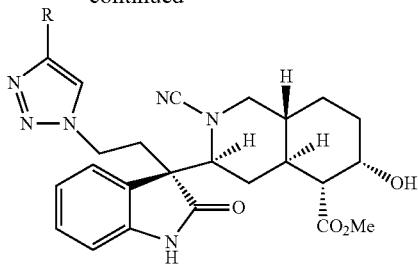
14 triazole derivatives
Y2c-Y2p
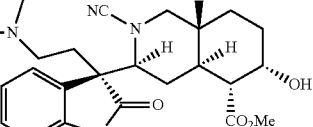
Y2c
(75%)
Y3h
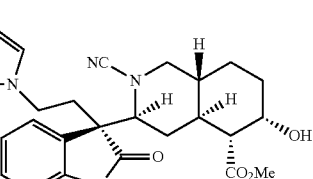
Y2d
(75%)
Y3i
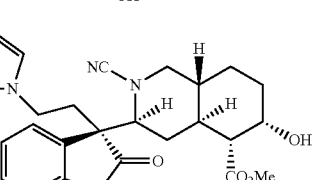
Y2e
(71%)
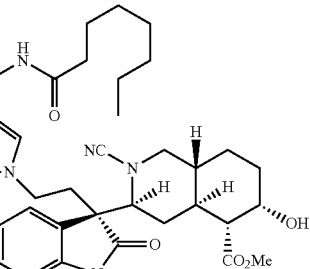
Y2f
(73%)

-continued
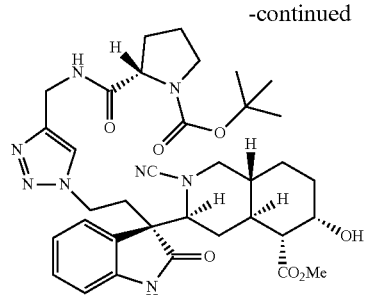
Y2g
(50%)
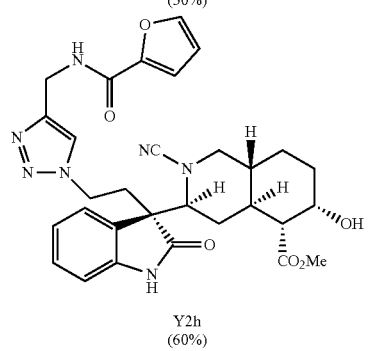
Y2h
(60%)
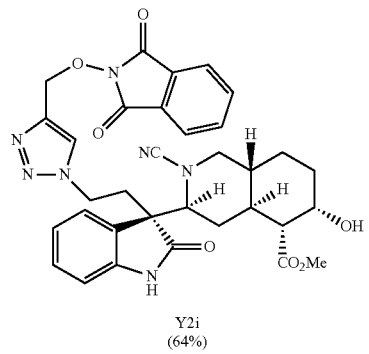
Y2i
(64%)
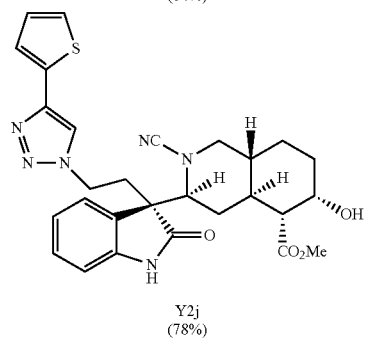
Y2j
(78%)
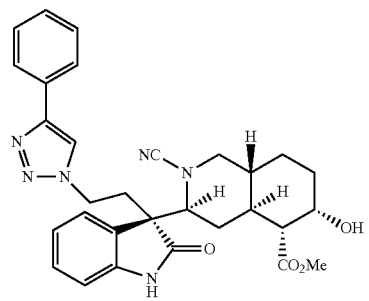
Y2k
(76%)
-continued
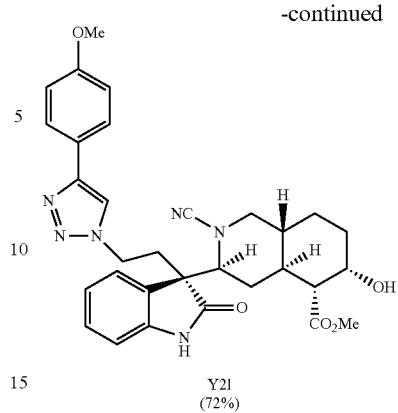
Y2l
(72%)
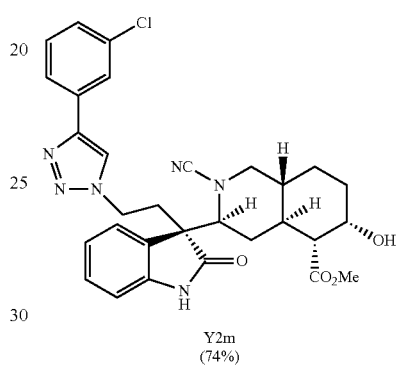
Y2m
(74%)
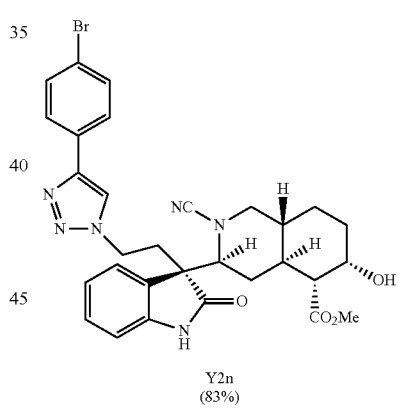
Y2n
(83%)
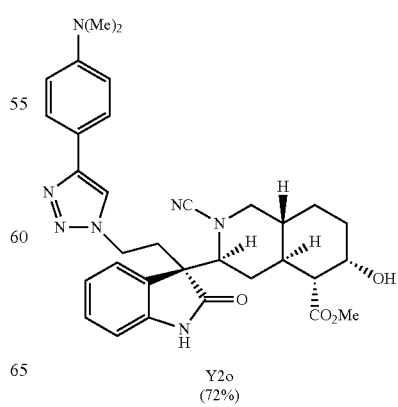
Y2o
(72%)

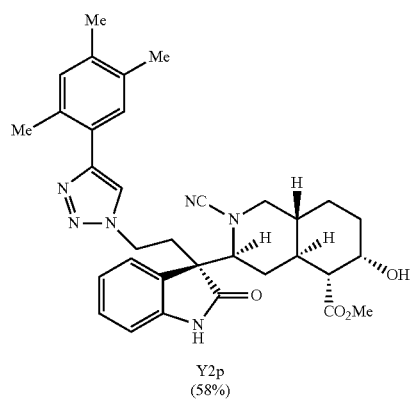
Y2p
(58%)
Scheme 3. Synthesis of Compounds Y1c-Y1h (Compounds of Formula (IV'))
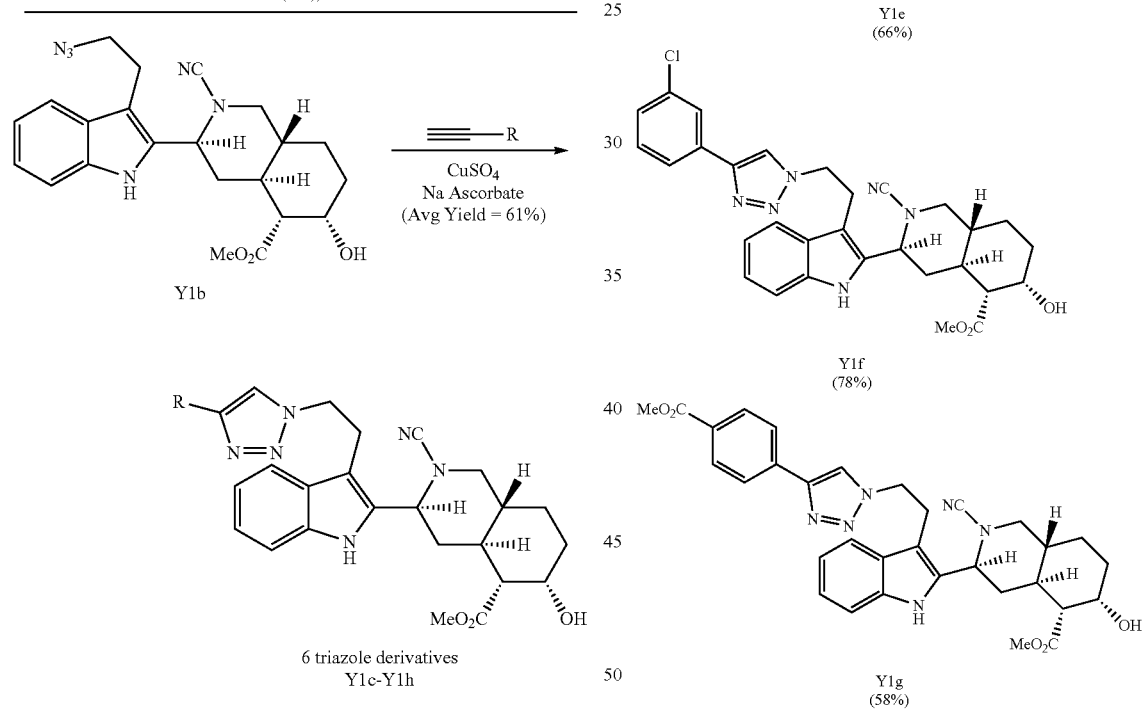
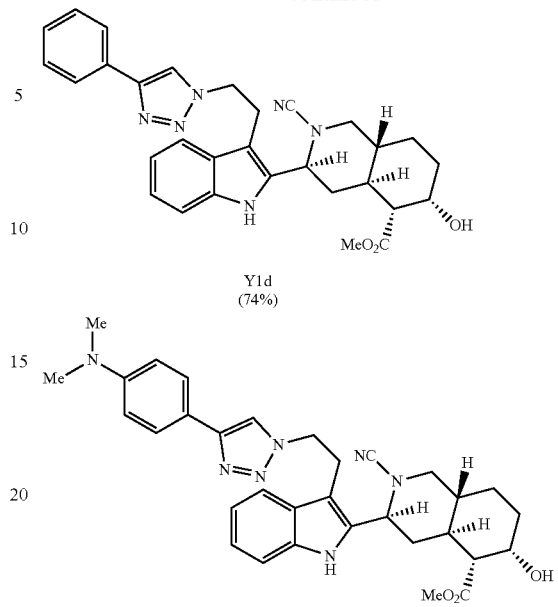
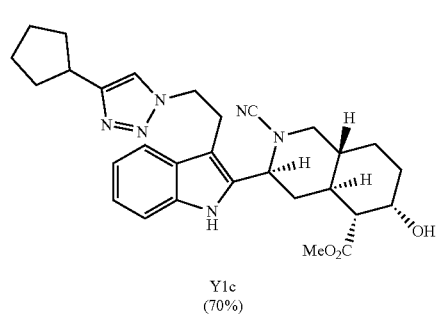

Scheme 4. Synthesis of Compounds Y6a-Y6s (Compounds of Formula (V-A))
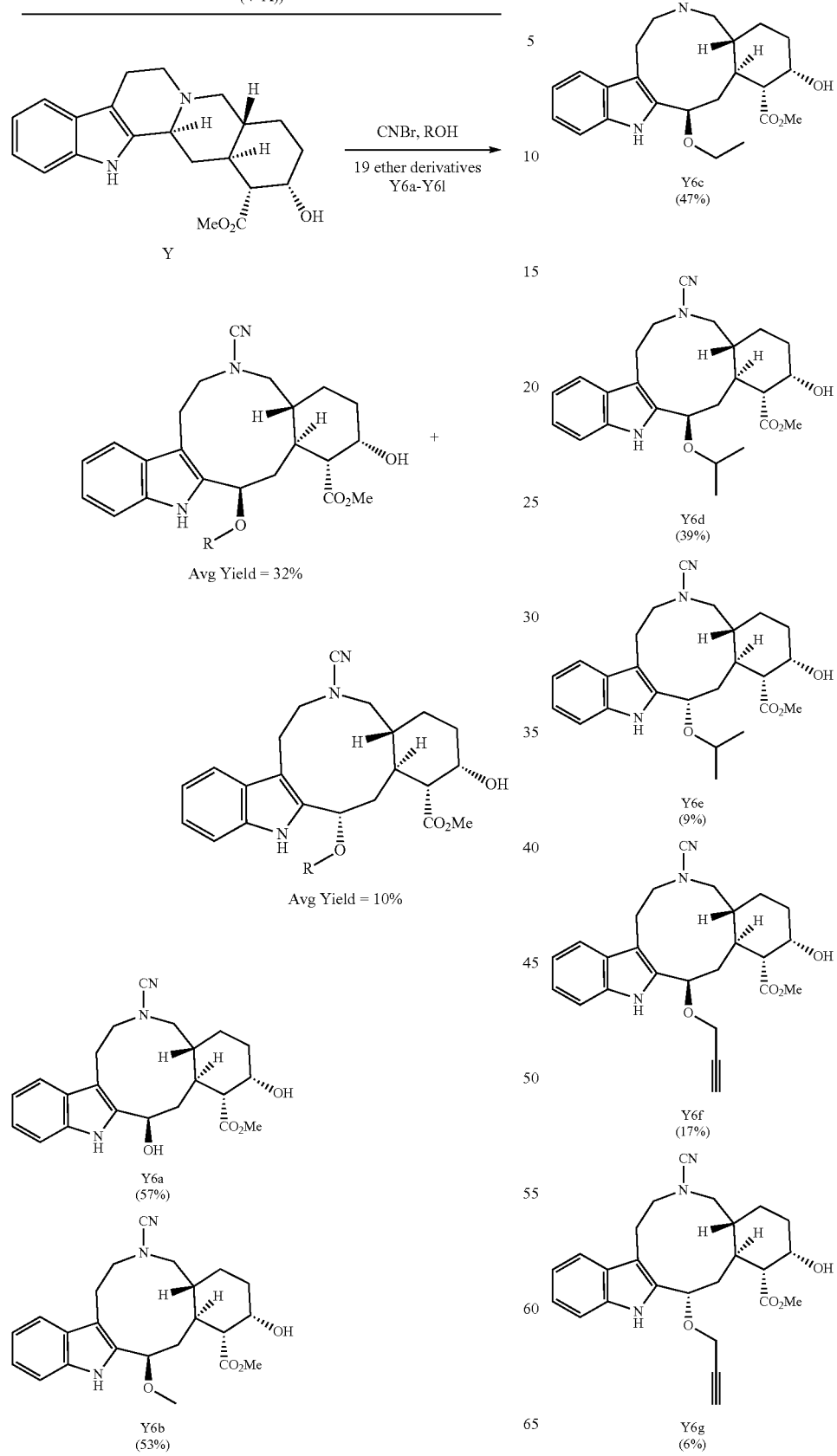

-continued
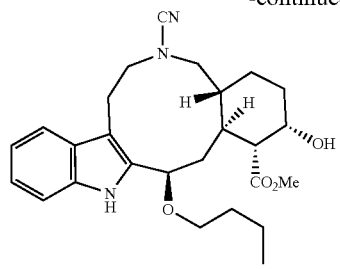
Y6h
(34%)
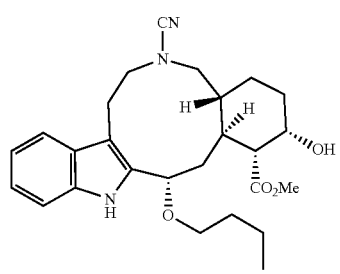
Y6i
(6%)
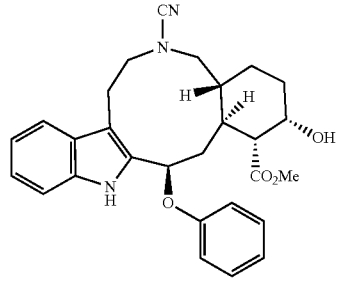
Y6j
(7%)
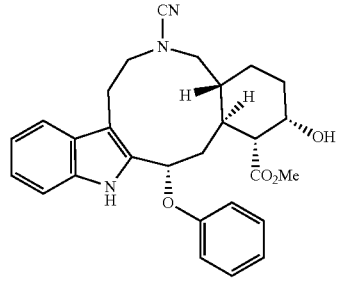
Y6k
(7%)
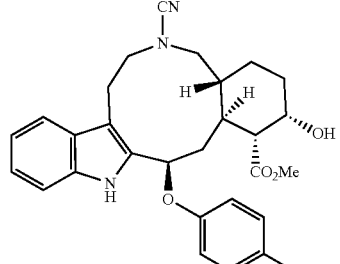
Y6l
(7%)
-continued
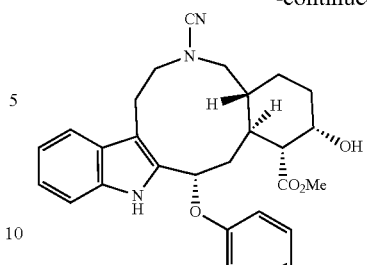
Y6m
(7%)
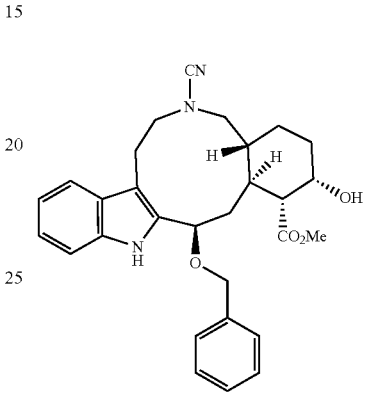
Y6n
(37%)
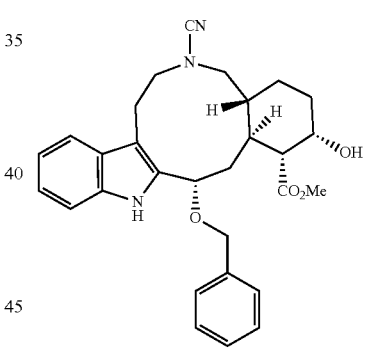
Y6o
(8%)
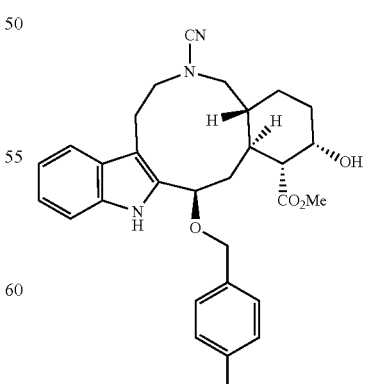
Y6p
(20%)

-continued
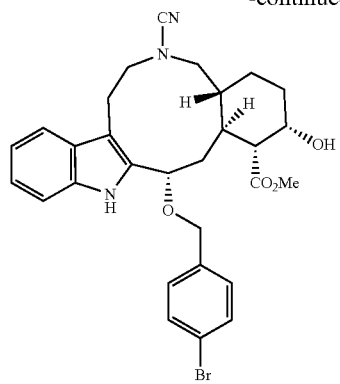
Y6q
(16%)
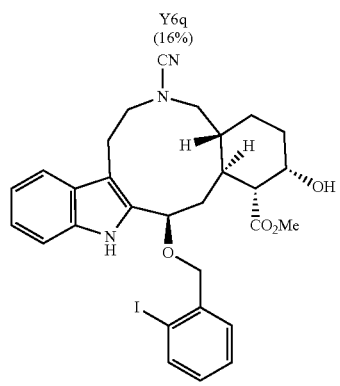
Y6r
(29%)
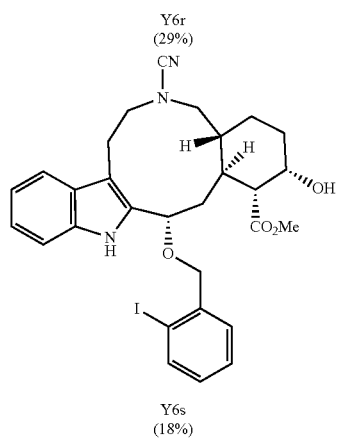
Y6s
(18%)
Yohimbine (Y): Tabulated Data with Key $^1$H and $^{13}$C Signals Labeled for Reference:
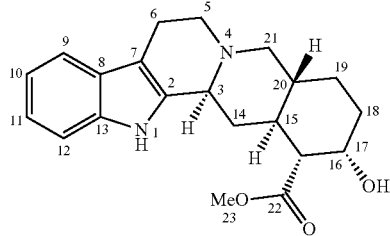
Y
$^1$H NMR: (400 MHz, CDCl$_3$) δ 7.80 (s, 1H), 7.47 (dd, J=7.5, 1.4 Hz, 1H), 7.30 (d, J=7.9 Hz, 1H), 7.13 (td, J=7.2, 1.4 Hz, 1H), 7.08 (td, J=7.4, 1.2 Hz, 1H), 4.23 (m, 1H), 3.81 (s, 3H), 3.32 (dd, J=11.4, 2.3 Hz, 1H), 3.08 (ddd, J=11.1, 5.9, 1.3 Hz, 1H), 3.04-2.90 (m, 2H), 2.71 (dd, J=15.2, 4.0 Hz, 1H), 2.62 (td, J=11.1, 4.3 Hz, 1H), 2.35 (dd, J=11.5, 2.1 Hz, 1H), 2.24 (t, J=10.5 Hz, 1H), 2.09-1.94 (m, 3H), 1.64-1.49 (m, 3H), 1.42 (m, 1H), 1.36 (q, J=11.9 Hz, 1H). $^{13}$C NMR: (100 MHz, CDCl$_3$) δ 175.8, 136.2, 134.7, 127.6, 121.6, 119.6, 118.3, 110.9, 108.5, 67.2, 61.5, 60.1, 53.1, 52.6, 52.2, 41.0, 36.9, 34.5, 31.7, 23.5, 21.9.
Key signals and correlations for Y
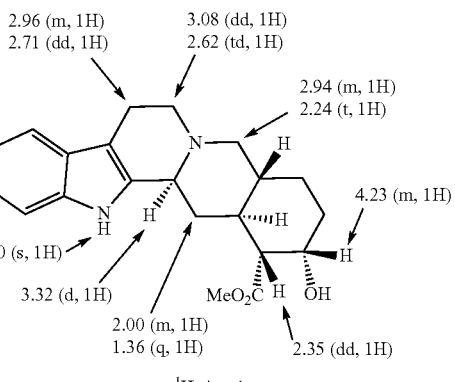
$^1$H signals
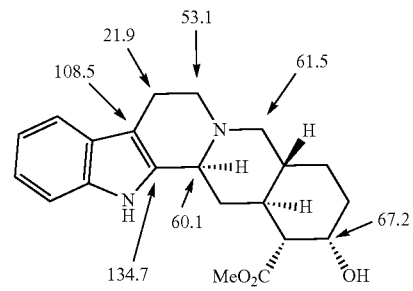
Key $^{13}$C signals
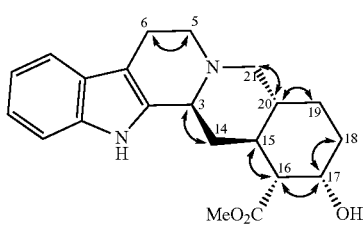
COSY correlations Key signals and correlations for Y

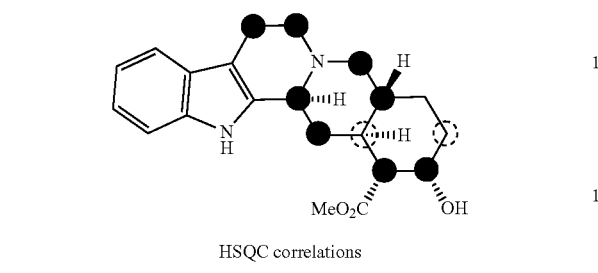

HSQC correlations

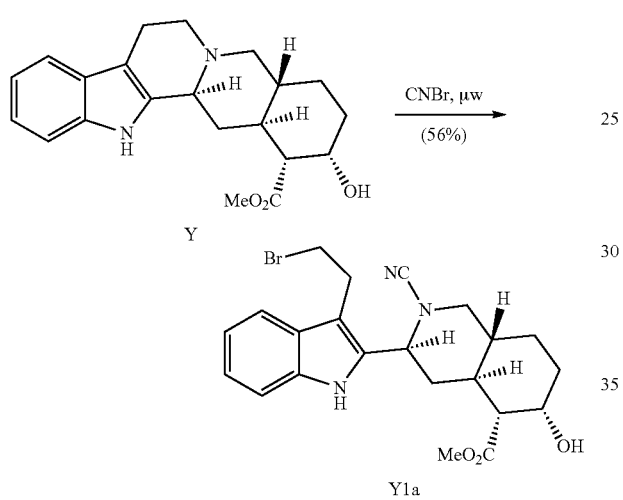

Procedure for the synthesis of Y1a: Y (435 mg, 1.23 mmol) was added to a flame-dried microwave flask and subsequently dissolved in N,N-dimethylformamide (17 mL). A 3M solution of cyanogen bromide in dichloromethane (1.23 mL, 3.68 mmol) was added drop wise to the resulting solution. The reaction was subjected to microwave irradiation at 100° C. for two minutes and forty-five seconds. The reaction was cooled to room temperature, diluted with ethyl acetate and quenched by addition of brine (3×100 mL). The ethyl acetate layer was dried with sodium sulfate, filtered and concentrated under reduced pressure. The crude material was purified via column chromatography using a gradient of 100% hexanes to 1:1 hexanes:ethyl acetate to 100% ethyl acetate to afford Y1a (316 mg, 56%) as a colorless solid. Note: This reaction was scaled up from Y (1.70 g, 4.79 mmol) to afford Y1a (985 mg, 45%).

$^1$H NMR: (400 MHz, CDCl$_3$) δ 8.17 (s, 1H), 7.55 (d, J=8.0 Hz, 1H), 7.34 (d, J=8.0 Hz, 1H), 7.22 (td, J=7.1, 1.0 Hz, 1H), 7.13 (td, J=7.4, 1.0 Hz, 1H), 4.44 (ddd, J=12.0, 2.2, 2.8, 0.4 Hz, 1H), 4.22 (m, 1H), 3.72-3.56 (m, 2H), 3.66 (s, 3H), 3.50 (dd, J=12.3, 3.1 Hz, 1H), 3.41 (m, 1H), 3.31 (m, 1H), 3.18 (s, 1H), 3.07 (t, J=11.3 Hz, 1H), 2.31 (d, J=11.1 Hz, 1H), 2.12 (q, J=11.2 Hz, 1H), 2.04 (dd, J=13.4, 2.5 Hz, 1H), 1.89 (dt, J=13.5, 2.6 Hz, 1H), 1.66 (q, J=12.4 Hz, 1H), 1.60-1.44 (m, 4H). $^{13}$C NMR: (100 MHz, CDCl$_3$) δ 175.2, 136.1, 131.0, 127.3, 123.4, 120.3, 119.0, 116.7, 113.1, 111.6, 66.3, 56.4, 55.7, 52.3, 51.9, 39.6, 36.5, 36.2, 33.0, 31.0, 28.5, 22.5. HRMS (ESI): calc. for $C_{22}H_{26}BrN_3O_3Na$ [M+Na]$^+$: 482.1050, found: 482.1038. MP: 171-173° C.

Key signals for Y1a

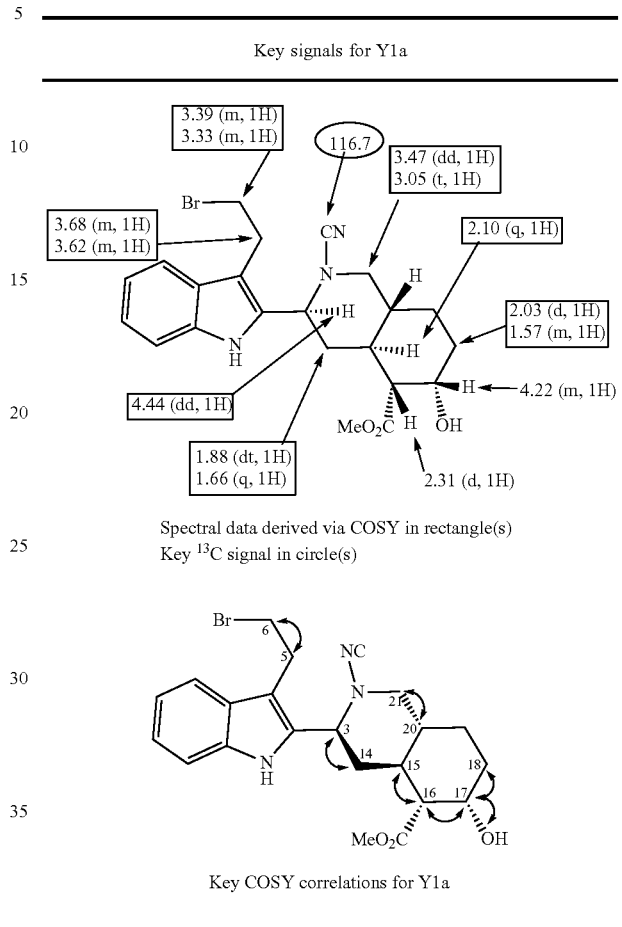

Spectral data derived via COSY in rectangle(s)
Key $^{13}$C signal in circle(s)

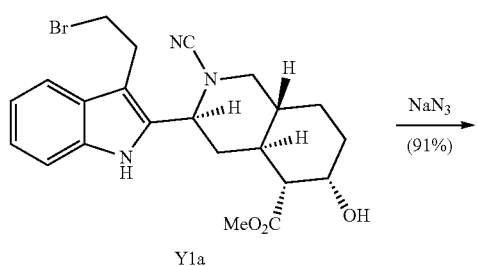

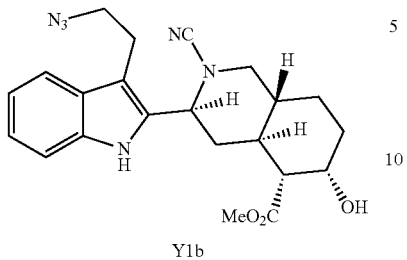

Y1b

Procedure for the synthesis of Y1b: Y1a (243 mg, 0.53 mmol) was added to a round-bottom flask and dissolved in N,N-dimethylformamide (9 mL). Sodium azide (86 mg, 1.32 mmol) was added and the reaction was stirred at room temperature and slowly warmed to 75° C. for 22 hours. The reaction was cooled to room temperature, diluted with ethyl acetate and quenched with brine (3×100 mL). The organic layer was dried with sodium sulfate, filtered and concentrated. The crude product was purified via column chromatography using a gradient of 100% hexanes to 1:1 hexanes: ethyl acetate to 100% ethyl acetate to afford Y1b (203 mg, 91%) as a pale-yellow foam. $^1$H NMR: (400 MHz, CDCl$_3$) δ 7.96 (d, J=8.0 Hz, 1H), 7.51 (d, J=8.0 Hz, 1H), 7.29 (t, J=8.9 Hz, 1H), 7.22 (t, J=7.6 Hz, 1H), 4.53 (dd, J=11.6, 3.4 Hz, 1H), 4.32 (br. s, 1H), 4.23 (s, 1H), 3.91 (dd, J=13.7, 4.4 Hz, 1H), 3.76 (s, 3H), 3.56-3.48 (m, 2H), 2.96-2.88 (m, 2H), 2.78 (dd, J=13.6, 11.2 Hz, 1H), 2.27-2.09 (m, 3H), 1.99 (m, 1H), 1.61 (m, 1H), 1.55-1.42 (m, 2H), 1.28 (m, 1H), 1.14 (q, J=11.9 Hz, 1H). Note: $^1$H spectrum referenced TMS at 0.00 ppm. $^{13}$C NMR: (100 MHz, CDCl$_3$) δ 175.1, 150.6, 137.2, 132.5, 130.6, 123.1, 121.8, 118.8, 112.0, 105.2, 66.5, 54.9, 52.2, 51.9, 51.5, 45.9, 39.9, 35.7, 35.2, 31.2, 24.3, 22.7.$^1$H NMR: (400 MHz, d$_6$-DMSO) δ 8.04 (d, J=7.9 Hz, 1H), 7.62 (d, J=7.8 Hz, 1H), 7.21 (t, J=7.4 Hz, 1H), 7.16 (t, J=7.4 Hz, 1H), 6.37 (br. s, 1H), 4.71 (dd, J=11.5, 4.4 Hz, 1H), 4.71 (dd, J=13.5, 3.4 Hz, 1H), 4.11 (m, 1H), 4.02 (dd, J=13.6, 4.2 Hz, 1H), 3.61 (s, 3H), 3.57 (dd, J=6.6, 6.6 Hz, 2H), 3.00-2.84 (m, 2H), 2.71 (t, J=12.3 Hz, 1H), 2.37 (dt, J=12.3, 3.4 Hz, 1H), 2.26 (dd, J=11.4, 2.7 Hz, 1H), 2.05 (qd, J=11.1, 2.8 Hz, 1H), 1.76 (dd, J=13.1, 1.9 Hz, 1H), 1.55 (tt, J=12.8, 2.5 Hz, 1H), 1.44 (qd, J=12.9, 1.6 Hz, 1H), 1.33 (m, 1H), 1.19 (m, 1H), 0.93 (q, J=11.9 Hz, 1H). HRMS (ESI): calc. for C$_{22}$H$_{27}$N$_6$O$_3$ [M+H]$^+$: 423.2139, found: 423.2143. MP: 53-55° C., decomposed.

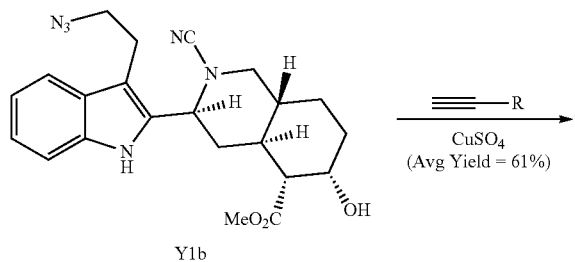

Y1b

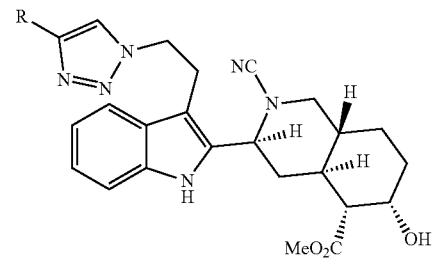

General procedure for the preparation of Y1c-Y1h: Anhydrous copper sulfate (4.4 mg, 0.03 mmol) and sodium ascorbate (17.0 mg, 0.09 mmol) were added to a vial and dissolved in a solution of tert-butanol:H$_2$O (1:2). This solution was then added to a round-bottom flask containing Y1b (24.7 mg, 0.06 mmol). Cyclopentylacetylene (20 μL, 0.18 mmol) was added, followed by dichloromethane (0.7 mL). The reaction was vigorously stirred at room temperature for 4.5 hours until starting material was fully consumed as determined by TLC analysis. The biphasic mixture was quenched with brine and the product was extracted with dichloromethane. The organics were collected, dried with sodium sulfate, filtered and concentrated. Crude product was purified via column chromatography using a gradient of 100% hexanes to 1:1 hexanes:ethyl acetate to 100% ethyl acetate to afford Y1c (21.1 mg, 70%) as a colorless solid.

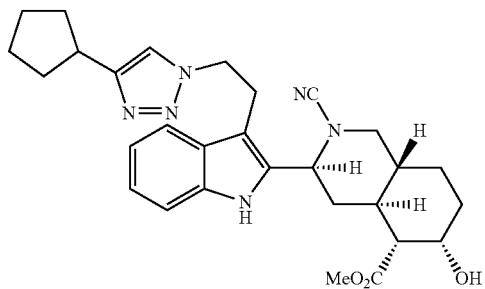

Y1c

Yield: 70%; 21.1 mg of Y1c isolated as a colorless solid. $^1$H NMR: (400 MHz, CDCl$_3$) δ 7.97 (d, J=8.1 Hz, 1H), 7.43 (d, J=8.1 Hz, 1H), 7.30 (t, J=7.5 Hz, 1H), 7.23 (t, J=7.5 Hz, 1H), 6.78 (s, 1H), 4.59 (dt, J=13.2, 6.5 Hz, 1H), 4.49 (dt, J=13.2, 6.5 Hz, 1H), 4.21 (m, 1H), 4.16 (dd, J=11.6, 3.5 Hz, 1H), 3.89 (dd, J=13.3, 4.3 Hz, 1H), 3.82 (s, 3H), 3.66 (br. s, 1H), 3.28-3.21 (m, 2H), 3.06 (p, J=8.2 Hz, 1H), 2.76 (dd, J=13.9, 11.4 Hz, 1H), 2.19 (dd, J=11.3, 1.9 Hz, 2H), 2.10 (qd, J=11.1, 2.6 Hz, 1H), 2.04-1.91 (m, 4H), 1.72-1.42 (m, 7H), 1.32-1.17 (m, 2H), 0.94 (q, J=11.9 Hz, 1H). $^{13}$C NMR: (100 MHz, CDCl$_3$) δ 175.2, 152.6, 150.6, 137.6, 132.2, 130.7, 123.4, 122.1, 120.5, 118.7, 112.2, 104.5, 66.6, 54.8, 52.4, 52.3, 50.2, 46.0, 40.1, 36.8, 35.3, 33.5, 33.4, 31.1, 26.0, 25.3, 22.9. HRMS (ESI): calc. for C$_{29}$H$_{37}$N$_6$O$_3$[M+H]$^+$: 517.2922, found: 517.2916. MP: 175-177° C.

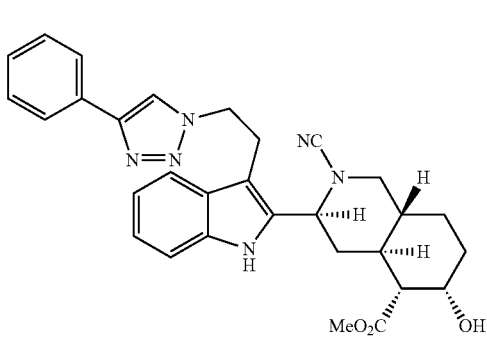

Y1d

Yield: 74%; 14.9 mg of Y1d isolated as a pale-yellow solid. $^1$H NMR: (400 MHz, CDCl$_3$) δ 8.01 (d, J=8.2 Hz, 1H), 7.70 (d, J=7.4 Hz, 2H), 7.54 (d, J=7.9 Hz, 1H), 7.38 (t, J=7.3 Hz, 2H), 7.36-7.23 (m, 4H), 4.72-4.62 (m, 2H), 4.26 (dd, J=11.7, 3.6 Hz, 1H), 4.19 (m, 1H), 3.86 (s, 3H), 3.83 (m, 1H, partially buried), 3.41-3.23 (m, 2H), 2.72 (dd, J=13.2, 12.2 Hz, 1H), 2.14-2.03 (m, 2H), 2.01-1.88 (m, 2H), 1.59 (m, 1H), 1.51-1.38 (m, 2H), 1.36-1.10 (m, 3H), 0.88 (q, J=11.5 Hz, 1H). Note: $^1$H spectrum referenced TMS at 0.00 ppm. $^{13}$C NMR: (100 MHz, CDCl$_3$) δ 175.2, 150.6, 147.8, 137.9, 132.1, 130.9, 130.7, 129.0, 128.3, 125.9, 123.5, 122.2, 120.4, 118.7, 112.4, 104.2, 66.7, 54.9, 52.5, 52.2, 50.3, 46.0, 40.0, 35.3, 35.3, 31.1, 26.2, 22.8. HRMS (ESI): calc. for C$_{30}$H$_{33}$N$_6$O$_3$ [M+H]$^+$: 525.2609, found: 525.2616. MP: 103-105° C.

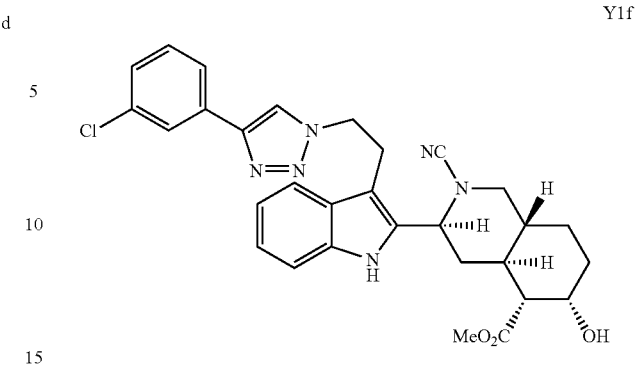

Y1f

Yield: 78%; 27.9 mg of Y1f isolated as a pale-yellow foam. $^1$H NMR: (400 MHz, CDCl$_3$) δ 7.99 (d, J=8.3 Hz, 1H), 7.71 (t, J=1.8 Hz, 1H), 7.54 (dt, J=7.3, 1.6 Hz, 1H), 7.50 (d, J=7.9 Hz, 1H), 7.35-7.21 (m, 5H), 4.66 (td, J=6.8, 3.5 Hz, 2H), 4.26 (dd, J=11.6, 3.7 Hz, 1H), 4.20 (m, 1H), 3.85 (s, 3H), 3.83 (dd, J=11.6, 3.7 Hz, 1H, buried), 3.63 (br. s, 1H), 3.36-3.26 (m, 2H), 2.71 (dd, J=13.6, 11.2 Hz, 1H), 2.14-1.88 (m, 4H), 1.57 (m, 1H), 1.52-1.39 (m, 2H), 1.22 (m, 1H), 0.82 (q, J=12.5 Hz, 1H). $^{13}$C NMR: (100 MHz, CDCl$_3$) δ 175.0, 150.5, 146.4, 137.8, 134.9, 132.4, 132.1, 130.8, 130.3, 128.3, 125.9, 123.9, 123.5, 122.2, 120.8, 118.6, 112.4, 104.1, 66.7, 54.9, 52.4, 52.2, 50.4, 46.0, 39.9, 35.3, 35.2, 31.2, 26.1, 22.8. HRMS (ESI): calc. for C$_{30}$H$_{32}$ClN$_6$O$_3$ [M+H]$^+$: 559.2219, found: 559.2215. MP: 70-72° C.

Y1e

Yield: 66%; 26.2 mg of Y1e isolated as a yellow solid. $^1$H NMR: (400 MHz, CDCl$_3$) δ 7.99 (d, J=8.2 Hz, 1H), 7.56 (d, J=8.7 Hz, 2H), 7.53 (d, J=8.0 Hz, 1H), 7.32 (t, J=7.6 Hz, 1H), 7.25 (t, J=7.6 Hz, 1H), 7.22 (s, 1H), 6.71 (d, J=8.7 Hz, 2H), 4.61 (t, J=6.5 Hz, 2H), 4.24 (dd, J=12.4, 3.5 Hz, 1H), 4.19 (m, 1H), 3.84 (s, 3H), 3.82 (dd, J=12.4, 4.0 Hz, 1H, partially buried), 3.65 (br. s, 1H), 3.29 (td, J=6.9, 2.9 Hz, 2H), 2.96 (s, 6H), 2.71 (dd, J=13.8, 12.1 Hz, 1H), 2.16-2.00 (m, 2H), 1.99-1.90 (m, 2H), 1.56 (m, 1H), 1.44 (tt, J=13.0, 2.4 Hz, 2H), 1.24 (m, 1H), 0.88 (q, J=11.2 Hz, 1H). 1$^{13}$C NMR: (100 MHz, CDCl$_3$) δ 175.2, 150.6, 150.5, 148.2, 137.8, 132.2, 130.8, 126.8, 123.4, 122.2, 118.9, 118.9, 118.7, 112.6, 112.3, 104.4, 66.7, 54.9, 52.5, 52.2, 50.2, 46.0, 40.7, 40.0, 35.3, 35.2, 31.1, 26.1, 22.8. HRMS (ESI): calc. for C$_{32}$H$_{38}$N$_7$O$_3$ [M+H]$^+$: 568.3031, found: 568.3041. MP: 200-202° C.

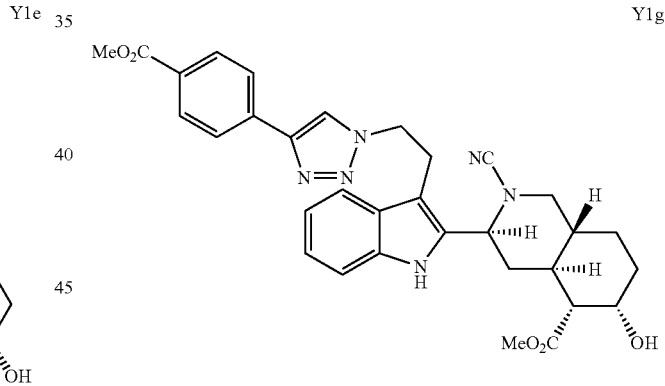

Y1g

Yield: 58%; 22.6 mg of Y1g isolated as a pale-yellow solid. $^1$H NMR: (400 MHz, CDCl$_3$) δ 7.90 (d, J=7.9 Hz, 2H), 7.86 (d, J=8.2 Hz, 1H), 7.62 (d, J=7.9 Hz, 2H), 7.36 (d, J=7.7 Hz, 1H), 7.18 (td, J=7.3, 0.8 Hz, 1H), 7.12 (s, 1H), 7.10 (td, J=7.4, 0.6 Hz, 1H), 4.57-4.50 (m, 2H), 4.12 (dd, J=11.4, 2.7 Hz, 1H), 4.06 (m, 1H), 3.77 (s, 3H), 3.71 (s, 3H), 3.68 (dd, J=13.1, 4.6 Hz, 1H, partially buried), 3.35 (br. s, 1H), 3.23-3.10 (m, 2H), 2.57 (dd, J=14.0, 11.5 Hz, 1H), 1.97-1.91 (m, 2H), 1.86-1.75 (m, 2H), 1.42 (m, 1H), 1.36-1.24 (m, 2H), 1.11 (m, 1H), 0.78 (q, J=11.8 Hz, 1H). $^{13}$C NMR: (100 MHz, CDCl$_3$) δ 175.1, 166.9, 150.5, 146.7, 137.9, 134.9, 132.0, 130.9, 130.4, 129.7, 125.6, 123.5, 122.2, 121.3, 118.6, 112.5, 104.1, 66.7, 54.9, 52.5, 52.4, 52.2, 50.4, 46.0, 39.9, 35.3, 35.2, 31.1, 26.1, 22.8. HRMS (ESI): calc. for C$_{32}$H$_{35}$N$_6$O$_5$ [M+H]$^+$: 583.2663, found: 583.2653. MP: 201-203° C.

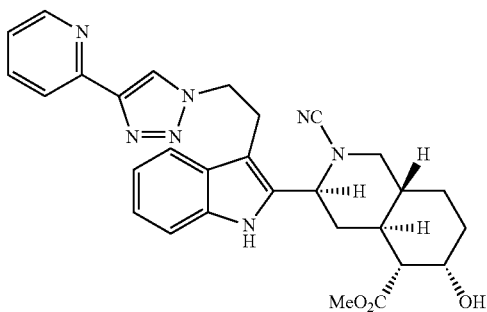

Y1h

Yield: 19%; 6.0 mg of Y1h isolated as a colorless solid. $^1$H NMR: (400 MHz, CDCl$_3$) δ 8.51 (ddd, J=4.9, 2.0, 0.9 Hz, 1H), 8.13 (dt, J=8.2, 0.8 Hz, 1H), 7.98 (d, J=8.0 Hz, 1H), 7.81 (s, 1H), 7.77 (td, J=8.0, 1.7 Hz, 1H), 7.54 (d, J=7.8 Hz, 1H), 7.32 (td, J=7.4, 1.0 Hz, 1H), 7.27 (m, 1H), 7.21 (ddd, J=7.6, 4.8, 1.2 Hz, 1H), 4.73-4.65 (m, 2H), 4.34 (dd, J=11.8, 3.6 Hz, 1H), 4.18 (m, 1H), 3.88 (dd, J=6.7, 4.4 Hz, 1H), 3.86 (s, 3H), 3.42-3.25 (m, 2H), 2.74 (dd, J=13.2, 11.2 Hz, 1H), 2.12-2.05 (m, 2H), 1.97 (dt, J=11.8, 3.0 Hz, 1H), 1.92 (dt, J=13.1, 3.0 Hz, 1H), 1.57 (td, J=12.0, 2.7 Hz, 1H), 1.51-1.40 (m, 2H), 1.32-1.17 (m, 2H), 0.94 (q, J=11.4 Hz, 1H). $^{13}$C NMR: (100 MHz, CDCl$_3$) δ 175.2, 150.5, 150.3, 149.6, 148.4, 137.7, 137.1, 132.2, 130.9, 123.6, 123.1, 122.7, 122.3, 120.3, 118.7, 112.4, 104.3, 66.7, 55.0, 52.5, 52.2, 50.4, 46.1, 40.0, 35.4, 35.3, 31.1, 26.1, 22.8. HRMS (ESI): calc. for C$_{29}$H$_{31}$N$_7$O$_3$Na [M+Na]$^+$: 548.2381, found: 548.2382. MP: 201-203° C.

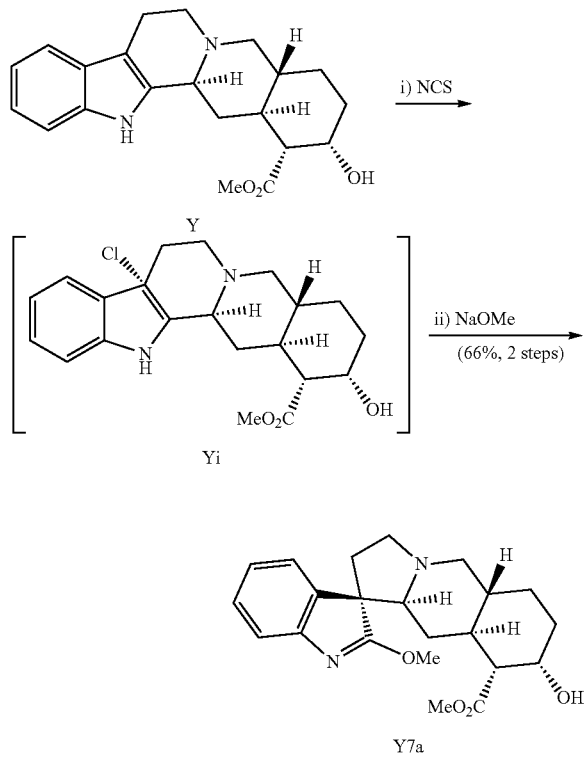

Procedure for synthesis of Y7a: Y (3.17 g, 8.95 mmol) was added to a round-bottom flask and dissolved in dichloromethane (90 mL). The solution was cooled to −41° C. (dry ice/acetonitrile bath) and was added a solution of N-chlorosuccinimide (1.31 g, 9.85 mmol) in dichloromethane (8 mL). The reaction was stirred for 45 minutes before being warmed to room temperature and concentrated in vacuo. Crude Yi was taken on to the next methanolysis step.

A flame-dried round-bottom flask was added methanol (100 mL) and cooled to 0° C. Sodium hydride (2.00 g, 50.0 mmol, 60% dispersion in mineral oil) was slowly added in several portions and the solution was gradually warmed to room temperature. To the fresh 0.5 M sodium methoxide solution was added a solution of crude Yi (3.38 g, 8.69 mmol) obtained above, dissolved in 10 mL of methanol. The solution was then allowed to stir at room temperature for 2.5 hours. The reaction was quenched with brine and ethyl acetate was used to extract the product. The ethyl acetate layer was then dried with sodium sulfate, filtered and concentrated under reduced pressure. The crude material was purified via column chromatography using a gradient of 99:1 hexanes:triethylamine to 49.5:49.5:1 hexanes:ethyl acetate:triethylamine to afford Y7a (2.20 g, 66%, 2 steps) as a pale yellow foam. Note: NMR tabulated data was consistent to previous literature data; however, no spectra were reported for visual inspection.[1] $^1$H NMR: (400 MHz, CDCl$_3$) δ 7.32 (d, J=7.4, 1H), 7.26 (dd, J=7.6, 0.4 1H), 7.18 (td, J=7.6, 1.2 Hz, 1H), 7.01 (td, J=7.4, 1.1 Hz, 1H), 4.04 (m, 1H), 4.02 (s, 3H), 3.51 (s, 3H), 3.24 (td, J=8.6, 2.3 Hz, 1H), 3.11 (s, 1H), 3.08 (dd, J=10.7, 3.6 Hz, 1H), 2.43 (dd, J=10.9, 2.4 Hz, 1H), 2.37 (q, J=8.8 Hz, 11H), 2.22 (ddd, J=13.1, 9.2, 2.4 Hz, 1H), 2.07 (dd, J=11.7, 2.2 Hz, 1H), 1.96 (dt, J=13.0, 8.5 Hz, 1H), 1.92-1.81 (m, 2H), 1.66 (qd, J=11.5, 3.4 Hz, 1H), 1.49 (td, J=11.7, 3.4 Hz, 1H), 1.41 (dt, J=13.3, 2.7 Hz, 1H), 1.34 (m, 1H), 1.26 (qt, J=9.6, 2.4 Hz, 1H), 0.87 (dt, J=12.4, 3.0 Hz, 1H), 0.61 (q, J=11.8 Hz, 1H). $^{13}$C NMR: (100 MHz, CDCl$_3$) δ 182.2, 175.7, 152.3, 140.6, 127.6, 123.5, 123.4, 118.1, 69.6, 66.8, 59.7, 59.1, 56.6, 53.5, 52.4, 51.8, 40.4, 36.3, 33.0, 31.5, 30.3, 23.5. MP: 184-186° C., lit: 184-186° C.

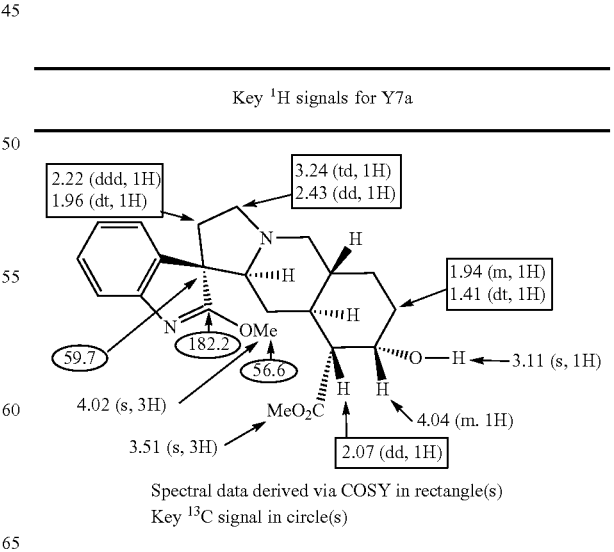

Key $^1$H signals for Y7a

Spectral data derived via COSY in rectangle(s)
Key $^{13}$C signal in circle(s)

Key COSY correlations for Y7a

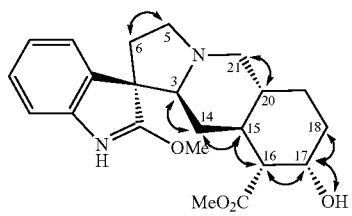 [SMILES: COC(=O)[C@@H]1[C@H]2C[C@@H]3N(CC[C@@]34C(OC)=Nc3ccccc34)C[C@@H]2CC[C@@H]1O]

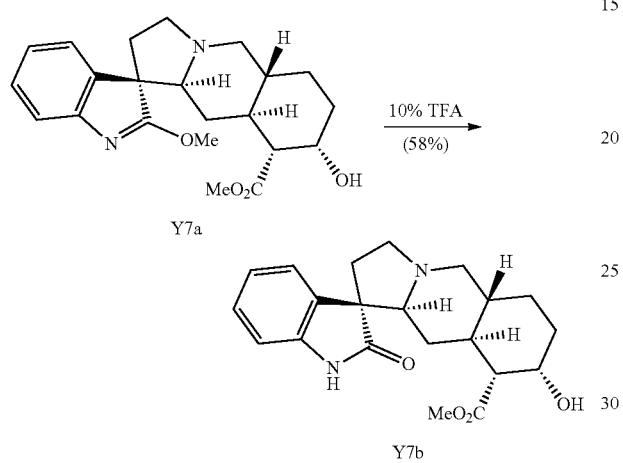

Y7a

10% TFA
(58%)

Y7b

Procedure for synthesis of Y7b: Y7a (760 mg, 1.98 mmol) was added to a round-bottom flask and dissolved in a 10% aqueous trifluoroacetic acid solution (44 mL). The resulting solution was refluxed for 1 hour. The reaction was then cooled to room temperature and basified to pH 10 via slow addition of concentrated ammonium hydroxide. The basified solution was transferred to a separatory funnel and ethyl acetate was used to extract the product. The ethyl acetate layer was then dried with sodium sulfate, filtered and concentrated under reduced pressure. The crude material was purified via column chromatography using a gradient of 99:1 hexanes:triethylamine to 49.5:49.5:1 hexanes:ethyl acetate:triethylamine to afford Y7b (426 mg, 58%) as a colorless foam. Note: NMR tabulated data was consistent to previous literature data; however, no spectra were reported for visual inspection.[1] $^1$H NMR: (400 MHz, CDCl$_3$) δ 8.04 (br. s, 1H), 7.37 (d, J=7.5 Hz, 1H), 7.19 (t, J=7.7 Hz, 1H), 7.02 (t, J=7.6, Hz, 1H), 6.87 (d, J=7.5 Hz, 1H), 4.08 (m, 1H), 3.57 (s, 3H), 3.27 (td, J=8.7, 2.4 Hz, 1H), 3.10 (dd, J=10.8, 3.7 Hz, 1H), 3.05 (s, 1H), 2.50 (m, 2H), 2.37 (ddd, J=12.8, 10.1, 1.5 Hz, 1H), 2.11 (dd, J=11.7, 2.1 Hz, 1H), 2.00 (m, 1H), 1.97-1.87 (m, 2H), 1.72 (qd, J=11.4, 3.4 Hz, 1H), 1.54 (qd, J=12.1, 10.5, 4.6 Hz, 1H), 1.44 (d, J=13.2 Hz, 1H), 1.38 (m, 1H), 1.28 (qd, J=11.1, 3.3 Hz, 1H), 1.05 (dt, J=12.2, 3.0 Hz, 1H), 0.67 (q, J=11.7 Hz, 1H). $^{13}$C NMR: (100 MHz, CDCl$_3$) δ 181.9, 175.7, 140.4, 134.0, 127.7, 125.2, 122.6, 109.7, 71.6, 66.9, 59.0, 56.9, 53.6, 52.6, 51.9, 40.6, 36.3, 35.5, 31.5, 30.6, 23.6. HRMS (ESI): calc. for C$_{21}$H$_{27}$N$_2$O$_4$ [M+H]$^+$: 371.1965, found: 371.1978. MP: free base: 89-91° C., TFA salt: 70-72° C.; lit: 221-222° C.[1] (Note: The MP was determined several times for Y7b and found the values were found to be reproducible.)

Key $^1$H signals for Y7b

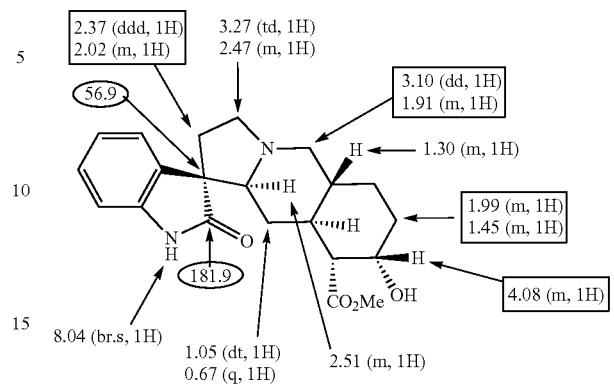

Spectral data derived via COSY in rectangle(s)
Key $^{13}$C signal in circle(s)

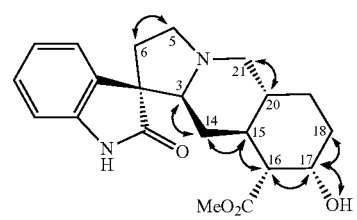

Key COSY correlations

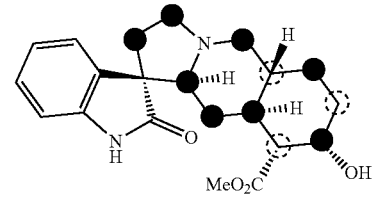

HSQC correlations for Y7b

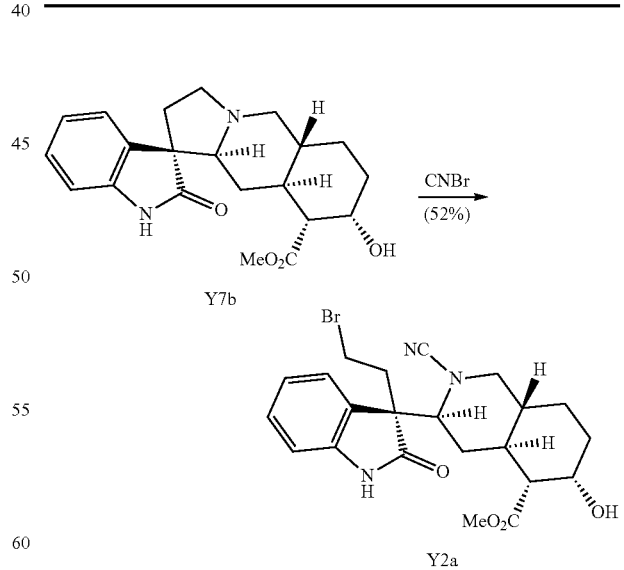

Y7b

CNBr
(52%)

Y2a

Procedure for the synthesis of Y2a: Y7b (351 mg, 0.95 mmol) was added to a flame-dried round-bottom flask and dissolved in N,N-dimethylformamide (14 mL). To the resulting solution was added a 3M solution of cyanogen bromide (0.95 mL, 2.84 mmol) in dichloromethane at room temperature. The reaction stirred at room temperature and slowly warmed to 60° C. for 22 hours. Upon completion of the reaction, as determined by TLC analysis, the reaction was quenched with brine and ethyl acetate was used to extract the product. The ethyl acetate layer was subsequently washed with additional H$_2$O (4×). The organic phases were collected, dried with sodium sulfate, filtered and concentrated in vacuo. The crude material was purified via column chromatography using a gradient of 100% hexanes to 1:2 hexanes:ethyl acetate to afford Y2a (233 mg, 52%) as a colorless foam.

$^1$H NMR: (400 MHz, CDCl$_3$) δ 9.16 (s, 1H), 7.42 (d, J=7.8 Hz, 1H), 7.24 (t, J=7.8 Hz, 1H), 7.05 (t, J=7.5 Hz, 1H), 6.91 (d, J=7.8 Hz, 1H), 4.17 (m, 1H), 3.66 (s, 3H), 3.44 (dd, J=11.6, 1.5 Hz, 1H), 3.28 (d, J=2.5 Hz, 1H), 3.24 (dd, J=13.9, 2.3 Hz, 1H), 3.06 (ddd, J=11.7, 9.7, 5.2 Hz, 1H), 2.84-2.75 (m, 2H), 2.54 (m, 1H), 2.43 (td, J=12.6, 4.9 Hz, 1H), 2.26 (dd, J=11.7, 2.3 Hz, 1H), 2.02-1.88 (m, 2H), 1.66 (dd, J=13.7, 2.9 Hz, 1H), 1.62-1.23 (m, 5H). $^{13}$C NMR: (100 MHz, CDCl$_3$) δ 177.7, 175.0, 141.4, 129.5, 127.7, 125.3, 123.4, 116.7, 110.6, 66.6, 65.4, 58.5, 56.0, 52.2, 52.0, 39.4, 39.0, 37.0, 31.2, 29.6, 26.2, 22.2. HRMS (ESI): calc. for C$_{22}$H$_{26}$BrN$_3$O$_4$Na [M+Na]$^+$: 498.0999, found: 498.0991. MP: 60-62° C.

Key signals for Y2a

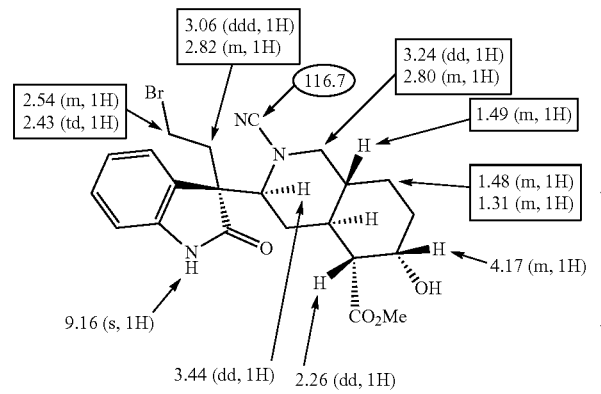

Spectral data derived via COSY in rectangles(s)
Key $^{13}$C signal in circle(s)

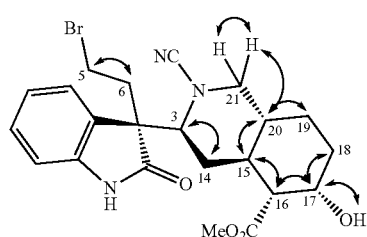

Key COSY correlations

Key signals for Y2a

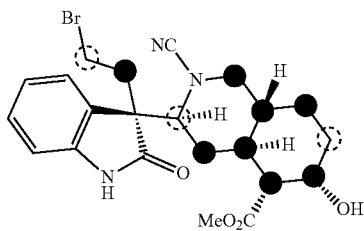

HSQC correlations

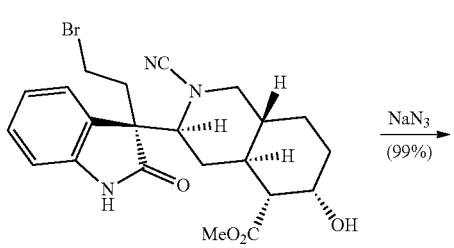

Y2a

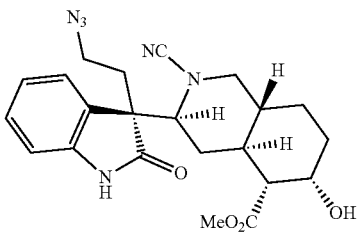

Y2b

Procedure for the synthesis of Y2b: Y2a (172 mg, 0.36 mmol) was added to a round-bottom flask and dissolved in N,N-dimethylformamide (5 mL). Sodium azide (70.4 mg, 1.08 mmol) was added and the reaction was stirred at room temperature for 30 minutes, then slowly warmed to 80° C. for 16.5 hours. The reaction was cooled to room temperature, diluted with ethyl acetate and quenched with brine (4×50 mL). The organic layer was collected, dried with sodium sulfate, filtered and concentrated. Crude material was purified via column chromatography using a gradient of 100% hexanes to 1:1 hexanes:ethyl acetate to 100% ethyl acetate to afford Y2b (156 mg, 99%) as a pale-yellow foam.

$^1$H NMR: (400 MHz, CDCl$_3$) δ 9.20 (s, 1H), 7.43 (d, J=7.5 Hz, 1H), 7.22 (t, J=7.6 Hz, 1H), 7.03 (t, J=7.6 Hz, 1H), 6.91 (d, J=7.8 Hz, 1H), 4.16 (m, 1H), 3.62 (s, 3H), 3.42 (d, J=11.6 Hz, 1H), 3.32 (d, J=1.5 Hz, 1H), 3.23 (d, J=12.3 Hz, 1H), 2.98 (dt, J=12.0, 7.7 Hz, 1H), 2.88 (ddd, J=13.0, 8.5, 5.6 Hz, 1H), 2.79 (t, J=11.9 Hz, 1H), 2.32-2.13 (m, 3H), 2.01-1.84 (m, 2H), 1.64 (d, J=12.5 Hz, 1H), 1.55-1.36 (m, 4H), 1.29 (m, 1H). $^{13}$C NMR: (100 MHz, CDCl$_3$) δ 178.4, 174.4, 141.6, 129.1, 127.8, 124.8, 122.8, 116.5, 110.6, 66.6, 65.2, 58.2, 54.0, 51.9, 51.8, 46.7, 39.1, 36.5, 34.4, 31.3, 29.4, 21.9. HRMS (ESI): calc. for C$_{22}$H$_{26}$N$_6$O$_4$Na [M+Na]$^+$: 461.1908, found: 461.1913. MP: 60-62° C.

Key signals for Y2b

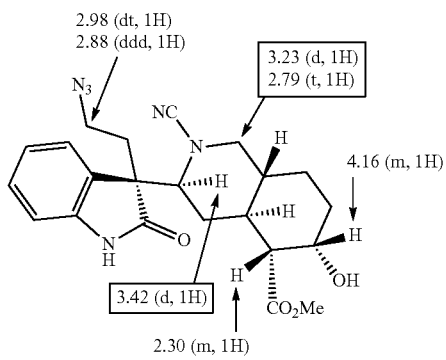

Spectral data derived via COSY in rectangles(s)
Key ¹³C signal in circle(s)

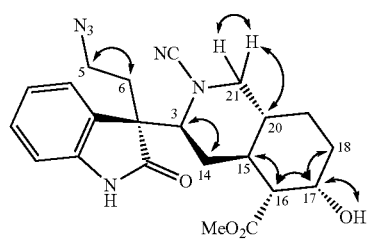

Key COSY correlations

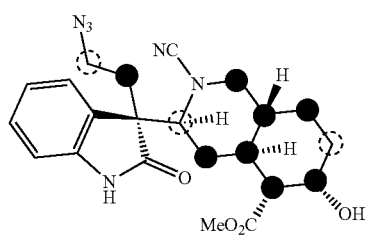

HSQC correlations

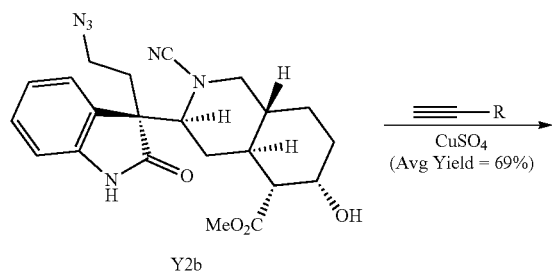

Y2b

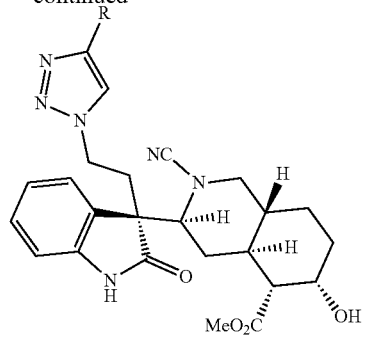

-continued

General procedure for the preparation of Y2c-Y2p: Anhydrous copper sulfate (4.4 mg, 0.03 mmol) and sodium ascorbate (17.2 mg, 0.09 mmol) were dissolved in a solution of tert-butanol:$H_2O$(1:2) and was added to a round-bottom flask containing Y2b (25.9 mg, 0.06 mmol). Cyclopropylacetylene (15 μL, 0.18 mmol) was added, followed by dichloromethane (0.7 mL). The biphasic mixture was vigorously stirred at room temperature for 1.25 hours until starting material was fully consumed as determined by TLC analysis. The mixture was quenched with brine (2×50 mL) and the product was extracted with dichloromethane. The organics were collected, dried with sodium sulfate, filtered and concentrated. Crude product was purified via column chromatography using a gradient of 100% hexanes to 1:1 hexanes:ethyl acetate to 100% ethyl acetate to afford Y2c (22.5 mg, 75%) as a colorless solid. Note: The alkynyl amides: N-(prop-2-yn-1-yl)-octanamide,[2] Boc-N-propargylamino-proline,[3] and N-(prop-2-yn-1-yl)-furan-2-carboxamide[4] used for synthesizing derivatives Y2f, Y2g, Y2h, respectively, matched previously reported spectral data.

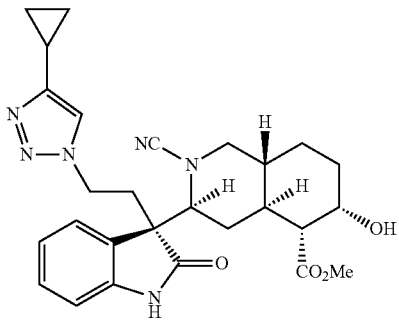

Y2c

Yield: 75%; 22.5 mg of Y2c isolated as a colorless solid. ¹H NMR: (400 MHz, $CDCl_3$) δ 8.92 (s, 1H), 7.53 (d, J=7.7 Hz, 1H), 7.27 (t, J=7.8 Hz, 1H), 7.07 (t, J=7.5 Hz, 1H), 7.03 (s, 1H), 6.94 (d, J=7.8 Hz, 1H), 4.18 (m, 1H), 4.12 (ddd, J=13.9, 8.8, 6.6 Hz, 1H), 3.95 (ddd, J=13.9, 8.8, 6.6 Hz, 1H), 3.64 (s, 3H), 3.44 (dd, J=11.7, 1.2 Hz, 1H), 3.30 (dd, J=13.6, 2.8 Hz, 1H), 3.13 (s, 1H), 2.84 (dd, J=14.1, 10.9 Hz, 1H), 2.70-2.56 (m, 2H), 2.23 (dd, J=11.6, 2.0 Hz, 1H), 2.03-1.91 (m, 2H), 1.85 (tt, J=8.7, 5.0 Hz, 1H), 1.54 (dt, J=13.3, 2.4 Hz, 1H), 1.51-1.43 (m, 2H), 1.39 (d, J=12.6 Hz, 1H), 1.36-1.22 (m, 2H), 0.92-0.85 (m, 2H), 0.77-0.70 (m, 2H). ¹³C NMR: (100 MHz, $CDCl_3$) δ 178.0, 174.7, 150.4, 141.5, 129.5, 127.5, 125.6, 123.4, 120.0, 117.1, 110.7, 66.7, 65.7, 58.5, 54.5, 52.1, 51.9, 45.7, 39.4, 36.7, 35.5, 31.3, 29.8, 22.1, 7.8, 7.8, 6.8. HRMS (ESI): calc. for $C_{27}H_{33}N_6O_4$ [M+H]⁺: 505.2558, found: 505.2561. MP: 119-121° C.

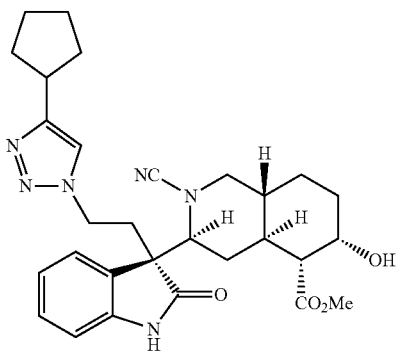

Y2d

Yield: 75%; 20.9 mg of Y2d isolated as a colorless foam. $^1$H NMR: (400 MHz, CDCl$_3$) δ 9.14 (s, 1H), 7.54 (d, J=7.6 Hz, 1H), 7.27 (t, J=9.0 Hz, 1H), 7.05 (s, 1H), 7.05 (t, J=9.0 Hz, 1H), 6.96 (d, J=7.6 Hz, 1H), 4.19 (m, 1H), 4.16 (ddd, J=14.4, 8.9, 6.6 Hz, 1H), 3.98 (ddd, J=14.4, 8.9, 6.6 Hz, 1H), 3.65 (s, 3H), 3.48 (d, J=11.4 Hz, 1H), 3.32 (dd, J=13.6, 3.0 Hz, 1H), 3.25 (m, 1H), 3.08 (p, J=8.0 Hz, 1H), 2.87 (t, J=11.3 Hz, 1H), 2.73-2.54 (m, 2H), 2.24 (dd, J=11.4, 2.1 Hz, 1H), 2.15 (m, 1H), 2.10-1.90 (m, 4H), 1.78-1.23 (m, 11H). Note: $^1$H spectrum referenced TMS at 0.00 ppm. $^{13}$C NMR: (100 MHz, CDCl$_3$) δ 178.0, 174.7, 152.8, 141.6, 129.5, 127.5, 125.6, 123.3, 119.9, 117.1, 110.8, 66.7, 65.7, 58.5, 54.5, 52.1, 51.9, 45.7, 39.4, 36.8, 36.7, 35.5, 33.3, 33.3, 31.3, 29.9, 29.8, 25.3, 22.1. HRMS (ESI): calc. for C$_{29}$H$_{37}$N$_6$O$_4$ [M+H]$^+$: 533.2871, found: 533.2870. MP: 93-95° C.

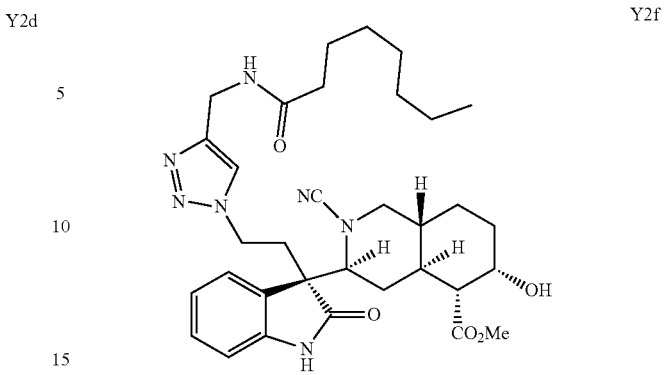

Y2f

Yield: 73%; 17.4 mg of Y2f isolated as a colorless foam. $^1$H NMR: (400 MHz, CDCl$_3$) δ 8.85 (s, 1H), 7.60 (d, J=7.9 Hz, 1H), 7.33-7.25 (m, 2H), 7.10 (td, J=8.0, 1.1 Hz, 1H), 6.96 (d, J=7.8 Hz, 1H), 6.50 (t, J=5.8 Hz, 1H), 4.43 (dd, J=15.2, 5.8 Hz, 1H), 4.34 (dd, J=15.2, 5.8 Hz, 1H), 4.17 (m, 1H), 4.15-4.05 (m, 2H), 3.64 (s, 3H), 3.37 (dd, J=11.6, 2.1 Hz, 1H), 3.35-3.29 (m, 2H), 3.07 (m, 1H), 2.83 (dd, J=13.3, 10.6 Hz, 1H), 2.72-2.64 (m, 2H), 2.22 (dd, J=11.5, 2.1 Hz, 1H), 2.20-2.13 (m, 2H), 2.01-1.91 (m, 2H), 1.85-1.70 (m, 2H), 1.65-1.55 (m, 2H), 1.54-1.44 (m, 2H), 1.42-1.21 (m, 9H), 0.86 (t, J=6.3 Hz, 3H). $^{13}$C NMR: (100 MHz, CDCl$_3$) δ 177.8, 174.7, 173.9, 144.8, 141.7, 129.6, 127.2, 126.0, 123.4, 122.9, 117.1, 110.8, 66.7, 65.8, 58.6, 54.6, 52.0, 51.9, 46.1, 39.4, 36.7, 35.2, 34.9, 31.9, 31.3, 29.9, 29.8, 29.5, 29.2, 25.8, 22.8, 22.2, 14.3. HRMS (ESI): calc. for C$_{33}$H$_{46}$N$_7$O$_5$ [M+H]$^+$: 620.3555, found: 620.3557. MP: 72-74° C.

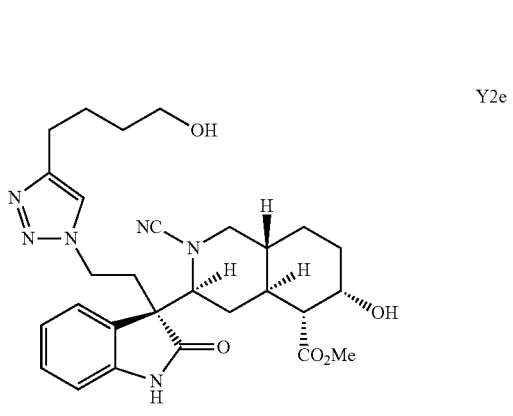

Y2e

Yield: 71%; 19.4 mg of Y2e isolated as a colorless foam. $^1$H NMR: (400 MHz, CDCl$_3$) δ 9.38 (s, 1H), 7.57 (d, J=7.3 Hz, 1H), 7.27 (m, 1H), 7.12 (br. s, 1H), 7.06 (t, J=7.6 Hz, 1H), 6.95 (d, J=7.6 Hz, 1H), 4.17 (m, 1H), 4.12 (dt, J=13.6, 6.9 Hz, 1H), 4.01 (dt, J=13.6, 6.9 Hz, 1H), 3.67-3.62 (m, 2H), 3.61 (s, 3H), 3.43 (d, J=11.4 Hz, 1H), 3.36 (m, 1H), 3.30 (d, J=13.3 Hz, 1H), 2.85 (t, J=11.9 Hz, 1H), 2.74-2.56 (m, 4H), 2.20 (d, J=11.4 Hz, 1H), 2.04-1.88 (m, 2H), 1.79-1.65 (m, 2H), 1.65-1.39 (m, 5H), 1.39-1.18 (m, 4H).

$^{13}$C NMR: (100 MHz, CDCl$_3$) δ 178.1, 174.6, 148.3, 141.8, 129.5, 127.3, 125.8, 123.3, 121.5, 117.3, 110.9, 66.7, 65.7, 62.3, 58.5, 54.7, 52.0, 51.9, 45.9, 39.4, 36.6, 35.1, 32.1, 31.4, 29.8, 25.6, 25.2, 22.1. HRMS (ESI): calc. for C$_{28}$H$_{37}$N$_6$O$_5$ [M+H]$^+$: 537.2820, found: 537.2822. MP: 55-57° C.

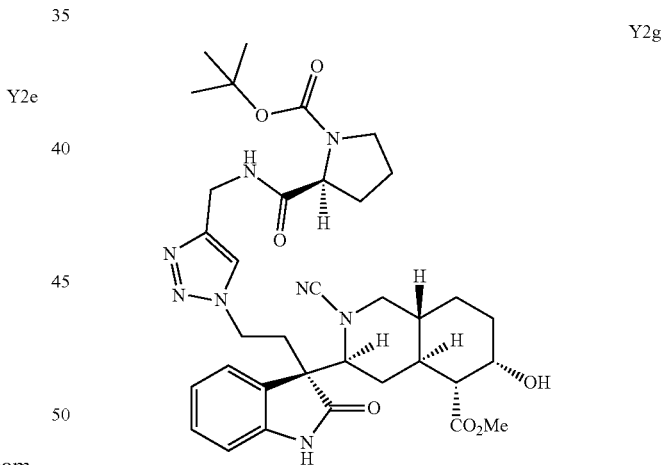

Y2g

Yield: 50%; 23.1 mg of Y2g isolated as a colorless solid. $^1$H NMR: (400 MHz, d$_6$-DMSO at 50° C.) δ 10.68 (s, 1H), 8.17 (t, J=5.8 Hz, 1H), 7.72 (br. s, 1H), 7.60 (d, J=7.5 Hz, 1H), 7.25 (td, J=7.7, 1.2 Hz, 1H), 7.03 (td, J=7.6, 1.0 Hz, 1H), 6.90 (d, J=7.8 Hz, 1H), 4.56 (d, J=4.4 Hz, 1H), 4.27 (dd, J=15.1, 5.8 Hz, 1H), 4.21 (dd, J=15.1, 5.8 Hz, 1H), 4.14-3.97 (m, 3H), 3.85 (ddd, J=13.3, 10.6, 5.6 Hz, 1H), 3.62 (dd, J=11.6, 1.9 Hz, 1H), 3.57 (s, 3H), 3.37 (m, 1H), 3.32-3.17 (m, 2H), 2.91 (dd, J=13.2, 10.7 Hz, 1H), 2.48-2.35 (m, 2H), 2.25 (dd, J=11.5, 2.8 Hz, 1H), 2.07 (m, 1H), 1.90 (qd, J=10.7, 2.5 Hz, 1H), 1.84-1.66 (m, 5H), 1.54 (t, J=12.4 Hz, 1H), 1.48-1.18 (m, 12H), 1.13 (q, J=12.1 Hz, 1H). $^{13}$C NMR: (100 MHz, d$_6$-DMSO at 50° C.) δ 177.0, 172.1, 172.1, 153.1, 144.6, 142.2, 128.5, 127.9, 124.9, 122.7, 121.7, 116.6, 109.7, 78.2, 66.1, 64.1, 59.5, 57.4, 53.3, 51.4, 50.8, 46.3, 44.7, 38.5, 35.5, 35.2, 33.9, 31.8, 30.8, 29.2, 27.8, 23.0, 21.4. Note: Spectrum represents a mixture of Boc-rotamers. HRMS (ESI): calc. for $C_{35}H_{47}N_8O_7$ [M+H]$^+$: 691.3562, found: 691.3557. MP: 248-250° C.

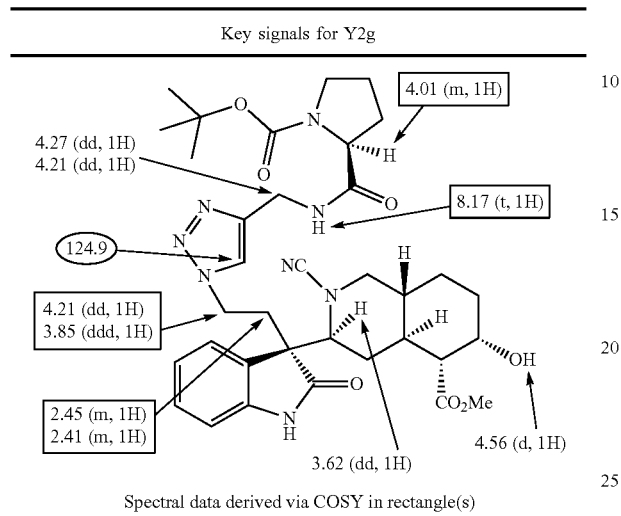

Spectral data derived via COSY in rectangle(s)
Key $^{13}$C signal in circle(s)

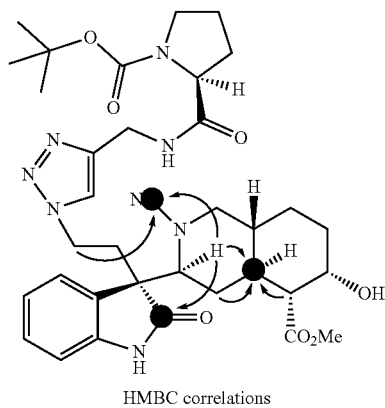

HMBC correlations

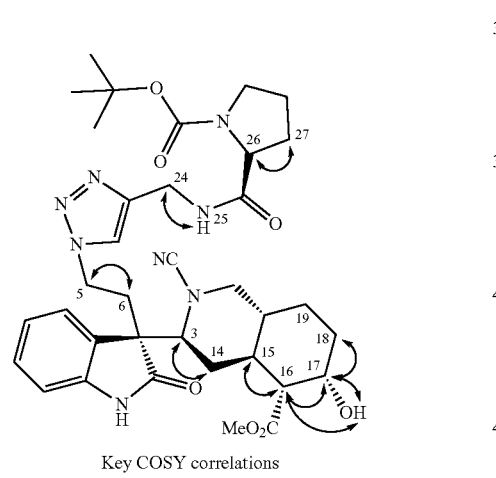

Key COSY correlations

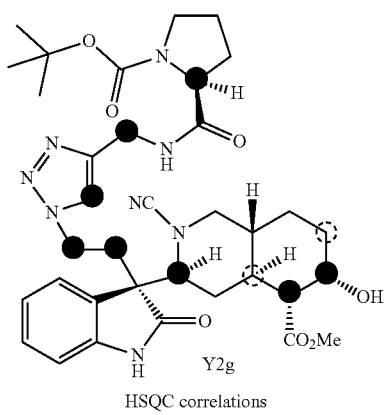

Y2g
HSQC correlations

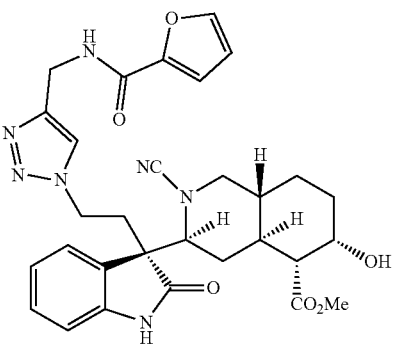

Y2h

Yield: 60%; 13.4 mg of Y2h isolated as a colorless solid. $^1$H NMR: (400 MHz, CDCl$_3$) δ 9.03 (s, 1H), 7.55 (d, J=7.2 Hz, 1H), 7.43 (s, 1H), 7.34 (s, 1H), 7.29-7.18 (m, 2H), 7.09 (d, J=3.1 Hz, 1H), 7.05 (t, J=7.5 Hz, 1H), 6.92 (d, J=7.8 Hz, 1H), 6.47 (dd, J=3.5, 1.8 Hz, 1H), 4.63-4.50 (m, 2H), 4.17 (m, 1H), 4.15 (dt, J=14.1, 7.2 Hz, 1H), 4.06 (dt, J=14.1, 7.2 Hz, 1H), 3.61 (s, 3H), 3.40 (d, J=11.4 Hz, 1H), 3.30 (dd, J=13.4, 1.9 Hz, 1H), 3.17 (s, 1H), 2.83 (dd, J=14.7, 11.1 Hz, 1H), 2.75-2.62 (m, 2H), 2.30 (m, 1H), 2.22 (dd, J=11.6, 1.4 Hz, 1H), 2.05-1.88 (m, 2H), 1.60-1.21 (m, 5H). $^{13}$C NMR: (100 MHz, CDCl$_3$) δ 177.9, 174.7, 158.8, 147.8, 144.5, 144.5, 141.7, 129.5, 127.3, 125.9, 123.3, 123.1, 117.1, 114.7, 112.3, 110.8, 66.7, 65.7, 58.6, 54.6, 52.0, 51.9, 46.1, 39.4, 36.7, 35.2, 34.6, 31.4, 29.7, 22.1. HRMS (ESI): calc. for $C_{30}H_{34}N_7O_6$[M+H]$^+$: 588.2565, found: 588.2576. MP: 115-117° C.

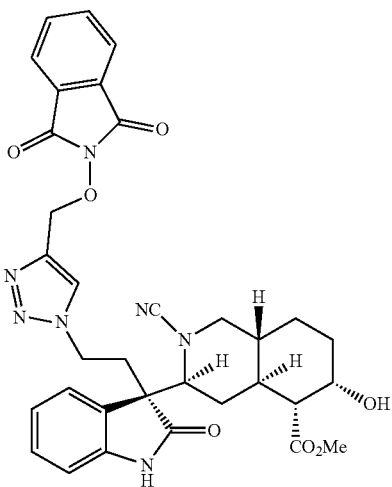

Y2i

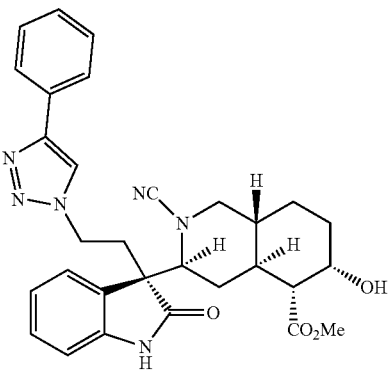

Y2k

Yield: 64%; 15.3 mg of Y2i isolated as a colorless solid. $^1$H NMR: (400 MHz, CDCl$_3$) δ 8.53 (s, 1H), 7.81-7.75 (m, 2H), 7.74-7.68 (m, 2H), 7.60 (s, 1H), 7.57 (d, J=7.9 Hz, 1H), 7.30 (t, J=7.7 Hz, 1H), 7.10 (t, J=7.7 Hz, 1H), 6.95 (d, J=7.7 Hz, 1H), 5.29 (d, J=12.4 Hz, 1H), 5.24 (d, J=12.4 Hz, 1H), 4.20 (dt, J=14.2, 7.4 Hz, 1H), 4.17 (m, 1H), 4.08 (dt, J=14.2, 7.4 Hz, 1H), 3.65 (s, 3H), 3.42 (dd, J=11.6, 2.3 Hz, 1H), 3.32 (dd, J=11.0, 2.3 Hz, 1H), 3.01 (s, 1H), 2.84 (dd, J=13.6 Hz, 11.8 Hz, 1H), 2.77-2.61 (m, 2H), 2.24 (dd, J=11.6, 2.1 Hz, 1H), 2.04-1.89 (m, 2H), 1.82-1.71 (m, 2H), 1.58-1.37 (m, 4H). $^{13}$C NMR: (100 MHz, CDCl$_3$) δ 177.7, 174.8, 163.7, 141.6, 141.6, 134.7, 129.6, 129.0, 127.3, 125.8, 125.1, 123.8, 123.5, 117.0, 110.8, 70.4, 66.7, 65.7, 58.6, 54.4, 52.1, 51.9, 46.2, 39.4, 36.8, 35.3, 31.3, 29.7, 22.2. HRMS (ESI): calc. for C$_{33}$H$_{33}$N$_7$O$_7$Na [M+Na]$^+$: 662.2334, found: 662.2323. MP: 220-222° C.

119.7, 117.0, 110.8, 66.7, 65.6, 58.5, 54.5, 52.1, 51.9, 46.1, 39.4, 36.7, 35.5, 31.3, 29.7, 22.1. HRMS (ESI): calc. for C$_{28}$H$_{31}$N$_6$O$_4$S [M+H]$^+$: 547.2112, found: 547.2102. MP: 125-127° C.

Yield: 76%; 14.7 mg of Y2k was isolated as a colorless foam. $^1$H NMR: (400 MHz, CDCl$_3$) δ 9.01 (s, 1H), 7.71 (dd, J=6.6, 1.5 Hz, 2H), 7.56-7.52 (m, 2H), 7.41-7.33 (m, 2H), 7.30 (dt, J=7.4, 1.0 Hz, 1H), 7.23 (m, 1H), 7.04 (td, J=7.6, 1.2 Hz, 1H), 6.96 (d, J=7.8 Hz, 1H), 4.25 (ddd, J=14.4, 8.6, 6.2 Hz, 1H), 4.18 (m, 1H), 4.07 (ddd, J=14.4, 8.6, 6.2 Hz, 1H), 3.63 (s, 3H), 3.48 (dd, J=11.7, 2.2 Hz, 1H), 3.30 (dd, J=13.8, 2.5 Hz, 1H), 3.11 (br. s, 1H), 2.84 (dd, J=13.4, 10.7 Hz, 1H), 2.80-2.65 (m, 2H), 2.23 (dd, J=11.6, 2.2 Hz, 1H), 2.08-1.88 (m, 2H), 1.59 (d, J=13.1 Hz, 1H), 1.55-1.20 (m, 5H). $^{13}$C NMR: (100 MHz, CDCl$_3$) δ 178.1, 174.7, 147.8, 141.5, 130.6, 129.5, 129.0, 128.3, 127.5, 125.9, 125.6, 123.4, 120.2, 117.0, 110.8, 66.7, 65.6, 58.5, 54.5, 52.1, 51.9, 46.0, 39.4, 36.7, 35.6, 31.3, 29.8, 22.1. HRMS (ESI): calc. for C$_{30}$H$_{33}$N$_6$O$_4$ [M+H]$^+$: 541.2558, found: 541.2543. MP: 200-202° C.

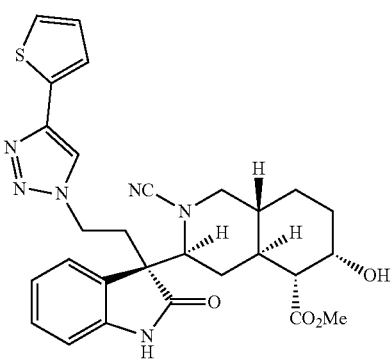

Y2j

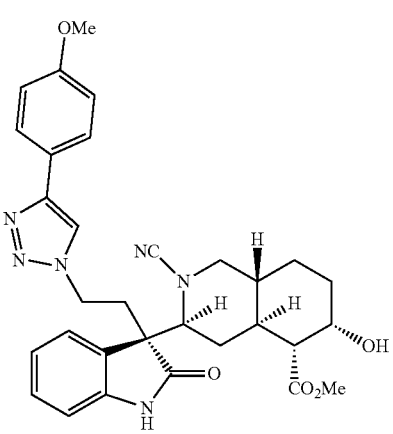

Y2l

Yield: 78%; 23.7 mg of Y2j isolated as a tan foam. $^1$H NMR: (400 MHz, CDCl$_3$) δ 9.11 (s, 1H), 7.53 (d, J=7.6 Hz, 1H), 7.46 (s, 1H), 7.31-7.21 (m, 3H), 7.09-7.01 (m, 2H), 6.97 (d, J=7.8 Hz, 1H), 4.25 (ddd, J=14.6, 8.8, 6.2 Hz, 1H), 4.19 (m, 1H), 4.07 (ddd, J=14.3, 8.6, 6.5 Hz, 1H), 3.64 (s, 3H), 3.49 (dd, J=11.6, 2.1 Hz, 1H), 3.31 (dd, J=13.5, 3.1 Hz, 1H), 3.15 (s, 1H), 2.85 (dd, J=13.4, 10.6 Hz, 1H), 2.80-2.63 (m, 2H), 2.24 (dd, J=11.6, 2.2 Hz, 1H), 2.05 (s, 1H), 2.02-1.92 (m, 2H), 1.60 (d, J=13.3 Hz, 1H), 1.57-1.21 (m, 4H). Note: $^1$H spectrum referenced TMS at 0.00 ppm. $^{13}$C NMR: (100 MHz, CDCl$_3$) δ 178.1, 174.6, 142.8, 141.6, 132.9, 129.5, 127.8, 127.4, 125.6, 125.2, 124.4, 123.4, Yield: 72%; 25.0 mg of Y2l isolated as a colorless foam. $^1$H NMR: (400 MHz, CDCl$_3$) δ 9.02 (s, 1H), 7.64 (d, J=8.6 Hz, 2H), 7.54 (d, J=7.7 Hz, 1H), 7.46 (s, 1H), 7.24 (t, J=7.8 Hz, 1H), 7.04 (t, J=7.7 Hz, 1H), 6.96 (d, J=7.8 Hz, 1H), 6.90 (d, J=8.7 Hz, 2H), 4.23 (ddd, J=14.3, 8.7, 6.5 Hz, 1H), 4.17 (m, 1H), 4.05 (ddd, J=14.3, 8.7, 6.5 Hz, 1H), 3.80 (s, 3H), 3.62 (s, 3H), 3.48 (dd, J=11.6, 2.1 Hz, 1H), 3.30 (dd, J=13.6, 3.1 Hz, 1H), 3.13 (s, 1H), 2.84 (dd, J=13.4, 11.0 Hz, 1H), 2.79-2.64 (m, 2H), 2.22 (dd, J=11.5, 2.2 Hz, 1H), 2.06-1.90

(m, 2H), 1.59 (dt, J=13.2, 2.1 Hz, 1H), 1.55-1.37 (m, 3H), 1.36-1.20 (m, 2H). $^{13}$C NMR: (100 MHz, CDCl$_3$) δ 178.0, 174.7, 159.7, 147.7, 141.6, 129.5, 127.5, 127.2, 125.6, 123.4, 123.3, 119.4, 117.1, 114.4, 110.8, 66.7, 65.6, 58.5, 55.5, 54.5, 52.1, 51.9, 45.9, 39.4, 36.7, 35.6, 31.3, 29.8, 22.1. HRMS (ESI): calc. for C$_{31}$H$_{34}$N$_6$O$_5$Na [M+Na]$^+$: 593.2483, found: 593.2476. MP: 102-104° C.

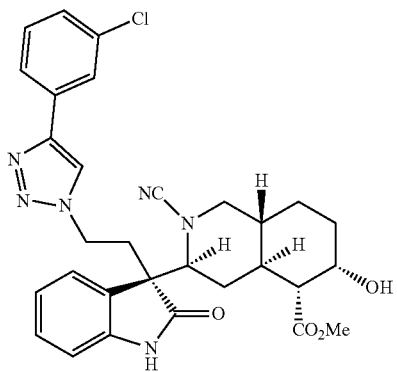

Y2m

Yield: 74%; 24.1 mg of Y2m isolated as a colorless foam. $^1$H NMR: (400 MHz, CDCl$_3$) δ 9.14 (s, 1H), 7.72 (s, 1H), 7.60 (dt, J=7.5, 1.0 Hz, 1H), 7.58 (s, 1H), 7.53 (d, J=7.5 Hz, 1H), 7.31 (t, J=7.7 Hz, 1H), 7.28-7.21 (m, 2H), 7.04 (t, J=7.6 Hz, 1H), 6.97 (d, J=7.8 Hz, 1H), 4.28 (ddd, J=14.3, 8.5, 6.1 Hz, 1H), 4.19 (m, 1H), 4.10 (ddd, J=14.3, 8.5, 6.1 Hz, 1H), 3.64 (s, 3H), 3.50 (d, J=11.3 Hz, 1H), 3.31 (dd, J=13.8, 2.5 Hz, 1H), 3.12 (s, 1H), 2.86 (dd, J=13.7, 11.3 Hz, 1H), 2.81-2.66 (m, 2H), 2.24 (dd, J=11.8, 1.2 Hz, 1H), 2.11-1.91 (m, 2H), 1.62 (dt, J=13.3, 2.4 Hz, 1H), 1.58-1.22 (m, 5H). Note: $^1$H spectrum referenced TMS at 0.00 ppm. $^{13}$C NMR: (100 MHz, CDCl$_3$) δ 178.1, 174.6, 146.5, 141.6, 134.8, 132.4, 130.3, 129.5, 128.2, 127.5, 125.9, 125.5, 123.9, 123.4, 120.7, 117.0, 110.8, 66.8, 65.6, 58.5, 54.5, 52.1, 51.9, 46.1, 39.4, 36.7, 35.6, 31.3, 29.7, 22.1. HRMS (ESI): calc. for C$_{30}$H$_{32}$ClN$_6$O$_4$[M+H]$^+$: 575.2168, found: 575.2163. MP: 106-108° C.

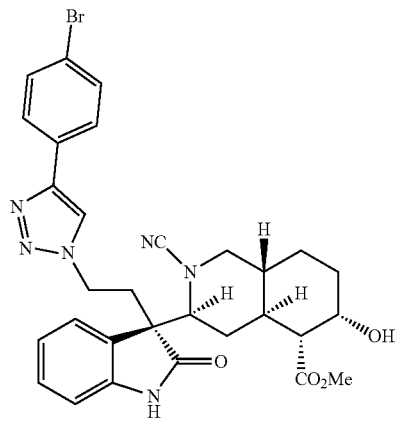

Y2n

Yield: 63%; 21.6 mg of Y2n isolated as a colorless foam. $^1$H NMR: (400 MHz, CDCl$_3$) δ 8.81 (s, 1H), 7.58 (dd, J=8.3, 1.5 Hz, 2H), 7.56 (s, 1H), 7.54 (d, J=1.2 Hz, 1H), 7.49 (dd, J=8.6, 1.5 Hz, 2H), 7.24 (t, J=7.7 Hz, 1H), 7.04 (t, J=7.7 Hz, 1H), 6.94 (d, J=7.7 Hz, 1H), 4.27 (ddd, J=14.5, 8.5, 6.4 Hz, 1H), 4.18 (m, 1H), 4.11 (ddd, J=14.5, 8.5, 6.4 Hz, 1H), 3.63 (s, 3H), 3.48 (d, J=12.1 Hz, 1H), 3.31 (d, J=13.6 Hz, 1H), 2.95 (s, 1H), 2.85 (dd, J=14.3, 11.0 Hz, 1H), 2.79-2.66 (m, 2H), 2.22 (dt, J=11.5, 1.7 Hz, 1H), 2.02-1.90 (m, 2H), 1.59 (d, J=13.2 Hz, 1H), 1.55-1.21 (m, 5H). $^{13}$C NMR: (100 MHz, CDCl$_3$) δ 178.0, 174.6, 146.9, 141.6, 132.1, 129.8, 129.6, 129.2, 127.5, 125.8, 123.5, 122.2, 120.2, 117.1, 110.8, 66.8, 65.7, 58.7, 54.7, 52.1, 52.0, 46.1, 39.5, 36.8, 35.5, 31.4, 30.0, 22.2. HRMS (ESI): calc. for C$_{30}$H$_{32}$BrN$_6$O$_4$ [M+H]$^+$: 619.1663, found: 619.1674. MP: 134-136° C.

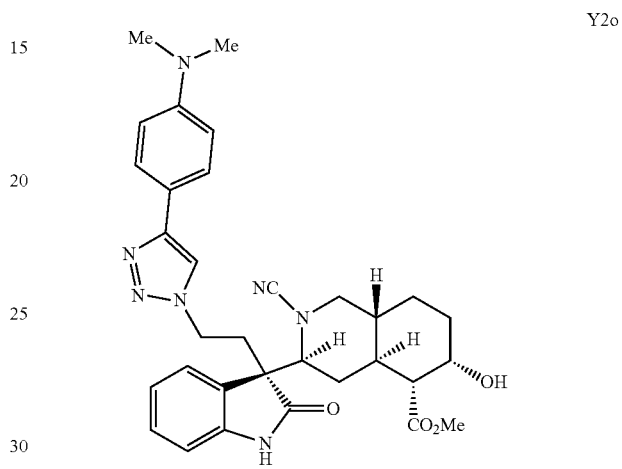

Y2o

Yield: 72%; 21.2 mg of Y2o isolated as a pale-yellow foam. $^1$H NMR: (400 MHz, CDCl$_3$) δ 9.18 (s, 1H), 7.58 (d, J=8.4 Hz, 2H), 7.54 (d, J=8.3 Hz, 1H), 7.40 (s, 1H), 7.24 (t, J=7.6 Hz, 1H), 7.04 (t, J=7.6 Hz, 1H), 6.96 (d, J=8.0 Hz, 1H), 6.70 (d, J=8.4 Hz, 2H), 4.17 (m, 1H), 4.15 (dt, J=14.5, 7.6 Hz, 1H), 4.01 (dt, J=14.5, 7.6 Hz, 1H), 3.62 (s, 3H), 3.48 (d, J=11.6 Hz, 1H), 3.28 (d, J=13.4 Hz, 1H), 2.94 (s, 6H), 2.84 (t, J=12.1 Hz, 1H), 2.75-2.62 (m, 2H), 2.21 (d, J=11.5 Hz, 1H), 2.02-1.89 (m, 2H), 1.59 (d, J=13.2 Hz, 1H), 1.54-1.21 (m, 6H). 13C NMR: (100 MHz, CDCl$_3$) δ 178.1, 174.6, 150.5, 148.3, 141.7, 129.5, 127.5, 126.8, 125.6, 123.3, 118.8, 118.7, 117.1, 112.6, 110.8, 66.7, 65.6, 58.5, 54.5, 52.1, 51.9, 45.8, 40.6, 39.4, 36.6, 35.5, 31.3, 29.8, 22.1. HRMS (ESI): calc. for C$_{32}$H$_{38}$N$_7$O$_4$ [M+H]$^+$: 584.2980, found: 584.2983. MP: 116-118° C.

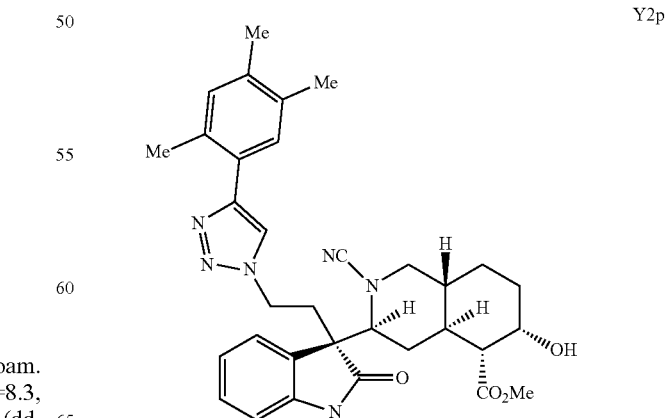

Y2p

Yield: 58%; 19.9 mg of Y2p isolated as a colorless foam. ¹H NMR: (400 MHz, CDCl₃) δ 8.90 (s, 1H), 7.56 (d, J=7.5 Hz, 1H), 7.47 (s, 1H), 7.43 (s, 1H), 7.26 (td, J=7.3, 1.1 Hz, 1H), 7.07 (td, J=7.6, 1.1 Hz, 1H), 6.99 (s, 1H), 6.95 (d, J=7.8 Hz, 1H), 4.24 (ddd, J=13.8, 8.9, 6.4 Hz, 1H), 4.18 (m, 1H), 4.07 (ddd, J=13.8, 8.9, 6.4 Hz, 1H), 3.63 (s, 3H), 3.49 (dd, J=11.4, 1.6 Hz, 1H), 3.31 (dd, J=13.5, 2.7 Hz, 1H), 3.10 (d, J=1.1 Hz, 1H), 2.85 (dd, J=13.5, 10.8 Hz, 1H), 2.80-2.67 (m, 2H), 2.32 (s, 3H), 2.24 (m, 1H), 2.23 (s, 6H), 2.06-1.87 (m, 3H), 1.59 (dt, J=13.6, 2.3 Hz, 1H), 1.55-1.22 (m, 4H). ¹³C NMR: (100 MHz, CDCl₃) δ 178.0, 174.7, 147.3, 141.5, 136.7, 134.3, 132.7, 132.3, 130.1, 129.5, 127.5, 127.2, 125.6, 123.4, 121.8, 117.0, 110.8, 66.7, 65.7, 58.5, 54.5, 52.1, 51.9, 45.9, 39.4, 36.7, 35.5, 31.3, 29.8, 22.1, 20.9, 19.6, 19.3. HRMS (ESI): calc. for C₃₃H₃₈N₆O₄Na [M+Na]⁺: 605.2847, found: 605.2852. MP: 102-104° C.

Yield: 26%; 15.8 mg of Y3a isolated as a colorless solid. ¹H NMR: (400 MHz, CDCl₃) δ 7.50 (t, J=7.5 Hz, 2H), 7.46 (d, J=7.5 Hz, 1H), 7.39 (d, J=7.5, 1H), 7.36 (dt, J=8.0, 1.1 Hz, 2H), 7.18 (td, J=7.7, 1.4 Hz, 1H), 7.08 (td, J=7.5, 1.2 Hz, 1H), 6.81 (d, J=7.8 Hz, 1H), 4.09 (m, 1H), 3.57 (s, 3H), 3.32 (td, J=8.5, 2.3 Hz, 1H), 3.12 (dd, J=10.9, 3.6 Hz, 1H), 2.60 (dd, J=11.1, 2.5 Hz, 1H), 2.54 (m, 1H), 2.47 (ddd, J=12.3, 9.5, 2.3 Hz, 1H), 2.15-2.03 (m, 2H), 2.01-1.88 (m, 2H), 1.73 (qd, J=11.5, 3.3 Hz, 1H), 1.54 (m, 1H), 1.49-1.21 (m, 4H), 1.09 (dt, J=12.3, 3.0 Hz, 1H), 0.70 (q, J=11.7 Hz, 1H). ¹³C NMR: (100 MHz, CDCl₃): δ 178.7, 175.7, 143.1, 134.9, 133.3, 129.7, 128.1, 127.6, 126.6, 125.2, 123.1, 109.1, 72.1, 66.8, 58.9, 56.7, 53.5, 52.5, 51.7, 40.6, 36.3, 35.3, 31.4, 30.6, 23.5. HRMS (ESI): calc. for C₂₇H₃₁N₂O₄ [M+H]⁺: 447.2278, found: 447.2286. MP: 63-65° C.

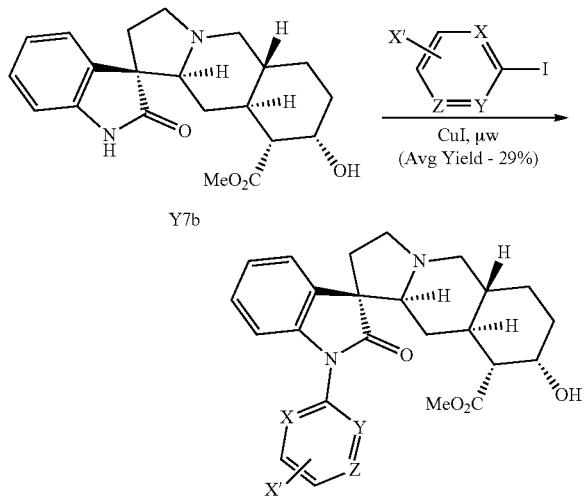

Y7b

General procedure for the preparation of Y3a-Y3i: Y7b (50.6 mg, 0.14 mmol) and iodobenzene (18 µL, 0.16 mmol) were added to a microwave vial and dissolved in acetonitrile (3 mL). The solution was allowed to stir for five minutes before the sequential addition of N,N'-dimethylethylenediamine (10 µL, 0.10 mmol), potassium carbonate (28.3 mg, 0.21 mmol) and copper(I) iodide (9.1 mg, 0.05 mmol). The reaction was then subjected to microwave irradiation at 160° C. for twelve minutes. The reaction was cooled to room temperature, diluted with ethyl acetate and brine was added to quench. The organic layers were dried with sodium sulfate, filtered and concentrated under reduced pressure. The resulting crude material was purified via column chromatography using a gradient of 99:1 hexanes:triethylamine to 49.5:49.5:1 hexanes:ethyl acetate:trimethylamine to afford Y3a (15.8 mg, 26%) as a colorless solid.

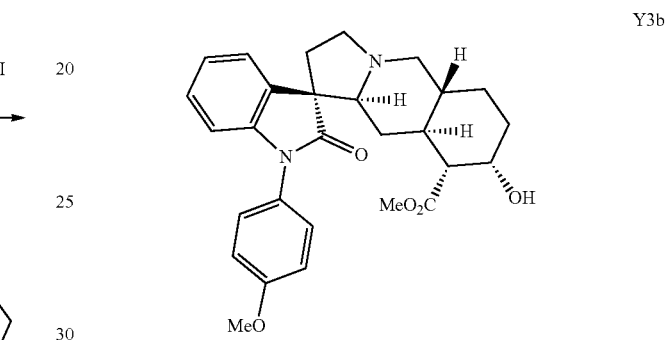

Y3b

Yield: 24%; 12.5 mg of Y3b isolated as a colorless, amorphous solid. ¹H NMR: (400 MHz, CDCl₃) δ 7.45 (d, J=7.3 Hz, 1H), 7.26 (d, J=7.3 Hz, 2H), 7.18 (t, J=7.5 Hz, 1H), 7.07 (t, J=7.5 Hz, 1H), 7.02 (d, J=8.7 Hz, 2H), 6.74 (d, J=7.8 Hz, 1H), 4.10 (m, 1H), 3.86 (s, 3H), 3.58 (s, 3H), 3.31 (td, J=8.5, 2.4 Hz, 1H), 3.12 (dd, J=10.9, 3.6 Hz, 1H), 2.60 (dd, J=11.2, 1.8 Hz, 1H), 2.54 (m, 1H), 2.46 (ddd, J=11.0, 9.6, 2.4 Hz, 1H), 2.16-2.03 (m, 2H), 2.01-1.88 (m, 2H), 1.73 (qd, J=11.5, 3.3 Hz, 1H), 1.55 (m, 1H), 1.48-1.36 (m 2H), 1.35-1.22 (m, 2H), 1.08 (dt, J=12.2, 3.1 Hz, 1H), 0.69 (q, J=11.7 Hz, 1H). Note: ¹H spectrum referenced TMS at 0.00 ppm. ¹³C NMR: (100 MHz, CDCl₃) δ 178.9, 175.7, 159.2, 143.6, 133.3, 128.0, 127.6, 127.5, 125.1, 122.9, 115.0, 109.0, 72.1, 66.8, 58.9, 56.6, 55.7, 53.6, 52.6, 51.7, 40.7, 36.4, 35.3, 31.5, 30.6, 23.6. HRMS (ESI): calc. for C₂₈H₃₃N₂O₅ [M+H]⁺: 477.2384, found: 477.2400.

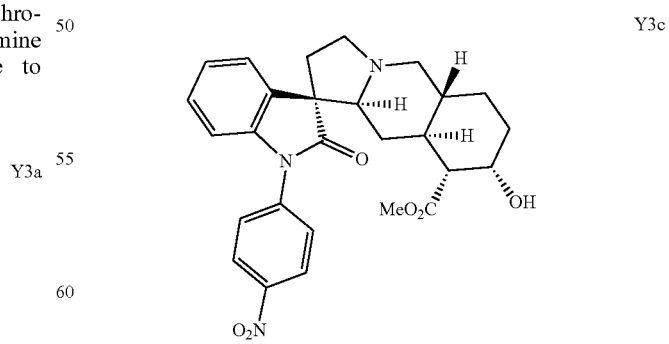

Y3c

Yield: 31%; 17.3 mg of Y3c isolated as a yellow foam. ¹H NMR: (400 MHz, CDCl₃) δ 8.38 (d, J=8.9 Hz, 2H), 7.66 (d, J=8.9 Hz, 2H), 7.51 (d, J=7.4 Hz, 1H), 7.25 (dd, J=7.8, 0.9 Hz, 1H), 7.16 (t, J=7.4 Hz, 1H), 6.95 (d, J=7.8 Hz, 1H), 4.10

(m, 1H), 3.56 (s, 3H), 3.32 (td, J=8.4, 0.7 Hz, 1H), 3.12 (dd, J=10.9, 3.6 Hz, 1H), 2.97 (br. s, 1H), 2.60 (dd, J=11.2, 2.4 Hz, 1H), 2.54 (m, 1H), 2.46 (ddd, J=12.2, 9.4, 2.3 Hz, 1H), 2.14-2.04 (m, 2H), 2.00-1.88 (m, 2H), 1.73 (qd, J=11.5, 3.4 Hz, 1H), 1.54 (m, 1H), 1.45 (dt, J=13.9, 2.3 Hz, 1H), 1.39 (m, 1H), 1.30 (m, 1H), 1.06 (dt, J=12.2, 3.1 Hz, 1H), 0.68 (q, J=11.7 Hz, 1H). $^{13}$C NMR: (100 MHz, CDCl$_3$) δ 178.6, 175.4, 146.3, 141.3, 140.7, 133.3, 127.9, 126.4, 125.7, 125.1, 124.1, 109.2, 72.2, 66.8, 58.8, 56.7, 53.5, 52.6, 51.8, 40.5, 36.2, 35.9, 31.5, 30.7, 23.5. HRMS (ESI): calc. for C$_{27}$H$_{30}$N$_3$O$_6$ [M+H]$^+$: 492.2129, found: 492.2142. MP: 188-190° C.

2H), 7.20 (td, J=7.2, 1.1 Hz, 1H), 7.16 (d, J=7.8 Hz, 1H), 7.13-7.03 (m, 5H), 6.80 (d, J=7.8 Hz, 1H), 4.10 (m, 1H), 3.57 (s, 3H), 3.32 (t, J=9.1 Hz, 1H), 3.12 (dd, J=11.0, 3.6 Hz, 1H), 2.60 (dd, J=10.0, 1.4 Hz, 1H), 2.55 (m, 1H), 2.47 (ddd, J=10.9, 9.6, 2.3 Hz, 1H), 2.15-2.03 (m, 2H), 2.01-1.87 (m, 2H), 1.73 (qd, J=11.6, 3.4 Hz, 1H), 1.55 (t, J=12.4 Hz, 1H), 1.44 (d, J=14.7 Hz, 1H), 1.40-1.22 (m, 3H), 1.07 (d, J=12.4 Hz, 1H), 0.69 (q, J=11.7 Hz, 1H). $^{13}$C NMR: (100 MHz, CDCl$_3$) δ 178.8, 175.7, 157.1, 156.8, 143.2, 133.3, 130.1, 129.6, 128.1, 127.7, 125.2, 124.0, 123.1, 119.6, 119.5, 109.0, 72.1, 66.8, 58.9, 56.6, 53.5, 52.6, 51.7, 40.6, 36.3, 35.4, 31.5, 30.6, 23.5. HRMS (ESI): calc. for C$_{33}$H$_{35}$N$_2$O$_5$ [M+H]$^+$: 539.2540, found: 539.2552.

Y3d

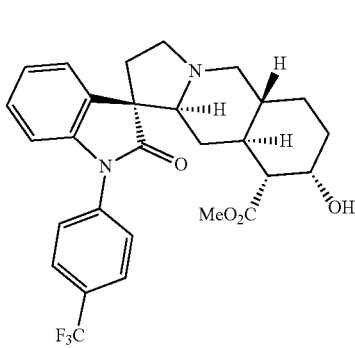

Y3f

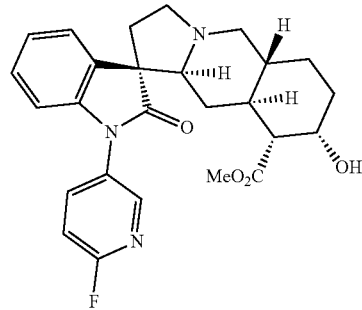

Yield: 26%; 14.9 mg of Y3d isolated as a yellow, amorphous solid. $^1$H NMR: (400 MHz, CDCl$_3$) δ 7.77 (d, J=8.3 Hz, 2H), 7.55 (d, J=8.3 Hz, 2H), 7.49 (d, J=7.2 Hz, 1H), 7.22 (td, J=7.8, 1.4 Hz, 1H), 7.12 (t, J=7.4 Hz, 1H), 6.88 (d, J=7.8 Hz, 1H), 4.10 (m, 1H), 3.57 (s, 3H), 3.32 (td, J=8.8, 2.5 Hz, 1H), 3.12 (dd, J=10.9, 3.6 Hz, 1H), 2.60 (dd, J=11.3, 2.5 Hz, 1H), 2.55 (m, 1H), 2.47 (ddd, J=12.3, 9.5, 2.4 Hz, 1H), 2.16-2.02 (m, 2H), 1.99-1.88 (m, 2H), 1.73 (qd, J=11.3, 3.4 Hz, 1H), 1.54 (dd, J=13.5, 10.5 Hz, 1H), 1.49-1.20 (m, 4H), 1.07 (dt, J=12.2, 3.1 Hz, 1H), 0.69 (q, J=11.7 Hz, 1H). $^{13}$C NMR: (100 MHz, CDCl$_3$) δ 178.6, 175.6, 142.1, 138.2, 133.4, 129.9 (q, J=33.0 Hz), 127.8, 126.9 (q, J=3.7 Hz), 126.5, 125.5, 124.0 (q, J=271.9 Hz), 123.6, 109.1, 72.2, 66.8, 58.9, 56.7, 53.5, 52.7, 51.7, 40.6, 36.3, 35.7, 31.5, 30.7, 23.6. HRMS (ESI): calc. for C$_{28}$H$_{30}$F$_3$N$_2$O$_4$ [M+H]$^+$: 515.2152, found: 515.2164.

Yield: 37%; 13.0 mg of Y3f isolated as colorless solid. $^1$H NMR: (400 MHz, CDCl$_3$) δ 8.28 (dd, J=2.8, 1.2 Hz, 1H), 7.87 (ddd, J=8.8, 6.7, 2.6 Hz, 1H), 7.49 (d, J=7.4 Hz, 1H), 7.23 (td, J=7.8, 1.4 Hz, 1H), 7.16-7.07 (m, 2H), 6.79 (d, J=7.8 Hz, 1H), 4.10 (m, 1H), 3.57 (s, 3H), 3.32 (td, J=8.6, 2.3 Hz, 1H), 3.12 (dd, J=10.9, 3.6 Hz, 1H), 3.00 (br. s, 1H), 2.59 (dd, J=11.7, 2.2 Hz, 1H), 2.54 (m, 1H), 2.46 (ddd, J=12.3, 9.5, 2.4 Hz, 1H), 2.11 (dd, J=11.8, 1.9 Hz, 1H), 2.06 (dd, J=14.1, 4.4 Hz, 1H), 1.99-1.88 (m, 2H), 1.73 (qd, J=11.5, 3.4 Hz, 1H), 1.53 (m, 1H), 1.45 (dt, J=13.5, 2.0 Hz, 1H), 1.42-1.21 (m, 2H), 1.07 (dt, J=12.2, 3.1 Hz, 1H), 0.68 (q, J=11.7 Hz, 1H). $^{13}$C NMR: (100 MHz, CDCl$_3$) δ 178.9, 175.5, 162.2 (d, J=242.3 Hz), 145.5 (d, J=15.9 Hz), 142.0, 139.6 (d, J=8.5 Hz), 133.2, 129.6 (d, J=4.7 Hz), 127.9, 125.2, 123.8, 110.7 (d, J=39.1 Hz), 108.6, 72.1, 66.8, 58.9, 56.7, 53.5, 52.6, 51.8, 40.6, 36.3, 35.7, 31.5, 30.7, 23.5. HRMS (ESI): calc. for C$_{26}$H$_{29}$FN$_3$O$_4$[M+H]$^+$: 466.2137, found: 466.2149. MP: 190-192° C., decomposed.

Y3e

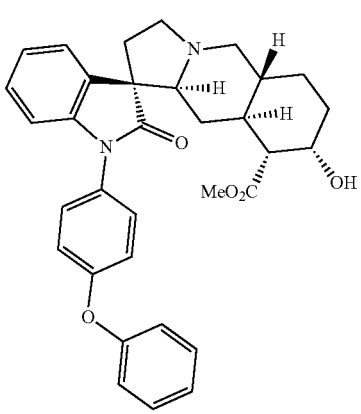

Y3g

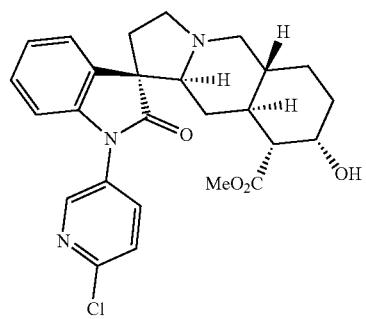

Yield: 30%; 18.4 mg of Y3e isolated as a colorless, amorphous solid. $^1$H NMR: (400 MHz, CDCl$_3$) δ 7.46 (d, J=7.3 Hz, 1H), 7.37 (t, J=7.8 Hz, 2H), 7.31 (d, J=8.7 Hz, Yield: 25%; 13.1 mg of Y3g isolated as a colorless solid. $^1$H NMR: (400 MHz, CDCl$_3$) δ 8.47 (d, J=2.7 Hz, 1H), 7.77 (dd, J=8.5, 2.7 Hz, 1H), 7.49 (d, J=8.3 Hz, 2H), 7.23 (t, J=8.0 Hz, 1H), 7.14 (t, J=7.4 Hz, 1H), 6.83 (d, J=7.8 Hz, 1H), 4.09

(m, 1H), 3.56 (s, 3H), 3.32 (td, J=9.0, 1.6 Hz 1H), 3.12 (dd, J=10.9, 3.6 Hz, 1H), 3.01 (s, 1H), 2.59 (dd, J=10.9, 1.6 Hz, 1H), 2.54 (m, 1H), 2.45 (ddd, J=12.3, 9.5, 2.4 Hz, 1H), 2.16-2.02 (m, 2H), 1.99-1.88 (m, 2H), 1.73 (qd, J=11.3, 3.4 Hz, 1H), 1.55 (dd, J=12.0, 2.6 Hz, 1H), 1.52-1.19 (m, 3H), 1.06 (dt, J=12.2, 3.1 Hz, 1H), 0.67 (q, J=11.7 Hz, 1H). $^{13}$C NMR: (100 MHz, CDCl$_3$) δ 178.8, 175.5, 150.1, 147.1, 141.6, 136.8, 133.3, 130.9, 127.9, 125.7, 125.2, 123.9, 108.7, 72.1, 66.8, 58.8, 56.7, 53.5, 52.6, 51.8, 40.5, 36.2, 35.7, 31.5, 30.7, 23.5. HRMS (ESI): calc. for C$_{26}$H$_{29}$ClN$_3$O$_4$[M+H]$^+$: 482.1841, found: 482.1843. MP: 218-220° C., decomposed.

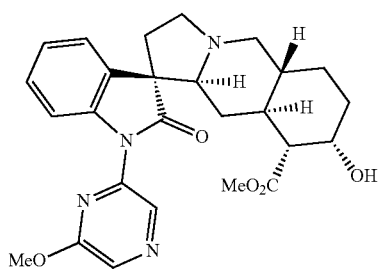

Y3h

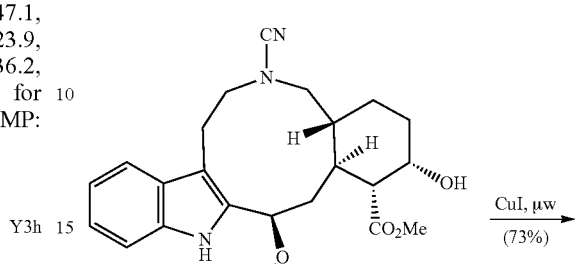

Y6k

Yield: 27%; 15.4 mg of Y3h isolated as a colorless solid. $^1$H NMR: (400 MHz, CDCl$_3$) δ 8.76 (s, 1H), 8.17 (s, 1H), 7.70 (d, J=8.0 Hz, 1H), 7.51 (d, J=7.4 Hz, 1H), 7.26 (m, 1H), 7.17 (t, J=7.5 Hz, 1H), 4.09 (m, 1H), 4.00 (s, 3H), 3.54 (s, 3H), 3.32 (t, J=9.1 Hz, 1H), 3.13 (d, J=10.8, Hz, 1H), 3.02 (br. s, 1H), 2.63 (dd, J=11.1, 1.8 Hz, 1H), 2.55 (m, 1H), 2.48 (ddd, J=12.3, 9.5, 2.4 Hz, 1H), 2.19-2.03 (m, 2H), 2.02-1.88 (m, 2H), 1.75 (q, J=11.3 Hz, 1H), 1.54 (t, J=12.7 Hz, 1H), 1.50-1.22 (m, 3H), 1.07 (d, J=12.3 Hz, 1H), 0.71 (q, J=11.8 Hz, 1H). Note: $^1$H spectrum referenced TMS at 0.00 ppm. $^{13}$C NMR: (100 MHz, CDCl$_3$) δ 178.9, 175.5, 159.0, 143.1, 140.6, 133.4, 132.1, 132.0, 127.6, 125.2, 124.0, 112.4, 72.3, 66.9, 58.9, 56.6, 54.2, 53.6, 52.6, 51.8, 40.5, 36.5, 36.3, 31.5, 30.7, 23.5. HRMS (ESI): calc. for C$_{26}$H$_{31}$N$_4$O$_5$ [M+H]$^+$: 479.2289, found: 479.2291. MP: 178-180° C., decomposed.

Y3i

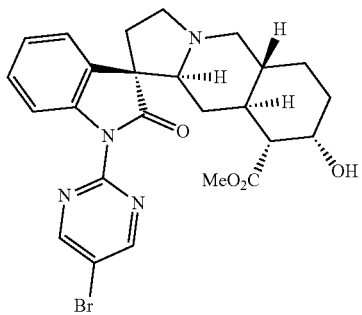

Yield: 20%; 11.0 mg of Y3i isolated as a colorless solid. $^1$H NMR: (400 MHz, CDCl$_3$) δ 9.00 (s, 1H), 8.88 (s, 1H), 7.63 (d, J=8.1 Hz, 1H), 7.50 (d, J=7.2 Hz, 1H), 7.27 (t, J=7.6 Hz, 1H), 7.16 (t, J=7.6 Hz, 1H), 4.06 (m, 1H), 3.52 (s, 3H), 3.29 (t, J=8.9 Hz, 1H), 3.15-3.04 (m, 2H), 2.65 (d, J=10.6 Hz, 1H), 2.56 (m, 1H), 2.49 (ddd, J=12.3, 9.5, 2.4 Hz, 1H), 2.15-2.01 (m, 2H), 2.00-1.87 (m, 2H), 1.71 (q, J=10.5 Hz, 1H), 1.55 (dd, J=13.1, 2.9 Hz, 1H), 1.52-1.21 (m, 3H), 1.08 (d, J=11.9 Hz, 1H), 0.70 (q, J=11.6 Hz, 1H). $^{13}$C NMR: (100 MHz, CDCl$_3$) δ 178.5, 175.6, 164.0, 159.3, 140.0, 132.9, 127.7, 125.2, 124.4, 116.7, 112.5, 72.3, 66.8, 58.9, 56.9, 53.5, 52.8, 51.9, 40.6, 36.8, 36.3, 31.4, 30.7, 23.5. Note: All $^{13}$C signals confirmed by HSQC and/or HMBC correlations. HRMS (ESI): calc. for C$_{25}$H$_{28}$BrN$_4$O$_4$[M+H]$^+$: 527.1288, found: 527.1307. MP: 55-57° C.

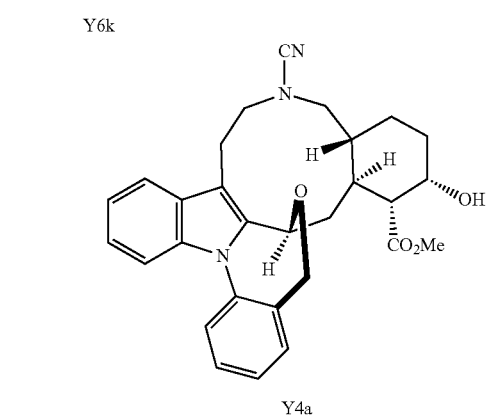

Y4a

Procedure for the preparation of Y4a: Y6k (120 mg, 0.20 mmol) was added to a flame-dried microwave vial and dissolved in dry acetonitrile (4 mL). Potassium carbonate (40.6 mg, 0.29 mmol), N,N'-dimethylethylenediamine (7 μL, 0.14 mmol), and copper(I) iodide (13.1 mg, 0.07 mmol) were added and the reaction was subjected to microwave irradiation at 160° C. for 13 minutes. The reaction was cooled to room temperature, diluted with ethyl acetate and quenched with brine (2×50 mL). The organic layers were collected, dried with sodium sulfate, filtered and concentrated. Crude product was purified via column chromatography using a gradient of 100% hexanes to 1:2 hexanes:ethyl acetate to afford Y4a (69.9 mg, 73%) as a colorless foam. $^1$H NMR: (400 MHz, CDCl$_3$) δ 7.81 (d, J=7.7 Hz, 1H), 7.69 (d, J=8.1 Hz, 1H), 7.60-7.51 (m, 2H), 7.43 (d, J=7.4 Hz, 1H), 7.33-7.27 (m, 2H), 7.22 (t, J=7.1 Hz, 1H), 5.06 (d, J=7.7 Hz, 1H), 4.59 (d, J=12.0 Hz, 1H), 4.44 (d, J=12.0 Hz, 1H), 4.00 (m, 1H), 3.56 (s, 3H), 3.52 (s, 1H), 3.42-3.27 (m, 2H), 3.14 (dd, J=12.2, 10.3 Hz, 1H), 3.08-3.00 (m, 2H), 2.95 (d, J=12.1 Hz, 1H), 2.30 (q, J=11.0 Hz, 1H), 2.15 (d, J=12.1 Hz, 1H), 1.91 (dq, J=13.5, 2.5 Hz, 1H), 1.81-1.67 (m, 2H), 1.57 (q, J=10.6 Hz, 1H), 1.42 (d, J=12.9 Hz, 1H), 1.33 (m, 1H), 1.15 (dd, J=15.3, 7.7 Hz, 1H). $^{13}$C NMR: (100 MHz, CDCl$_3$) δ 176.1, 139.1, 138.5, 136.0, 132.4, 130.3, 129.8, 127.6, 126.0, 123.4, 123.1, 121.1, 118.8, 118.1, 110.8, 110.1, 72.9, 67.0, 66.2, 54.7, 54.4, 53.2, 52.1, 42.0, 40.7, 38.5, 31.3, 26.1, 21.6. HRMS (ESI): calc. for C$_{29}$H$_{32}$N$_3$O$_4$ [M+H]$^+$: 486.2387, found: 486.2396. MP: 122-124° C.

Key ¹H signals for Y4a

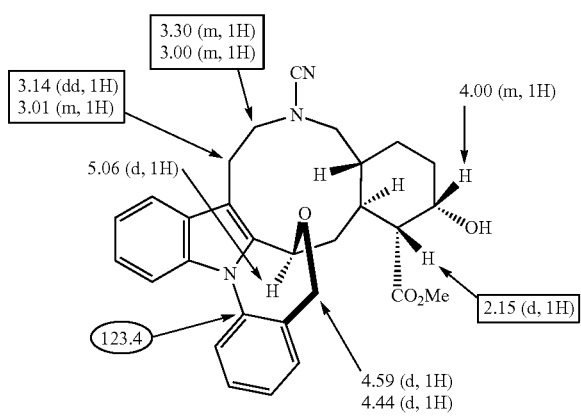

Spectral data derived via COSY in rectangle(s)
Key ¹³C signal in circle(s)

Key COSY correlations for Y4a

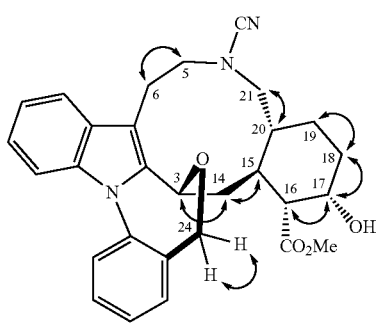

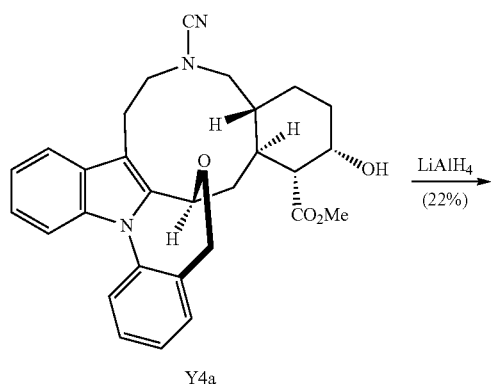

Y4a

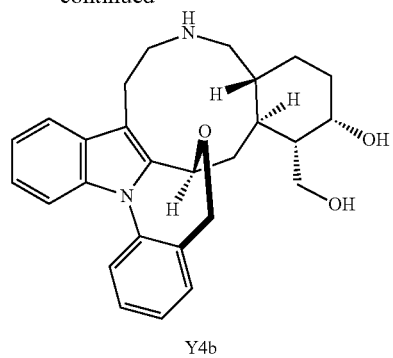

Y4b

Procedure for the preparation of Y4b: Y4a (113 mg, 0.23 mmol) was added to a round-bottom flask and dissolved in tetrahydrofuran (4 mL). The reaction was added a 1M solution of lithium aluminum hydride in tetrahydrofuran (1.4 mL, 1.40 mmol) at room temperature. The reaction was stirred for 1.5 hours and subsequently quenched by slow addition of water (3 mL), then 1M NaOH (1 mL) and celite. The slurry was allowed to stir for 30 minutes before being filtered through a plug of celite and washed with hot ethyl acetate. The filtrate was collected, dried with sodium sulfate, filtered and concentrated. Crude product was purified via column chromatography using a gradient of 99:1 hexanes:triethylamine to 49.5:49.5:1 hexanes:ethyl acetate:trimethylamine to 98:1:1 ethyl acetate:methanol:trimethylamine to afford Y4b (22.3 mg, 22%) as a colorless foam. 1H NMR: (400 MHz, CDCl$_3$) δ 7.77 (d, J=7.8 Hz, 1H), 7.73 (d, J=8.1 Hz, 1H), 7.63 (d, J=7.7 Hz, 1H), 7.55-7.46 (m, 2H), 7.33-7.18 (m, 3H), 5.37 (d, J=8.0 Hz, 1H), 4.77 (d, J=12.2 Hz, 1H), 4.49 (d, J=12.2 Hz, 1H), 4.08 (m, 1H), 3.81 (dd, J=12.6, 3.8 Hz, 1H), 3.70-3.58 (m, 2H), 3.05-2.89 (m, 3H), 2.86 (dd, J=15.9, 2.1 Hz, 1H), 2.79 (dd, J=11.7, 2.8 Hz, 1H), 2.72 (m, 1H), 2.16-1.96 (m, 2H), 1.80 (m, 1H), 1.67 (m, 1H), 1.57 (td, J=13.2, 3.7 Hz, 1H), 1.38-1.22 (m, 4H), 1.00 (q, J=9.7 Hz, 1H), 0.94 (d, J=12.5 Hz, 1H). Note: ¹H spectrum referenced TMS at 0.00 ppm. ¹³C NMR: (100 MHz, CDCl$_3$) δ 139.6, 138.2, 135.6, 131.8, 130.5, 129.9, 128.6, 126.1, 123.0, 122.3, 120.8, 119.2, 114.1, 110.9, 76.2, 72.5, 67.2, 64.6, 62.9, 54.3, 48.8, 45.8, 45.0, 38.2, 37.6, 32.5, 26.3. HRMS (ESI): calc. for C$_{27}$H$_{33}$N$_2$O$_3$ [M+H]$^+$: 433.2486, found: 433.2491. MP: 99-101° C.

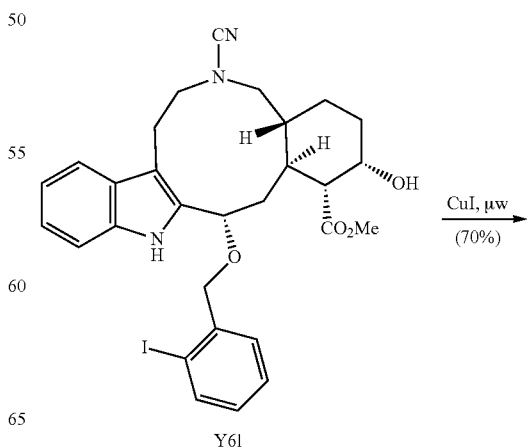

Y6l

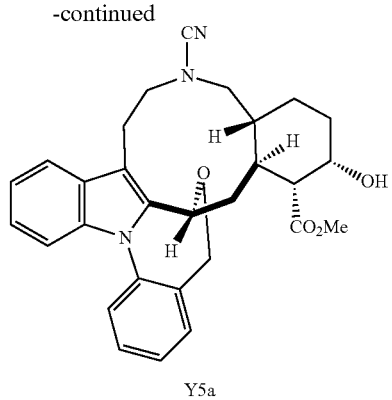

Y5a

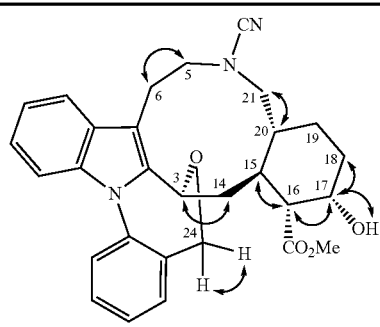

Key COSY correlations for Y5a

Procedure for the preparation of Y5a: Y6l (292 mg, 0.48 mmol) was added to a flame-dried microwave vial and dissolved in dry acetonitrile (8 mL). Potassium carbonate (98.8 mg, 0.72 mmol), N,N'-dimethylethylenediamine (36 μL, 0.33 mmol), and copper(I) iodide (31.8 mg, 0.17 mmol) were added and the reaction was subjected to microwave irradiation at 160° C. for 13 minutes. The reaction was cooled to room temperature, diluted with ethyl acetate and quenched with brine (2×50 mL). The organic layers were collected, dried with sodium sulfate, filtered and concentrated. Crude product was purified via column chromatography using a gradient of 100% hexanes to 1:2 hexanes:ethyl acetate to afford Y5a (163 mg, 70%) as a colorless foam. $^1$H NMR: (400 MHz, CDCl$_3$) δ 7.81 (d, J=7.6 Hz, 1H), 7.70 (d, J=8.6 Hz, 1H), 7.58 (d, J=7.6 Hz, 1H), 7.53 (td, J=7.6, 1.3 Hz, 1H), 7.39 (dd, J=7.4, 1.3 Hz, 1H), 7.32 (d, J=7.5 Hz, 1H), 7.28 (m, 1H), 7.22 (td, J=7.5, 0.9 Hz, 1H), 5.50 (t, J=6.0 Hz, 1H), 4.66 (d, J=12.2 Hz, 1H), 4.41 (d, J=12.2 Hz, 1H), 3.91 (m, 1H), 3.58 (s, 3H), 3.56 (m, 1H), 3.45 (m, 1H), 3.22 (dt, J=15.2, 3.2 Hz, 1H), 3.10 (m, 1H), 2.96 (dd, J=14.2, 2.3 Hz, 1H), 2.81 (dd, J=14.2, 9.8 Hz, 1H), 2.71 (m, 1H), 2.45 (dd, J=9.6, 2.0 Hz, 1H), 1.94-1.66 (m, 5H), 1.57-1.40 (m, 3H). $^{13}$C NMR: (100 MHz, CDCl$_3$) δ 175.2, 138.8, 136.4, 136.4, 132.5, 130.0, 129.7, 128.0, 126.2, 123.6, 123.5, 121.2, 118.9, 118.5, 111.1, 111.0, 70.1, 67.3, 66.8, 59.3, 53.2, 52.2, 51.1, 38.9, 37.4, 35.5, 30.1, 24.8, 24.8. HRMS (ESI): calc. for C$_{29}$H$_{32}$N$_3$O$_4$ [M+H]$^+$: 486.2387, found: 486.2382. MP: 75-77° C.

Key $^1$H signals for Y5a

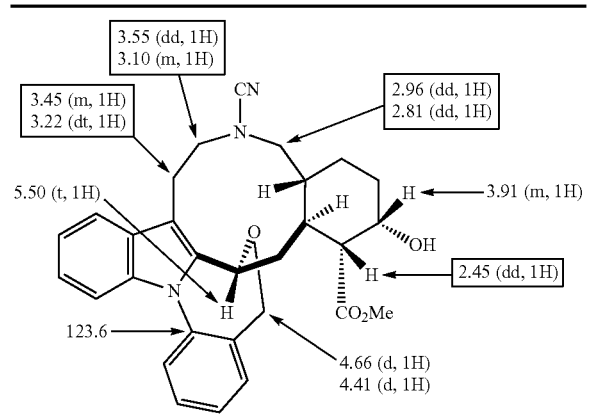

Spectral data derived via COSY in rectangle(s)
Key $^{13}$C signal in circle(s)

Procedure for the preparation of Y5b: Y5a (117 mg, 0.24 mmol) was added to a round-bottom flask and dissolved in tetrahydrofuran (5 mL). The reaction was added a 1M solution of lithium aluminum hydride in tetrahydrofuran (1.4 mL, 1.44 mmol) at room temperature. The reaction was stirred for 2 hours and subsequently quenched by slow addition of water (3 mL), then 1M NaOH (1 mL) and celite. The slurry was allowed to stir for 30 minutes before being filtered through a plug of celite and washed with hot ethyl acetate. The filtrate was collected, dried with sodium sulfate, filtered and concentrated. Crude product was purified via column chromatography using a gradient of 99:1 hexanes:triethylamine to 49.5:49.5:1 hexanes:ethyl acetate:trimethylamine to 98:1:1 ethyl acetate:methanol:trimethylamine to afford Y5b (29.7 mg, 29%) as a pale-brown foam. $^1$H NMR: (400 MHz, CDCl$_3$) δ 7.87 (d, J=7.8 Hz, 1H), 7.70 (d, J=8.1 Hz, 1H), 7.65 (dd, J=8.1, 1.0 Hz, 1H), 7.59 (td, J=7.7, 1.4 Hz, 1H), 7.44 (dd, J=7.7, 1.4 Hz, 1H), 7.35 (dd, J=7.4, 1.1

Hz, 1H), 7.33-7.19 (m, 2H), 5.76 (dd, J=11.2, 6.8 Hz, 1H), 4.51 (d, J=12.3 Hz, 1H), 4.40 (d, J=12.3 Hz, 1H), 3.80 (m, 1H), 3.22-3.11 (m, 2H), 3.11-3.06 (m, 2H), 3.05-2.98 (m, 2H), 2.91 (m, 1H), 2.53 (dd, J=12.0, 2.8 Hz, 1H), 2.05-1.85 (m, 2H), 1.80 (m, 1H), 1.70 (dd, J=12.0, 3.3 Hz, 1H), 1.67-1.55 (m, 2H), 1.40-1.20 (m, 6H). Note: $^1$H spectrum referenced TMS at 0.00 ppm. $^{13}$C NMR: (100 MHz, CDCl$_3$) δ 138.8, 137.0, 135.6, 132.6, 130.2, 129.4, 127.8, 126.7, 123.8, 123.6, 121.0, 119.5, 113.0, 110.8, 71.7, 68.9, 66.8, 63.7, 60.6, 49.1, 46.7, 44.7, 43.4, 41.3, 32.6, 24.7, 21.8. HRMS (ESI): calc. for $C_{27}H_{33}N_2O_3$ [M+H]$^+$: 433.2486, found: 433.2483. MP: 60-62° C.

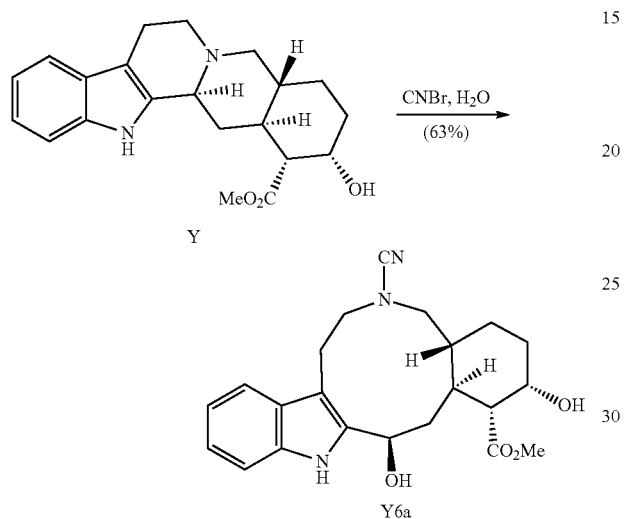

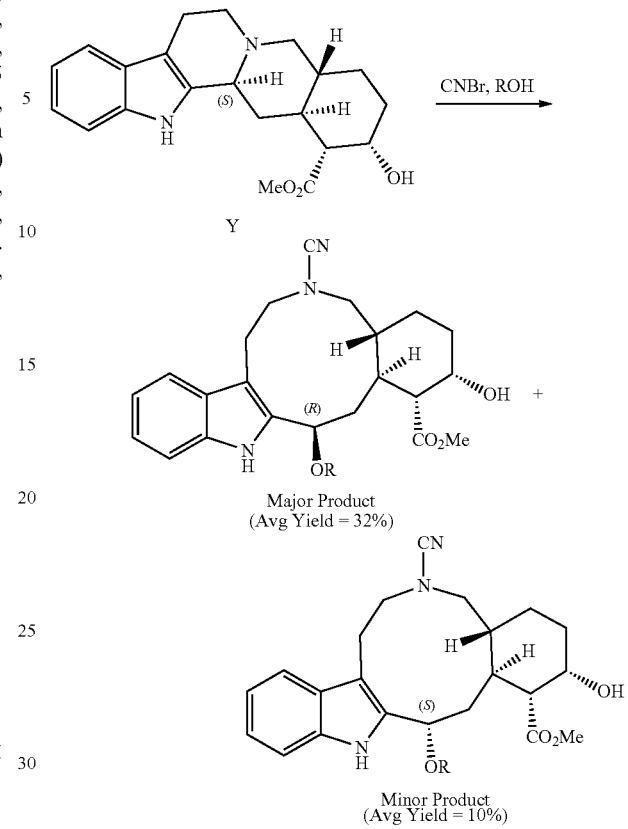

Procedure for synthesis of Y6a: Y (104 mg, 0.29 mmol) was added to a round-bottom flask and subsequently dissolved in a 2.5:1 tetrahydrofuran:water solution. To the solution was added dropwise a 3M solution of cyanogen bromide in dichloromethane (0.29 mL, 0.88 mmol). The reaction was allowed to stir at room temperature for 23 hours before being quenched with brine. The product was extracted with dichloromethane, dried with sodium sulfate, filtered and concentrated under reduced pressure. Crude material was purified via column chromatography using a gradient of 100% hexanes to 1:1 hexanes:ethyl acetate to afford Y6a (73.8 mg, 63%) as a colorless foam. Notes. A.) Compound Y6a has been previously reported; however, no melting point data was given.[5] B.) This reaction was scaled up to isolate Y6a in 208 mg, 57%. $^1$H NMR: (400 MHz, CDCl$_3$) δ 8.92 (s, 1H), 7.43 (d, J=7.7 Hz, 1H), 7.28 (dt, J=8.2, 1.0 Hz, 1H), 7.14 (td, J=7.1, 1.2 Hz, 1H), 7.08 (td, J=7.1, 1.2 Hz, 1H), 4.78 (t, J=5.0 Hz, 1H), 4.16 (m, 1H), 4.00 (br. s, 1H), 3.61 (s, 3H), 3.38 (m, 1H), 3.26-3.09 (m, 2H), 2.93-2.83 (m, 2H), 2.80 (d, J=12.3 Hz, 1H), 2.51-2.33 (m, 3H), 1.86 (m, 1H), 1.82 (dd, J=13.9, 2.9 Hz, 1H), 1.61 (ddd, J=15.9, 6.9, 2.6 Hz, 1H), 1.57-1.41 (m, 2H), 1.31 (dq, J=12.8, 2.8 Hz, 1H), 1.20 (m, 1H). $^{13}$C NMR: (100 MHz, CDCl$_3$) δ 176.0, 138.9, 135.4, 128.1, 121.9, 119.5, 118.1, 117.9, 111.4, 106.7, 69.5, 67.2, 56.0, 54.3, 53.5, 52.3, 43.2, 40.2, 37.6, 31.9, 25.1, 23.2. HRMS (ESI): calc. for $C_{22}H_{27}N_3O_4Na$ [M+Na]$^+$: 420.1894, found: 420.1902. MP: 93-95° C.

General procedure for the preparation of Y6b-Y6s: Y (103 mg, 0.29 mmol) was added to a round-bottom flask and dissolved in a 1:3 methanol:chloroform solution. A 3M solution of cyanogen bromide in dichloromethane (0.29 mL, 0.87 mmol) was added dropwise and the reaction was stirred at room temperature for 6.5 hours. The reaction was diluted with dichloromethane and filtered through a frit funnel. The resulting filtrate was purified via column chromatography using a gradient of 100% hexanes to 1:1 hexanes:ethyl acetate to afford Y6b (65.1 mg, 55%) as a colorless foam. Note: Major diastereomer products have two characteristic multiplets each integrating for one proton. These signals occur at 2.82-2.60 ppm and 2.30-2.17 ppm (refer to comprehensive NMR data for compound Y6b). However, minor diastereomer products do not contain these multiplets.

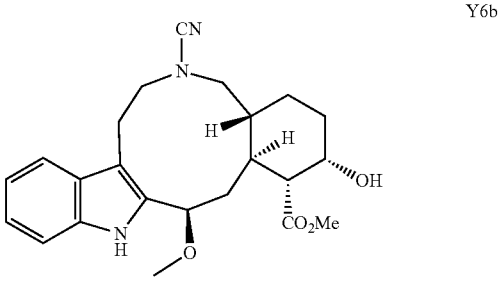

Yield: 55%; 65.1 mg of Y6b isolated as a colorless foam. Note: This reaction was scaled up to isolate Y6b in 498 mg, 36%. $^1$H NMR: (400 MHz, CDCl$_3$ at 50° C.) δ 8.29 (s, 1H), 7.48 (d, J=7.7 Hz, 1H), 7.36 (d, J=8.0, Hz, 11H), 7.20 (td, J=7.3, 1.0 Hz, 11H), 7.12 (td, J=7.3, 1.1 Hz, 1H), 4.25 (dd, J=8.5, 6.1 Hz, 11H), 4.09 (m, 1H), 3.84 (s, 3H), 3.50 (m, 1H), 3.41-3.29 (m, 2H), 3.18 (s, 3H), 2.98 (dd, J=12.7, 6.3 Hz, 1H), 2.91 (d, J=12.7 Hz, 1H), 2.80 (br. s, 1H), 2.65 (m, 1H), 2.48 (dd, J=11.5, 2.2 Hz, 1H), 2.27 (m, 1H), 1.96-1.74 (m, 3H), 1.61 (qd, J=10.1, 4.7 Hz, 1H), 1.45 (tt, J=13.6, 2.0 Hz, 1H), 1.40-1.18 (m, 2H). $^{13}$C NMR: (100 MHz, CDCl$_3$ at 50° C.) δ 175.6, 135.9, 135.4, 127.7, 121.8, 119.4, 118.1, 117.7, 111.4, 108.7, 78.3, 66.4, 56.9, 56.4, 54.9, 53.2, 51.9, 39.9, 39.5, 35.6, 31.3, 25.0, 23.9. HRMS (ESI): calc. for C$_{23}$H$_{29}$N$_3$O$_4$Na [M+Na]$^+$: 434.2050, found: 434.2051. MP: 97-99° C.

Key signals for Y6b

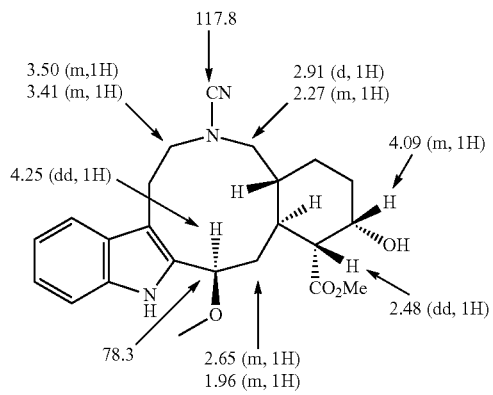

Spectral data derived via COSY in rectangle(s)
Key $^{13}$C signal in circle(s)

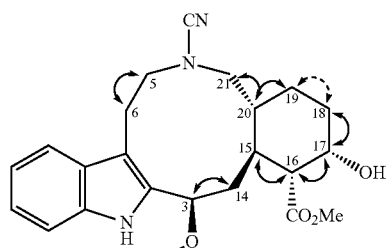

Key COSY correlations

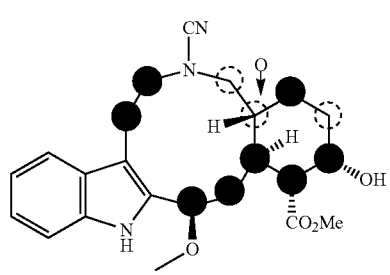

HSQC correlations for Y6b

Key signals for Y6b

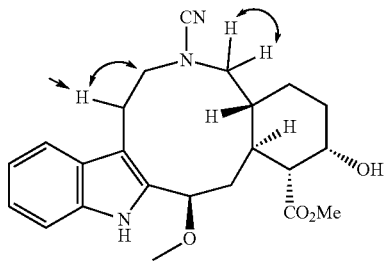

Key nOe correlations

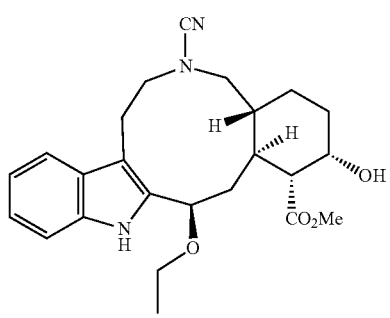

Y6c

Yield: 47%; 171 mg of Y6c isolated as a colorless foam. $^1$H NMR: (400 MHz, CDCl$_3$ at 50° C.) δ 8.70 (s, 1H), 7.46 (d, J=7.8 Hz, 1H), 7.28 (d, J=8.1, Hz, 1H), 7.14 (td, J=7.8, 0.8 Hz, 1H), 7.09 (td J=7.4, 0.6 Hz, 1H), 4.39 (dd, J=9.4, 5.8 Hz, 1H), 4.13 (m, 1H), 3.80 (s, 3H), 3.54-3.29 (m, 3H), 3.29-3.19 (m, 3H), 2.96 (dd, J=13.6, 5.9 Hz, 1H), 2.82 (d, J=12.7 Hz, 1H), 2.70 (m, 1H), 2.48 (dd, J=11.6, 1.7 Hz, 1H), 2.17 (m, 1H), 1.94-1.71 (m, 3H), 1.58 (qd, J=11.1, 3.5 Hz, 1H), 1.46 (t, J=12.7 Hz, 1H), 1.28 (m, 1H), 1.20 (m, 1H), 1.08 (t, J=7.0 Hz, 3H). $^{13}$C NMR: (100 MHz, CDCl$_3$ at 50° C.) δ 176.0, 136.8, 135.4, 127.9, 121.9, 119.5, 118.3, 117.8, 111.4, 108.6, 76.4, 66.5, 64.2, 57.2, 55.0, 53.4, 52.0, 40.1, 39.5, 35.7, 31.3, 25.1, 24.1, 15.2. HRMS (ESI): calc. for C$_{24}$H$_{31}$N$_3$O$_4$Na [M+Na]$^+$: 448.2207, found: 448.2219. MP: 50-52° C., lit: 115-125° C.$^5$ Note: Previously reported $^1$H NMR in CDCl$_3$ only contained three reported signals: 1.07 (t, 3H), 3.80 (s, 3H), and 4.33 (m, 1H). All previously reported signals were accounted for in our sample.$^5$

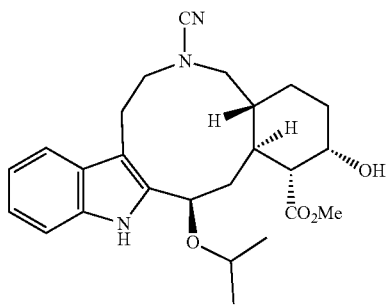

Y6d

Yield: 39%; 145 mg of Y6d isolated as a colorless foam. $^1$H NMR: (400 MHz, CDCl$_3$ at 50° C.) δ 8.66 (s, 1H), 7.47

(d, J=7.7, 1H), 7.29 (d, J=7.7 Hz, 1H), 7.14 (t, J=7.0 Hz, 1H), 7.10 (t, J=7.7 Hz, 1H), 4.46 (dd, J=8.8, 5.9 Hz, 1H), 4.13 (m, 1H), 3.82 (s, 3H), 3.57-3.26 (m, 5H), 2.96 (dd, J=14.0, 5.8 Hz, 1H), 2.86 (d, J=12.7 Hz, 1H), 2.71 (m, 1H), 2.48 (d, J=11.5 Hz, 1H), 2.17 (m, 1H), 1.93-1.70 (m, 3H), 1.61 (qd, J=10.0, 3.8 Hz, 1H), 1.46 (t, J=13.2 Hz, 1H), 1.38-1.16 (m, 2H), 1.11 (d, J=5.9 Hz, 3H), 1.00 (d, J=5.9 Hz, 3H). $^{13}$C NMR: (100 MHz, CDCl$_3$ at 50° C.) δ 176.3, 137.4, 135.4, 128.0, 122.0, 119.6, 118.3, 117.9, 111.4, 108.6, 73.6, 69.0, 66.4, 57.4, 54.9, 53.5, 52.1, 40.3, 39.6, 36.0, 31.3, 25.2, 24.2, 23.2, 21.2. HRMS (ESI): calc. for $C_{25}H_{33}N_3O_4Na$ [M+Na]$^+$: 462.2363, found: 462.2375. MP: 58-60° C.

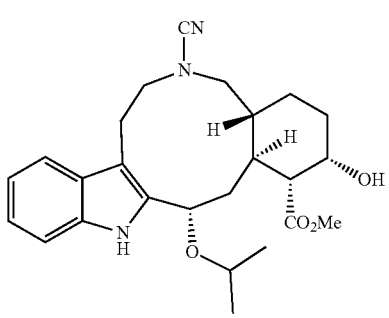

Y6e

Yield: 9% as the minor product; 22.2 mg of Y6e isolated as a colorless solid. $^1$H NMR: (400 MHz, CDCl$_3$) δ 8.53 (s, 1H), 7.46 (d, J=7.7 Hz, 1H), 7.42 (dd, J=8.1 Hz, 1H), 7.20 (td, J=8.1, 0.8 Hz, 1H), 7.11 (td, J=7.6, 0.8 Hz, 1H), 4.95 (dd, J=6.9, 2.8 Hz, 1H), 4.05 (m, 1H), 3.82 (s, 3H), 3.60 (dt, J=14.1, 3.6 Hz, 1H), 3.49 (p, J=6.1 Hz, 1H), 3.19 (td, J=13.4, 2.4 Hz, 1H), 3.14-3.05 (m, 2H), 3.00-2.89 (m, 2H), 2.53-2.42 (m, 2H), 2.10-1.98 (m, 2H), 1.94-1.77 (m, 2H), 1.74 (br. s, 1H), 1.63 (m, 1H), 1.44 (m, 1H), 1.25 (m, 1H), 1.17 (d, J=6.1 Hz, 3H), 1.12 (d, J=6.1 Hz, 3H). $^{13}$C NMR: (100 MHz, CDCl$_3$) δ 176.1, 137.5, 135.5, 127.9, 122.2, 119.7, 118.4, 117.9, 111.6, 107.9, 70.2, 70.2, 66.6, 59.8, 53.9, 53.6, 52.2, 40.8, 39.3, 35.5, 30.9, 24.9, 24.8, 23.5, 21.5. HRMS (ESI): calc. for $C_{25}H_{34}N_3O_4$ [M+H]$^+$: 440.2544, found: 440.2526. MP: 50-52° C.

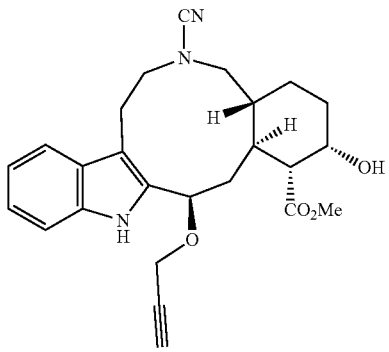

Y6f

Yield: 17%; 46.6 mg of Y6f isolated as a colorless foam. $^1$H NMR: (400 MHz, CDCl$_3$ at 50° C.) δ 8.43 (s, 1H), 7.48 (d, J=7.9 Hz, 1H), 7.35 (d, J=7.9 Hz, 1H), 7.20 (td, J=8.1, 0.9 Hz, 1H), 7.12 (td, J=7.0, 0.9 Hz, 1H), 4.66 (dd, J=9.1, 6.3 Hz, 1H), 4.10 (m, 1H), 4.08 (dd, J=16.0, 2.4 Hz, 1H), 3.85 (s, 3H), 3.82 (dd, J=16.0, 2.4 Hz, 1H), 3.52 (m, 1H), 3.43-3.28 (m, 2H), 3.08-2.96 (m, 2H), 2.93 (d, J=12.8 Hz, 1H), 2.71 (m, 1H), 2.48 (dd, J=11.6, 2.0 Hz, 1H), 2.41 (td, J=2.4, 0.8 Hz, 1H), 2.28 (m, 1H), 1.98-1.77 (m, 3H), 1.64 (dq, J=10.6, 3.8 Hz, 1H), 1.47 (tt, J=12.5, 2.7 Hz, 1H), 1.41-1.19 (m, 2H). 1C NMR: (100 MHz, CDCl$_3$ at 50° C.) δ 176.5, 135.8, 135.0, 128.1, 122.6, 120.0, 118.3, 118.2, 111.7, 109.8, 80.1, 74.9, 74.7, 66.5, 57.7, 55.9, 54.8, 53.7, 52.4, 39.8 (2, confirmed by HSQC), 36.2, 31.3, 25.2, 24.2. HRMS (ESI): calc. for $C_{25}H_{29}N_3O_4Na$ [M+Na]$^+$: 458.2050, found: 458.2041. MP: 96-98° C.

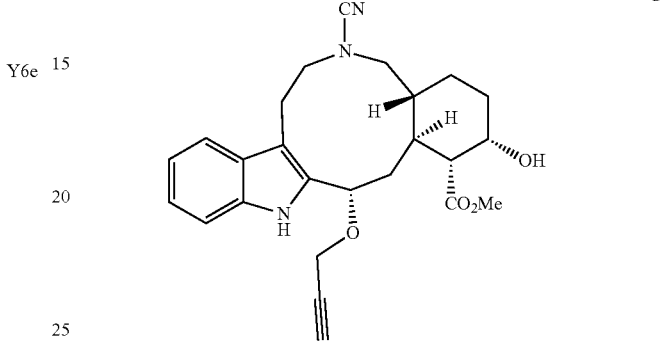

Y6g

Yield: 6% as the minor product; 12.9 mg of Y6g isolated as a colorless solid. $^1$H NMR: (400 MHz, CDCl$_3$) δ 8.62 (s, 1H), 7.48 (d, J=7.8 Hz, 1H), 7.42 (d, J=8.1 Hz, 1H), 7.21 (td, J=7.5, 1.1 Hz, 1H), 7.12 (td, J=7.4, 1.0 Hz, 1H), 5.13 (dd, J=6.5, 3.5 Hz, 1H), 4.15 (dd, J=15.8, 2.4 Hz, 1H), 4.06 (m, 1H), 3.93 (dd, J=15.8, 2.4 Hz, 1H), 3.83 (s, 3H), 3.60 (dt, J=13.8, 3.5 Hz, 1H), 3.20 (td, J=12.7, 2.3 Hz, 1H), 3.14-3.06 (m, 2H), 3.00 (m, 1H), 2.92 (dd, J=13.2, 1.6 Hz, 1H), 2.55 (ddd, J=16.1, 6.5, 4.8 Hz, 1H), 2.50-2.44 (m, 2H), 2.16 (dt, J=16.1, 3.6 Hz, 1H), 1.97 (dd, J=12.9, 9.8 Hz, 1H), 1.91-1.77 (m, 2H), 1.71 (s, 1H), 1.63 (m, 1H), 1.41 (td, J=12.1, 5.6 Hz, 1H), 1.23 (m, 1H). $^{13}$C NMR: (100 MHz, CDCl$_3$) δ 176.6, 135.6, 134.9, 127.5, 122.5, 119.8, 118.5, 118.0, 111.8, 109.0, 79.6, 75.1, 72.3, 66.3, 59.8, 56.8, 53.8, 53.4, 52.5, 40.0, 39.1, 35.4, 30.7, 24.9, 24.6. HRMS (ESI): calc. for $C_{25}H_{29}N_3O_4Na$ [M+Na]$^+$: 458.2050, found: 458.2071. MP: 56-58° C.

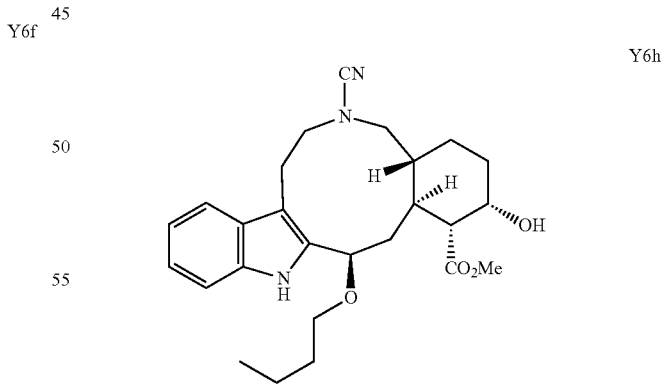

Y6h

Yield: 34%; 59.2 mg of Y6h isolated as a colorless foam. $^1$H NMR: (400 MHz, CDCl$_3$ at 50° C.) δ 8.49 (s, 1H), 7.47 (d, J=7.6 Hz, 1H), 7.32 (d, J=7.6 Hz, 1H), 7.17 (t, J=7.2 Hz, 1H), 7.11 (t, J=7.2 Hz, 1H), 4.33 (dd, J=9.4, 6.3 Hz, 1H), 4.11 (m, 1H), 3.82 (s, 3H), 3.50 (m, 2H), 3.45-3.30 (m, 2H), 3.26-3.17 (m, 2H), 3.10 (m, 1H), 2.96 (dd, J=13.5, 4.8 Hz, 1H), 2.87 (d, J=12.7 Hz, 1H), 2.69 (m, 1H), 2.48 (d, J=11.9

Hz, 1H), 2.20 (m, 1H), 1.99-1.70 (m, 3H), 1.60 (qd, J=11.4, 3.2 Hz, 1H), 1.54-1.40 (m, 3H), 1.39-1.15 (m, 4H), 0.86 (t, J=7.3 Hz, 3H). $^{13}$C NMR: (100 MHz, CDCl$_3$ at 50° C.) δ 176.4, 137.0, 135.5, 128.1, 122.2, 119.8, 118.4, 118.1, 111.5, 108.8, 76.9, 69.0, 66.6, 57.5, 54.9, 53.6, 52.2, 40.3, 39.6, 36.2, 32.1, 31.4, 25.2, 24.3, 19.4, 13.9. HRMS (ESI): calc. for C$_{26}$H$_{35}$N$_3$O$_4$Na [M+Na]$^+$: 476.2520, found: 476.2519. MP: 48-50° C.

Y6i

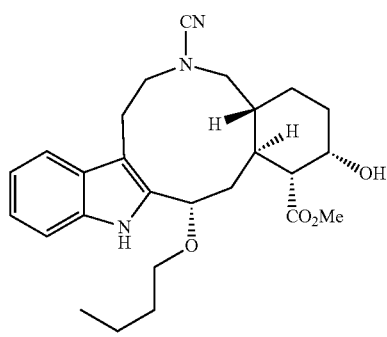

Yield: 6% as the minor product; 6.9 mg of Y6i isolated as a colorless solid. 1H NMR: (400 MHz, CDCl$_3$) δ 8.51 (s, 1H), 7.47 (d, J=7.9 Hz, 1H), 7.42 (d, J=8.2 Hz, 1H), 7.20 (tt, J=7.5, 0.9 Hz, 1H), 7.11 (tt, J=7.5, 0.9 Hz, 1H), 4.79 (dd, J=6.6, 3.1 Hz, 1H), 4.04 (m, 1H), 3.80 (s, 3H), 3.59 (dt, J=13.9, 3.4 Hz, 1H), 3.36-3.29 (m, 2H), 3.19 (td, J=13.9, 12.9, 2.6 Hz, 1H), 3.12-3.03 (m, 2H), 2.99-2.87 (m, 2H), 2.51 (ddd, J=16.1, 6.7, 4.8 Hz, 1H), 2.44 (dd, J=11.5, 2.2 Hz, 1H), 2.09 (dt, J=15.9, 3.4 Hz, 1H), 1.97 (dd, J=13.0, 9.9 Hz, 1H), 1.91-1.77 (m, 2H), 1.67-1.48 (m, 4H), 1.48-1.17 (m, 4H), 0.90 (t, J=7.4 Hz, 3H). $^{13}$C NMR: (100 MHz, CDCl$_3$) δ 176.5, 136.8, 135.4, 127.7, 122.2, 119.7, 118.6, 117.9, 111.7, 108.0, 73.5, 70.1, 66.4, 59.8, 53.9, 53.5, 52.4, 40.3, 39.1, 35.4, 32.2, 30.7, 25.1, 24.7, 19.5, 14.2. HRMS (ESI): calc. for C$_{26}$H$_{36}$N$_3$O$_4$ [M+H]$^+$: 454.2700, found: 454.2719. MP: 68-70° C.

Y6j

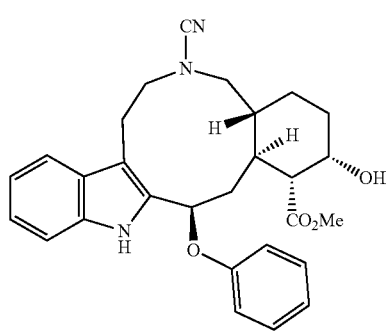

Yield: 8%; 26.4 mg of Y6j isolated as a colorless foam. Note: Y6j was synthesized via refluxing in chloroform for 7.5 hours. $^1$H NMR: (400 MHz, CDCl$_3$ at 50° C.) δ 8.60 (s, 1H), 7.45 (d, J=7.8 Hz, 1H), 7.32 (d, J=7.8 Hz 1H), 7.20-7.13 (m, 3H), 7.10 (tt, J=7.7, 1.1 Hz, 1H), 6.91-6.83 (m, 3H), 5.23 (dd, J=8.6, 7.2 Hz, 1H), 4.15 (m, 1H), 3.80 (s, 3H), 3.57 (m, 1H), 3.52-3.32 (m, 2H), 3.04-2.76 (m, 4H), 2.54 (dd, J=11.6, 2.0 Hz, 1H), 2.30 (m, 1H), 2.11 (ddd, J=15.0, 6.4, 4.0 Hz, 1H), 1.92-1.80 (m, 2H), 1.67 (qd, J=10.3, 4.2 Hz, 1H), 1.51 (td, J=13.3, 3.9 Hz, 1H), 1.36-1.19 (m, 2H).

$^{13}$C NMR: (100 MHz, CDCl$_3$ at 50° C.) δ 176.4, 158.2, 135.8, 135.7, 129.6, 128.0, 122.5, 121.5, 119.9, 118.4, 118.3, 116.1, 111.7, 109.0, 75.6, 66.8, 57.8, 55.1, 53.6, 52.4, 40.7, 39.5, 35.8, 31.5, 25.1, 24.5. Note: HMBC and HSQC have been included in the spectra section. HRMS (ESI): calc. for C$_{28}$H$_{32}$N$_3$O$_4$ [M+H]$^+$: 474.2387, found: 474.2386. MP: 100-102° C.

Key signals for Y6J

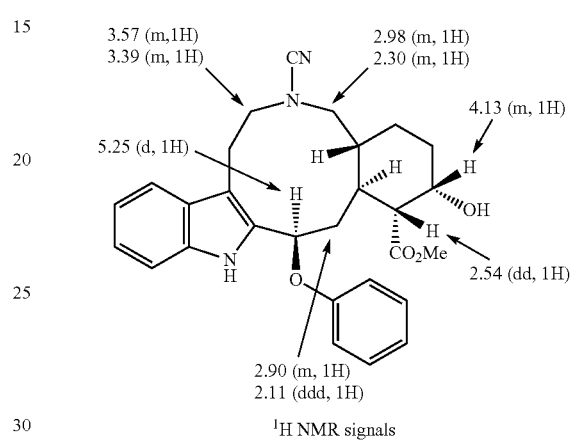

$^1$H NMR signals

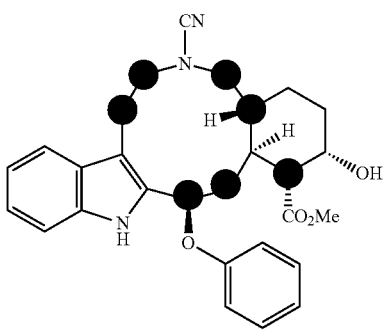

HSQC correlations

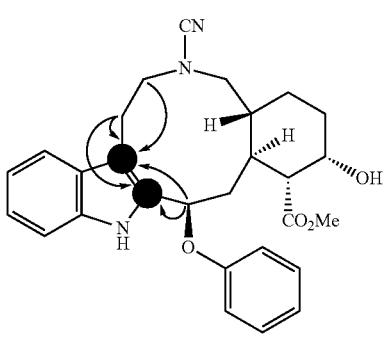

HMBC correlations

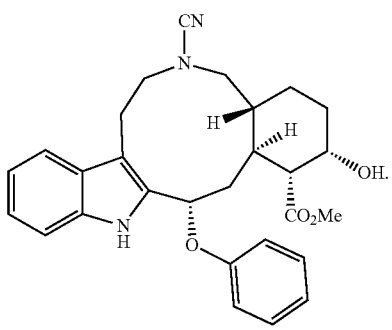

Y6k

Yield: 7% as the minor product; 25.3 mg of Y6k isolated as a colorless solid. Note: Y6k was synthesized via refluxing in chloroform for 7.5 hours. $^1$H NMR: (400 MHz, CDCl$_3$) δ 8.48 (s, 1H), 7.48 (d, J=7.7 Hz, 1H), 7.32 (dd, J=7.8 Hz, 1H), 7.24-7.08 (m, 4H), 6.94-6.86 (m, 3H), 5.68 (dd, J=5.9, 2.4 Hz, 1H), 4.08 (m, 1H), 3.78 (s, 3H), 3.65 (m, 1H), 3.42 (m, 1H), 3.28 (td, J=12.2, 2.3 Hz, 1H), 3.19 (dt, J=15.1, 2.8 Hz, 1H), 3.05 (ddd, J=15.4, 12.1, 3.4 Hz, 1H), 2.91 (d, J=13.0 Hz, 1H), 2.82 (ddd, J=16.3, 5.9, 3.8 Hz, 1H), 2.49 (dd, J=11.8, 2.0 Hz, 1H), 2.37 (dt, J=16.5, 3.1 Hz, 1H), 2.09 (m, 1H), 1.94 (dd, J=13.0, 10.0 Hz, 1H), 1.83 (dq, J=13.7, 3.5 Hz, 1H), 1.75 (br. s, 1H), 1.67 (m, 1H), 1.43 (td, J=13.1, 2.9 Hz, 1H), 1.23 (m, 1H). $^{13}$C NMR: (100 MHz, CDCl$_3$) δ 176.5, 157.7, 135.4, 135.2, 129.9, 127.6, 122.4, 121.7, 119.9, 118.5, 118.0, 115.4, 111.9, 107.1, 72.3, 66.4, 59.1, 53.5, 53.4, 52.4, 39.5, 39.0, 35.6, 30.9, 25.4, 25.1. HRMS (ESI): calc. for C$_{28}$H$_{32}$N$_3$O$_4$ [M+H]$^+$: 474.2387, found: 474.2395. MP: 115-117° C.

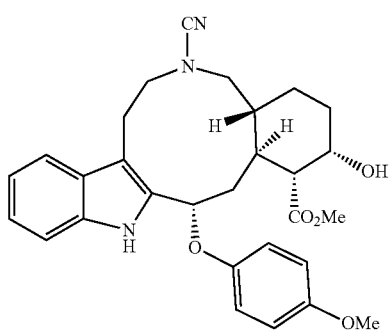

Y6m

Yield: 7% as the minor product; 24.8 mg of Y6m isolated as a colorless solid. Note: Y6m was synthesized via refluxing in chloroform for 9 hours. $^1$H NMR: (400 MHz, CDCl$_3$) δ 8.45 (s, 1H), 7.47 (d, J=7.8 Hz, 1H), 7.34 (dt, J=8.1, 1.0 Hz, 1H), 7.17 (td, J=7.2, 1.2 Hz, 1H), 7.11 (td, J=7.6, 1.0 Hz, 1H), 6.84-6.78 (m, 2H), 6.76-6.71 (m, 2H), 5.58 (dd, J=6.0, 2.5 Hz, 1H), 4.07 (m, 1H), 3.79 (s, 3H), 3.70 (s, 3H), 3.65 (dt, J=13.7, 3.3 Hz, 1H), 3.36 (s, 1H), 3.27 (td, J=12.6, 2.2 Hz, 1H), 3.16 (dt, J=15.1, 2.7 Hz, 1H), 3.02 (ddd, J=15.5, 12.2, 3.5 Hz, 1H), 2.92 (d, J=12.7 Hz, 1H), 2.80 (ddd, J=16.4, 5.9, 3.8 Hz, 1H), 2.49 (dd, J=11.7, 2.0 Hz, 1H), 2.36 (dt, J=16.3, 3.2 Hz, 1H), 2.06 (m, 1H), 1.94 (dd, J=13.0, 10.0 Hz, 1H), 1.84 (dq, J=13.7, 3.5 Hz, 1H), 1.66 (m, 1H), 1.43 (m, 1H), 1.37-1.18 (m, 2H). $^{13}$C NMR: (100 MHz, CDCl$_3$) δ 176.5, 154.4, 151.9, 135.5, 135.4, 127.6, 122.4, 119.9, 118.5, 117.9, 116.4, 115.0, 111.9, 107.1, 73.1, 66.4, 59.2, 55.8, 53.5, 53.4, 52.4, 39.4, 39.2, 35.6, 30.9, 25.3, 25.1. HRMS (ESI): calc. for C$_{29}$H$_{37}$N$_4$O$_5$ [M+NH$_4$]$^+$: 521.2758, found: 521.2754. MP: 78-80° C.

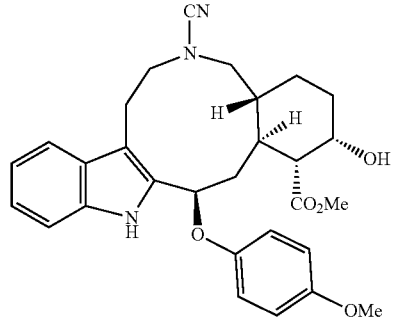

Y6l

Yield: 7%; 28.3 mg of Y6l isolated as a colorless foam. Note: Y6l was synthesized via refluxing in chloroform for 9 hours. $^1$H NMR: (400 MHz, CDCl$_3$ at 50° C.) δ 8.43 (s, 1H), 7.46 (d, J=7.9 Hz, 1H), 7.33 (d, J=8.1 Hz, 1H), 7.18 (ddd, J=8.2, 7.0, 1.2 Hz, 1H), 7.11 (ddd, J=8.0, 7.0, 1.1 Hz, 1H), 6.79-6.74 (m, 2H), 6.72-6.66 (m, 2H), 5.06 (dd, J=8.3, 6.7 Hz, 1H), 4.12 (m, 1H), 3.81 (s, 3H), 3.69 (s, 3H), 3.56 (m, 1H), 3.51-3.31 (m, 2H), 3.03-2.91 (m, 2H), 2.82 (m, 1H), 2.52 (dd, J=11.6, 2.2 Hz, 1H), 2.28 (m, 1H), 2.10 (ddd, J=14.9, 6.4, 3.9 Hz, 1H), 1.93-1.80 (m, 2H), 1.74-1.60 (m, 2H), 1.49 (td, J=13.8, 3.9 Hz, 1H), 1.42-1.19 (m, 2H). $^{13}$C NMR: (100 MHz, CDCl$_3$ at 50° C.) δ 176.5, 154.7, 152.5, 136.2, 135.8, 128.2, 122.6, 120.0, 118.4, 118.3, 117.6, 115.0, 111.7, 109.0, 77.0, 66.7, 57.9, 55.9, 54.9, 53.7, 52.4, 40.8, 39.8, 36.3, 31.4, 25.1, 24.4. HRMS (ESI): calc. for C$_{29}$H$_{33}$N$_3$O$_5$Na [M+Na]$^+$: 526.2312, found: 526.2305. MP: 97-99° C.

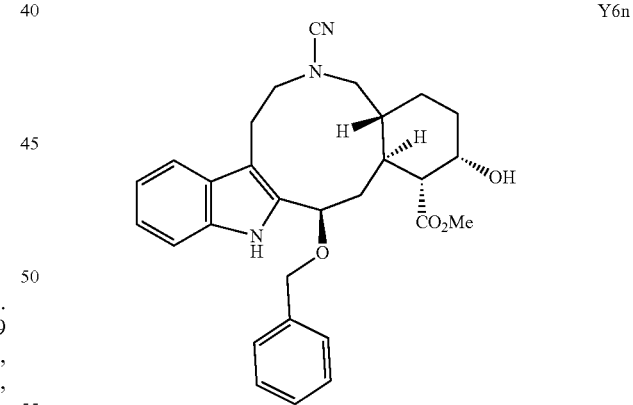

Y6n

Yield: 37%; 560 mg of Y6n isolated as a colorless foam. Note: Y6n was synthesized via refluxing in chloroform for 4 hours. $^1$H NMR: (400 MHz, CDCl$_3$ at 50° C.) δ 8.23 (s, 1H), 7.48 (d, J=7.8 Hz, 1H), 7.36 (d, J=8.2 Hz, 1H), 7.32 (d, J=6.5 Hz, 1H), 7.30-7.23 (m, 4H), 7.20 (td, J=7.6, 0.8 Hz, 1H), 7.12 (td, J=7.8, 0.6 Hz, 1H), 4.46 (d, J=12.1 Hz, 1H), 4.31 (t, J=6.9 Hz, 1H), 4.17 (d, J=12.1 Hz, 1H), 4.04 (m, 1H), 3.69 (s, 3H), 3.46 (m, 1H), 3.42-3.20 (m, 2H), 3.26 (m, 1H), 2.97-2.84 (m, 2H), 2.60 (m, 1H), 2.42 (dd, J=11.6, 2.0 Hz, 1H), 2.17 (m, 1H), 1.98-1.70 (m, 3H), 1.61 (qd, J=10.3, 3.7 Hz, 1H), 1.43 (t, J=13.3 Hz, 1H), 1.37-1.16 (m, 2H).

Note: [1]H spectrum referenced TMS at 0.00 ppm. $^{13}$C NMR: (100 MHz, CDCl$_3$ at 50° C.) δ 175.9, 138.2, 136.0, 135.5, 128.2, 127.8, 127.8, 127.5, 122.0, 119.5, 118.0, 117.9, 111.4, 108.9, 74.9, 70.3, 66.3, 57.0, 54.8, 53.2, 51.9, 39.9, 39.6, 35.7, 31.2, 25.1, 24.0. $^1$H NMR: (400 MHz, d$_6$-DMSO at 50° C.) δ 10.86 (s, 1H), 7.50 (d, J=7.8 Hz, 1H), 7.42-7.30 (m, 5H), 7.27 (m, 1H), 7.08 (td, J=7.3, 1.2 Hz, 1H), 7.00 (t, J=7.5 Hz, 1H), 4.71 (t, J=4.6 Hz, 1H), 4.42 (br. s, 1H), 4.31 (d, J=12.3 Hz, 1H), 4.29 (d, J=12.3 Hz, 1H), 4.03 (m, 1H), 3.62 (s, 3H), 3.38-3.20 (m, 3H), 3.14 (m, 1H), 2.95 (dt, J=15.1, 5.5 Hz, 1H), 2.87 (d, J=12.3 Hz, 1H), 2.37 (dd, J=11.5, 2.6 Hz, 1H), 2.22 (m, 1H), 2.02 (m, 1H), 1.84 (dd, J=14.2, 4.7 Hz, 1H), 1.68 (d, J=12.2 Hz, 1H), 1.50 (td, J=11.1, 10.5, 6.0 Hz, 1H), 1.45-1.32 (m, 2H), 1.19 (m, 1H). $^{13}$C NMR: (100 MHz, d$_6$-DMSO at 50° C.) S 173.2, 138.6, 136.9, 135.7, 127.8, 127.2, 127.0, 127.0, 120.7, 118.2, 117.9, 117.6, 111.3, 107.8, 74.9, 69.6, 65.9, 54.9 (2, confirmed by HSQC), 53.0, 50.9, 40.6 (2, confirmed by HSQC), 35.9, 32.2, 25.1, 22.4. HRMS (ESI): calc. for C$_{29}$H$_{33}$N$_3$O$_4$Na [M+Na]$^+$: 510.2363, found: 510.2363. MP: 98-100° C.

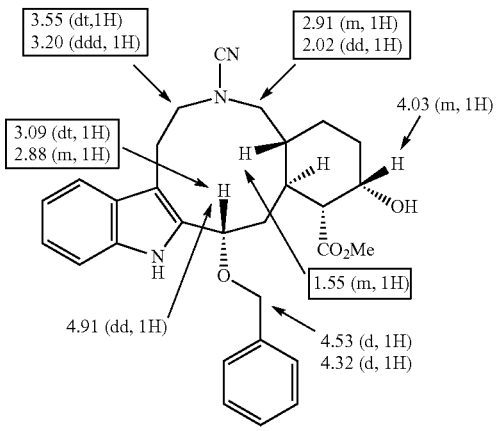

Key signals for Y6o
Spectral data derived via COSY in rectangle

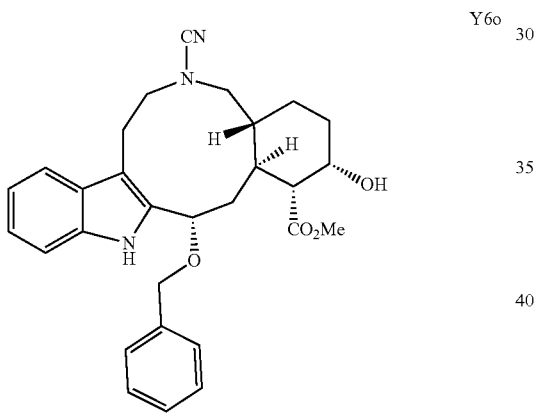

Y6o

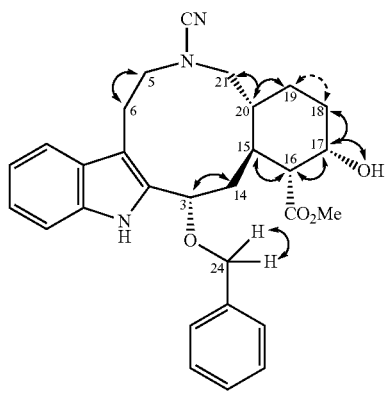

Key COSY correlations

Yield: 8% as the minor product; 13.8 mg of Y6o isolated as a colorless solid. Note: Y6o was synthesized via refluxing in chloroform for 4 hours. $^1$H NMR: (400 MHz, CDCl$_3$) δ 8.64 (s, 1H), 7.49 (d, J=7.8 Hz, 1H), 7.44 (dt, J=8.1, 0.9 Hz, 1H), 7.39-7.34 (m, 3H), 7.34-7.28 (m, 2H), 7.23 (td, J=7.6, 0.9 Hz, 1H), 7.14 (td, J=7.4, 1.0 Hz, 1H), 4.91 (dd, J=6.6, 3.1 Hz, 1H), 4.53 (d, J=12.1 Hz, 1H), 4.32 (d, J=12.1 Hz, 1H), 4.03 (m, 1H), 3.65 (s, 3H), 3.55 (dt, J=13.9, 3.6 Hz, 1H), 3.20 (ddd, J=14.1, 12.1, 2.6 Hz, 1H), 3.09 (dt, J=15.2, 2.7 Hz, 1H), 3.03 (br. s, 1H), 2.96-2.82 (m, 2H), 2.51 (ddd, J=16.2, 6.7, 4.6 Hz, 1H), 2.42 (dd, J=11.5, 2.3 Hz, 1H), 2.18 (dt, J=16.2, 3.4 Hz, 1H), 2.02 (dd, J=13.0, 9.9 Hz, 1H), 1.95-1.70 (m, 2H), 1.55 (m, 1H), 1.37 (m, 1H), 1.31-1.15 (m, 2H). $^{13}$C NMR: (100 MHz, CDCl$_3$) δ 176.4, 137.9, 136.0, 135.5, 128.7, 128.5, 128.1, 127.7, 122.4, 119.8, 118.5, 117.9, 111.8, 108.5, 72.4, 71.6, 66.3, 59.9, 53.8, 53.4, 52.4, 40.2, 38.9, 35.5, 30.7, 25.0, 24.5. HRMS (ESI): calc. for C$_{29}$H$_{33}$N$_3$O$_4$Na [M+Na]$^+$: 510.2363, found: 510.2381. MP: 53-55° C.

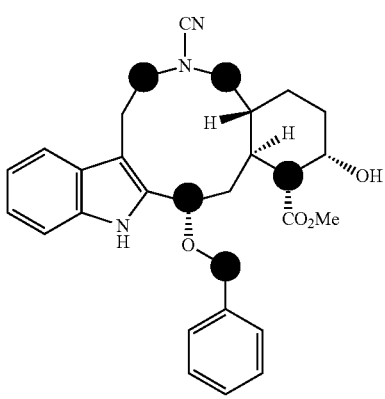

Key HSQC correlations

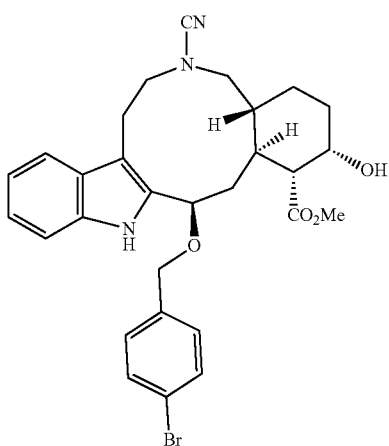

Y6p

Yield: 20%; 109 mg of Y6p isolated as a colorless foam. ¹H NMR: (400 MHz, CDCl₃ at 50° C.) δ 8.58 (s, 1H), 7.49 (d, J=7.7 Hz, 1H), 7.46 (d, J=7.7 Hz, 2H), 7.32 (d, J=8.0 Hz, 1H), 7.19 (t, J=7.5 Hz, 1H), 7.16-7.09 (m, 3H), 4.39 (t, J=7.2 Hz, 1H), 4.34 (d, J=12.2 Hz, 1H), 4.14 (d, J=12.2 Hz, 1H), 4.10 (m, 1H), 3.73 (s, 3H), 3.49 (m, 1H), 3.44-3.25 (m, 2H), 3.12 (m, 1H), 2.94 (dd, J=14.0, 6.0 Hz, 1H), 2.87 (d, J=12.7 Hz, 1H), 2.71 (m, 1H), 2.47 (d, J=11.4 Hz, 1H), 2.16 (m, 1H), 1.98-1.68 (m, 3H), 1.62 (q, J=10.5 Hz, 1H), 1.48 (t, J=13.0 Hz, 1H), 1.41-1.17 (m, 2H). 13C NMR: (100 MHz, CDCl₃ at 50° C.) δ 176.3, 137.5, 136.0, 135.7, 131.6, 129.6, 128.0, 122.4, 121.6, 119.9, 118.2, 118.1, 111.6, 109.3, 75.6, 69.9, 66.6, 57.4, 54.9, 53.6, 52.2, 40.2, 39.8, 36.2, 31.4, 25.2, 24.1. HRMS (ESI): calc. for C₂₉H₃₃BrN₃O₄[M+H]⁺: 566.1649, found: 566.1645. MP: 83-85° C.

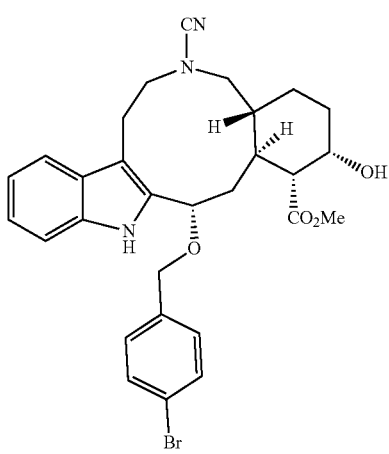

Y6q

Yield: 16% as the minor product; 27.1 mg of Y6q isolated as a colorless solid. ¹H NMR: (400 MHz, CDCl₃) δ 8.64 (s, 1H), 7.52-7.46 (m, 3H), 7.44 (d, J=8.1 Hz, 1H), 7.23 (t, J=7.3 Hz, 1H), 7.20-7.11 (m, 3H), 4.90 (dd, J=6.8, 3.3 Hz, 1H), 4.44 (d, J=12.2 Hz, 1H), 4.27 (d, J=12.2 Hz, 1H), 4.05 (m, 1H), 3.67 (s, 3H), 3.56 (dt, J=13.9, 3.6 Hz, 1H), 3.18 (td, J=13.4, 2.5 Hz, 1H), 3.09 (dt, J=15.2, 2.5 Hz, 1H), 2.96-2.83 (m, 3H), 2.51 (ddd, J=16.1, 6.7, 4.9 Hz, 1H), 2.42 (dd, J=11.5, 2.3 Hz, 1H), 2.15 (dt, J=16.2, 3.4 Hz, 1H), 2.03 (m, 1H), 1.89 (m, 1H), 1.81 (m, 1H), 1.58 (m, 1H), 1.39 (m, 1H), 1.33-1.15 (m, 2H). ¹³C NMR: (100 MHz, CDCl₃) δ 176.3, 137.0, 135.7, 135.6, 131.8, 129.6, 127.5, 122.5, 121.9, 119.8, 118.5, 117.9, 111.8, 108.8, 72.6, 70.7, 66.4, 59.9, 53.8, 53.4, 52.4, 40.3, 39.0, 35.3, 30.7, 24.9, 24.4. HRMS (ESI): calc. for C₂₉H₃₃BrN₃O₄[M+H]⁺: 566.1649, found: 566.1618. MP: 66-68° C.

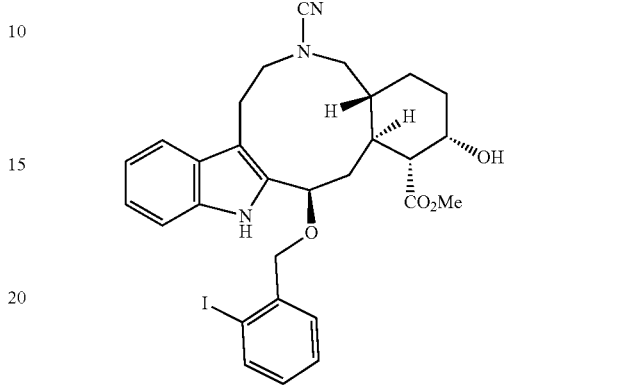

Y6r

Yield: 29%; 31.4 mg of Y6r isolated as a colorless foam. Note: This reaction was scaled up to isolate Y6r in 576 mg, 23%. ¹H NMR: (400 MHz, CDCl₃ at 50° C.) δ 8.82 (s, 1H), 7.80 (d, J=7.8 Hz, 1H), 7.51 (d, J=7.8 Hz, 1H), 7.39 (m, 1H), 7.36-7.30 (m, 2H), 7.19 (t, J=7.4 Hz, 1H), 7.14 (t, J=7.4 Hz, 1H), 6.97 (t, J=7.5 Hz, 1H), 4.50 (dd, J=9.0, 6.0 Hz, 1H), 4.36 (d, J=12.6 Hz, 1H), 4.30 (d, J=12.6 Hz, 1H), 4.13 (m, 1H), 3.74 (s, 3H), 3.59-3.40 (m, 2H), 3.39-3.26 (m, 2H), 3.01 (dd, J=14.9, 4.1 Hz, 1H), 2.86 (d, J=12.6 Hz, 1H), 2.77 (m, 1H), 2.51 (d, J=11.6 Hz, 1H), 2.17 (m, 1H), 1.99 (dt, J=14.3, 4.3 Hz, 1H), 1.86 (dd, J=13.9, 2.4 Hz, 1H), 1.79 (m, 1H), 1.63 (qd, J=10.1, 3.8 Hz, 1H), 1.48 (t, J=13.4 Hz, 1H), 1.39-1.18 (m, 2H). ¹³C NMR: (100 MHz, CDCl₃ at 50° C.) δ 176.0, 140.5, 139.1, 135.7, 135.5, 129.3, 129.2, 128.1, 127.9, 122.2, 119.6, 118.2, 118.0, 111.5, 109.1, 98.1, 76.2, 74.5, 66.4, 57.3, 55.0, 53.3, 52.1, 39.8, 39.6, 35.5, 31.3, 25.2, 24.4. HRMS (ESI): calc. for C₂₉H₃₃IN₃O₄[M+H]⁺: 614.1510, found: 614.1511. MP: 62-64° C.

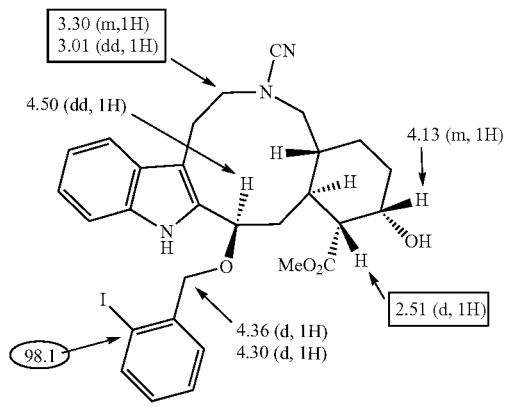

Key signals for Y6r

Spectral data derived via COSY in rectangle(s)
Key ¹³C signal in circle(s)

Key signals for Y6r

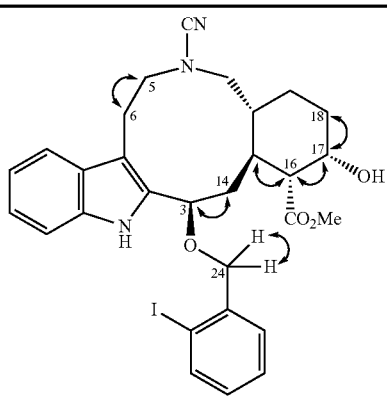

Key COSY correlations

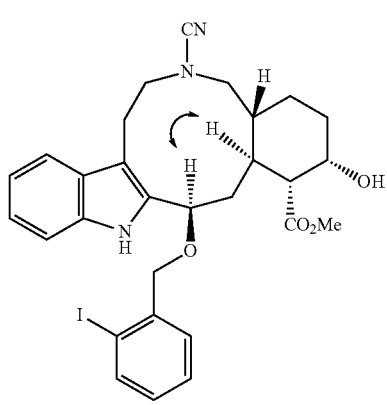

Key nOe correlations

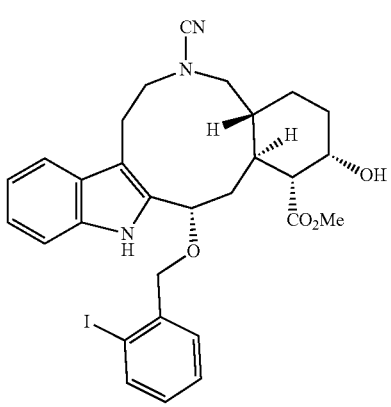

Y6s

Yield: 21% as the minor product; 518 mg of Y6s isolated as a colorless foam. $^1$H NMR: (400 MHz, CDCl$_3$) δ 8.84 (s, 1H), 7.81 (d, J=7.8 Hz, 1H), 7.48 (t, J=8.2 Hz, 2H), 7.41 (d, J=8.0 Hz, 1H), 7.36 (t, J=7.4 Hz, 1H), 7.20 (t, J=7.5 Hz, 1H), 7.13 (t, J=7.5 Hz, 1H), 6.98 (td, J=7.6, 0.9 Hz, 1H), 5.01 (dd, J=6.7, 3.8 Hz, 1H), 4.46 (d, J=12.5 Hz, 1H), 4.38 (d, J=12.5 Hz, 1H), 4.06 (m, 1H), 3.59 (s, 3H), 3.54 (dt, J=13.9, 3.4 Hz, 1H), 3.22 (td, J=13.1, 2.2 Hz, 1H), 3.12 (dt, J=14.9, 2.8 Hz, 1H), 3.04-2.86 (m, 3H), 2.55 (dt, J=15.7, 6.0 Hz, 1H), 2.49 (dd, J=11.3, 1.7 Hz, 1H), 2.24 (dt, J=15.9, 3.7 Hz, 1H), 2.15 (dd, J=13.4, 9.8 Hz, 1H), 1.97 (m, 1H), 1.80 (dt, J=13.6, 3.2 Hz, 1H), 1.62 (m, 1H), 1.41 (t, J=13.3, 1H), 1.35-1.16 (m, 2H). $^{13}$C NMR: (100 MHz, CDCl$_3$) δ 176.5, 140.3, 139.5, 135.6, 135.6, 129.6, 129.3, 128.5, 127.6, 122.4, 119.8, 118.6, 117.9, 111.9, 108.5, 98.4, 75.8, 73.8, 66.3, 59.8, 53.8, 53.5, 52.4, 40.4, 39.0, 35.3, 30.6, 25.1, 24.5. HRMS (ESI): calc. for C$_{29}$H$_{33}$IN$_3$O$_4$[M+H]$^+$: 614.1510, found: 614.1497. MP: 58-60° C.

Key signals for Y6s

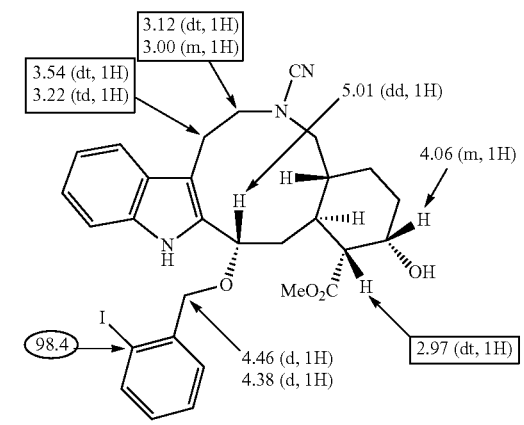

Spectral data derived via COSY in rectangle(s)
Key $^{13}$C signal in circles(s)

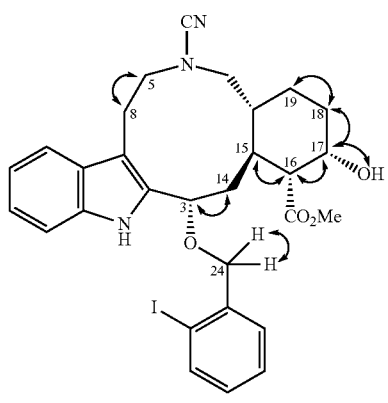

Key COSY correlations

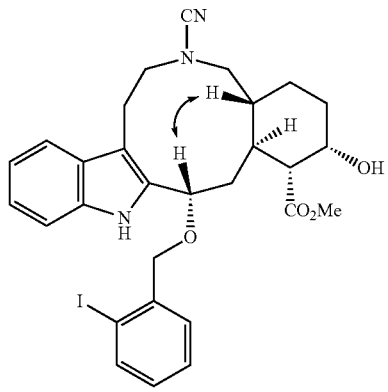

Key nOe correlations

X-ray crystallographic data for Y6s: Crystallographic data for Y6s have been deposited with the Cambridge Crystallographic Data Centre as supplementary publication no. CCDC 1497688-1497689.

TABLE 1

Crystal data and structure refinement for Y6s.

| | |
|---|---|
| Identification code | huig1 |
| Empirical formula | C30 H33 Cl3.07 I0.93 N3 O4 |
| Formula weight | 726.44 |
| Temperature | 243(2) K |
| Wavelength | 0.71073 Å |
| Crystal system | Orthorhombic |
| Space group | $P2_12_12_1$ |
| Unit cell dimensions | a = 10.1661(6) Å α = 90°. |
| | b = 12.3608(8) Å β = 90°. |
| | c = 25.4845(17) Å γ = 90°. |
| Volume | 3202.4(4) Å$^3$ |
| Z | 4 |
| Density (calculated) | 1.507 Mg/m$^3$ |
| Absorption coefficient | 1.227 mm$^{-1}$ |
| F(000) | 1470 |
| Crystal size | 0.428 × 0.282 × 0.180 mm$^3$ |
| Theta range for data collection | 1.598 to 27.499°. |
| Index ranges | $-13 \le h \le 13, -16 \le k \le 16, -33 \le l \le 33$ |
| Reflections collected | 40732 |
| Independent reflections | 7349 [R(int) = 0.0210] |
| Completeness to theta = 25.242° | 99.8% |
| Absorption correction | Analytical |
| Max. and min. transmission | 0.8536 and 0.7346 |
| Refinement method | Full-matrix least-squares on F$^2$ |
| Data/restraints/parameters | 7349/15/410 |
| Goodness-of-fit on F$^2$ | 1.024 |
| Final R indices [I > 2sigma(I)] | R1 = 0.0334, wR2 = 0.0815 [6714] |
| R indices (all data) | R1 = 0.0385, wR2 = 0.0858 |
| Absolute structure parameter | −0.024(3) |
| Extinction coefficient | n/a |
| Largest diff. peak and hole | 0.755 and −0.480 e · Å$^{-3}$ |

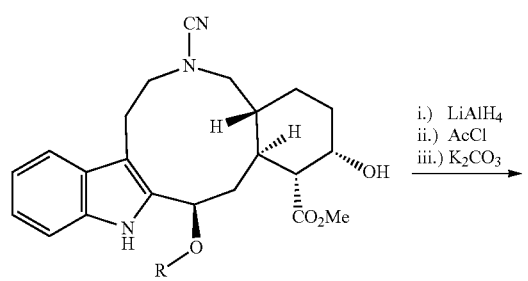

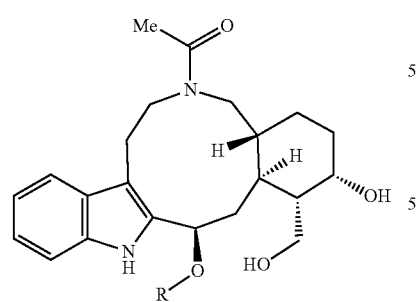

General procedure for synthesis of Y6t-Y6u: Y6b (689 mg, 1.68 mmol) was added to a round-bottom flask and dissolved in tetrahydrofuran (30 mL). The reaction was cooled to 0° C. and a 1M solution of lithium aluminum hydride in tetrahydrofuran (10 mL, 10.1 mmol) was added dropwise. The reaction was slowly warmed to room temperature and stirred for 1.5 hours. The reaction was quenched by slow addition of water (3 mL), then 1M sodium hydroxide (1 mL) and celite. The slurry was allowed to stir for 30 minutes before being filtered through a plug of celite and subsequently washed with hot ethyl acetate. The filtrate was collected, dried with sodium sulfate, filtered and concentrated. Crude product was taken onto next acylation step.

Crude aminodiol (146 mg, 0.406 mmol) obtained above was added to a round-bottom flask and dissolved in dichloromethane (7 mL) and pyridine (130 µL, 1.62 mmol). Catalytic N,N-dimethylaminopyridine and acetyl chloride (290 µL, 4.06 mmol) were added and reaction was stirred at room temperature for 30 minutes. The reaction was quenched with 0.5 N hydrochloric acid followed by brine and product was extracted with dichloromethane. The organic layer was dried with sodium sulfate, filtered and concentrated. The crude triacyl product was taken onto next saponification step.

Crude triacyl product (59.8 mg, 0.12 mmol) obtained above was added to a round-bottom flask and dissolved in methanol (4 mL). Potassium carbonate (102 mg, 0.74 mol) was added and the reaction was stirred at room temperature for 9 hours. The reaction was quenched with brine and the product was extracted with ethyl acetate. Organics were collected, dried with sodium sulfate, filtered and concentrated. Crude diol was purified via column chromatography using a gradient of 100% hexanes to 1:1 hexanes:ethyl acetate to 100% ethyl acetate to afford Y6t (36.4 mg, 22%, 3 steps) as a colorless foam.

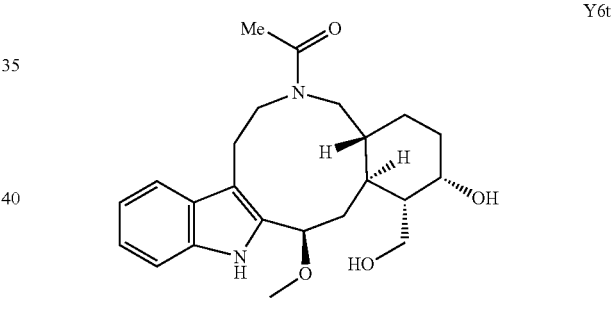

Yield: 22%, 3 steps; 36.4 mg of Y6t isolated as a colorless foam. $^1$H NMR: (400 MHz, CDCl$_3$ at 22° C.) δ 8.88 (s, 1H), 7.49 (d, J=7.8 Hz, 1H), 7.34 (d, J=8.1 Hz, 1H), 7.18 (t, J=7.3 Hz, 11H), 7.12 (t, J=7.3 Hz, 1H), 4.46 (dd, J=11.6, 4.2 Hz, 11H), 4.03 (m, 1H), 4.01 (d, J=11.0 Hz, 1H), 3.93 (d, J=11.0 Hz, 1H), 3.85 (m, 1H), 3.41 (m, 1H), 3.17 (s, 3H), 3.15 (m, 1H), 3.09-2.94 (m, 2H), 2.52 (m, 1H), 2.16 (s, 3H), 2.08 (m, 1H), 1.85 (m, 1H), 1.58-1.42 (m, 4H), 1.38-1.21 (m, 4H), 0.90 (m, 1H). $^1$H NMR: (400 MHz, CDCl$_3$ at 45° C.) δ 8.57 (s, 1H), 7.50 (d, J=8.0 Hz, 1H), 7.36 (dd, J=8.1, 1.1 Hz, 1H), 7.20 (td, J=7.7, 0.8 Hz, 1H), 7.13 (td, J=7.5, 0.8 Hz, 1H), 4.47 (dd, J=11.4, 5.2 Hz, 1H), 4.14-3.91 (m, 3H), 3.83 (m, 1H), 3.65 (m, 1H), 3.43 (m, 1H), 3.22 (s, 3H), 3.11 (m, 1H), 3.02 (dd, J=14.7, 4.9 Hz, 1H), 2.51 (t, J=11.5 Hz, 1H), 2.16 (s, 3H), 2.03 (m, 1H), 1.87 (m, 1H), 1.64 (s, 1H), 1.60-1.48 (m, 2H), 1.41-1.21 (m, 5H), 0.88 (m, 1H). $^{13}$C NMR: (100 MHz, CDCl$_3$ at 22° C.) δ 173.3, 136.6, 135.6, 128.5, 121.9, 119.5, 118.1, 111.7, 109.6, 78.6, 72.6, 64.6, 59.2, 56.7, 52.8, 48.7, 41.1, 36.6, 33.0, 32.8, 25.2, 24.9, 23.1. HRMS (ESI): calc. for C$_{23}$H$_{33}$N$_2$O$_4$ [M+H]$^+$: 401.2435, found: 401.2446. MP: 74-76° C.

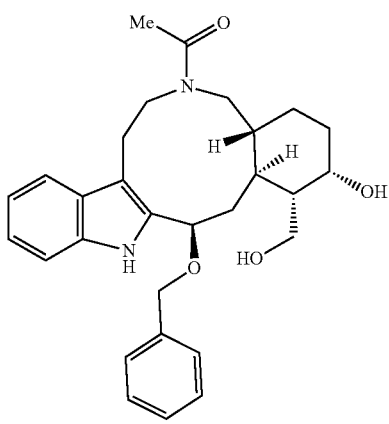

Y6u

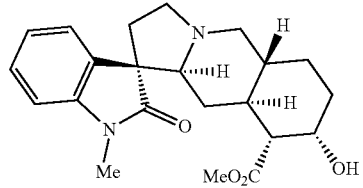

Y7c

Yield: 17%, 3 steps; 50.8 mg of Y6u isolated as a colorless foam. ¹H NMR: (400 MHz, CDCl₃) δ 8.72 (s, 1H), 7.49 (d, J=7.6 Hz, 1H), 7.36-7.20 (m, 6H), 7.17 (t, J=7.4 Hz, 1H), 7.11 (t, J=7.4 Hz, 1H), 4.63 (dd, J=12.3, 4.4 Hz, 1H), 4.40 (d, J=12.3 Hz, 1H), 4.29 (d, J=12.3 Hz, 1H), 3.99 (m, 1H), 3.93-3.72 (m, 3H), 3.49 (q, J=13.0 Hz, 1H), 3.38 (m, 1H), 3.05 (m, 1H), 3.00 (dd, J=14.6, 3.4 Hz, 1H), 2.57 (t, J=11.5 Hz, 1H), 2.11 (s, 3H), 2.06-1.93 (m, 2H), 1.89 (dd, J=13.1, 5.9 Hz, 1H), 1.56-1.39 (m, 3H), 1.36-1.19 (m, 4H), 0.89 (m, 1H). Note: ¹H spectrum referenced TMS at 0.00 ppm. ¹³C NMR: (100 MHz, CDCl₃) δ 173.1, 138.6, 137.0, 135.8, 128.6, 128.5, 127.9, 127.7, 122.0, 119.6, 118.1, 111.7, 110.2, 76.3, 72.4, 70.9, 64.5, 59.0, 52.8, 48.9, 41.3, 36.6, 33.0, 32.2, 25.4, 24.9, 23.0. HRMS (ESI): calc. for $C_{29}H_{36}N_2O_4Na$ [M+Na]⁺: 499.2567, found: 499.2569. MP: 66-68° C.

Yield: 80%; 22.9 mg of Y7c isolated as a colorless, amorphous solid. ¹H NMR: (400 MHz, CDCl₃) δ 7.39 (d, J=7.3 Hz, 1H), 7.25 (m, 1H), 7.04 (t, J=7.5 Hz, 1H), 6.80 (d, J=7.5 Hz, 1H), 4.07 (m, 1H), 3.56 (s, 3H), 3.26 (td, J=8.5, 1.2 Hz, 1H), 3.20 (s, 3H), 3.09 (dd, J=10.5, 3.2 Hz, 1H), 2.98 (s, 1H), 2.56-2.46 (m, 2H), 2.33 (ddt, J=13.0, 9.4, 2.0 Hz, 1H), 2.09 (dt, J=11.6, 1.8 Hz, 1H), 2.03-1.87 (m, 3H), 1.71 (qd, J=11.1, 3.1 Hz, 1H), 1.52 (td, J=12.0, 2.4 Hz, 1H), 1.47-1.19 (m, 3H), 0.95 (dt, J=12.2, 2.6 Hz, 1H), 0.64 (q, J=11.6 Hz, 1H). ¹³C NMR: (100 MHz, CDCl₃) δ 179.4, 175.5, 143.5, 133.6, 127.7, 124.9, 122.6, 107.8, 71.4, 66.9, 59.0, 56.5, 53.6, 52.7, 51.8, 40.7, 36.3, 35.5, 31.5, 30.7, 26.6, 23.6. ¹H NMR: (400 MHz, d₆-DMSO) δ 7.31-7.19 (m, 2H), 7.05-6.94 (m, 2H), 4.56 (d, J=4.8 Hz, 1H), 3.99 (m, 1H), 3.46 (s, 3H), 3.21 (t, J=9.1 Hz, 1H), 3.13 (s, 3H), 3.04 (dd, J=10.7, 3.4 Hz, 1H), 2.39-2.27 (m, 2H), 2.17 (ddd, J=12.3, 9.3, 2.4 Hz, 1H), 2.01 (dd, J=11.3, 2.8 Hz, 1H), 1.89-1.73 (m, 2H), 1.67 (dt, J=12.8, 3.2 Hz, 1H), 1.60-1.42 (m, 2H), 1.36 (qd, J=13.0, 12.5, 3.1 Hz, 1H), 1.29-1.08 (m, 3H), 0.35 (q, J=11.5 Hz, 1H). HRMS (ESI): calc. for $C_{22}H_{29}N_2O_4$ [M+H]⁺: 385.2104, found: 385.2104.

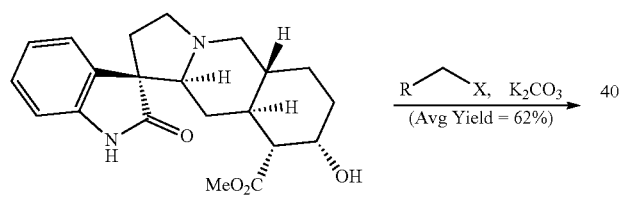

Y7b

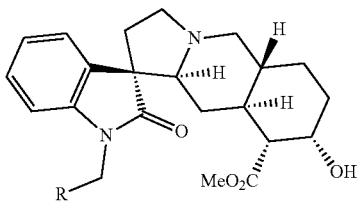

Y7d

General procedure for the synthesis of Y7c and Y7d: Y7b (27.6 mg, 0.08 mmol) was added to a round-bottom flask and dissolved in N,N-dimethylformamide (1.75 mL). Potassium carbonate (41.2 mg, 0.30 mmol) and iodomethane (9 µL, 0.15 mmol) were added. The reaction was stirred at room temperature for 15 hours. The reaction was quenched with brine (3×50 mL) and extracted with ethyl acetate. Organics were dried with sodium sulfate, filtered and concentrated. The crude material was purified via column chromatography using a gradient of 99:1 hexanes:triethylamine to 49.5:49.5:1 hexanes:ethyl acetate:trimethylamine to afford Y7c (22.9 mg, 80%) as a colorless, amorphous solid.

Yield: 44%; 15.1 mg of Y7d isolated as a colorless, amorphous solid. ¹H NMR: (400 MHz, CDCl₃) δ 7.39 (d, J=7.2 Hz, 1H), 7.23 (t, J=7.6 Hz, 1H), 7.02 (t, J=7.6 Hz, 1H), 6.81 (d, J=7.6 Hz, 1H), 4.06 (m, 1H), 3.80 (dt, J=14.4, 7.3 Hz, 1H), 3.58 (dt, J=14.4, 7.3 Hz, 1H), 3.52 (s, 3H), 3.25 (t, J=7.6 Hz, 1H), 3.15-3.01 (m, 3H), 2.55-2.43 (m, 2H), 2.32 (dd, J=13.0, 9.9 Hz, 1H), 2.07 (d, J=11.6 Hz, 1H), 2.01-1.85 (m, 3H), 1.69 (qd, J=11.2, 2.8 Hz, 1H), 1.66-1.47 (m, 3H), 1.46-1.22 (m, 4H), 0.93 (t, J=7.3 Hz, 3H), 0.90 (m, 1H), 0.61 (q, J=11.8 Hz, 1H). ¹³C NMR: (100 MHz, CDCl₃) δ 179.1, 175.7, 142.7, 133.8, 127.6, 125.0, 122.3, 108.1, 71.6, 66.8, 59.0, 56.4, 53.6, 52.6, 51.6, 40.6, 39.9, 36.3, 35.1, 31.5, 30.5, 29.7, 23.5, 20.2, 14.0. ¹H NMR: (400 MHz, d₆-DMSO) δ 7.27 (d, J=7.3 Hz, 1H), 7.22 (t, J=7.6 Hz, 1H), 7.03-6.97 (m, 2H), 4.54 (d, J=4.8 Hz, 1H), 3.99 (m, 1H), 3.77 (dt, J=14.0, 7.1 Hz, 1H), 3.59 (dt, J=14.0, 7.1 Hz, 1H), 3.44 (s, 3H), 3.23 (t, J=8.9 Hz, 1H), 3.04 (dd, J=10.8, 3.4 Hz, 1H), 2.38-2.27 (m, 2H), 2.17 (t, J=12.6 Hz, 1H), 2.00 (dd, J=11.3, 2.7 Hz, 1H), 1.90-1.72 (m, 2H), 1.67 (dd, J=13.2, 3.1 Hz, 1H), 1.60-1.42 (m, 4H), 1.35 (qd, J=12.4, 2.0 Hz, 1H), 1.29-1.09 (m, 5H), 0.87 (t, J=7.3 Hz, 3H), 0.31 (q, J=11.5 Hz, 1H). HRMS (ESI): calc. for $C_{25}H_{35}N_2O_4$ [M+H]⁺: 427.2591, found: 427.2591.

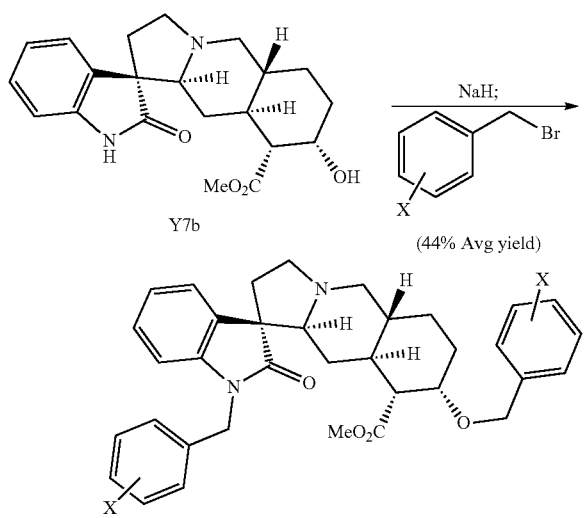

Y7b (44% Avg yield)

General procedure for the synthesis of Y7e-Y7l: To a flame-dried, round-bottom flask was added tetrahydrofuran (2.0 mL) followed by sodium hydride (6.8 mg, 0.17 mmol, 60% dispersion in mineral oil). The resulting suspension was cooled to 0° C. and a solution of Y7b (16 mg, 0.04 mmol) in tetrahydrofuran (0.25 mL) was added drop wise. The reaction was stirred at 0° C. for 15 minutes before benzyl bromide (10 μL, 0.08 mmol) was added. The reaction was stirred at 0° C. for an additional 20 minutes then slowly warmed to room temperature over 16 hours. The reaction was quenched with brine and the product was extracted with ethyl acetate. The ethyl acetate layer was dried with sodium sulfate, filtered and concentrated under reduced pressure. The crude material was purified via column chromatography using a gradient of 99:1 hexanes:triethylamine to 74.5: 24.5:1 hexanes:ethyl acetate:trimethylamine to afford Y7e (13.1 mg, 56%) as a pale-yellow, amorphous solid.

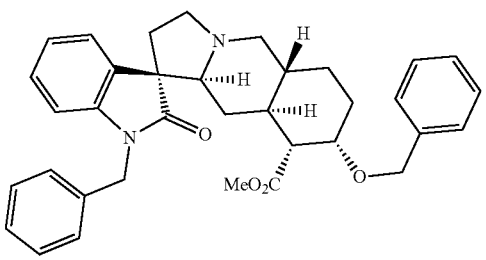

Y7e

Yield: 56%; 13.1 mg of Y7e isolated as a pale-yellow, amorphous solid. $^1$H NMR: (400 MHz, CDCl$_3$) δ 7.38 (d, J=7.2 Hz, 1H), 7.35-7.29 (m, 4H), 7.27-7.19 (m, 6H), 7.10 (td, J=7.7, 0.9 Hz, 1H), 6.98 (t, J=7.4 Hz, 1H), 6.65 (d, J=7.6 Hz, 1H), 5.12 (d, J=15.5 Hz, 1H), 4.68 (d, J=15.5 Hz, 1H), 4.55 (d, J=12.3 Hz, 1H), 4.28 (d, J=12.3 Hz, 1H), 3.92 (m, 1H), 3.47 (s, 3H), 3.29 (td, J=8.1, 2.2 Hz, 1H), 3.11 (dd, J=10.7, 3.5 Hz, 1H), 2.68 (d, J=10.9 Hz, 1H), 2.54 (q, J=8.9 Hz, 1H), 2.42 (ddd, J=12.7, 9.3, 2.2 Hz, 1H), 2.15-2.01 (m, 3H), 1.97 (t, J=10.6 Hz, 1H), 1.84 (qd, J=11.3, 3.3 Hz, 1H), 1.49 (dt, J=11.8, 2.3 Hz, 1H), 1.45-1.20 (m, 4H), 0.46 (q, J=11.5 Hz, 1H). Note: $^1$H spectrum referenced TMS at 0.00 ppm. $^{13}$C NMR: (100 MHz, CDCl$_3$) δ 179.6, 172.6, 142.5, 138.8, 136.3, 133.8, 129.0, 128.4, 127.6, 127.6, 127.5, 127.4, 124.9, 122.4, 108.9, 75.0, 72.2, 70.5, 59.1, 56.5, 53.9, 52.8, 51.3, 44.0, 40.5, 36.1, 35.4, 31.1, 28.1, 23.8. $^1$H NMR: (400 MHz, d$_6$-DMSO) δ 7.36-7.28 (m, 5H), 7.28-7.19 (m, 6H), 7.13 (td, J=7.9, 1.0 Hz, 1H), 6.98 (t, J=7.6 Hz, 1H), 6.83 (d, J=7.9 Hz, 1H), 5.09 (d, J=16.3 Hz, 1H), 4.72 (d, J=16.3 Hz, 1H), 4.50 (d, J=12.8 Hz, 1H), 4.22 (d, J=12.8 Hz, 1H), 3.84 (m, 1H), 3.45 (s, 3H), 3.26 (m, 1H), 3.09 (d, J=10.3 Hz, 1H), 2.44 (dd, J=11.2, 2.4 Hz, 1H), 2.37 (d, J=8.8 Hz, 1H), 2.26 (dd, J=12.9, 11.5 Hz, 1H), 2.18 (dd, J=11.9, 2.4 Hz, 1H), 2.06 (d, J=14.3 Hz, 1H), 1.91 (m, 1H), 1.81 (t, J=9.6 Hz, 1H), 1.55 (q, J=9.7 Hz, 1H), 1.45-1.17 (m, 5H), 0.33 (q, J=11.4 Hz, 1H). $^{13}$C NMR: (100 MHz, d$_6$-DMSO) δ 178.3, 171.9, 141.8, 138.6, 136.5, 133.0, 128.7, 128.1, 127.5, 127.4, 127.3, 127.3, 126.9, 124.3, 122.2, 108.8, 74.5, 71.8, 69.5, 58.5, 55.6, 53.0, 51.0, 50.9, 42.6, 39.2, 35.8, 34.5, 30.3, 26.9, 23.2. HRMS (ESI): calc. for C$_{35}$H$_{39}$N$_2$O$_4$ [M+H]): 551.2904, found: 551.2907.

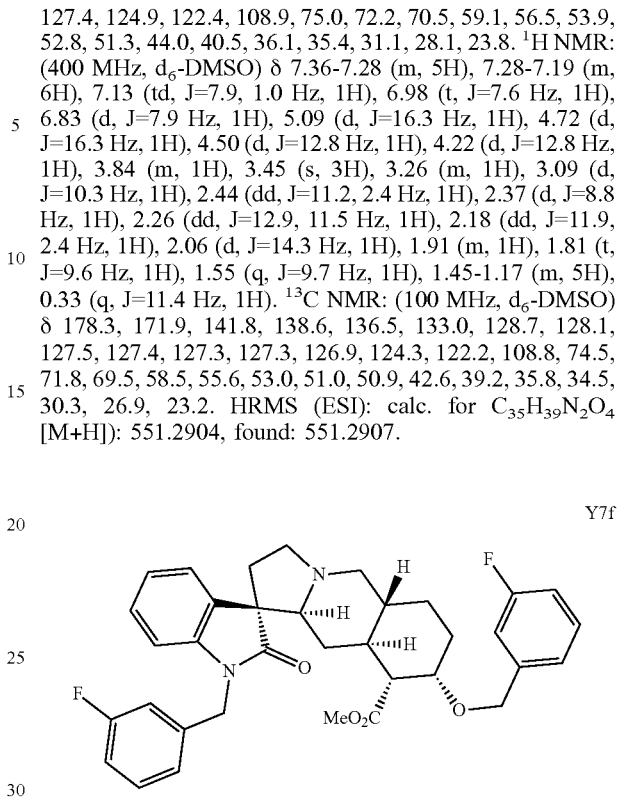

Y7f

Yield: 39%; 25.7 mg of Y7f isolated as a pale-yellow foam. $^1$H NMR: (400 MHz, CDCl$_3$) δ 7.40 (d, J=7.3 Hz, 11H), 7.35-7.22 (m, 2H), 7.13 (td, J=7.7, 1.3 Hz, 11H), 7.06-6.89 (m, 7H), 6.63 (d, J=7.7 Hz, 1H), 5.09 (d, J=16.2 Hz, 1H), 4.70 (d, J=16.2 Hz, 1H), 4.54 (d, J=12.7 Hz, 1H), 4.26 (d, J=12.7 Hz, 1H), 3.91 (m, 1H), 3.52 (s, 3H), 3.29 (td, J=8.5, 2.2 Hz, 1H), 3.12 (dd, J=10.8, 3.5 Hz, 1H), 2.69 (dd, J=11.2, 2.5 Hz, 1H), 2.55 (q, J=8.7 Hz, 1H), 2.42 (ddd, J=11.9, 9.3, 2.2 Hz, 1H), 2.15-2.01 (m, 3H), 1.97 (t, J=10.6 Hz, 1H), 1.83 (qd, J=11.3, 3.2 Hz, 11H), 1.48 (dt, J=12.1, 3.0 Hz, 1H), 1.44-1.21 (m, 4H), 0.49 (q, J=11.3 Hz, 1H). Note: $^1$H spectrum referenced TMS at 0.00 ppm. $^{13}$C NMR: (100 MHz, CDCl$_3$) δ 179.5, 172.6, 163.2 (d, J=247 Hz), 163.0 (d, J=246 Hz), 142.2, 141.4 (d, J=7.2 Hz), 138.9 (d, J=7.1 Hz), 133.7, 130.7 (d, J=8.2 Hz), 129.9 (d, J=8.2 Hz), 127.6, 125.0, 122.9 (d, J=2.9 Hz), 122.9 (d, J=2.9 Hz), 122.6, 114.6 (d, J=20.6 Hz), 114.3 (d, J=22.0 Hz), 114.3, 114.2, 108.7, 75.4, 72.0, 69.7 (d, J=1.9 Hz), 59.0, 56.4, 53.8, 52.7, 51.4 (d, J=1.5 Hz), 43.6 (d, J=1.9 Hz), 40.4, 36.1, 35.6, 31.1, 28.1, 23.8. HRMS (ESI): calc. for C$_{35}$H$_{37}$F2N$_2$O$_6$[M+H]$^+$: 587.2716, found: 587.2727. MP: 55-57° C.

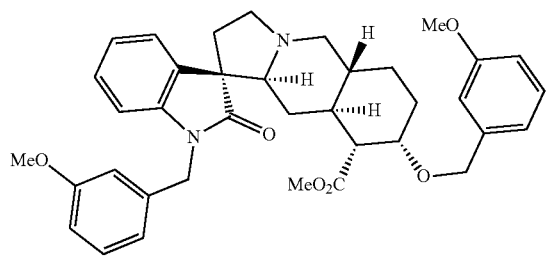

Y7g

Yield: 29%; 21.5 mg of Y7g isolated as a colorless, amorphous solid. $^1$H NMR: (400 MHz, CDCl$_3$) δ 7.39 (d, J=7.4 Hz, 11H), 7.25-7.18 (m, 2H), 7.10 (td, J=7.7, 1.3 Hz, 1H), 6.98 (t, J=7.5 Hz, 1H), 6.85-6.74 (m, 6H), 6.67 (d, J=7.7 Hz, 1H), 5.01 (d, J=15.7 Hz, 1H), 4.73 (d, J=15.7 Hz, 1H), 4.53 (d, J=12.3 Hz, 1H), 4.26 (d, J=12.3 Hz, 1H), 3.91 (m, 1H), 3.81 (s, 3H), 3.77 (s, 3H), 3.48 (s, 3H), 3.29 (t, J=8.5 Hz, 1H), 3.11 (dd, J=11.0, 3.4 Hz, 1H), 2.69 (d, J=11.0 Hz, 1H), 2.55 (q, J=8.7 Hz, 1H), 2.41 (ddd, J=11.8, 9.2, 2.2 Hz, 1H), 2.14-1.92 (m, 4H), 1.83 (qd, J=11.1, 3.1 Hz, 1H), 1.51-1.22 (m, 5H), 0.50 (q, J=11.6 Hz, 1H). $^{13}$C NMR: (100 MHz, CDCl$_3$) δ 179.6, 172.6, 160.1, 159.8, 142.5, 140.4, 137.9, 133.8, 130.1, 129.4, 127.6, 124.9, 122.4, 119.8, 119.6, 113.2, 113.1, 113.0, 113.0, 108.9, 75.2, 71.8, 70.4, 59.0, 56.4, 55.4, 53.8, 52.8, 51.3, 44.1, 40.5, 36.1, 35.8, 31.2, 29.9, 28.2, 23.8. HRMS (ESI): calc. for C$_{37}$H$_{43}$N$_2$O$_6$ [M+H]$^+$: 611.3116, found: 611.3134.

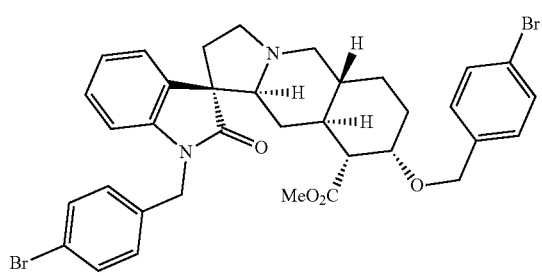

Y7h

Yield: 45%; 14.2 mg of Y7h isolated as a colorless, amorphous solid. $^1$H NMR: (400 MHz, CDCl$_3$) δ 7.50-7.42 (m, 4H), 7.37 (d, J=7.3 Hz, 1H), 7.19-7.08 (m, 5H), 6.99 (td, J=7.5, 1.0 Hz, 1H), 6.62 (d, J=7.7 Hz, 1H), 5.15 (d, J=15.7 Hz, 1H), 4.52 (d, J=15.7 Hz, 1H), 4.49 (d, J=12.4 Hz, 1H), 4.22 (d, J=12.4 Hz, 1H), 3.90 (m, 1H), 3.50 (s, 3H), 3.29 (td, J=8.4, 2.2 Hz, 1H), 3.11 (dd, J=10.7, 3.5 Hz, 1H), 2.66 (dd, J=11.1, 2.5 Hz, 1H), 2.53 (q, J=8.7 Hz, 1H), 2.41 (ddd, J=13.0, 9.3, 2.2 Hz, 1H), 2.11-2.00 (m, 3H), 1.95 (t, J=10.7 Hz, 1H), 1.80 (qd, J=11.4, 3.2 Hz, 1H), 1.49-1.18 (m, 5H), 0.39 (q, J=11.6 Hz, 1H). $^{13}$C NMR: (100 MHz, CDCl$_3$) δ 179.5, 172.4, 142.1, 137.8, 135.5, 133.8, 132.2, 131.6, 129.3, 129.2, 127.6, 124.9, 122.6, 121.6, 121.5, 108.6, 75.2, 72.4, 69.8, 59.1, 56.5, 53.9, 52.5, 51.5, 43.4, 40.4, 36.1, 35.1, 31.0, 28.1, 23.8. HRMS (ESI): calc. for C$_{35}$H$_{37}$Br$_2$N$_2$O$_4$ [M+H]$^+$: 709.1098, found: 709.1103.

Y7i

Yield: 32%; 26.2 mg of Y7i isolated as a tan solid. $^1$H NMR: (400 MHz, CDCl$_3$) δ 7.42-7.30 (m, 5H), 7.22-7.15 (m, 4H), 7.12 (td, J=7.7, 1.3 Hz, 1H), 6.99 (t, J=7.5 Hz, 1H), 6.68 (d, J=7.8 Hz, 1H), 5.07 (d, J=16.4 Hz, 1H), 4.68 (d, J=16.4 Hz, 1H), 4.53 (d, J=12.1 Hz, 1H), 4.25 (d, J=12.1 Hz, 1H), 3.94 (m, 1H), 3.48 (s, 3H), 3.30 (t, J=9.0 Hz, 1H), 3.12 (dd, J=10.7, 2.0 Hz, 1H), 2.69 (d, J=10.8 Hz, 1H), 2.55 (q, J=7.6 Hz, 1H), 2.42 (ddd, J=11.7, 9.2, 2.0 Hz, 1H), 2.16-1.91 (m, 4H), 1.85 (qd, J=11.3, 3.1 Hz, 1H), 1.53 (dt, J=12.2, 2.6 Hz, 1H), 1.45 (m, 1H), 1.39-1.33 (m, 3H), 1.31 (s, 9H), 1.28 (s, 9H), 0.50 (q, J=11.3 Hz, 1H). $^{13}$C NMR: (100 MHz, CDCl$_3$) δ 179.5, 172.6, 150.5, 150.4, 142.7, 135.7, 133.8, 133.1, 127.5, 127.0, 125.9, 125.3, 124.8, 122.3, 108.9, 74.9, 72.1, 70.3, 59.1, 56.4, 53.9, 52.8, 51.3, 43.6, 40.5, 36.1, 35.5, 34.7, 34.6, 31.6, 31.5, 31.1, 28.1, 23.8. Note: Missing one aromatic carbon signal most likely due to signal overlap. $^1$HMR: (400 MHz, d$_6$-DMSO) δ 7.37-7.32 (m, 4H), 7.30 (d, J=7.2 Hz, 1H), 7.17-7.10 (m, 5H), 6.98 (t, J=7.6 Hz, 1H), 6.81 (d, J=7.0 Hz, 1H), 5.04 (d, J=15.5 Hz, 1H), 4.69 (d, J=15.5 Hz, 1H), 4.45 (d, J=11.9 Hz, 1H), 4.16 (d, J=11.9 Hz, 1H), 3.86 (m, 1H), 3.43 (s, 3H), 3.30-3.19 (m, 2H), 3.09 (d, J=9.7 Hz, 1H), 2.47-2.32 (m, 2H), 2.25 (t, J=12.7, 2.1 Hz, 1H), 2.19 (dd, J=11.6, 2.7 Hz, 1H), 2.06 (d, J=13.4 Hz, 1H), 1.99-1.77 (m, 2H), 1.55 (q, J=10.0 Hz, 1H), 1.45-1.29 (m, 4H), 1.25 (s, 9H), 1.24 (s, 9H), 0.37 (q, J=11.8 Hz, 1H). $^{13}$C NMR: (100 MHz, d$_6$-DMSO) δ 178.3, 171.9, 149.7, 149.6, 141.9, 135.5, 133.4, 133.0, 127.5, 127.4, 126.4, 125.4, 124.9, 124.3, 122.2, 108.8, 74.3, 71.8, 69.3, 58.6, 55.6, 53.1, 50.9, 50.7, 42.2, 35.8, 34.7, 34.2, 34.2, 31.2, 31.1, 31.1, 30.3, 26.8, 23.2. HRMS (ESI): calc. for C$_{43}$H$_{55}$N$_2$O$_4$ [M+H]$^+$: 663.4156, found: 663.4161. MP: 55-57° C.

Y7j

Yield: 47%; 38.1 mg of Y7j isolated as a colorless foam. $^1$H NMR: (400 MHz, CDCl$_3$) δ 7.39 (d, J=7.4 Hz, 1H), 7.31 (d, J=8.5 Hz, 1H), 7.13 (td, J=7.7, 1.3 Hz, 1H), 7.03-6.96 (m, 2H), 6.91 (d, J=2.6 Hz, 1H), 6.86 (d, J=2.6 Hz, 1H), 6.81 (t, J=3.2 Hz, 1H), 6.79 (t, J=3.0 Hz, 1H), 6.67 (d, J=7.7 Hz, 1H), 5.11 (d, J=16.1 Hz, 1H), 4.80 (d, J=16.1 Hz, 1H), 4.56 (d, J=12.4 Hz, 1H), 4.28 (d, J=12.4 Hz, 1H), 3.95 (m, 1H), 3.77 (s, 3H), 3.74 (s, 3H), 3.50 (s, 3H), 3.29 (t, J=8.6 Hz, 1H), 3.12 (dd, J=10.9, 3.4 Hz, 1H), 2.68 (d, J=10.9 Hz, 1H), 2.54 (q, J=8.7 Hz, 1H), 2.42 (ddd, J=11.7, 9.2, 2.1 Hz, 1H), 2.16 (dt, J=11.3, 2.9 Hz, 1H), 2.11-2.00 (m, 2H), 1.97 (t, J=10.7 Hz, 1H), 1.83 (qd, J=11.3, 3.1 Hz, 1H), 1.51 (dt, J=12.2, 2.9 Hz, 1H), 1.48-1.22 (m, 4H), 0.48 (q, J=11.6 Hz, 1H). $^{13}$C NMR: (100 MHz, CDCl$_3$) δ 179.7, 172.5, 159.5, 159.5, 142.3, 133.7, 133.4, 133.4, 130.3, 129.2, 128.4, 127.7, 125.3, 124.9, 122.6, 114.9, 114.7, 114.0, 112.9, 108.8, 75.4, 72.2, 67.2, 59.1, 56.5, 55.7, 55.6, 53.9, 52.7, 51.4, 40.7, 40.4, 36.1, 35.4, 31.2, 28.1, 23.8. HRMS (ESI): calc. for C$_{37}$H$_{41}$Cl$_2$N$_2$O$_6$ [M+H]$^+$: 679.2336, found: 679.2318. MP: 64-66° C.

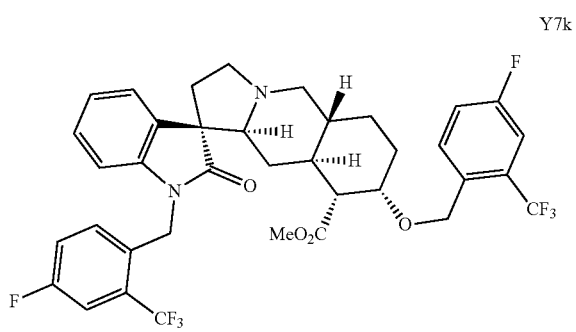

Y7k

Yield: 34%; 34.2 mg of Y7k isolated as a tan, amorphous solid. $^1$H NMR: (400 MHz, CDCl$_3$) δ 7.65 (dd, J=8.7, 5.8 Hz, 1H), 7.46-7.37 (m, 2H), 7.34-7.22 (m, 3H), 7.17-7.07 (m, 2H), 7.04 (t, J=7.3 Hz, 1H), 6.56 (d, J=7.6 Hz, 1H), 5.30 (d, J=16.8 Hz, 1H), 4.85 (d, J=16.8 Hz, 1H), 4.69 (d, J=13.5 Hz, 1H), 4.38 (d, J=13.5 Hz, 1H), 4.03 (m, 1H), 3.54 (s, 3H), 3.33 (t, J=7.9 Hz, 1H), 3.15 (dd, J=11.0, 2.7 Hz, 1H), 2.72 (d, J=10.5 Hz, 1H), 2.56 (q, J=8.6 Hz, 1H), 2.45 (ddd, J=13.0, 9.2, 2.1 Hz, 1H), 2.22-2.03 (m, 3H), 1.98 (t, J=10.4 Hz, 1H), 1.87 (qd, J=10.8, 3.0 Hz, 1H), 1.61 (dt, J=12.0, 2.8 Hz, 1H), 1.48-1.23 (m, 4H), 0.52 (q, J=11.3 Hz, 1H). Note: $^1$H spectrum referenced TMS at 0.00 ppm. $^{13}$C NMR: (100 MHz, CDCl$_3$) δ 180.1, 172.5, 161.5 (d, J=247.5 Hz), 161.4 (d, J=247.2 Hz), 141.8, 133.6, 133.3 (q, J=2.6 Hz), 131.1 (d, J=8.1 Hz), 130.3 (d, J=2.3 Hz), 129.8 (d, J=8.2 Hz), 129.6 (d, J=31.9 Hz), 129.5 (d, J=31.9 Hz), 128.7 (d, J=31.7 Hz), 128.7 (d, J=31.7 Hz), 127.8, 125.1, 123.0, 119.8 (d, J=21.9 Hz), 119.1 (d, J=20.3 Hz), 114.0 (dq, J=25.1, 5.8 Hz), 113.2 (dq, J=25.4, 5.6 Hz), 108.5, 76.3, 72.5, 65.9 (q, J=2.7 Hz), 59.1, 56.6, 54.1, 52.4, 51.4, 40.3, 39.9 (q, J=3.2 Hz), 36.2, 35.3, 31.3, 28.1, 23.8. HRMS (ESI): calc. for C$_{37}$H$_{35}$F8N$_2$O$_4$[M+H]$^+$: 723.2464, found: 723.2473.

REFERENCES

1. Newman, D. J.; Cragg, G. M. *J. Nat. Prod.* 2012, 75, 311-335.
2. Swinney, D. C.; Anthony, *J. Nat. Rev. Drug Discov.* 2011, 10, 507-519.
3. Payne, D. J.; Gwynn, M. N.; Holmes, D. J.; Pompliano, D. L. *Nat. Rev. Drug Discov.* 2007, 6, 29-40.
4. Dömling, A. *Curr. Opin. Chem. Biol.* 2008, 12, 281-291.
5. Villoutreix, B. O.; Kuenemann, M. A.; Poyet, J. L.; Bruzzoni-Giovanelli, H.; Labbé, C.; Lagorce, D.; Sperandio, O.; Miteva, M. A. Mol. Inform. 2014, 33, 414-437.
6. Corbi-Verge, C.; Kim, P. M. Cell Commun. *Signal.* 2016, 14, p. 12.
7. Grivas, P. D.; Kiaris, H.; Papavassiliou, A. G. *Trends Mol. Med.* 2011, 17, 537-538.
8. Grivas, P. D.; Papavassiliou, A. G. *Cancer* 2013, 119, 1120-1128.
9. Schreiber, S. L. *Nature* 2009, 457, 153-154.
10. Bauer, R. A.; Wurst, J. M.; Tan, D. S. *Curr. Opin. Chem. Biol.* 2010, 14, 308-314.
11. Dandapani, S.; Marcaurelle, L. A. *Nat. Chem. Biol.* 2010, 6, 861-863.
12. Schreiber, S. L. *Science* 2000, 287, 1964-1969.
13. Hung, A. W.; Ramek, A.; Wang, Y.; Kaya, T.; Wilson, J. A.; Clemons, P. A.; Young, D. W. *Proc. Natl. Acad. Sci.* 2011, 108, 6799-6804.
14. Kopp, F.; Stratton, C. F.; Akella, L. B.; Tan, D. S. *Nat. Chem. Biol.* 2012, 8, 358-365.
15. Bauer, R. A.; Wenderski, T. A.; Tan, D. S. *Nat. Chem. Biol.* 2013, 9, 21-29.
16. Beckmann, H. S.; Nie, F.; Hagerman, C. E.; Johansson, H.; Tan, Y. S.; Wilcke, D.; Spring, D. R. *Nat. Chem.* 2013, 5, 861-867.
17. Grossmann, A.; Bartlett, S.; Janecek, M.; Hodgkinson, J. T.; Spring, D. R. *Angew. Chem. Int. Ed.* 2014, 53, 13093-13097.
18. Antonchick, A. P.; Gerding-Reimers, C.; Catarinella, M.; Schurmann, M.; Preut, H.; Ziegler, S.; Rauh, D.; Waldmann, H. *Nat. Chem.* 2010, 2, 735-740.
19. Wetzel, S.; Bon, R. S.; Kumar, K.; Waldmann, H. *Angew. Chem. Int. Ed.* 2011, 50, 10800-10826.
20. Basu, S.; Ellinger, B.; Rizzo, S.; Deraeve, C.; Schurmann, M.; Preut, H.; Arndt, H. D.; Waldmann, H. *Proc. Natl. Acad. Sci.* 2011, 108, 6805-6810.
21. van Hattum, H.; Waldmann, H. *J. Am. Chem. Soc.* 2014, 136, 11853-11859.
22. Antonchick, A. P.; López-Tosco, S.; Parga, J.; Sievers, S.; Schurmann, M.; Preut, H.; Hing, S.; Schöler, H. R.; Sterneckert, J.; Rauh, D.; Waldmann, H. *Chem. Biol.* 2013, 20, 500-509.
23. § venda, J.; Sheremet, M.; Kremer, L.; Maier, L.; Bauer, J. O.; Strohmann, C.; Ziegler, S.; Kumar, K.; Waldmann, H. *Angew. Chem. Int. Ed.* 2015, 54, 5596-5602.
24. Balthaser, B. R.; Maloney, M. C.; Beeler, A. B.; Porco, J. A.; Snyder, J. K. *Nat. Chem.* 2011, 3, 969-973.
25. McLeod, M. C.; Singh, G.; Plampin III, J. N.; Rane, D.; Wang, J. L.; Day, V. W.; Aubé, *J. Nat. Chem.* 2014, 6, 133-140.
26. Aquino, C.; Sarkar, M.; Chalmers, M. J.; Mendes, K.; Kodadek, T.; Micalizio, G. C. *Nat. Chem.* 2012, 4, 99-104.
27. Tan, D. S. *Nat. Chem. Biol.* 2005, 1, 74-84.
28. Goess, B. C.; Hannoush, R. N.; Chan, L. K.; Kirchhausen, T.; Shair, M. D. *J. Am. Chem. Soc.* 2006, 128, 5391-5403.
29. Collins, I.; Jones, A. M. Molecules 2014, 19, 17221-17255.
30. Huigens III, R. W.; Morrison, K. C.; Hicklin, R. W.; Flood, T. A.; Richer, M. F.; Hergenrother, P. *J. Nat. Chem.* 2013, 5, 195-202.
31. Rafferty, R. J.; Hicklin, R. W.; Maloof, K. A.; Hergenrother, P. *J. Angew. Chem. Int. Ed.* 2014, 53, 220-224.
32. Hicklin, R. W.; López Sliva, T. L.; Hergenrother, P. *J. Angew. Chem. Int. Ed.* 2014, 53, 9880-9883.
33. Friesen, K.; Palatnick, W.; Tenebein, M. *J. Emerg. Med.* 1993, 11, 287-288.
34. Albright, J. D.; Goldman, L., *J. Org. Chem.* 1965, 30, 1107-1110.
35. N. Kagawa, J. Malerich, V. Rawal, *Org. Lett.* 2008, 10, 2381-2384.
36. U. G. Bhat, M. A. Winter, H. L. Pearce, W. T. Beck, *Mol. Pharm.* 1995, 48, 682-689.
37. M. Somei, K. Noguchi, F., Yamada, *Heterocycles.* 2001, 55, 1237-1240.
38. M. Somei, K. Noguchi, K. Yoshino, K. Mori, M. Asada, F. Yamada, Y. Tanaka, K. Shigenobu, K. Koike *Heterocycles,* 2006, 69, 259-269.
39. H. Takayama, K. Misawa, N. Okada, H. Ishikawa, M. Kitajima, Y. Hatori, T. Murayama, S. Wongseripipatana, K. Tashima, K. Matsumoto, S. Horie, *Org. Lett.* 2006, 8, 5705-5708.
40. J. D. Albright, L. Goldman, *J. Am. Chem. Soc.* 1969, 91, 4317-4318.
41. Stahl, R.; Borschberg, H. *J. Helv. Chim. Acta* 1996, 79, 1361-1378.

42. Burkitt, K.; Chun, S. Y.; Dang, D. T.; Dang, L. H. *Mol. Cancer Ther.* 2009, 8, 1148-1156.
43. Bousquet, M. S.; Ma, J. J.; Ratnayake, R.; Havre, P. A.; Yao, J.; Dang, N. H.; Paul, V. J.; Carney, T. J.; Dang, L. H.; Luesch, H. *ACS Chem. Biol.* 2016, 11, 1322-1331.
44. Lau, A.; Villeneuve, N. F.; Sun, Z.; Wong, P. K.; Zhang, D. D. *Pharmacol. Res.* 2008, 58, 262-270.
45. Du, Y.; Villeneuve, N. F.; Wang, X. J.; Sun, Z.; Chen, W.; Li, J.; Lou, H.; Wong, P. K.; Zhang, D. D. *Environ. Health Perspect.* 2008, 116, 1154-1161.
46. Ren, D.; Villeneuve, N. F.; Jiang, T.; Wu, T.; Lau, A.; Toppin, H. A.; Zhang D. D. *Proc. Natl. Acad. Sci.* 2011, 108, 1433-1438.
47. Yates M. S.; Tauchi, M.; Katsuoka, F.; Flanders, K. C.; Liby, K. T.; Honda, T.; Gribble, G. W.; Johnson, D. A.; Johnson, J. A.; Burton, N. C.; Guilarte, T. R.; Yamamoto, M.; Sporn, M. B.; Kensler, T. W. *Mol. Cancer Ther.* 2007, 6, 154-162.
48. Moehlenkamp J. D.; Johnson J. A. *Arch. Biochem. Biophys.* 1999, 363, 98-106.
49. Ratnayake, R.; Liu, Y.; Paul, V. J.; Luesch, H. *Cancer Prev. Res.* 2013, 6, 989-999.
50. O'Connor, S. E., Maresh, J. *J. Nat. Prod. Rep.* 2006, 23, 532-547.
51. Kaushik, N. K.; Kaushik, N.; Attri, P.; Kumar, N.; Kim, C. H.; Verma, A. K.; Choi, E. H. Molecules 2013, 18, 6620-6662.
52. Woodward, R. B.; Bader, F. E.; Bickel, H.; Frey, A. J.; Kierstead, R. W. *J. Am. Chem. Soc.* 1956, 78, 2023-2025.
53. Yang, Y.; Bai, Y.; Sun, S.; Dai, M. *Org. Lett.* 2014, 16, 6216-6219.
54. Rajapaksa, N. S.; McGowan, M. A.; Rienzo, M.; Jacobsen, E. N. *Org. Lett.* 2013, 15, 706-709.
55. Podoll, J. D.; Liu, Y.; Chang, L.; Walls, S.; Wang, W.; Wang, X. *Proc. Natl. Acad. Sci.* 2013, 110, 15573-15578.
56. Xu, W.; Wang, W.; Wang, X. *Angew. Chem. Int. Ed.* 2015, 54, 9546-9549.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (II'):

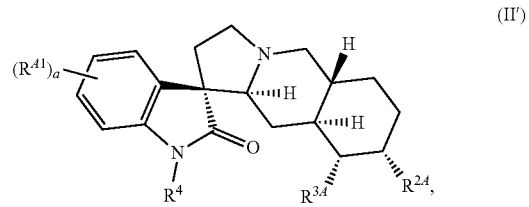

or a pharmaceutically acceptable salt thereof, wherein:
$R^{2A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;
$R^{3A}$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^b)_2$, or —$SR^a$;

R⁴ is —CN, unsubstituted alkyl, alkyl substituted with optionally substituted phenyl, substituted or unsubstituted benzyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $R^{A1}$ is independently halogen, —CN, —SCN, —NO$_2$, —N$_3$, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted sulfonyl, —OR$^a$, —N(R$^b$)$_2$, or —SR$^a$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, or a sulfur protecting group when attached to a sulfur atom; and each instance of R$^b$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group; or optionally two R$^b$ are joined together with the intervening atoms to form substituted or unsubstituted heterocyclyl or substituted or unsubstituted heteroaryl; and a is 0, 1, 2, 3, or 4.

2. A pharmaceutical composition comprising a compound of claim 1, or a pharmaceutically acceptable salt thereof, and optionally a pharmaceutically acceptable excipient.

3. A method of treating cancer in a subject in need thereof, the method comprising administering to the subject an effective amount of a compound of claim 1, or a pharmaceutically acceptable salt thereof, wherein the cancer is colon cancer, skin cancer, breast cancer, bladder cancer, or liver cancer.

4. The method of claim 3, wherein the cancer is colon cancer.

5. The method of claim 3, wherein the cancer is breast cancer.

6. The method of claim 3, wherein the subject is a human.

7. A kit comprising:
a compound of claim 1, a pharmaceutically acceptable salt thereof, or a pharmaceutical composition thereof.

8. The compound of claim 1, or a pharmaceutically acceptable salt thereof, wherein $R^{24}$ is: —O(CH$_2$)$_z$R$^{6b}$, wherein:
R$^{6b}$ is substituted or unsubstituted C$_{1-6}$ alkyl, substituted or unsubstituted heterocyclyl, substituted or unsubstituted aryl, or substituted or unsubstituted heteroaryl; and
z is 0, 1, 2, 3, or 4.

9. The compound of claim 1, or a pharmaceutically acceptable salt thereof, wherein $R^{24}$ is —O(R$^3$), and R$^{a3}$ is hydrogen or substituted or unsubstituted C$_{1-6}$ alkyl.

10. The compound of claim 8, or a pharmaceutically acceptable salt thereof, wherein $R^{24}$ is of the formula:

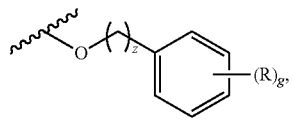

wherein:
R is hydrogen, halogen, substituted or unsubstituted C$_{1-6}$ alkyl, or —OR$^{a1}$;
R$^{a1}$ is substituted or unsubstituted C$_{1-6}$ alkyl;
z is 0 or 1; and
g is 1, 2, 3, 4, or 5.

11. The compound of claim 10, or a pharmaceutically acceptable salt thereof, wherein $R^{2A}$ is of the formula:

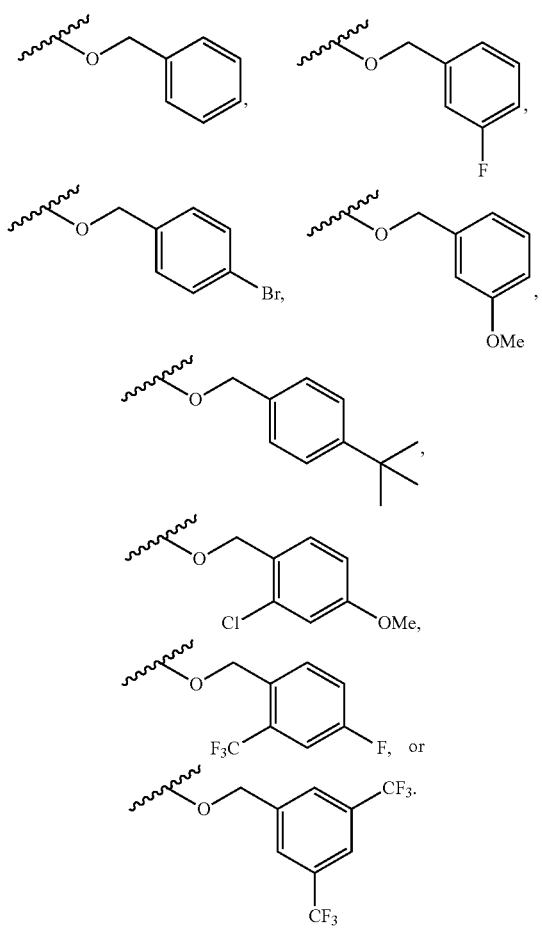

12. The compound of claim 10, or a pharmaceutically acceptable salt thereof, wherein $R^{2A}$ is of the formula:

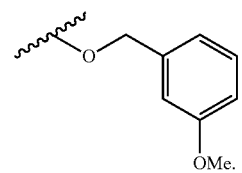 [SMILES: *OCc1cccc(OC)c1]

13. The compound of claim 1, or a pharmaceutically acceptable salt thereof, wherein $R^{3A}$ is

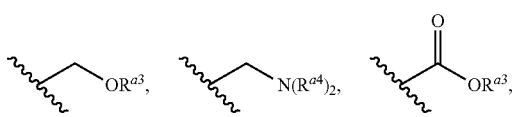

or —C(=O)N($R^{a4}$)₂;

$R^{a3}$ is hydrogen or substituted or unsubstituted $C_{1-6}$ alkyl; and each instance of $R^{a4}$ is independently hydrogen, substituted or unsubstituted $C_{1-6}$ alkyl, or nitrogen protecting group.

14. The compound of claim 13, or a pharmaceutically acceptable salt thereof, wherein $R^{3A}$

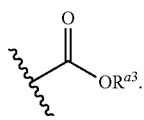

15. The compound of claim 1, a pharmaceutically acceptable salt thereof, wherein $R^{3A}$ is

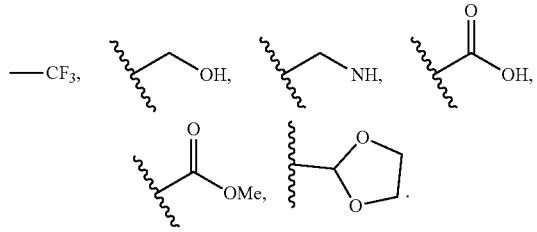

16. The compound of claim 1, or a pharmaceutically acceptable salt thereof, wherein $R^4$ is unsubstituted $C_{1-6}$ alkyl, $C_{1-6}$ alkyl substituted with optionally substituted phenyl, substituted or unsubstituted benzyl, substituted or unsubstituted phenyl, substituted or unsubstituted pyridine, substituted or unsubstituted pyrimidine, or substituted or unsubstituted pyrazine.

17. The compound of claim 1, or a pharmaceutically acceptable salt thereof, wherein $R^4$ is of the formula:

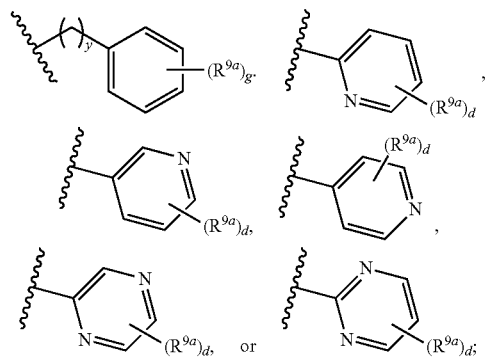

wherein:

$R^{9a}$ is hydrogen, halogen, substituted or unsubstituted $C_{1-6}$ alkyl, —$OR^a$, or —$NO_2$;

$R^a$ is substituted or unsubstituted $C_{1-6}$ alkyl or substituted or unsubstituted aryl;

Y is 0 or 1;

d is 1, 2, 3, or 4; and g is 1, 2, 3, 4, or 5.

18. The compound of claim 17, or a pharmaceutically acceptable salt thereof, wherein $R^4$ is of the formula:

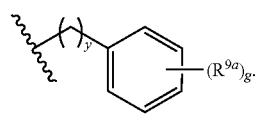

19. The compound of claim 1, wherein the compound is of the formula:

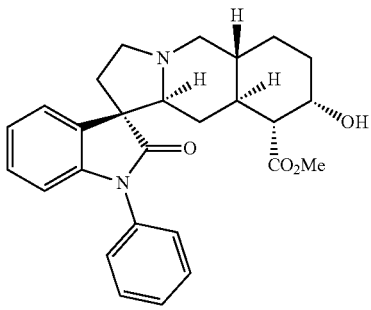

Y3a

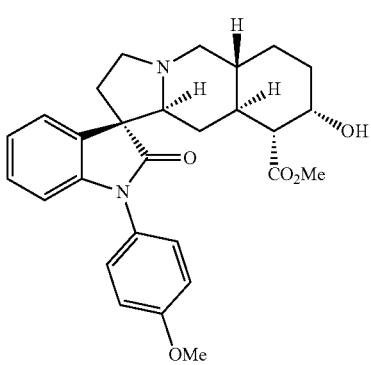

Y3b

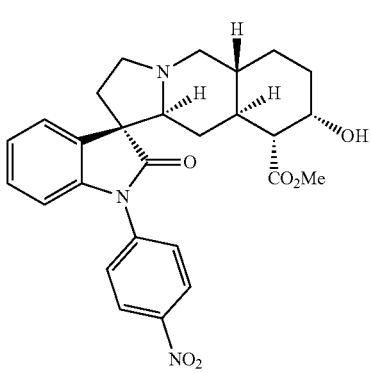

Y3c

229
-continued
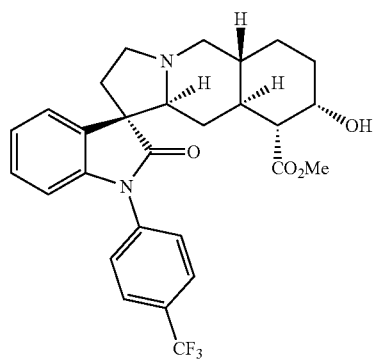
Y3d
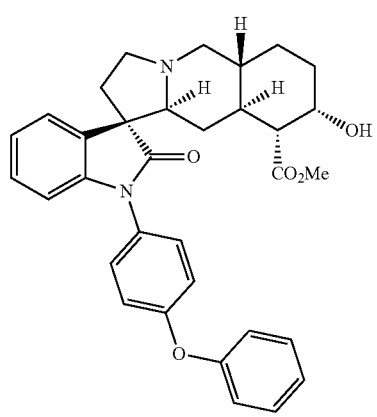
Y3e
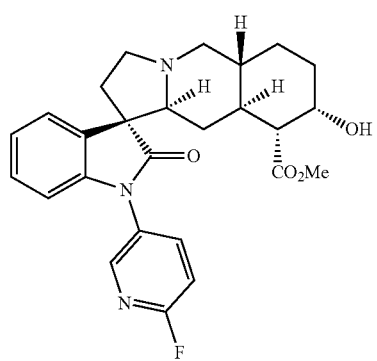
Y3f
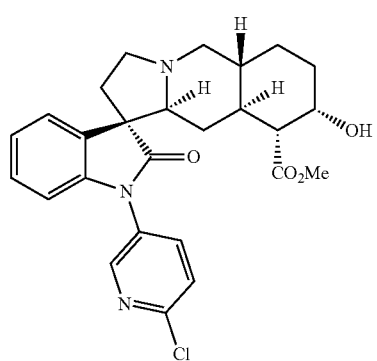
Y3g
230
-continued
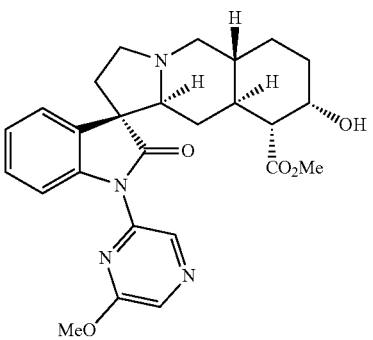
Y3h
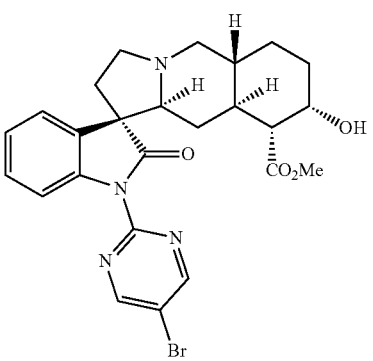
Y3i
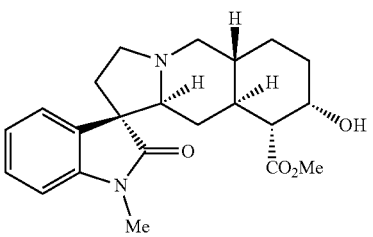
Y7c
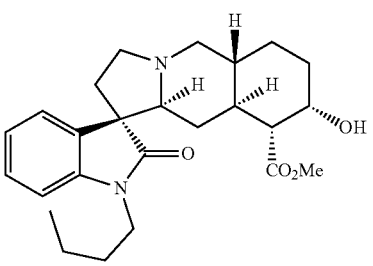
Y7d
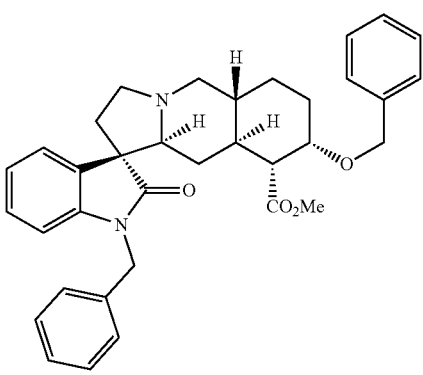
Y7e 231
-continued
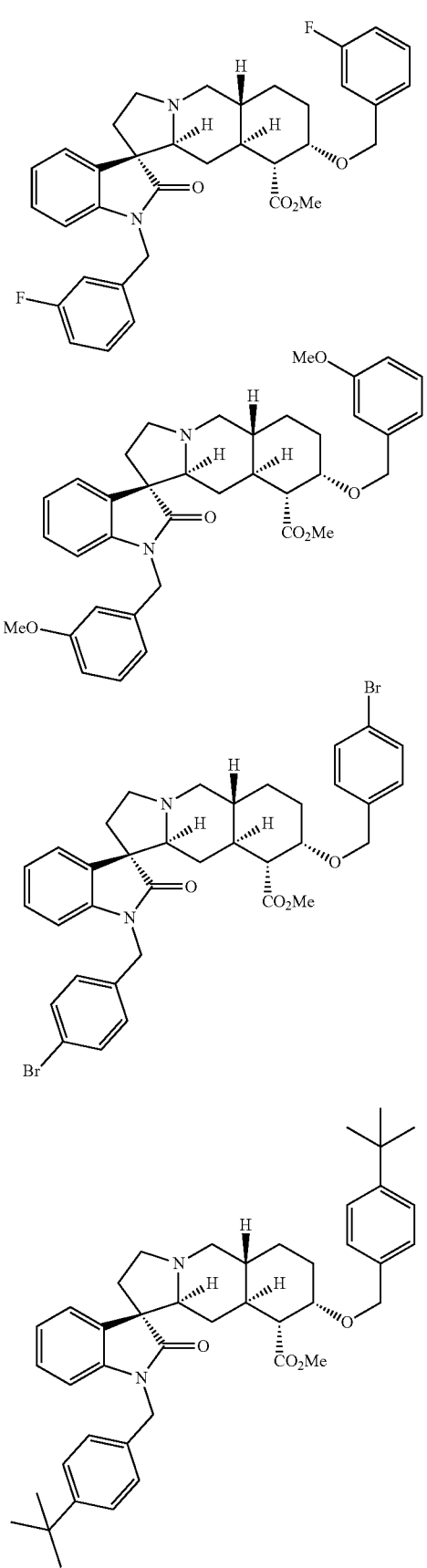
232
-continued
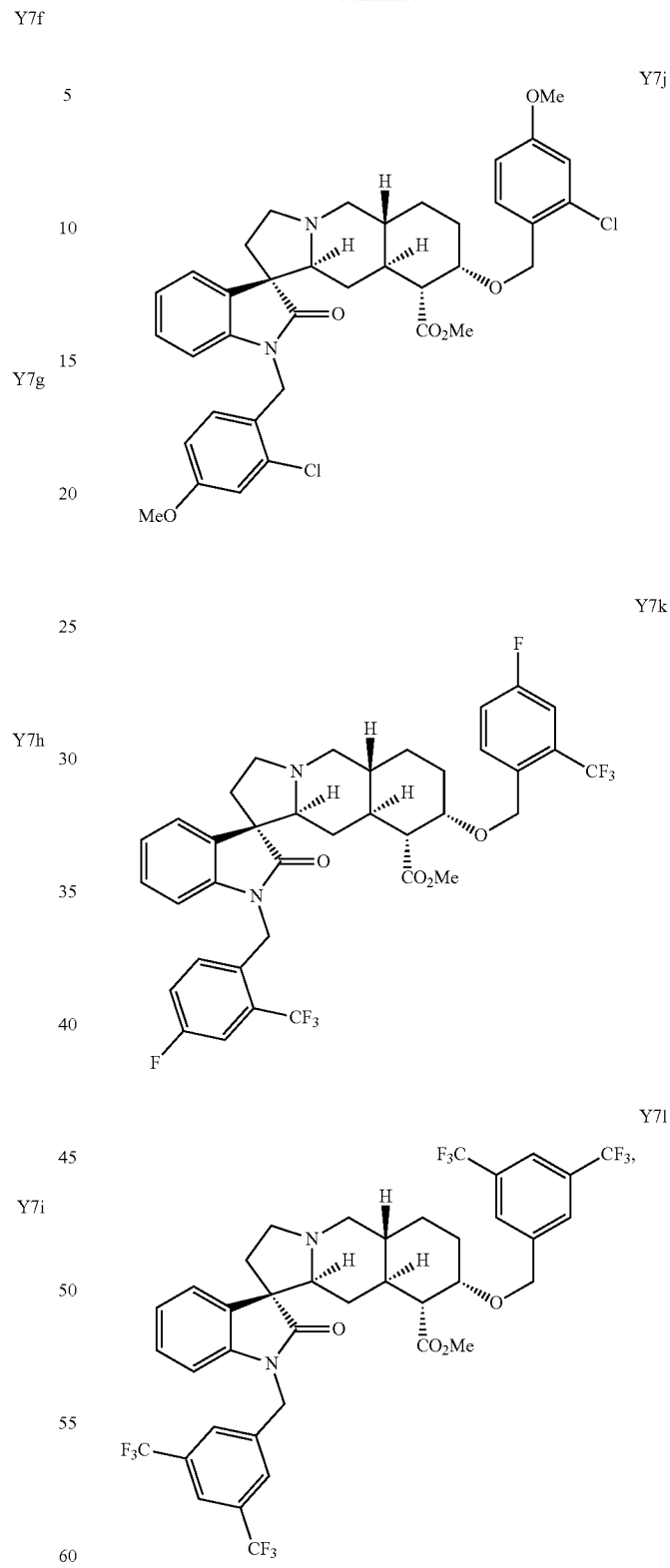
or a pharmaceutically acceptable salt thereof.
20. The compound of claim 1, wherein $R^4$ is unsubstituted $C_{1-6}$ alkyl.
21. The compound of claim 1, wherein $R^4$ is of the formula:

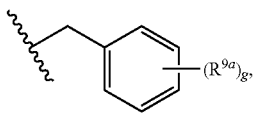

wherein each instance of $R^{9a}$ is independently halogen, substituted or unsubstituted $C_{1-6}$ alkyl, —$OR^a$, or —CN; $R^a$ is substituted or unsubstituted $C_{1-6}$ alkyl or substituted or unsubstituted aryl; and g is 0, 1, or 2.

22. The compound of claim 1, wherein $R^4$ is of the formula:

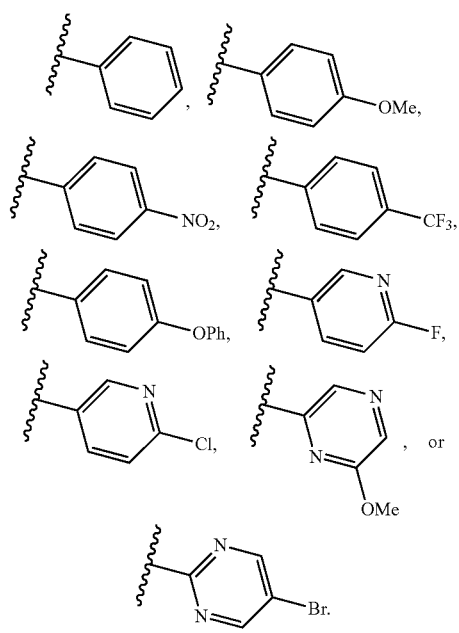

23. The compound of claim 1, wherein $R^{24}$ is —OH.

24. The compound of claim 1, or a pharmaceutically acceptable salt thereof, wherein $R^{34}$ is

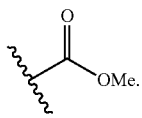

25. The compound of claim 1, or a pharmaceutically acceptable salt thereof, wherein $R^4$ is of the formula:

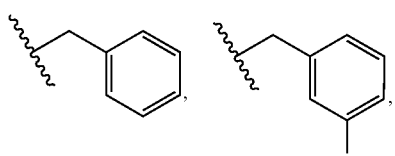

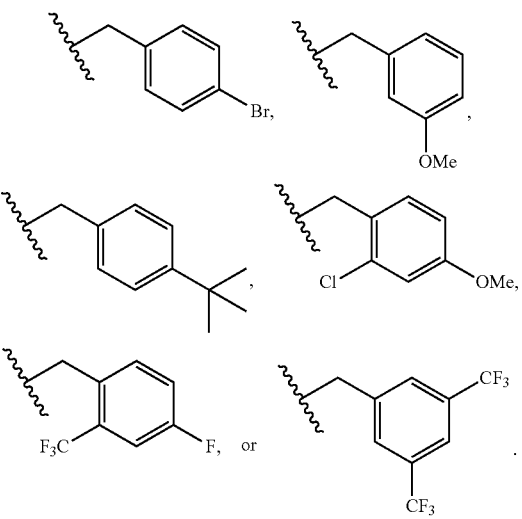

26. The compound of claim 1, a pharmaceutically acceptable salt thereof, wherein $R^4$ is

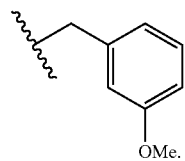 [SMILES: *Cc1cccc(OC)c1]

27. The compound of claim 1, or a pharmaceutically acceptable salt thereof, wherein a is 0.

28. A method of treating malaria in a subject in need thereof, the method comprising administering to the subject an effective amount of a compound of claim 1, or a pharmaceutically acceptable salt thereof.

29. The method of claim 3, wherein the cancer is bladder cancer.

30. The method of claim 3, wherein the cancer is liver cancer.

* * * * *

UNITED STATES PATENT AND TRADEMARK OFFICE
CERTIFICATE OF CORRECTION

PATENT NO. : 11,242,331 B2
APPLICATION NO. : 16/097167
DATED : February 8, 2022
INVENTOR(S) : Huigens, III et al.

Page 1 of 1

It is certified that error appears in the above-identified patent and that said Letters Patent is hereby corrected as shown below:

In the Claims

In Claim 15, at Column 227, Lines 30-35, the formula: "  " should be replaced with the formula: --  --.

In Claim 17, at Column 227, Lines 51-57, the formula: " 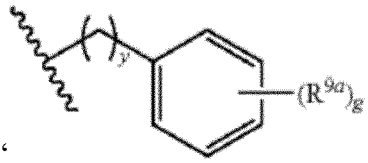 " should be replaced with the formula: -- 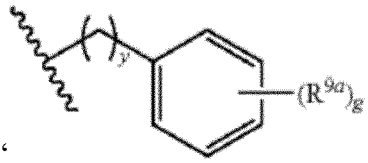 --.

In Claim 17, at Column 227, Line 55, the "." should be replaced with a --,--.

In Claim 18, at Column 228, Lines 15-20, the formula: " 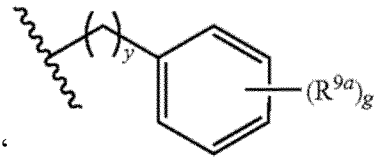 " should be replaced with the formula: -- 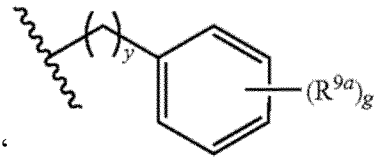 --.

Signed and Sealed this
Seventeenth Day of May, 2022

Katherine Kelly Vidal
*Director of the United States Patent and Trademark Office*